US010730938B2

(12) United States Patent
Bedoucha et al.

(10) Patent No.: US 10,730,938 B2
(45) Date of Patent: *Aug. 4, 2020

(54) BISPECIFIC ANTIBODIES AND METHODS OF USE IN OPHTHALMOLOGY

(71) Applicant: Hoffmann-La Roche Inc., Little Falls, NJ (US)

(72) Inventors: Marc Bedoucha, Ranspach-le-Haut (FR); Sebastian Breuer, Penzberg (DE); Stefan Dengl, Munich (DE); Christian Gassner, Penzberg (DE); Guy Georges, Habach (DE); Sabine Gruener, Grenzach-Wyhlen (DE); Guido Hartmann, Loerrach (DE); Peter Michael Huelsmann, Habach (DE); Hubert Kettenberger, Munich (DE); Joerg Moelleken, Munich (DE); Michael Molhoj, Munich (DE); Olaf Mundigl, Weilheim (DE); Joerg Thomas Regula, Munich (DE); Ralf Schumacher, Penzberg (DE); Barbara Weiser, Sindelsdorf (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/590,176

(22) Filed: May 9, 2017

(65) Prior Publication Data

US 2017/0240629 A1 Aug. 24, 2017

Related U.S. Application Data

(63) Continuation of application No. PCT/EP2015/075879, filed on Nov. 6, 2015.

(30) Foreign Application Priority Data

Nov. 10, 2014 (EP) ..................................... 14192517

(51) Int. Cl.
*C07K 16/22* (2006.01)
*C07K 16/24* (2006.01)

(52) U.S. Cl.
CPC ............ *C07K 16/245* (2013.01); *C07K 16/22* (2013.01); *C07K 2317/24* (2013.01); *C07K 2317/31* (2013.01); *C07K 2317/33* (2013.01); *C07K 2317/35* (2013.01); *C07K 2317/52* (2013.01); *C07K 2317/522* (2013.01); *C07K 2317/55* (2013.01); *C07K 2317/56* (2013.01); *C07K 2317/62* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 4,935,343 | A | 6/1990 | Allison et al. |
|---|---|---|---|
| 7,993,878 | B2 | 8/2011 | Gram et al. |
| 8,268,314 | B2 | 9/2012 | Baehner et al. |
| 8,703,130 | B2 | 4/2014 | Baehner et al. |
| 9,151,761 | B2 | 10/2015 | Anderson et al. |
| 9,695,233 | B2 | 7/2017 | Duerr et al. |
| 9,708,396 | B2 | 7/2017 | Baehner et al. |
| 2010/0111967 | A1 | 5/2010 | Baehner et al. |
| 2012/0321627 | A1 | 12/2012 | Baehner et al. |
| 2013/0142783 | A1 | 6/2013 | Coyle et al. |
| 2013/0330355 | A1 | 12/2013 | Ke et al. |
| 2014/0093498 | A1 | 4/2014 | Gschwind et al. |
| 2014/0093499 | A1 | 4/2014 | Gschwind et al. |
| 2014/0271458 | A1 | 9/2014 | Ghayur et al. |
| 2014/0348824 | A1 | 11/2014 | Anderson et al. |
| 2015/0004166 | A1 | 1/2015 | Baehner et al. |
| 2015/0232548 | A1 | 8/2015 | Klein et al. |
| 2017/0240629 | A1 | 8/2017 | Bedoucha et al. |
| 2017/0247440 | A1 | 8/2017 | Bedoucha et al. |
| 2017/0247441 | A1 | 8/2017 | Dengl et al. |
| 2017/0247447 | A1 | 8/2017 | Dengl et al. |
| 2017/0369566 | A1 | 12/2017 | Baehner et al. |
| 2018/0134780 | A1 | 5/2018 | Klein et al. |
| 2018/0346559 | A1 | 12/2018 | Hilberg et al. |
| 2019/0004048 | A1 | 1/2019 | Anderson et al. |

FOREIGN PATENT DOCUMENTS

| RU | 2368359 | | 9/2009 |
|---|---|---|---|
| WO | 2003/073982 | | 9/2003 |
| WO | 2004/003019 | A2 | 1/2004 |
| WO | 2004/067568 | A2 | 8/2004 |
| WO | 2004/067563 | | 12/2004 |
| WO | 2005/052002 | | 9/2005 |
| WO | 2005/087812 | A1 | 9/2005 |
| WO | 2006/045049 | | 4/2006 |
| WO | 2006/068953 | A2 | 6/2006 |

(Continued)

OTHER PUBLICATIONS

Hessen et al., "Dry Eye: and Inflammatory Ocular Disease" Journal of Ophthalmic and Vision Research 9(2):240-250 ( 2014).
Planck et al., "Impact of IL-1 signalling on experimental uveitis and arthritis" Ann Rheum Dis 71(5):753-760 ( 2012).
Solomon et al., "Pro- and Anti-inflammatory Forms of Interleukin-1 in the Tear Fluid and Conjuctiva of Patients with Dry Eye Disease" Investigative Ophthalmology & Visual Science 42(10):2283-2292 ( 2001).

(Continued)

*Primary Examiner* — Marianne P Allen
(74) *Attorney, Agent, or Firm* — Grant Kalinowski

(57) ABSTRACT

Herein are reported novel bispecific antibodies that specifically bind to two different antigens selected from the group consisting of human ANG2, human VEGF, human IL-1beta and human PDGF-B.

13 Claims, No Drawings

Specification includes a Sequence Listing.

(56) References Cited

FOREIGN PATENT DOCUMENTS

| | | |
|---|---|---|
| WO | 2006/138181 A2 | 12/2006 |
| WO | 2008/024188 A2 | 2/2008 |
| WO | 2009/080252 A1 | 7/2009 |
| WO | 2009/136352 | 11/2009 |
| WO | 2009/149370 | 12/2009 |
| WO | 2010/040508 A1 | 4/2010 |
| WO | 2010/087972 | 8/2010 |
| WO | 2011/047266 A1 | 4/2011 |
| WO | 2011/117329 A1 | 9/2011 |
| WO | 2011/117330 A1 | 9/2011 |
| WO | 2011/140522 | 11/2011 |
| WO | 2012/021773 A1 | 2/2012 |
| WO | 2012/034039 | 3/2012 |
| WO | 2012/121775 | 9/2012 |
| WO | 2012/125850 A1 | 9/2012 |
| WO | 2014/001442 A1 | 1/2014 |
| WO | 2014/009465 | 1/2014 |
| WO | 2014/072876 A1 | 5/2014 |
| WO | 2014/074823 A1 | 5/2014 |
| WO | 2014/109999 A1 | 7/2014 |
| WO | 2014/177460 | 11/2014 |
| WO | 2014/177460 A1 | 11/2014 |
| WO | 2015/107026 A1 | 7/2015 |
| WO | 2015/150447 A1 | 10/2015 |

OTHER PUBLICATIONS

IPRP for PCT/EP2015/075879 (May 16, 2017).
ISR for PCT/EP2015/075879 (Dated Dec. 21, 2015).
Jo, N. et al., "Inhibition of Platelet-Derived Growth Factor B Signaling Enhances the Efficacy of Anti-Vascular Endothelial Growth Factor Therapy in Multiple Models of Ocular Neovascularization" American Journal of Pathology 168(6):2036-2053 ( 2006).
Kienast et al., "Ang-2 VEGF-A CrossMab, a Novel Bispecific Human IgG1 Antibody Blocking VEGF-A and Ang-2 Functions Simultaneously, Mediates Potent Antitumor, Antiangiogenic, and Antimetastatic Efficacy" Clin Cancer Res 19(24):6730-6740 (Dec. 15, 2013).
Kontermann, "Dual targeting strategies with bispecific antibodies" mAbs (Mar./Apr. 2012), 4(2):182-197.
Leonardzehr et al., "Molecular Partners continues to valiate DARPin platform" BioTuesdays:1-8 ( 2012).
Li, Q. et al., "Therapeutic efficacy of three bispecific antibodies on collagen-induced arthritis mouse model" International Immunopharmacology 21:119-127 ( 2014).
Mabry, R. et al., "A dual-targeting PDGFRβ/VEGF-A molecule assembled from stable antibody fragments demonstrates antiangiogenic activity in vitro and in vivo" mAbs 2(1):20-34 ( 2010).
Papadopoulos, K.P. et al., "A phase I first-in-human study of REGN910 (SAR307746), a fully human and selective angiopoietin-2 (Ang2) monoclonal antibody (MAb), in patients with advanced solid tumor malignancies" Abstract (Abstract 2517) ASCO Annual Meeting, (2013) http://meetinglibrary.asco.org/print/1155681.
Schaefer et al., "Immunoglobulin domain crossover as a generic approach for the production of bispecific IgG antibodies" Proceedings of the National Academy of Sciences 108(27):11187-11192 (Jul. 5, 2011).
Thomas et al., "A Novel Angiopoietin-2 Selective Fully Human Antibody with Potent Anti-Tumoral and Anti-Angiogenic Efficacy and Superior Side Effect Profile Compared to Pan-Angiopoietin-1/-2 Inhibitors" PLOS-One 8(2):e54923 (Feb. 2013).
Vassbotn, F.S. et al., "A monoclonal antibody against PDGF B-chain inhibits PDGF-induced DNA synthesis in C3H fibroblasts and prevents binding of PDGF to its receptor" Biochimica et Biophysica Acta 1054(2):246-249 ( 1990).
Wu, C. et al., "Molecular construction and optimization of antihuman IL-1α/β dual variable domain immunoglobulin (DVD-IgTM) molecules" mAbs 1(4):339-347 ( 2009).
Bessho et al., "Effect of Ang-2-VEGF-A bispecific antibody in renal cell carcinoma" Cancer Investigation 33(8):378-86 (2015).
Bezuidenhout et al., "Association of Ang-2 with Integrin β2 Controls Ang-2/PDGF-BB-Dependent Unpregulation of Human Peripheral Blood Monocyte Fibrinolysis" Inflammation 32(6):393 (2009).
Bezuidenthout et al., "Ang-2 and PGDF-BB cooperatively stimulate human peripheral blood monocyte fibrinolysis" Journal of Leukoeyte Biology 81:1469 (2007).
Bogdanovic et al., "Activation of Tie2 by angiopoietin-1 and angiopoietin-2 results in their release and receptor internalization" J. Cell Sci. 119(17):3551-33560 (2006).
Fenn, S et al., "Crystal Structure of an Anti-Ang2 CrossFab Demonstrates Complete Structural and Functional Integrity of the Variable Domain" PLOS ONE 8(4):e61953 (Apr. 1, 2013).
Gassner, C. et al., "Development and validation of a novel SPR-based assay principle for bispecific molecules" Journal of Pharmaceutical and Biomedical Analysis 102:144-149 (2015).
Hansen et al., "Effects of angiopoetins-1 and -2 on the recepter tyrosine kinase Tie2 are differentially regulated at the endothelial cell surface" Cell Signal 22(3):527-532 (2010).
Klein et al., "The Use of CrossMAB technology for the generation of bi- and multispecific antibodies" MABS 8(6):1010-1020 (2016).
Kloepper et al., "Ang-2/VEGF bispecific antibody reprograms macrophages and resident microglia to anti-tumor phenotype and prolongs glioblastoma survival" Proc. Natl. Acad. Sci. USA 113(16):4476-4481 (2016).
Regula et al., "Targeting key angiogenic pathways with a bispecific CrossMAB optimized for neovascular eye diseases" EMBO Molecular Medicine 8(11):1265 (2016).
Scheuer et al., "Anti-tumoral, anti-angiogenic and anti-metastatic efficacy of a tetravalent bispecific antibody (TAvi6) targeting VEGF-A and angiopoietin-2" MABS 8(3):562-573 (2016).
Stubenrauch et al., "An immunodepletion procedure advances free angiopoietin-2 determination in human plasma samples during anticancer therapy with bispecific anti-Ang2/VEGF Cross Mab" J. of Pharm and Biomedical Analysis 102:459-67 (2015).
Ward et al., "Binding activities of a reportoire of sigle immunoglobin variable domainds" Nature 341:544-546 (Oct. 12, 1989).
Karamysheva, "The Mechanisms of Angiogenesis" Biochimia 73(7):935-948 (Jul. 2008).
Ogawa et al., "Anti-PGDF-B monoclonal antibody reduces livel fibrosis development" Hepatology Research 40:1128-1141 (2010).
Pakula et al., "Genetic analysis of protein stability and function" Annu. Rev. Genet. 23:289-310 (1989).
Peppercorn et al., "Toward Improved Understanding of the Ethical and Clinical Issues Surrounding Mandatory Research Biopsies" Journal of Clinical Oncoloy 31(1):1-2 (2013).
Rudikoff et al., "Single amino acid substitution altering antigen-binding specificity," Proc. Nat. Acad. Sci. USA, vol. 79, pp. 1979-1983, Mar. 1982.
Alten et al., "The Human anti-ilβMonoclonal Antibody ACZ885 is Effective in Joint Inflammation Models in Mice and in a Proof-of-Concept Study in Patients with Rheumatoid Arthritis" Arthritis Research & Therapy 10(3) (2008).
Rondeau et al., "The Molecular Human Monoclonal Antibody Mode of Action and Species Neutralizing Il-1 β" MABS 7(6):1151-1160 (2015).
Ohno et al., "Antigen binding specificities of antibodies are primarily determined by seven residues of VH" Proc. Natl. Acad Sci. USA 829(9):2945-2949 (1985).
Wu et al., "Research progress of bispecific antibodies in potential clinical applications" J. of Gastroenterology and Hepatology 21(10):971-974 (2012).
Almagro, J., et al., "Humanization of antibodies" Front Biosci 13:1619-1633 (Jan. 1, 2008).

SEQUENCE LISTING

```
<160> NUMBER OF SEQ ID NOS: 189

<210> SEQ ID NO 1
<211> LENGTH: 118
<212> TYPE: PRT
<213> ORGANISM: Artificial sequence
<220> FEATURE:
<223> OTHER INFORMATION: huH34-1 VH

<400> SEQUENCE: 1

Gln Val Gln Leu Val Gln Ser Gly Ala Glu Val Lys Lys Pro Gly Ala
```

```
                1               5                  10                  15
            Ser Val Lys Val Ser Cys Lys Ala Ser Gly Tyr Thr Phe Thr Gly Tyr
                        20                  25                  30

Tyr Met His Trp Val Arg Gln Ala Pro Gly Gln Gly Leu Glu Trp Met
                        35                  40                  45

Gly Tyr Ile Ser Ser Tyr Ser Gly Phe Thr Thr Tyr Ala Gln Lys Phe
                    50                  55                  60

Gln Gly Arg Val Thr Met Thr Arg Asp Thr Ser Ile Ser Thr Ala Tyr
            65                  70                  75                  80

Met Glu Leu Ser Arg Leu Arg Ser Asp Asp Thr Ala Val Tyr Tyr Cys
                        85                  90                  95

Ala Arg Ser Asp Tyr Tyr Gly Thr Ser Leu Tyr Trp Gly Gln Gly Thr
                        100                 105                 110

Leu Val Thr Val Ser Ser
                    115

<210> SEQ ID NO 2
<211> LENGTH: 7
<212> TYPE: PRT
<213> ORGANISM: Artificial sequence
<220> FEATURE:
<223> OTHER INFORMATION: huH34-1-HVR-H1

<400> SEQUENCE: 2

Gly Tyr Thr Phe Thr Gly Tyr
1               5

<210> SEQ ID NO 3
<211> LENGTH: 3
<212> TYPE: PRT
<213> ORGANISM: Artificial sequence
<220> FEATURE:
<223> OTHER INFORMATION: huH34-1-HVR-H2s

<400> SEQUENCE: 3

Tyr Ser Gly
1

<210> SEQ ID NO 4
<211> LENGTH: 17
<212> TYPE: PRT
<213> ORGANISM: Artificial sequence
<220> FEATURE:
<223> OTHER INFORMATION: huH34-1-HVR-H2

<400> SEQUENCE: 4

Tyr Ile Ser Ser Tyr Ser Gly Phe Thr Thr Tyr Ala Gln Lys Phe Gln
1               5                   10                  15

Gly

<210> SEQ ID NO 5
<211> LENGTH: 7
<212> TYPE: PRT
<213> ORGANISM: Mus musculus

<400> SEQUENCE: 5

Asp Tyr Tyr Gly Thr Ser Leu
1               5

<210> SEQ ID NO 6
<211> LENGTH: 118
<212> TYPE: PRT
```

```
<213> ORGANISM: Artificial sequence
<220> FEATURE:
<223> OTHER INFORMATION: huH34-2 VH

<400> SEQUENCE: 6
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Ile
        35                  40                  45

Gly Tyr Ile Ser Ser Tyr Asn Ala Phe Thr Thr Tyr Asn Gln Lys Phe
    50                  55                  60

Arg Gly Arg Ala Thr Phe Thr Val Asp Thr Ser Ile Ser Thr Ala Tyr
65              70                  75                  80

Met Glu Leu Ser Arg Leu Arg Ser Asp Asp Thr Ala Val Tyr Tyr Cys
                85                  90                  95

Val Arg Ser Asp Tyr Tyr Gly Thr Ser Leu Tyr Trp Gly Gln Gly Thr
            100                 105                 110

Leu Val Thr Val Ser Ser
            115

```
<210> SEQ ID NO 7
<211> LENGTH: 7
<212> TYPE: PRT
<213> ORGANISM: Mus musculus

<400> SEQUENCE: 7
```

Gly Tyr Thr Phe Thr Gly Tyr
1               5

```
<210> SEQ ID NO 8
<211> LENGTH: 3
<212> TYPE: PRT
<213> ORGANISM: Mus musculus

<400> SEQUENCE: 8
```

Tyr Asn Ala
1

```
<210> SEQ ID NO 9
<211> LENGTH: 17
<212> TYPE: PRT
<213> ORGANISM: Artificial sequence
<220> FEATURE:
<223> OTHER INFORMATION: huH34-2-HVR-H2

<400> SEQUENCE: 9
```

Tyr Ile Ser Ser Tyr Asn Ala Phe Thr Thr Tyr Asn Gln Lys Phe Arg
1               5                   10                  15

Gly

```
<210> SEQ ID NO 10
<211> LENGTH: 7
<212> TYPE: PRT
<213> ORGANISM: Mus musculus

<400> SEQUENCE: 10
```

Asp Tyr Tyr Gly Thr Ser Leu
1               5

```
<210> SEQ ID NO 11
<211> LENGTH: 118
<212> TYPE: PRT
<213> ORGANISM: Artificial sequence
<220> FEATURE:
<223> OTHER INFORMATION: huH34-3 VH

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Ile
        35                  40                  45

Gly Tyr Ile Ser Ser Tyr Ser Ala Phe Thr Thr Tyr Asn Gln Lys Phe
    50                  55                  60

Arg Gly Arg Ala Thr Phe Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Val Arg Ser Asp Tyr Tyr Gly Thr Ser Leu Tyr Trp Gly Gln Gly Thr
            100                 105                 110

Leu Val Thr Val Ser Ser
        115

<210> SEQ ID NO 12
<211> LENGTH: 7
<212> TYPE: PRT
<213> ORGANISM: Mus musculus

<400> SEQUENCE: 12

Gly Tyr Thr Phe Thr Gly Tyr
1               5

<210> SEQ ID NO 13
<211> LENGTH: 3
<212> TYPE: PRT
<213> ORGANISM: Artificial sequence
<220> FEATURE:
<223> OTHER INFORMATION: huH34-3-HVR-H2s

<400> SEQUENCE: 13

Tyr Ser Ala
1

<210> SEQ ID NO 14
<211> LENGTH: 17
<212> TYPE: PRT
<213> ORGANISM: Artificial sequence
<220> FEATURE:
<223> OTHER INFORMATION: huH34-3-HVR-H2

<400> SEQUENCE: 14

Tyr Ile Ser Ser Tyr Ser Ala Phe Thr Thr Tyr Asn Gln Lys Phe Arg
1               5                   10                  15

Gly

<210> SEQ ID NO 15
<211> LENGTH: 7
<212> TYPE: PRT
<213> ORGANISM: Mus musculus

<400> SEQUENCE: 15
```

Asp Tyr Tyr Gly Thr Ser Leu
1               5

<210> SEQ ID NO 16
<211> LENGTH: 105
<212> TYPE: PRT
<213> ORGANISM: Artificial sequence
<220> FEATURE:
<223> OTHER INFORMATION: huH34 VK

<400> SEQUENCE: 16

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
            20                  25                  30

His Trp Ser Gln Gln Lys Pro Gly Gln Ala Pro Arg Leu Leu Ile Tyr
        35                  40                  45

Ser Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys His Gln Trp Ser Asn Tyr Tyr Thr Phe
                85                  90                  95

Gly Gln Gly Thr Lys Leu Glu Ile Lys
            100                 105

<210> SEQ ID NO 17
<211> LENGTH: 6
<212> TYPE: PRT
<213> ORGANISM: Mus musculus

<400> SEQUENCE: 17

Ser Ser Ser Val Ser Tyr
1               5

<210> SEQ ID NO 18
<211> LENGTH: 3
<212> TYPE: PRT
<213> ORGANISM: Mus musculus

<400> SEQUENCE: 18

Ser Thr Ser
1

<210> SEQ ID NO 19
<211> LENGTH: 5
<212> TYPE: PRT
<213> ORGANISM: Mus musculus

<400> SEQUENCE: 19

Trp Ser Asn Tyr Tyr
1               5

<210> SEQ ID NO 20
<211> LENGTH: 121
<212> TYPE: PRT
<213> ORGANISM: Mus musculus

<400> SEQUENCE: 20

Glu Val Gln Leu Gln Gln Ser Gly Pro Glu Leu Glu Lys Pro Gly Ala
1               5                   10                  15

```
Ser Val Lys Ile Ser Cys Lys Ala Ser Gly Tyr Ser Phe Thr Asp Tyr
            20                  25                  30

Asn Met Asn Trp Val Arg Gln Ser Asn Gly Lys Ser Leu Glu Trp Ile
         35                  40                  45

Gly Asn Ile Asp Pro Tyr Tyr Gly Gly Thr Thr Tyr Asn Gln Lys Phe
     50                  55                  60

Lys Asp Lys Ala Thr Leu Thr Val Asp Lys Ser Ser Thr Ala Tyr
 65                  70                  75                  80

Met Gln Leu Lys Ser Leu Thr Ser Glu Asp Ser Ala Val Tyr Tyr Cys
                 85                  90                  95

Ala Arg Glu Gly Ser Pro Thr Arg Tyr Tyr Val Met Asp Tyr Trp Gly
            100                 105                 110

Gln Gly Thr Ser Val Thr Val Ser Ser
            115                 120

<210> SEQ ID NO 21
<211> LENGTH: 7
<212> TYPE: PRT
<213> ORGANISM: Mus musculus

<400> SEQUENCE: 21

Gly Tyr Ser Phe Thr Asp Tyr
1               5

<210> SEQ ID NO 22
<211> LENGTH: 3
<212> TYPE: PRT
<213> ORGANISM: Mus musculus

<400> SEQUENCE: 22

Tyr Tyr Gly
1

<210> SEQ ID NO 23
<211> LENGTH: 17
<212> TYPE: PRT
<213> ORGANISM: Mus musculus

<400> SEQUENCE: 23

Asn Ile Asp Pro Tyr Tyr Gly Gly Thr Thr Tyr Asn Gln Lys Phe Lys
1               5                   10                  15

Asp

<210> SEQ ID NO 24
<211> LENGTH: 10
<212> TYPE: PRT
<213> ORGANISM: Mus musculus

<400> SEQUENCE: 24

Gly Ser Pro Thr Arg Tyr Tyr Val Met Asp
1               5                   10

<210> SEQ ID NO 25
<211> LENGTH: 107
<212> TYPE: PRT
<213> ORGANISM: Mus musculus

<400> SEQUENCE: 25

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Asn
```

```
                20                  25                  30
Leu Ala Trp Tyr Gln Gln Lys Gln Gly Lys Ser Pro Gln Leu Leu Val
            35                  40                  45
Tyr Ala Ala Thr Asn Leu Ala Asp Gly Val Pro Ser Arg Phe Ser Gly
        50                  55                  60
Ser Gly Ser Gly Thr Gln Phe Ser Leu Lys Ile Asn Ser Leu Gln Pro
65                  70                  75                  80
Glu Asp Phe Gly Ser Tyr Tyr Cys His His Phe Tyr Asn Thr Pro Trp
                85                  90                  95
Thr Phe Gly Gly Gly Thr Lys Leu Glu Ile Lys
                100                 105
```

<210> SEQ ID NO 26
<211> LENGTH: 7
<212> TYPE: PRT
<213> ORGANISM: Mus musculus

<400> SEQUENCE: 26

```
Ser Glu Asn Ile Tyr Ser Asn
1               5
```

<210> SEQ ID NO 27
<211> LENGTH: 3
<212> TYPE: PRT
<213> ORGANISM: Mus musculus

<400> SEQUENCE: 27

```
Ala Ala Thr
1
```

<210> SEQ ID NO 28
<211> LENGTH: 6
<212> TYPE: PRT
<213> ORGANISM: Mus musculus

<400> SEQUENCE: 28

```
Phe Tyr Asn Thr Pro Trp
1               5
```

<210> SEQ ID NO 29
<211> LENGTH: 116
<212> TYPE: PRT
<213> ORGANISM: Mus musculus

<400> SEQUENCE: 29

```
Gln Val Gln Leu Gln Gln Ser Gly Ala Glu Leu Met Lys Pro Gly Ala
1               5                   10                  15
Ser Val Lys Ile Ser Cys Lys Ala Thr Gly Tyr Thr Phe Ser Ser Tyr
                20                  25                  30
Trp Ile Glu Trp Val Lys Gln Arg Pro Gly His Gly Leu Glu Trp Ile
            35                  40                  45
Gly Glu Ile Leu Pro Gly Ser Gly Ser Thr Asn Tyr Asn Glu Lys Phe
        50                  55                  60
Lys Val Lys Ala Thr Phe Thr Ala Asp Thr Ser Ser Asn Thr Ala Tyr
65                  70                  75                  80
Met Gln Leu Ser Ser Leu Thr Ser Glu Asp Ser Ala Val Tyr Tyr Cys
                85                  90                  95
Ala Gln Thr Thr Gln Asp Phe Asp Ser Trp Gly Gln Gly Thr Thr Leu
                100                 105                 110
```

Thr Val Ser Ser
        115

<210> SEQ ID NO 30
<211> LENGTH: 7
<212> TYPE: PRT
<213> ORGANISM: Mus musculus

<400> SEQUENCE: 30

Gly Tyr Thr Phe Ser Ser Tyr
1               5

<210> SEQ ID NO 31
<211> LENGTH: 3
<212> TYPE: PRT
<213> ORGANISM: Mus musculus

<400> SEQUENCE: 31

Gly Ser Gly
1

<210> SEQ ID NO 32
<211> LENGTH: 17
<212> TYPE: PRT
<213> ORGANISM: Mus musculus

<400> SEQUENCE: 32

Glu Ile Leu Pro Gly Ser Gly Ser Thr Asn Tyr Asn Glu Lys Phe Lys
1               5                   10                  15

Val

<210> SEQ ID NO 33
<211> LENGTH: 5
<212> TYPE: PRT
<213> ORGANISM: Mus musculus

<400> SEQUENCE: 33

Thr Gln Asp Phe Asp
1               5

<210> SEQ ID NO 34
<211> LENGTH: 111
<212> TYPE: PRT
<213> ORGANISM: Mus musculus

<400> SEQUENCE: 34

Asp Ile Val Leu Thr Gln Ser Pro Gly Ser Leu Ala Val Ser Leu Gly
1               5                   10                  15

Gln Arg Ala Thr Ile Ser Cys Arg Ala Ser Glu Ser Val Asp Ile Tyr
            20                  25                  30

Gly Tyr Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Arg Thr Phe Gly Gly Gly Thr Lys Leu Glu Ile Lys
            100                 105                 110

```
<210> SEQ ID NO 35
<211> LENGTH: 11
<212> TYPE: PRT
<213> ORGANISM: Mus musculus

<400> SEQUENCE: 35

Ser Glu Ser Val Asp Ile Tyr Gly Tyr Ser Phe
1               5                   10

<210> SEQ ID NO 36
<211> LENGTH: 3
<212> TYPE: PRT
<213> ORGANISM: Mus musculus

<400> SEQUENCE: 36

Arg Ala Ser
1

<210> SEQ ID NO 37
<211> LENGTH: 6
<212> TYPE: PRT
<213> ORGANISM: Mus musculus

<400> SEQUENCE: 37

Ser Asn Glu Asp Pro Arg
1               5

<210> SEQ ID NO 38
<211> LENGTH: 120
<212> TYPE: PRT
<213> ORGANISM: Artificial sequence
<220> FEATURE:
<223> OTHER INFORMATION: PDGFB-0085 VH

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ser Thr Ile Ser Asp Gly Gly Gly Leu Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Glu Ser Gly Gly Tyr Thr Asp Trp Leu Phe Gly Tyr Trp Gly Gln
            100                 105                 110

Gly Thr Leu Val Thr Val Ser Ser
        115                 120

<210> SEQ ID NO 39
<211> LENGTH: 5
<212> TYPE: PRT
<213> ORGANISM: Artificial sequence
<220> FEATURE:
<223> OTHER INFORMATION: PDGFB-0085 HVR-H1

<400> SEQUENCE: 39

Ser Tyr Trp Met Ser
1               5
```

```
<210> SEQ ID NO 40
<211> LENGTH: 6
<212> TYPE: PRT
<213> ORGANISM: Artificial sequence
<220> FEATURE:
<223> OTHER INFORMATION: PDGFB-0085 HVR-H2s

<400> SEQUENCE: 40

Ser Asp Gly Gly Gly Leu
1               5

<210> SEQ ID NO 41
<211> LENGTH: 17
<212> TYPE: PRT
<213> ORGANISM: Artificial sequence
<220> FEATURE:
<223> OTHER INFORMATION: PDGFB-0085 HVR-H2

<400> SEQUENCE: 41

Thr Ile Ser Asp Gly Gly Gly Leu Thr Tyr Tyr Ala Asp Ser Val Lys
1               5                   10                  15

Gly

<210> SEQ ID NO 42
<211> LENGTH: 11
<212> TYPE: PRT
<213> ORGANISM: Artificial sequence
<220> FEATURE:
<223> OTHER INFORMATION: PDGFB-0085 HVR-H3

<400> SEQUENCE: 42

Ser Gly Gly Tyr Thr Asp Trp Leu Phe Gly Tyr
1               5                   10

<210> SEQ ID NO 43
<211> LENGTH: 107
<212> TYPE: PRT
<213> ORGANISM: Artificial sequence
<220> FEATURE:
<223> OTHER INFORMATION: PDGFB-0085 VL kappa

<400> SEQUENCE: 43

Asp Ile Gln Met Thr Gln Ser Pro Ser Ser Leu Ser Ala Ser Val Gly
1               5                   10                  15

Asp Arg Val Ala Ile Thr Cys Arg Ala Ser Gln Ser Ile Ser Asn Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 44
<211> LENGTH: 11
<212> TYPE: PRT
<213> ORGANISM: Artificial sequence
<220> FEATURE:
<223> OTHER INFORMATION: PDGFB-0085 HVR-L1
```

<400> SEQUENCE: 44

Arg Ala Ser Gln Ser Ile Ser Asn Tyr Leu Asn
1               5                   10

<210> SEQ ID NO 45
<211> LENGTH: 7
<212> TYPE: PRT
<213> ORGANISM: Artificial sequence
<220> FEATURE:
<223> OTHER INFORMATION: PDGFB-0085 HVR-L2

<400> SEQUENCE: 45

Ala Ala Ser Ser Leu Gln Ser
1               5

<210> SEQ ID NO 46
<211> LENGTH: 9
<212> TYPE: PRT
<213> ORGANISM: Artificial sequence
<220> FEATURE:
<223> OTHER INFORMATION: PDGFB-0085 HVR-L3

<400> SEQUENCE: 46

Gln Gln Ser Tyr Ser Thr Pro Leu Thr
1               5

<210> SEQ ID NO 47
<211> LENGTH: 120
<212> TYPE: PRT
<213> ORGANISM: Artificial sequence
<220> FEATURE:
<223> OTHER INFORMATION: PDGFB-0086 VH

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ser Thr Ile Ser Asp Gly Gly Leu Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Glu Ser Gly Gly Tyr Thr Asp Trp Leu Phe Gly Tyr Trp Gly Gln
            100                 105                 110

Gly Thr Leu Val Thr Val Ser Ser
        115                 120

<210> SEQ ID NO 48
<211> LENGTH: 5
<212> TYPE: PRT
<213> ORGANISM: Artificial sequence
<220> FEATURE:
<223> OTHER INFORMATION: PDGFB-0086 HVR-H1

<400> SEQUENCE: 48

Ser Tyr Trp Met Ser
1               5

-continued

<210> SEQ ID NO 49
<211> LENGTH: 6
<212> TYPE: PRT
<213> ORGANISM: Artificial sequence
<220> FEATURE:
<223> OTHER INFORMATION: PDGFB-0086 HVR-H2s

<400> SEQUENCE: 49

Ser Asp Gly Gly Gly Leu
1               5

<210> SEQ ID NO 50
<211> LENGTH: 17
<212> TYPE: PRT
<213> ORGANISM: Artificial sequence
<220> FEATURE:
<223> OTHER INFORMATION: PDGFB-0086 HVR-H2

<400> SEQUENCE: 50

Thr Ile Ser Asp Gly Gly Gly Leu Thr Tyr Tyr Ala Asp Ser Val Lys
1               5                   10                  15

Gly

<210> SEQ ID NO 51
<211> LENGTH: 11
<212> TYPE: PRT
<213> ORGANISM: Artificial sequence
<220> FEATURE:
<223> OTHER INFORMATION: PDGFB-0086 HVR-H3

<400> SEQUENCE: 51

Ser Gly Gly Tyr Thr Asp Trp Leu Phe Gly Tyr
1               5                   10

<210> SEQ ID NO 52
<211> LENGTH: 107
<212> TYPE: PRT
<213> ORGANISM: Artificial sequence
<220> FEATURE:
<223> OTHER INFORMATION: PDGFB-0086 VL kappa

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 53
<211> LENGTH: 11
<212> TYPE: PRT
<213> ORGANISM: Artificial sequence
<220> FEATURE:
<223> OTHER INFORMATION: PDGFB-0086 HVR-L1

```
<400> SEQUENCE: 53

Arg Ala Ser Gln Ser Ile Ser Ser Tyr Leu Asn
1               5                   10

<210> SEQ ID NO 54
<211> LENGTH: 7
<212> TYPE: PRT
<213> ORGANISM: Artificial sequence
<220> FEATURE:
<223> OTHER INFORMATION: PDGFB-0086 HVR-L2

<400> SEQUENCE: 54

Ala Ala Ser Ser Leu Gln Ser
1               5

<210> SEQ ID NO 55
<211> LENGTH: 9
<212> TYPE: PRT
<213> ORGANISM: Artificial sequence
<220> FEATURE:
<223> OTHER INFORMATION: PDGFB-0086 HVR-L3

<400> SEQUENCE: 55

Gln Gln Ser Tyr Ser Thr Pro Leu Thr
1               5

<210> SEQ ID NO 56
<211> LENGTH: 129
<212> TYPE: PRT
<213> ORGANISM: Artificial sequence
<220> FEATURE:
<223> OTHER INFORMATION: Ang2 LC10 VH

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
                100                 105                 110

Pro Gly Ala Phe Asp Ile Trp Gly Gln Gly Thr Met Val Thr Val Ser
            115                 120                 125

Ser

<210> SEQ ID NO 57
<211> LENGTH: 7
<212> TYPE: PRT
<213> ORGANISM: Artificial sequence
<220> FEATURE:
<223> OTHER INFORMATION: Ang2 LC10 HVR-H1

<400> SEQUENCE: 57

Gly Tyr Thr Phe Thr Gly Tyr
```

```
<210> SEQ ID NO 58
<211> LENGTH: 3
<212> TYPE: PRT
<213> ORGANISM: Artificial sequence
<220> FEATURE:
<223> OTHER INFORMATION: Ang2 LC10 HVR-H2s

<400> SEQUENCE: 58

Asn Ser Gly
1

<210> SEQ ID NO 59
<211> LENGTH: 17
<212> TYPE: PRT
<213> ORGANISM: Artificial sequence
<220> FEATURE:
<223> OTHER INFORMATION: Ang2 LC10 HVR-H2

<400> SEQUENCE: 59

Trp Ile Asn Pro Asn Ser Gly Gly Thr Asn Tyr Ala Gln Lys Phe Gln
1               5                   10                  15

Gly

<210> SEQ ID NO 60
<211> LENGTH: 18
<212> TYPE: PRT
<213> ORGANISM: Artificial sequence
<220> FEATURE:
<223> OTHER INFORMATION: Ang2 LC10 HVR-H3

<400> SEQUENCE: 60

Pro Asn Pro Tyr Tyr Tyr Asp Ser Ser Gly Tyr Tyr Tyr Pro Gly Ala
1               5                   10                  15

Phe Asp

<210> SEQ ID NO 61
<211> LENGTH: 110
<212> TYPE: PRT
<213> ORGANISM: Artificial sequence
<220> FEATURE:
<223> OTHER INFORMATION: Ang2 LC10 VL

<400> SEQUENCE: 61

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser
            100                 105                 110

<210> SEQ ID NO 62
<211> LENGTH: 7
```

```
<212> TYPE: PRT
<213> ORGANISM: Artificial sequence
<220> FEATURE:
<223> OTHER INFORMATION: Ang2 LC10 HVR-L1

<400> SEQUENCE: 62

Asn Asn Ile Gly Ser Lys Ser
1               5

<210> SEQ ID NO 63
<211> LENGTH: 3
<212> TYPE: PRT
<213> ORGANISM: Artificial sequence
<220> FEATURE:
<223> OTHER INFORMATION: Ang2 LC10 HVR-L2

<400> SEQUENCE: 63

Asp Asp Ser
1

<210> SEQ ID NO 64
<211> LENGTH: 8
<212> TYPE: PRT
<213> ORGANISM: Artificial sequence
<220> FEATURE:
<223> OTHER INFORMATION: Ang2 LC10 HVR-L3

<400> SEQUENCE: 64

Trp Asp Ser Ser Ser Asp His Trp
1               5

<210> SEQ ID NO 65
<211> LENGTH: 129
<212> TYPE: PRT
<213> ORGANISM: Artificial sequence
<220> FEATURE:
<223> OTHER INFORMATION: Ang2 LC10 wt + G114A, S360P, T28N, T30A (HC) VH

<400> SEQUENCE: 65

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Pro Gly Tyr Tyr Tyr
            100                 105                 110

Pro Ala Ala Phe Asp Ile Trp Gly Gln Gly Thr Met Val Thr Val Ser
        115                 120                 125

Ser

<210> SEQ ID NO 66
<211> LENGTH: 7
<212> TYPE: PRT
<213> ORGANISM: Artificial sequence
<220> FEATURE:
<223> OTHER INFORMATION: Ang2 LC10 wt + G114A, S360P, T28N, T30A (HC)
```

-continued

HVR-H1

<400> SEQUENCE: 66

Gly Tyr Asn Phe Ala Gly Tyr
1               5

<210> SEQ ID NO 67
<211> LENGTH: 3
<212> TYPE: PRT
<213> ORGANISM: Artificial sequence
<220> FEATURE:
<223> OTHER INFORMATION: Ang2 LC10 wt + G114A, S360P, T28N, T30A (HC)
      HVR-H2s

<400> SEQUENCE: 67

Asn Ser Gly
1

<210> SEQ ID NO 68
<211> LENGTH: 17
<212> TYPE: PRT
<213> ORGANISM: Artificial sequence
<220> FEATURE:
<223> OTHER INFORMATION: Ang2 LC10 wt + G114A, S360P, T28N, T30A (HC)
      HVR-H2

<400> SEQUENCE: 68

Trp Ile Asn Pro Asn Ser Gly Gly Thr Asn Tyr Ala Gln Lys Phe Gln
1               5                   10                  15

Gly

<210> SEQ ID NO 69
<211> LENGTH: 18
<212> TYPE: PRT
<213> ORGANISM: Artificial sequence
<220> FEATURE:
<223> OTHER INFORMATION: Ang2 LC10 wt + G114A, S360P, T28N, T30A (HC)
      HVR-H3

<400> SEQUENCE: 69

Pro Asn Pro Tyr Tyr Tyr Asp Ser Pro Gly Tyr Tyr Tyr Pro Ala Ala
1               5                   10                  15

Phe Asp

<210> SEQ ID NO 70
<211> LENGTH: 110
<212> TYPE: PRT
<213> ORGANISM: Artificial sequence
<220> FEATURE:
<223> OTHER INFORMATION: Ang2 LC10 wt + G114A, S360P, T28N, T30A (HC) VL

<400> SEQUENCE: 70

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His

```
                    85                  90                  95

Trp Val Phe Gly Gly Gly Thr Lys Leu Thr Val Leu Ser Ser
            100                 105                 110

<210> SEQ ID NO 71
<211> LENGTH: 7
<212> TYPE: PRT
<213> ORGANISM: Artificial sequence
<220> FEATURE:
<223> OTHER INFORMATION: Ang2 LC10 wt + G114A, S360P, T28N, T30A (HC)
      HVR-L1

<400> SEQUENCE: 71

Asn Asn Ile Gly Ser Lys Ser
1               5

<210> SEQ ID NO 72
<211> LENGTH: 3
<212> TYPE: PRT
<213> ORGANISM: Artificial sequence
<220> FEATURE:
<223> OTHER INFORMATION: Ang2 LC10 wt + G114A, S360P, T28N, T30A (HC)
      HVR-L2

<400> SEQUENCE: 72

Asp Asp Ser
1

<210> SEQ ID NO 73
<211> LENGTH: 8
<212> TYPE: PRT
<213> ORGANISM: Artificial sequence
<220> FEATURE:
<223> OTHER INFORMATION: Ang2 LC10 wt + G114A, S360P, T28N, T30A (HC)
      HVR-L3

<400> SEQUENCE: 73

Trp Asp Ser Ser Ser Asp His Trp
1               5

<210> SEQ ID NO 74
<211> LENGTH: 129
<212> TYPE: PRT
<213> ORGANISM: Artificial sequence
<220> FEATURE:
<223> OTHER INFORMATION: Ang2 LC10 wt + G114A, S360P, T28N, T30A (HC) +
      D50T (LC) VH

<400> SEQUENCE: 74

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Pro Gly Tyr Tyr Tyr
            100                 105                 110
```

Pro Ala Ala Phe Asp Ile Trp Gly Gln Gly Thr Met Val Thr Val Ser
            115                 120                 125
Ser

<210> SEQ ID NO 75
<211> LENGTH: 7
<212> TYPE: PRT
<213> ORGANISM: Artificial sequence
<220> FEATURE:
<223> OTHER INFORMATION: Ang2 LC10 wt + G114A, S360P, T28N, T30A (HC) +
      D50T (LC) HVR-H1

<400> SEQUENCE: 75

Gly Tyr Asn Phe Ala Gly Tyr
1               5

<210> SEQ ID NO 76
<211> LENGTH: 3
<212> TYPE: PRT
<213> ORGANISM: Artificial sequence
<220> FEATURE:
<223> OTHER INFORMATION: Ang2 LC10 wt + G114A, S360P, T28N, T30A (HC) +
      D50T (LC) HVR-H2s

<400> SEQUENCE: 76

Asn Ser Gly
1

<210> SEQ ID NO 77
<211> LENGTH: 17
<212> TYPE: PRT
<213> ORGANISM: Artificial sequence
<220> FEATURE:
<223> OTHER INFORMATION: Ang2 LC10 wt + G114A, S360P, T28N, T30A (HC) +
      D50T (LC) HVR-H2

<400> SEQUENCE: 77

Trp Ile Asn Pro Asn Ser Gly Gly Thr Asn Tyr Ala Gln Lys Phe Gln
1               5                   10                  15
Gly

<210> SEQ ID NO 78
<211> LENGTH: 18
<212> TYPE: PRT
<213> ORGANISM: Artificial sequence
<220> FEATURE:
<223> OTHER INFORMATION: Ang2 LC10 wt + G114A, S360P, T28N, T30A (HC) +
      D50T (LC) HVR-H3

<400> SEQUENCE: 78

Pro Asn Pro Tyr Tyr Tyr Asp Ser Pro Gly Tyr Tyr Tyr Pro Ala Ala
1               5                   10                  15
Phe Asp

<210> SEQ ID NO 79
<211> LENGTH: 110
<212> TYPE: PRT
<213> ORGANISM: Artificial sequence
<220> FEATURE:
<223> OTHER INFORMATION: Ang2 LC10 wt + G114A, S360P, T28N, T30A (HC) +
      D50T (LC) VL

<400> SEQUENCE: 79

Ser Tyr Val Leu Thr Gln Pro Pro Ser Val Ser Val Ala Pro Gly Gln
1               5                   10                  15

-continued

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
            35                  40                  45

Asp Thr Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser
            100                 105                 110

<210> SEQ ID NO 80
<211> LENGTH: 7
<212> TYPE: PRT
<213> ORGANISM: Artificial sequence
<220> FEATURE:
<223> OTHER INFORMATION: Ang2 LC10 wt + G114A, S360P, T28N, T30A (HC) +
      D50T (LC) HVR-L1

<400> SEQUENCE: 80

Asn Asn Ile Gly Ser Lys Ser
1               5

<210> SEQ ID NO 81
<211> LENGTH: 3
<212> TYPE: PRT
<213> ORGANISM: Artificial sequence
<220> FEATURE:
<223> OTHER INFORMATION: Ang2 LC10 wt + G114A, S360P, T28N, T30A (HC) +
      D50T (LC) HVR-L2

<400> SEQUENCE: 81

Asp Thr Ser
1

<210> SEQ ID NO 82
<211> LENGTH: 8
<212> TYPE: PRT
<213> ORGANISM: Artificial sequence
<220> FEATURE:
<223> OTHER INFORMATION: Ang2 LC10 wt + G114A, S360P, T28N, T30A (HC) +
      D50T (LC) HVR-L3

<400> SEQUENCE: 82

Trp Asp Ser Ser Ser Asp His Trp
1               5

<210> SEQ ID NO 83
<211> LENGTH: 129
<212> TYPE: PRT
<213> ORGANISM: Artificial sequence
<220> FEATURE:
<223> OTHER INFORMATION: Ang2 LC10 wt + G114A, S360P, T28N, T30A, D106S
      (HC) + D50T (in LC) VH

<400> SEQUENCE: 83

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
            35                  40                  45

```
Gly Trp Ile Asn Pro Asn Ser Gly Gly Thr Asn Tyr Ala Gln Lys Phe
         50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Ser Pro Asn Pro Tyr Tyr Tyr Ser Ser Pro Gly Tyr Tyr Tyr
             100                 105                 110

Pro Ala Ala Phe Asp Ile Trp Gly Gln Gly Thr Met Val Thr Val Ser
             115                 120                 125
Ser
```

<210> SEQ ID NO 84
<211> LENGTH: 7
<212> TYPE: PRT
<213> ORGANISM: Artificial sequence
<220> FEATURE:
<223> OTHER INFORMATION: Ang2 LC10 wt + G114A, S360P, T28N, T30A, D106S
      (HC) + D50T (in LC) HVR-H1

<400> SEQUENCE: 84

```
Gly Tyr Asn Phe Ala Gly Tyr
1               5
```

<210> SEQ ID NO 85
<211> LENGTH: 3
<212> TYPE: PRT
<213> ORGANISM: Artificial sequence
<220> FEATURE:
<223> OTHER INFORMATION: Ang2 LC10 wt + G114A, S360P, T28N, T30A, D106S
      (HC) + D50T (in LC) HVR-H2s

<400> SEQUENCE: 85

```
Asn Ser Gly
1
```

<210> SEQ ID NO 86
<211> LENGTH: 17
<212> TYPE: PRT
<213> ORGANISM: Artificial sequence
<220> FEATURE:
<223> OTHER INFORMATION: Ang2 LC10 wt + G114A, S360P, T28N, T30A, D106S
      (HC) + D50T (in LC) HVR-H2

<400> SEQUENCE: 86

```
Trp Ile Asn Pro Asn Ser Gly Gly Thr Asn Tyr Ala Gln Lys Phe Gln
1               5                   10                  15
Gly
```

<210> SEQ ID NO 87
<211> LENGTH: 18
<212> TYPE: PRT
<213> ORGANISM: Artificial sequence
<220> FEATURE:
<223> OTHER INFORMATION: Ang2 LC10 wt + G114A, S360P, T28N, T30A, D106S
      (HC) + D50T (in LC) HVR-H3

<400> SEQUENCE: 87

```
Pro Asn Pro Tyr Tyr Tyr Ser Ser Pro Gly Tyr Tyr Tyr Pro Ala Ala
1               5                   10                  15
Phe Asp
```

```
<210> SEQ ID NO 88
<211> LENGTH: 110
<212> TYPE: PRT
<213> ORGANISM: Artificial sequence
<220> FEATURE:
<223> OTHER INFORMATION: Ang2 LC10 wt + G114A, S360P, T28N, T30A, D106S
      (HC) + D50T (in LC) VL

<400> SEQUENCE: 88

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Thr Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

Trp Val Phe Gly Gly Gly Thr Lys Leu Thr Val Leu Ser Ser
            100                 105                 110

<210> SEQ ID NO 89
<211> LENGTH: 7
<212> TYPE: PRT
<213> ORGANISM: Artificial sequence
<220> FEATURE:
<223> OTHER INFORMATION: Ang2 LC10 wt + G114A, S360P, T28N, T30A, D106S
      (HC) + D50T (in LC) HVR-L1

<400> SEQUENCE: 89

Asn Asn Ile Gly Ser Lys Ser
1               5

<210> SEQ ID NO 90
<211> LENGTH: 3
<212> TYPE: PRT
<213> ORGANISM: Artificial sequence
<220> FEATURE:
<223> OTHER INFORMATION: Ang2 LC10 wt + G114A, S360P, T28N, T30A, D106S
      (HC) + D50T (in LC) HVR-L2

<400> SEQUENCE: 90

Asp Thr Ser
1

<210> SEQ ID NO 91
<211> LENGTH: 8
<212> TYPE: PRT
<213> ORGANISM: Artificial sequence
<220> FEATURE:
<223> OTHER INFORMATION: Ang2 LC10 wt + G114A, S360P, T28N, T30A, D106S
      (HC) + D50T (in LC) HVR-L3

<400> SEQUENCE: 91

Trp Asp Ser Ser Ser Asp His Trp
1               5

<210> SEQ ID NO 92
<211> LENGTH: 269
<212> TYPE: PRT
<213> ORGANISM: Homo sapiens
```

<400> SEQUENCE: 92

```
Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
            20                  25                  30

Lys Cys Ser Phe Gln Asp Leu Asp Leu Cys Pro Leu Asp Gly Gly Ile
        35                  40                  45

Gln Leu Arg Ile Ser Asp His His Tyr Ser Lys Gly Phe Arg Gln Ala
    50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
            100                 105                 110

Tyr Val His Asp Ala Pro Val Arg Ser Leu Asn Cys Thr Leu Arg Asp
        115                 120                 125

Ser Gln Gln Lys Ser Leu Val Met Ser Gly Pro Tyr Glu Leu Lys Ala
    130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
            180                 185                 190

Lys Pro Thr Leu Gln Leu Glu Ser Val Asp Pro Lys Asn Tyr Pro Lys
        195                 200                 205

Lys Lys Met Glu Lys Arg Phe Val Phe Asn Lys Ile Glu Ile Asn Asn
    210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

Gln Asp Ile Thr Asp Phe Thr Met Gln Phe Val Ser Ser
            260                 265
```

<210> SEQ ID NO 93
<211> LENGTH: 231
<212> TYPE: PRT
<213> ORGANISM: Homo sapiens

<400> SEQUENCE: 93

```
Met Asn Arg Cys Trp Ala Leu Phe Leu Ser Leu Cys Cys Tyr Leu Arg
1               5                   10                  15

Leu Val Ser Ala Glu Gly Asp Pro Ile Pro Glu Glu Leu Tyr Glu Met
            20                  25                  30

Leu Ser Asp His Ser Ile Arg Ser Asp Pro Gly Glu Asp Gly Ala
        35                  40                  45

Glu Leu Asp Leu Asn Met Thr Arg Ser His Ser Gly Gly Glu Leu Glu
    50                  55                  60

Ser Leu Ala Arg Gly Arg Arg Ser Leu Gly Ser Leu Thr Ile Ala Glu
65                  70                  75                  80

Pro Ala Met Ile Ala Glu Cys Lys Thr Arg Thr Glu Val Phe Glu Ile
                85                  90                  95
```

-continued

```
Ser Arg Arg Leu Ile Asp Arg Thr Asn Ala Asn Phe Leu Val Trp Pro
                100                 105                 110

Pro Cys Val Glu Val Gln Arg Cys Ser Gly Cys Cys Asn Asn Arg Asn
            115                 120                 125

Val Gln Cys Arg Pro Thr Gln Val Gln Leu Arg Pro Val Gln Val Arg
        130                 135                 140

Lys Ile Glu Ile Val Arg Lys Lys Pro Ile Phe Lys Lys Ala Thr Val
145                 150                 155                 160

Thr Leu Glu Asp His Leu Ala Cys Lys Cys Glu Thr Val Ala Ala Ala
                165                 170                 175

Arg Pro Val Thr Arg Ser Pro Gly Gly Ser Gln Glu Gln Arg Ala Lys
            180                 185                 190

Thr Pro Gln Thr Arg Val Thr Ile Arg Thr Val Arg Val Arg Arg Pro
        195                 200                 205

Pro Lys Gly Lys His Arg Lys Phe Lys His Thr His Asp Lys Thr Ala
    210                 215                 220

Leu Lys Glu Thr Leu Gly Ala
225                 230

<210> SEQ ID NO 94
<211> LENGTH: 191
<212> TYPE: PRT
<213> ORGANISM: Homo sapiens

<400> SEQUENCE: 94

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
        50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190

<210> SEQ ID NO 95
<211> LENGTH: 496
<212> TYPE: PRT
<213> ORGANISM: Homo sapiens

<400> SEQUENCE: 95
```

```
Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
            20                  25                  30

Gln Tyr Gln Val Gln His Gly Ser Cys Ser Tyr Thr Phe Leu Leu Pro
        35                  40                  45

Glu Met Asp Asn Cys Arg Ser Ser Ser Ser Pro Tyr Val Ser Asn Ala
50                  55                  60

Val Gln Arg Asp Ala Pro Leu Glu Tyr Asp Ser Val Gln Arg Leu
65                  70                  75                  80

Gln Val Leu Glu Asn Ile Met Glu Asn Asn Thr Gln Trp Leu Met Lys
            85                  90                  95

Leu Glu Asn Tyr Ile Gln Asp Asn Met Lys Lys Glu Met Val Glu Ile
            100                 105                 110

Gln Gln Asn Ala Val Gln Asn Thr Ala Val Met Ile Glu Ile Gly
            115                 120                 125

Thr Asn Leu Leu Asn Gln Thr Ala Glu Gln Thr Arg Lys Leu Thr Asp
    130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
            180                 185                 190

Lys Lys Val Leu Ala Met Glu Asp Lys His Ile Ile Gln Leu Gln Ser
        195                 200                 205

Ile Lys Glu Glu Lys Asp Gln Leu Gln Val Leu Val Ser Lys Gln Asn
    210                 215                 220

Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Glu Thr Val Asn
                245                 250                 255

Asn Leu Leu Thr Met Met Ser Thr Ser Asn Ser Ala Lys Asp Pro Thr
            260                 265                 270

Val Ala Lys Glu Glu Gln Ile Ser Phe Arg Asp Cys Ala Glu Val Phe
        275                 280                 285

Lys Ser Gly His Thr Thr Asn Gly Ile Tyr Thr Leu Thr Phe Pro Asn
        290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
            340                 345                 350

Tyr Trp Leu Gly Asn Glu Phe Val Ser Gln Leu Thr Asn Gln Gln Arg
        355                 360                 365

Tyr Val Leu Lys Ile His Leu Lys Asp Trp Glu Gly Asn Glu Ala Tyr
    370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
                405                 410                 415

Ser Gln Pro Gly Asn Asp Phe Ser Thr Lys Asp Gly Asp Asn Asp Lys
```

```
                420              425              430
Cys Ile Cys Lys Cys Ser Gln Met Leu Thr Gly Gly Trp Trp Phe Asp
            435              440              445
Ala Cys Gly Pro Ser Asn Leu Asn Gly Met Tyr Tyr Pro Gln Arg Gln
    450              455              460
Asn Thr Asn Lys Phe Asn Gly Ile Lys Trp Tyr Tyr Trp Lys Gly Ser
465              470              475              480
Gly Tyr Ser Leu Lys Ala Thr Thr Met Met Ile Arg Pro Ala Asp Phe
                485              490              495
```

<210> SEQ ID NO 96
<211> LENGTH: 225
<212> TYPE: PRT
<213> ORGANISM: Artificial Sequence
<220> FEATURE:
<223> OTHER INFORMATION: IgG1 LALAPGAAA

<400> SEQUENCE: 96

```
Asp Lys Thr His Thr Cys Pro Pro Cys Pro Ala Pro Glu Ala Ala Gly
1               5                   10                  15
Gly Pro Ser Val Phe Leu Phe Pro Pro Lys Pro Lys Asp Thr Leu Met
            20                  25                  30
Ala Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu Ala Gln Asp Trp Leu Asn Gly
                85                  90                  95
Lys Glu Tyr Lys Cys Lys Val Ser Asn Lys Ala Leu Gly Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Thr
    130                 135                 140
Leu Ala Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn Ala Tyr Thr Gln Lys Ser Leu Ser Leu Ser
    210                 215                 220
Pro
225
```

<210> SEQ ID NO 97
<211> LENGTH: 229
<212> TYPE: PRT
<213> ORGANISM: Artificial sequence
<220> FEATURE:
<223> OTHER INFORMATION: IgG4 SPLEPGAAA

<400> SEQUENCE: 97

```
Glu Ser Lys Tyr Gly Pro Pro Cys Pro Pro Cys Pro Ala Pro Glu Phe
1               5                  10                 15

Glu Gly Gly Pro Ser Val Phe Leu Phe Pro Pro Lys Pro Lys Asp Thr
            20                  25                  30

Leu Met Ala Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu Ala Gln Asp Trp Leu
                85                  90                  95

Asn Gly Lys Glu Tyr Lys Cys Lys Val Ser Asn Lys Gly Leu Gly Ser
                100                 105                 110

Ser Ile Glu Lys Thr Ile Ser Lys Ala Lys Gly Gln Pro Arg Glu Pro
                115                 120                 125

Gln Val Tyr Thr Leu Pro Pro Ser Gln Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
                180                 185                 190

Thr Val Asp Lys Ser Arg Trp Gln Gln Gly Asn Val Phe Ser Cys Ser
                195                 200                 205

Val Met His Glu Ala Leu His Asn Ala Tyr Thr Gln Lys Ser Leu Ser
210                 215                 220

Leu Ser Leu Gly Lys
225

<210> SEQ ID NO 98
<211> LENGTH: 107
<212> TYPE: PRT
<213> ORGANISM: Homo sapiens

<400> SEQUENCE: 98

Arg Thr Val Ala Ala Pro Ser Val Phe Ile Phe Pro Pro Ser Asp Glu
1               5                  10                 15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 99
<211> LENGTH: 105
<212> TYPE: PRT
<213> ORGANISM: Homo sapiens
```

<400> SEQUENCE: 99

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 100
<211> LENGTH: 438
<212> TYPE: PRT
<213> ORGANISM: Artificial sequence
<220> FEATURE:
<223> OTHER INFORMATION: Ang2_wt VHVL cross HC IgG1 LALAPGAAA knob

<400> SEQUENCE: 100

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys Asp Lys Thr His Thr Cys Pro Pro Cys Pro Ala
    210                 215                 220

Pro Glu Ala Ala Gly Gly Pro Ser Val Phe Leu Phe Pro Pro Lys Pro
225                 230                 235                 240

```
Lys Asp Thr Leu Met Ala Ser Arg Thr Pro Glu Val Thr Cys Val Val
                245                 250                 255

Val Asp Val Ser His Glu Asp Pro Glu Val Lys Phe Asn Trp Tyr Val
            260                 265                 270

Asp Gly Val Glu Val His Asn Ala Lys Thr Lys Pro Arg Glu Glu Gln
        275                 280                 285

Tyr Asn Ser Thr Tyr Arg Val Val Ser Val Leu Thr Val Leu Ala Gln
    290                 295                 300

Asp Trp Leu Asn Gly Lys Glu Tyr Lys Cys Lys Val Ser Asn Lys Ala
305                 310                 315                 320

Leu Gly Ala Pro Ile Glu Lys Thr Ile Ser Lys Ala Lys Gly Gln Pro
                325                 330                 335

Arg Glu Pro Gln Val Tyr Thr Leu Pro Pro Cys Arg Asp Glu Leu Thr
            340                 345                 350

Lys Asn Gln Val Ser Leu Trp Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
                405                 410                 415

Ser Cys Ser Val Met His Glu Ala Leu His Asn Ala Tyr Thr Gln Lys
            420                 425                 430

Ser Leu Ser Leu Ser Pro
        435

<210> SEQ ID NO 101
<211> LENGTH: 236
<212> TYPE: PRT
<213> ORGANISM: Artificial sequence
<220> FEATURE:
<223> OTHER INFORMATION: Ang2_wt VHVL cross LC kappa

<400> SEQUENCE: 101

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160
```

```
Phe Tyr Pro Arg Glu Ala Lys Val Gln Trp Lys Val Asp Asn Ala Leu
            165                 170                 175

Gln Ser Gly Asn Ser Gln Glu Ser Val Thr Glu Gln Asp Ser Lys Asp
        180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
        210                 215                 220

Ser Pro Val Thr Lys Ser Phe Asn Arg Gly Glu Cys
225                 230                 235

<210> SEQ ID NO 102
<211> LENGTH: 446
<212> TYPE: PRT
<213> ORGANISM: Artificial sequence
<220> FEATURE:
<223> OTHER INFORMATION: huH34-2 HC IgG1 non-crossed LALAPGAAA hole

<400> SEQUENCE: 102

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Ile
        35                  40                  45

Gly Tyr Ile Ser Ser Tyr Asn Ala Phe Thr Thr Tyr Asn Gln Lys Phe
    50                  55                  60

Arg Gly Arg Ala Thr Phe Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Val Arg Ser Asp Tyr Tyr Gly Thr Ser Leu Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Glu Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Glu Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ala Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285
```

```
Lys Thr Lys Pro Arg Glu Glu Gln Tyr Asn Ser Thr Tyr Arg Val Val
    290                 295                 300

Ser Val Leu Thr Val Leu Ala Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Cys Thr Leu
                340                 345                 350

Pro Pro Ser Arg Asp Glu Leu Thr Lys Asn Gln Val Ser Leu Ser Cys
            355                 360                 365

Ala Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn Ala Tyr Thr Gln Lys Ser Leu Ser Leu Ser Pro
            435                 440                 445

<210> SEQ ID NO 103
<211> LENGTH: 211
<212> TYPE: PRT
<213> ORGANISM: Artificial sequence
<220> FEATURE:
<223> OTHER INFORMATION: huH34-2 LC kappa non-crossed

<400> SEQUENCE: 103

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
                20                  25                  30

His Trp Ser Gln Gln Lys Pro Gly Gln Ala Pro Arg Leu Leu Ile Tyr
            35                  40                  45

Ser Thr Ser Asn Leu Ala Ser Gly Ile Pro Ala Arg Phe Ser Gly Ser
        50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys His Gln Trp Ser Asn Tyr Tyr Thr Phe
                85                  90                  95

Gly Gln Gly Thr Lys Leu Glu Ile Lys Thr Val Ala Ala Pro Ser Val
                100                 105                 110

Phe Ile Phe Pro Pro Ser Asp Arg Lys Leu Lys Ser Gly Thr Ala Ser
            115                 120                 125

Val Val Cys Leu Leu Asn Asn Phe Tyr Pro Arg Glu Ala Lys Val Gln
130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205
```

Gly Glu Cys
    210

<210> SEQ ID NO 104
<211> LENGTH: 440
<212> TYPE: PRT
<213> ORGANISM: Artificial sequence
<220> FEATURE:
<223> OTHER INFORMATION: Ang2 wt mut4 + D50T VHVL cross HC IgG1
      LALAPGAAA knob

<400> SEQUENCE: 104

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Thr Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys Asp Lys Thr His Thr Cys Pro Pro Cys Pro Ala
    210                 215                 220

Pro Glu Ala Ala Gly Gly Pro Ser Val Phe Leu Phe Pro Pro Lys Pro
225                 230                 235                 240

Lys Asp Thr Leu Met Ala Ser Arg Thr Pro Glu Val Thr Cys Val Val
                245                 250                 255

Val Asp Val Ser His Glu Asp Pro Glu Val Lys Phe Asn Trp Tyr Val
            260                 265                 270

Asp Gly Val Glu Val His Asn Ala Lys Thr Lys Pro Arg Glu Glu Gln
        275                 280                 285

Tyr Asn Ser Thr Tyr Arg Val Val Ser Val Leu Thr Val Leu Ala Gln
    290                 295                 300

Asp Trp Leu Asn Gly Lys Glu Tyr Lys Cys Lys Val Ser Asn Lys Ala
305                 310                 315                 320

Leu Gly Ala Pro Ile Glu Lys Thr Ile Ser Lys Ala Lys Gly Gln Pro
                325                 330                 335

Arg Glu Pro Gln Val Tyr Thr Leu Pro Pro Cys Arg Asp Glu Leu Thr
            340                 345                 350

```
Lys Asn Gln Val Ser Leu Trp Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
                405                 410                 415

Ser Cys Ser Val Met His Glu Ala Leu His Asn Ala Tyr Thr Gln Lys
            420                 425                 430

Ser Leu Ser Leu Ser Pro Gly Lys
            435                 440

<210> SEQ ID NO 105
<211> LENGTH: 236
<212> TYPE: PRT
<213> ORGANISM: Artificial sequence
<220> FEATURE:
<223> OTHER INFORMATION: Ang2-wt 4 mut+ D50T VHVL cross kappa LC

<400> SEQUENCE: 105

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Asp Ser Pro Gly Tyr Tyr Tyr
            100                 105                 110

Pro Ala Ala Phe Asp Ile Trp Gly Gln Gly Thr Met Val Thr Val Ser
            115                 120                 125

Ser Ala Ser Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 106
<211> LENGTH: 236
<212> TYPE: PRT
<213> ORGANISM: Artificial sequence
```

<220> FEATURE:
<223> OTHER INFORMATION: Ang2-wt mut4 + D50T + D106S VHVL cross kappa LC

<400> SEQUENCE: 106

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Ser Ser Pro Gly Tyr Tyr Tyr
            100                 105                 110

Pro Ala Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 107
<211> LENGTH: 437
<212> TYPE: PRT
<213> ORGANISM: Artificial sequence
<220> FEATURE:
<223> OTHER INFORMATION: VEGF_B20.4.1 VHVL cross HC IgG1 LALAPGAAA knob

<400> SEQUENCE: 107

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Ile Arg Arg Ser
            20                  25                  30

Leu Ala Trp Tyr Gln Gln Lys Pro Gly Lys Ala Pro Lys Leu Leu Ile
        35                  40                  45

Tyr Ala Ala Ser Asn Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Thr Ser Pro Leu
                85                  90                  95

Thr Phe Gly Gln Gly Thr Lys Val Glu Ile Lys Ser Ser Ala Ser Thr
```

```
            100                 105                 110
Lys Gly Pro Ser Val Phe Pro Leu Ala Pro Ser Ser Lys Ser Thr Ser
            115                 120                 125

Gly Gly Thr Ala Ala Leu Gly Cys Leu Val Lys Asp Tyr Phe Pro Glu
            130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
            195                 200                 205

Pro Lys Ser Cys Asp Lys Thr His Thr Cys Pro Pro Cys Pro Ala Pro
210                 215                 220

Glu Ala Ala Gly Gly Pro Ser Val Phe Leu Phe Pro Pro Lys Pro Lys
225                 230                 235                 240

Asp Thr Leu Met Ala Ser Arg Thr Pro Glu Val Thr Cys Val Val Val
                245                 250                 255

Asp Val Ser His Glu Asp Pro Glu Val Lys Phe Asn Trp Tyr Val Asp
            260                 265                 270

Gly Val Glu Val His Asn Ala Lys Thr Lys Pro Arg Glu Glu Gln Tyr
            275                 280                 285

Asn Ser Thr Tyr Arg Val Val Ser Val Leu Thr Val Leu Ala Gln Asp
290                 295                 300

Trp Leu Asn Gly Lys Glu Tyr Lys Cys Lys Val Ser Asn Lys Ala Leu
305                 310                 315                 320

Gly Ala Pro Ile Glu Lys Thr Ile Ser Lys Ala Lys Gly Gln Pro Arg
                325                 330                 335

Glu Pro Gln Val Tyr Thr Leu Pro Pro Cys Arg Asp Glu Leu Thr Lys
            340                 345                 350

Asn Gln Val Ser Leu Trp Cys Leu Val Lys Gly Phe Tyr Pro Ser Asp
            355                 360                 365

Ile Ala Val Glu Trp Glu Ser Asn Gly Gln Pro Glu Asn Asn Tyr Lys
370                 375                 380

Thr Thr Pro Pro Val Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
                405                 410                 415

Cys Ser Val Met His Glu Ala Leu His Asn Ala Tyr Thr Gln Lys Ser
            420                 425                 430

Leu Ser Leu Ser Pro
            435

<210> SEQ ID NO 108
<211> LENGTH: 228
<212> TYPE: PRT
<213> ORGANISM: Artificial sequence
<220> FEATURE:
<223> OTHER INFORMATION: VEGF_B20.4.1 VHVL cross LC kappa

<400> SEQUENCE: 108

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Ile Asn Gly Ser
```

```
                20                  25                  30
Trp Ile Phe Trp Val Arg Gln Ala Pro Gly Lys Gly Leu Glu Trp Val
             35                  40                  45

Gly Ala Ile Trp Pro Phe Gly Gly Tyr Thr His Tyr Ala Asp Ser Val
         50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Trp Gly His Ser Thr Ser Pro Trp Ala Met Asp Tyr Trp Gly
            100                 105                 110

Gln Gly Thr Leu Val Thr Val Ser Ser Ala Ser Val Ala Ala Pro Ser
        115                 120                 125

Val Phe Ile Phe Pro Pro Ser Asp Glu Gln Leu Lys Ser Gly Thr Ala
    130                 135                 140

Ser Val Val Cys Leu Leu Asn Asn Phe Tyr Pro Arg Glu Ala Lys Val
145                 150                 155                 160

Gln Trp Lys Val Asp Asn Ala Leu Gln Ser Gly Asn Ser Gln Glu Ser
                165                 170                 175

Val Thr Glu Gln Asp Ser Lys Asp Ser Thr Tyr Ser Leu Ser Ser Thr
            180                 185                 190

Leu Thr Leu Ser Lys Ala Asp Tyr Glu Lys His Lys Val Tyr Ala Cys
        195                 200                 205

Glu Val Thr His Gln Gly Leu Ser Ser Pro Val Thr Lys Ser Phe Asn
    210                 215                 220

Arg Gly Glu Cys
225

<210> SEQ ID NO 109
<211> LENGTH: 437
<212> TYPE: PRT
<213> ORGANISM: Artificial sequence
<220> FEATURE:
<223> OTHER INFORMATION: VEGF_VHVL cross IgG HC LALAPGAAA knob

<400> SEQUENCE: 109

Asp Ile Gln Leu Thr Gln Ser Pro Ser Ser Leu Ser Ala Ser Val Gly
  1               5                  10                  15

Asp Arg Val Thr Ile Thr Cys Ser Ala Ser Gln Asp Ile Ser Asn Tyr
             20                  25                  30

Leu Asn Trp Tyr Gln Gln Lys Pro Gly Lys Ala Pro Lys Val Leu Ile
         35                  40                  45

Tyr Phe Thr Ser Ser Leu His Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Val Pro Trp
                 85                  90                  95

Thr Phe Gly Gln Gly Thr Lys Val Glu Ile Lys Ser Ser Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
```

```
                145                 150                 155                 160
        Thr Phe Pro Ala Val Leu Gln Ser Ser Gly Leu Tyr Ser Leu Ser Ser
                        165                 170                 175
        Val Val Thr Val Pro Ser Ser Ser Leu Gly Thr Gln Thr Tyr Ile Cys
                        180                 185                 190
        Asn Val Asn His Lys Pro Ser Asn Thr Lys Val Asp Lys Lys Val Glu
                        195                 200                 205
        Pro Lys Ser Cys Asp Lys Thr His Thr Cys Pro Pro Cys Pro Ala Pro
        210                 215                 220
        Glu Ala Ala Gly Gly Pro Ser Val Phe Leu Phe Pro Pro Lys Pro Lys
        225                 230                 235                 240
        Asp Thr Leu Met Ala Ser Arg Thr Pro Glu Val Thr Cys Val Val Val
                        245                 250                 255
        Asp Val Ser His Glu Asp Pro Glu Val Lys Phe Asn Trp Tyr Val Asp
                        260                 265                 270
        Gly Val Glu Val His Asn Ala Lys Thr Lys Pro Arg Glu Glu Gln Tyr
                        275                 280                 285
        Asn Ser Thr Tyr Arg Val Val Ser Val Leu Thr Val Leu Ala Gln Asp
        290                 295                 300
        Trp Leu Asn Gly Lys Glu Tyr Lys Cys Lys Val Ser Asn Lys Ala Leu
        305                 310                 315                 320
        Gly Ala Pro Ile Glu Lys Thr Ile Ser Lys Ala Lys Gly Gln Pro Arg
                        325                 330                 335
        Glu Pro Gln Val Tyr Thr Leu Pro Pro Cys Arg Asp Glu Leu Thr Lys
                        340                 345                 350
        Asn Gln Val Ser Leu Trp Cys Leu Val Lys Gly Phe Tyr Pro Ser Asp
                        355                 360                 365
        Ile Ala Val Glu Trp Glu Ser Asn Gly Gln Pro Glu Asn Asn Tyr Lys
                        370                 375                 380
        Thr Thr Pro Pro Val Leu Asp Ser Asp Gly Ser Phe Phe Leu Tyr Ser
        385                 390                 395                 400
        Lys Leu Thr Val Asp Lys Ser Arg Trp Gln Gln Gly Asn Val Phe Ser
                        405                 410                 415
        Cys Ser Val Met His Glu Ala Leu His Asn Ala Tyr Thr Gln Lys Ser
                        420                 425                 430
        Leu Ser Leu Ser Pro
                        435

<210> SEQ ID NO 110
<211> LENGTH: 230
<212> TYPE: PRT
<213> ORGANISM: Artificial sequence
<220> FEATURE:
<223> OTHER INFORMATION: VEGF_LC VHVL cross LC kappa

<400> SEQUENCE: 110

Glu Val Gln Leu Val Glu Ser Gly Gly Gly Leu Val Gln Pro Gly Gly
        1               5                   10                  15
        Ser Leu Arg Leu Ser Cys Ala Ala Ser Gly Tyr Asp Phe Thr His Tyr
                        20                  25                  30
        Gly Met Asn Trp Val Arg Gln Ala Pro Gly Lys Gly Leu Glu Trp Val
                        35                  40                  45
        Gly Trp Ile Asn Thr Tyr Thr Gly Glu Pro Thr Tyr Ala Ala Asp Phe
                        50                  55                  60
        Lys Arg Arg Phe Thr Phe Ser Leu Asp Thr Ser Lys Ser Thr Ala Tyr
```

```
                65                  70                  75                  80
Leu Gln Met Asn Ser Leu Arg Ala Glu Asp Thr Ala Val Tyr Tyr Cys
                        85                  90                  95
Ala Lys Tyr Pro Tyr Tyr Gly Thr Ser His Trp Tyr Phe Asp Val
                100                 105                 110
Trp Gly Gln Gly Thr Leu Val Thr Val Ser Ser Ala Ser Val Ala Ala
                115                 120                 125
Pro Ser Val Phe Ile Phe Pro Pro Ser Asp Glu Gln Leu Lys Ser Gly
130                 135                 140
Thr Ala Ser Val Val Cys Leu Leu Asn Asn Phe Tyr Pro Arg Glu Ala
145                 150                 155                 160
Lys Val Gln Trp Lys Val Asp Asn Ala Leu Gln Ser Gly Asn Ser Gln
                165                 170                 175
Glu Ser Val Thr Glu Gln Asp Ser Lys Asp Ser Thr Tyr Ser Leu Ser
                180                 185                 190
Ser Thr Leu Thr Leu Ser Lys Ala Asp Tyr Glu Lys His Lys Val Tyr
                195                 200                 205
Ala Cys Glu Val Thr His Gln Gly Leu Ser Ser Pro Val Thr Lys Ser
210                 215                 220
Phe Asn Arg Gly Glu Cys
225                 230
```

<210> SEQ ID NO 111
<211> LENGTH: 461
<212> TYPE: PRT
<213> ORGANISM: Artificial sequence
<220> FEATURE:
<223> OTHER INFORMATION: Ang2_wt CHCk cross IgG1 HC LALAPGAAA knob

<400> SEQUENCE: 111

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
                20                  25                  30
Tyr Met His Trp Val Arg Gln Ala Pro Gly Gln Gly Leu Glu Trp Met
            35                  40                  45
Gly Trp Ile Asn Pro Asn Ser Gly Gly Thr Asn Tyr Ala Gln Lys Phe
        50                  55                  60
Gln Gly Arg Val Thr Met Thr Arg Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Ser Pro Asn Pro Tyr Tyr Tyr Asp Ser Ser Gly Tyr Tyr Tyr
                100                 105                 110
Pro Gly Ala Phe Asp Ile Trp Gly Gln Gly Thr Met Val Thr Val Ser
            115                 120                 125
Ser Ala Ser Val Ala Ala Pro Ser Val Phe Ile Phe Pro Pro Ser Asp
        130                 135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
                165                 170                 175
Gln Ser Gly Asn Ser Gln Glu Ser Val Thr Glu Gln Asp Ser Lys Asp
                180                 185                 190
Ser Thr Tyr Ser Leu Ser Ser Thr Leu Thr Leu Ser Lys Ala Asp Tyr
```

-continued

```
                195                 200                 205
Glu Lys His Lys Val Tyr Ala Cys Glu Val Thr His Gln Gly Leu Ser
    210                 215                 220
Ser Pro Val Thr Lys Ser Phe Asn Arg Gly Glu Cys Asp Lys Thr His
225                 230                 235                 240
Thr Cys Pro Pro Cys Pro Ala Pro Glu Ala Gly Gly Pro Ser Val
                245                 250                 255
Phe Leu Phe Pro Pro Lys Pro Lys Asp Thr Leu Met Ala Ser Arg Thr
                260                 265                 270
Pro Glu Val Thr Cys Val Val Val Asp Val Ser His Glu Asp Pro Glu
                275                 280                 285
Val Lys Phe Asn Trp Tyr Val Asp Gly Val Glu Val His Asn Ala Lys
    290                 295                 300
Thr Lys Pro Arg Glu Glu Gln Tyr Asn Ser Thr Tyr Arg Val Val Ser
305                 310                 315                 320
Val Leu Thr Val Leu Ala Gln Asp Trp Leu Asn Gly Lys Glu Tyr Lys
                325                 330                 335
Cys Lys Val Ser Asn Lys Ala Leu Gly Ala Pro Ile Glu Lys Thr Ile
                340                 345                 350
Ser Lys Ala Lys Gly Gln Pro Arg Glu Pro Gln Val Tyr Thr Leu Pro
                355                 360                 365
Pro Cys Arg Asp Glu Leu Thr Lys Asn Gln Val Ser Leu Trp Cys Leu
    370                 375                 380
Val Lys Gly Phe Tyr Pro Ser Asp Ile Ala Val Glu Trp Glu Ser Asn
385                 390                 395                 400
Gly Gln Pro Glu Asn Asn Tyr Lys Thr Thr Pro Pro Val Leu Asp Ser
                405                 410                 415
Asp Gly Ser Phe Phe Leu Tyr Ser Lys Leu Thr Val Asp Lys Ser Arg
                420                 425                 430
Trp Gln Gln Gly Asn Val Phe Ser Cys Ser Val Met His Glu Ala Leu
                435                 440                 445
His Asn Ala Tyr Thr Gln Lys Ser Leu Ser Leu Ser Pro
    450                 455                 460

<210> SEQ ID NO 112
<211> LENGTH: 213
<212> TYPE: PRT
<213> ORGANISM: Artificial sequence
<220> FEATURE:
<223> OTHER INFORMATION: Ang2_wt CHCk cross LC kappa

<400> SEQUENCE: 112

Ser Tyr Val Leu Thr Gln Pro Pro Ser Val Ser Val Ala Pro Gly Gln
1               5                   10                  15
Thr Ala Arg Ile Thr Cys Gly Gly Asn Asn Ile Gly Ser Lys Ser Val
                20                  25                  30
His Trp Tyr Gln Gln Lys Pro Gly Gln Ala Pro Val Leu Val Val Tyr
                35                  40                  45
Asp Asp Ser Asp Arg Pro Ser Gly Ile Pro Glu Arg Phe Ser Gly Ser
    50                  55                  60
Asn Ser Gly Asn Thr Ala Thr Leu Thr Ile Ser Arg Val Glu Ala Gly
65                  70                  75                  80
Asp Glu Ala Asp Tyr Tyr Cys Gln Val Trp Asp Ser Ser Ser Asp His
                85                  90                  95
Trp Val Phe Gly Gly Gly Thr Lys Leu Thr Val Leu Ser Ser Ala Ser
```

```
              100                 105                 110
Thr Lys Gly Pro Ser Val Phe Pro Leu Ala Pro Ser Ser Lys Ser Thr
            115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys
    210

<210> SEQ ID NO 113
<211> LENGTH: 461
<212> TYPE: PRT
<213> ORGANISM: Artificial sequence
<220> FEATURE:
<223> OTHER INFORMATION: Ang2-wt mut4 + D50T CHCk cross HC IgG1
      LALAPGAAA knob

<400> SEQUENCE: 113

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Pro Gly Tyr Tyr Tyr
            100                 105                 110

Pro Ala Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Asp Lys Thr His
225                 230                 235                 240
```

```
Thr Cys Pro Pro Cys Pro Ala Pro Glu Ala Ala Gly Gly Pro Ser Val
                245                 250                 255

Phe Leu Phe Pro Pro Lys Pro Lys Asp Thr Leu Met Ala Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu Ala Gln Asp Trp Leu Asn Gly Lys Glu Tyr Lys
                325                 330                 335

Cys Lys Val Ser Asn Lys Ala Leu Gly Ala Pro Ile Glu Lys Thr Ile
            340                 345                 350

Ser Lys Ala Lys Gly Gln Pro Arg Glu Pro Gln Val Tyr Thr Leu Pro
        355                 360                 365

Pro Cys Arg Asp Glu Leu Thr Lys Asn Gln Val Ser Leu Trp Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn Ala Tyr Thr Gln Lys Ser Leu Ser Leu Ser Pro
    450                 455                 460

<210> SEQ ID NO 114
<211> LENGTH: 213
<212> TYPE: PRT
<213> ORGANISM: Artificial sequence
<220> FEATURE:
<223> OTHER INFORMATION: Ang2-wt mut4 + D50T CHCk cross LC

<400> SEQUENCE: 114

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Thr Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140
```

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
            195                 200                 205

Glu Pro Lys Ser Cys
    210

<210> SEQ ID NO 115
<211> LENGTH: 461
<212> TYPE: PRT
<213> ORGANISM: Artificial sequence
<220> FEATURE:
<223> OTHER INFORMATION: Xang2-0098 Ang2 LC 10 VH wt IgG1

<400> SEQUENCE: 115

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

```
Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
                340                 345                 350

Ser Lys Ala Lys Gly Gln Pro Arg Glu Pro Gln Val Tyr Thr Leu Pro
                355                 360                 365

Pro Ser Arg Asp Glu Leu Thr Lys Asn Gln Val Ser Leu Thr Cys Leu
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Lys Leu Thr Val Asp Lys Ser Arg
                420                 425                 430

Trp Gln Gln Gly Asn Val Phe Ser Cys Ser Val Met His Glu Ala Leu
                435                 440                 445

His Asn His Tyr Thr Gln Lys Ser Leu Ser Leu Ser Pro
450                 455                 460

<210> SEQ ID NO 116
<211> LENGTH: 461
<212> TYPE: PRT
<213> ORGANISM: Artificial sequence
<220> FEATURE:
<223> OTHER INFORMATION: Xang2-0099 Ang2 LC10 wt + G114A, S360P, T28N,
      T30A (HC)

<400> SEQUENCE: 116

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Pro Gly Tyr Tyr Tyr
                100                 105                 110

Pro Ala Ala Phe Asp Ile Trp Gly Gln Gly Thr Met Val Thr Val Ser
                115                 120                 125

Ser Ala Ser Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190
```

Ser Thr Tyr Ser Leu Ser Ser Thr Leu Thr Leu Ser Lys Ala Asp Tyr
             195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Arg Asp Glu Leu Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro
    450                 455                 460

<210> SEQ ID NO 117
<211> LENGTH: 461
<212> TYPE: PRT
<213> ORGANISM: Artificial sequence
<220> FEATURE:
<223> OTHER INFORMATION: Xang2-0103

<400> SEQUENCE: 117

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

```
Ala Arg Ser Pro Asn Pro Tyr Tyr Ser Pro Gly Tyr Tyr
            100                 105                 110

Pro Ala Ala Phe Asp Ile Trp Gly Gln Gly Thr Met Val Thr Val Ser
                115                 120                 125

Ser Ala Ser Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
                195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
                260                 265                 270

Pro Glu Val Thr Cys Val Val Val Asp Val Ser His Glu Asp Pro Glu
                275                 280                 285

Val Lys Phe Asn Trp Tyr Val Asp Gly Val Glu Val His Asn Ala Lys
                290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
                340                 345                 350

Ser Lys Ala Lys Gly Gln Pro Arg Glu Pro Gln Val Tyr Thr Leu Pro
                355                 360                 365

Pro Ser Arg Asp Glu Leu Thr Lys Asn Gln Val Ser Leu Thr Cys Leu
                370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Lys Leu Thr Val Asp Lys Ser Arg
                420                 425                 430

Trp Gln Gln Gly Asn Val Phe Ser Cys Ser Val Met His Glu Ala Leu
                435                 440                 445

His Asn His Tyr Thr Gln Lys Ser Leu Ser Leu Ser Pro
                450                 455                 460

<210> SEQ ID NO 118
<211> LENGTH: 461
<212> TYPE: PRT
<213> ORGANISM: Artificial sequence
<220> FEATURE:
<223> OTHER INFORMATION: Xang2-0101

<400> SEQUENCE: 118
```

```
Gln Val Gln Leu Val Gln Ser Gly Ala Glu Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
            35                  40                  45

Gly Trp Ile Asn Pro Asn Ser Gly Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Glu Ser Pro Gly Tyr Tyr Tyr
                100                 105                 110

Pro Ala Ala Phe Asp Ile Trp Gly Gln Gly Thr Met Val Thr Val Ser
            115                 120                 125

Ser Ala Ser Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
                195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
                260                 265                 270

Pro Glu Val Thr Cys Val Val Val Asp Val Ser His Glu Asp Pro Glu
            275                 280                 285

Val Lys Phe Asn Trp Tyr Val Asp Gly Val Glu Val His Asn Ala Lys
            290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Tyr Thr Leu Pro
            355                 360                 365

Pro Ser Arg Asp Glu Leu Thr Lys Asn Gln Val Ser Leu Thr Cys Leu
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415
```

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro
    450                 455                 460

<210> SEQ ID NO 119
<211> LENGTH: 461
<212> TYPE: PRT
<213> ORGANISM: Artificial sequence
<220> FEATURE:
<223> OTHER INFORMATION: Xang2-0102

<400> SEQUENCE: 119

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Ser Pro Asn Pro Tyr Tyr Tyr Thr Ser Pro Tyr Tyr Tyr
            100                 105                 110

Pro Ala Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
            325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Tyr Thr Leu Pro
            355                 360                 365

Pro Ser Arg Asp Glu Leu Thr Lys Asn Gln Val Ser Leu Thr Cys Leu
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
            405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
            435                 440                 445

His Asn His Tyr Thr Gln Lys Ser Leu Ser Leu Ser Pro
            450                 455                 460

<210> SEQ ID NO 120
<211> LENGTH: 461
<212> TYPE: PRT
<213> ORGANISM: Artificial sequence
<220> FEATURE:
<223> OTHER INFORMATION: Xang2-0112 Ang2 wt LC10 VH hole

<400> SEQUENCE: 120

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Ser Pro Asn Pro Tyr Tyr Asp Ser Ser Gly Tyr Tyr Tyr
            100                 105                 110

Pro Gly Ala Phe Asp Ile Trp Gly Gln Gly Thr Met Val Thr Val Ser
            115                 120                 125

Ser Ala Ser Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
            165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
            210                 215                 220

```
Ser Pro Val Thr Lys Ser Phe Asn Arg Gly Glu Cys Asp Lys Thr His
225                 230                 235                 240

Thr Cys Pro Pro Cys Pro Ala Pro Glu Leu Leu Gly Gly Pro Ser Val
            245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
            275                 280                 285

Val Lys Phe Asn Trp Tyr Val Asp Gly Val Glu Val His Asn Ala Lys
            290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
                340                 345                 350

Ser Lys Ala Lys Gly Gln Pro Arg Glu Pro Gln Val Cys Thr Leu Pro
                355                 360                 365

Pro Ser Arg Asp Glu Leu Thr Lys Asn Gln Val Ser Leu Ser Cys Ala
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Val Ser Lys Leu Thr Val Asp Lys Ser Arg
                420                 425                 430

Trp Gln Gln Gly Asn Val Phe Ser Cys Ser Val Met His Glu Ala Leu
                435                 440                 445

His Asn His Tyr Thr Gln Lys Ser Leu Ser Leu Ser Pro
                450                 455                 460

<210> SEQ ID NO 121
<211> LENGTH: 214
<212> TYPE: PRT
<213> ORGANISM: Artificial sequence
<220> FEATURE:
<223> OTHER INFORMATION: VL-DIG

<400> SEQUENCE: 121

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Lys Asn Tyr
            20                  25                  30

Leu Asn Trp Tyr Gln Gln Lys Pro Gly Lys Ala Pro Lys Leu Leu Ile
        35                  40                  45

Tyr Tyr Ser Ser Thr Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ile Thr Leu Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 122
<211> LENGTH: 453
<212> TYPE: PRT
<213> ORGANISM: Artificial sequence
<220> FEATURE:
<223> OTHER INFORMATION: DIG-Knob

<400> SEQUENCE: 122

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
        35                  40                  45

Ser Ser Ile Asn Ile Gly Ala Thr Tyr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Ser Pro Tyr Glu Tyr Asp Lys Ala Tyr Tyr Ser Met
            100                 105                 110

Ala Tyr Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270
```

```
Asp Val Ser His Glu Asp Pro Glu Val Lys Phe Asn Trp Tyr Val Asp
            275                 280                 285
Gly Val Glu Val His Asn Ala Lys Thr Lys Pro Arg Glu Glu Gln Tyr
        290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Cys Arg Asp Glu Leu Thr Lys
        355                 360                 365
Asn Gln Val Ser Leu Trp Cys Leu Val Lys Gly Phe Tyr Pro Ser Asp
370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
        435                 440                 445
Leu Ser Leu Ser Pro
    450

<210> SEQ ID NO 123
<211> LENGTH: 461
<212> TYPE: PRT
<213> ORGANISM: Artificial sequence
<220> FEATURE:
<223> OTHER INFORMATION: Xang2-0113 Ang2 LC10 wt + G114A, S360P, T28N,
      T30A (HC) hole

<400> SEQUENCE: 123

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Asn Phe Ala Gly Tyr
            20                  25                  30
Tyr Met His Trp Val Arg Gln Ala Pro Gly Gln Gly Leu Glu Trp Met
        35                  40                  45
Gly Trp Ile Asn Pro Asn Ser Gly Gly Thr Asn Tyr Ala Gln Lys Phe
    50                  55                  60
Gln Gly Arg Val Thr Met Thr Arg Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Ser Pro Asn Pro Tyr Tyr Tyr Asp Ser Pro Gly Tyr Tyr Tyr
            100                 105                 110
Pro Ala Ala Phe Asp Ile Trp Gly Gln Gly Thr Met Val Thr Val Ser
        115                 120                 125
Ser Ala Ser Val Ala Ala Pro Ser Val Phe Ile Phe Pro Pro Ser Asp
    130                 135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
                165                 170                 175
```

```
Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Cys Thr Leu Pro
        355                 360                 365

Pro Ser Arg Asp Glu Leu Thr Lys Asn Gln Val Ser Leu Ser Cys Ala
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Val Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro
    450                 455                 460

<210> SEQ ID NO 124
<211> LENGTH: 461
<212> TYPE: PRT
<213> ORGANISM: Artificial sequence
<220> FEATURE:
<223> OTHER INFORMATION: Xang2-0114 VH hole

<400> SEQUENCE: 124

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80
```

```
Met Glu Leu Ser Arg Leu Arg Ser Asp Asp Thr Ala Val Tyr Tyr Cys
                85                  90                  95

Ala Arg Ser Pro Asn Pro Tyr Tyr Ser Ser Pro Gly Tyr Tyr
            100                 105                 110

Pro Ala Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Cys Thr Leu Pro
        355                 360                 365

Pro Ser Arg Asp Glu Leu Thr Lys Asn Gln Val Ser Leu Ser Cys Ala
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Val Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro
450                 455                 460

<210> SEQ ID NO 125
<211> LENGTH: 442
<212> TYPE: PRT
<213> ORGANISM: Artificial Sequence
<220> FEATURE:
```

<223> OTHER INFORMATION: Ang2_WT + PDGFB_0044

<400> SEQUENCE: 125

```
Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Ser Thr Asn Tyr Asn Glu Lys Phe
    50                  55                  60

Lys Val Lys Ala Thr Phe Thr Ala Asp Thr Ser Ser Asn Thr Ala Tyr
65                  70                  75                  80

Met Gln Leu Ser Ser Leu Thr Cys Glu Asp Ser Ala Val Tyr Tyr Cys
                85                  90                  95

Ala Gln Thr Thr Gln Asp Phe Asp Ser Trp Gly Gln Gly Thr Thr Leu
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Glu Lys Val Ser Pro Asn Leu Val Thr Lys Leu Thr His
    210                 215                 220

Ala His Arg Ala Gln Pro Glu Ala Ala Gly Gly Pro Ser Val Phe Leu
225                 230                 235                 240

Phe Pro Pro Lys Pro Lys Asp Thr Leu Met Ala Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu Ala Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

Ala Lys Gln Pro Arg Glu Pro Gln Val Cys Thr Leu Pro Pro Ser Arg
            340                 345                 350

Asp Glu Leu Thr Lys Asn Gln Val Ser Leu Ser Cys Ala Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400
```

```
Phe Phe Leu Val Ser Lys Leu Thr Val Asp Lys Ser Arg Trp Gln Gln
                405                 410                 415

Gly Asn Val Phe Ser Cys Ser Val Met His Glu Ala Leu His Asn Ala
            420                 425                 430

Tyr Thr Gln Lys Ser Leu Ser Leu Ser Pro
        435                 440

<210> SEQ ID NO 126
<211> LENGTH: 217
<212> TYPE: PRT
<213> ORGANISM: Artificial sequence
<220> FEATURE:
<223> OTHER INFORMATION: Ang2_wt + PDGFB_0044

<400> SEQUENCE: 126

Asp Ile Val Leu Thr Gln Ser Pro Gly Ser Leu Ala Val Ser Leu Gly
1               5                   10                  15

Gln Arg Ala Thr Ile Ser Cys Arg Ala Ser Glu Ser Val Asp Ile Tyr
            20                  25                  30

Gly Tyr Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Arg Thr Phe Gly Gly Gly Thr Lys Leu Glu Ile Lys Thr
            100                 105                 110

Val Ala Ala Pro Ser Val Phe Ile Phe Pro Pro Ser Asp Arg Lys Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 127
<211> LENGTH: 213
<212> TYPE: PRT
<213> ORGANISM: Artificial sequence
<220> FEATURE:
<223> OTHER INFORMATION: Ang2_wt + PDGFB_0058 VH-VL cross

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45
```

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Thr Val Ala Ala Pro
            100                 105                 110

Ser Val Phe Ile Phe Pro Pro Ser Asp Arg Lys Leu Lys Ser Gly Thr
                115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
                195                 200                 205

Asn Arg Gly Glu Cys
    210

<210> SEQ ID NO 128
<211> LENGTH: 446
<212> TYPE: PRT
<213> ORGANISM: Artificial sequence
<220> FEATURE:
<223> OTHER INFORMATION: Ang2_wt + PDGFB_0058 VH-VL cross

<400> SEQUENCE: 128

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
                20                  25                  30

Trp Met Thr Trp Val Arg Gln Ala Pro Gly Lys Gly Leu Glu Trp Val
            35                  40                  45

Ala Ser Ile Ser Ala Gly Gly Gly Ile Thr His Tyr Pro Asp Ser Val
        50                  55                  60

Lys Asp Arg Phe Thr Val Ser Arg Asp Asn Ala Lys Asn Ser Leu Tyr
65                  70                  75                  80

Leu Gln Leu Asn Ser Leu Arg Cys Glu Asp Thr Ala Val Tyr Tyr Cys
                85                  90                  95

Ala Glu Ser Gly Gly Asp Ile Tyr Ser Asp Phe Asp Tyr Trp Gly Gln
            100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
130                 135                 140

Leu Gly Cys Leu Val Glu Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Glu Lys Val Ser Pro Asn Leu Val Thr
210                 215                 220

Lys Leu Thr His Ala His Arg Ala Gln Pro Glu Ala Ala Gly Gly Pro
225                 230                 235                 240

Ser Val Phe Leu Phe Pro Pro Lys Pro Lys Asp Thr Leu Met Ala Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu Ala Gln Asp Trp Leu Asn Gly Lys Glu
305                 310                 315                 320

Tyr Lys Cys Lys Val Ser Asn Lys Ala Leu Gly Ala Pro Ile Glu Lys
            325                 330                 335

Thr Ile Ser Lys Ala Lys Gln Pro Arg Glu Pro Gln Val Cys Thr Leu
            340                 345                 350

Pro Pro Ser Arg Asp Glu Leu Thr Lys Asn Gln Val Ser Leu Ser Cys
            355                 360                 365

Ala Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn Ala Tyr Thr Gln Lys Ser Leu Ser Leu Ser Pro
            435                 440                 445

<210> SEQ ID NO 129
<211> LENGTH: 446
<212> TYPE: PRT
<213> ORGANISM: Artificial sequence
<220> FEATURE:
<223> OTHER INFORMATION: Ang2_wt + PDGFB_0085 cross

<400> SEQUENCE: 129

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ser Thr Ile Ser Asp Gly Gly Gly Leu Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Cys Glu Asp Thr Ala Val Tyr Tyr Cys
            85                  90                  95

Ala Glu Ser Gly Gly Tyr Thr Asp Trp Leu Phe Gly Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Glu Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Glu Lys Val Ser Pro Asn Leu Val Thr
    210                 215                 220

Lys Leu Thr His Ala His Arg Ala Gln Pro Glu Ala Ala Gly Gly Pro
225                 230                 235                 240

Ser Val Phe Leu Phe Pro Pro Lys Pro Lys Asp Thr Leu Met Ala Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu Ala Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gln Pro Arg Glu Pro Gln Val Cys Thr Leu
            340                 345                 350

Pro Pro Ser Arg Asp Glu Leu Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn Ala Tyr Thr Gln Lys Ser Leu Ser Leu Ser Pro
        435                 440                 445

<210> SEQ ID NO 130
<211> LENGTH: 213
<212> TYPE: PRT
<213> ORGANISM: Artificial sequence
<220> FEATURE:
<223> OTHER INFORMATION: Ang2_wt + PDGFB_0085 VH-VL cross

<400> SEQUENCE: 130

Asp Ile Gln Met Thr Gln Ser Pro Ser Ser Leu Ser Ala Ser Val Gly
1               5                   10                  15

Asp Arg Val Ala Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Thr Val Ala Ala Pro
                100                 105                 110

Ser Val Phe Ile Phe Pro Pro Ser Asp Arg Lys Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
            195                 200                 205

Asn Arg Gly Glu Cys
            210

<210> SEQ ID NO 131
<211> LENGTH: 213
<212> TYPE: PRT
<213> ORGANISM: Artificial sequence
<220> FEATURE:
<223> OTHER INFORMATION: Ang2_wt + PDGFB_0086 VH-VL cross

<400> SEQUENCE: 131

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Thr Val Ala Ala Pro
                100                 105                 110

Ser Val Phe Ile Phe Pro Pro Ser Asp Arg Lys Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 132
<211> LENGTH: 37
<212> TYPE: DNA
<213> ORGANISM: Artificial sequence
<220> FEATURE:
<223> OTHER INFORMATION: rbHC.up

<400> SEQUENCE: 132
aagcttgcca ccatggagac tgggctgcgc tggcttc                                37

<210> SEQ ID NO 133
<211> LENGTH: 21
<212> TYPE: DNA
<213> ORGANISM: Artificial sequence
<220> FEATURE:
<223> OTHER INFORMATION: rbHCf.do

<400> SEQUENCE: 133
ccattggtga gggtgcccga g                                                 21

<210> SEQ ID NO 134
<211> LENGTH: 34
<212> TYPE: DNA
<213> ORGANISM: Artificial sequence
<220> FEATURE:
<223> OTHER INFORMATION: rbLC.up

<400> SEQUENCE: 134
aagcttgcca ccatggacay gagggccccc actc                                   34

<210> SEQ ID NO 135
<211> LENGTH: 26
<212> TYPE: DNA
<213> ORGANISM: Artificial sequence
<220> FEATURE:
<223> OTHER INFORMATION: rbLC.do

<400> SEQUENCE: 135
cagagtrctg ctgaggttgt aggtac                                            26

<210> SEQ ID NO 136
<211> LENGTH: 20
<212> TYPE: DNA
<213> ORGANISM: Artificial sequence
<220> FEATURE:
<223> OTHER INFORMATION: BcPCR_FHLC_leader.fw

<400> SEQUENCE: 136
atggacatga gggtccccgc                                                   20

<210> SEQ ID NO 137
<211> LENGTH: 24
<212> TYPE: DNA
<213> ORGANISM: Artificial Sequence
<220> FEATURE:
<223> OTHER INFORMATION: BcPCR_huCkappa.rev

<400> SEQUENCE: 137
gatttcaact gctcatcaga tggc                                              24

<210> SEQ ID NO 138
<211> LENGTH: 446
<212> TYPE: PRT
<213> ORGANISM: Artificial Sequence
<220> FEATURE:
<223> OTHER INFORMATION: huH34-2 HC non-cross for CH1Ck

<400> SEQUENCE: 138

```
Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Ile
            35                  40                  45

Gly Tyr Ile Ser Ser Tyr Asn Ala Phe Thr Thr Tyr Asn Gln Lys Phe
        50                  55                  60

Arg Gly Arg Ala Thr Phe Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Val Arg Ser Asp Tyr Tyr Gly Thr Ser Leu Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ala Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu Ala Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Cys Thr Leu
            340                 345                 350
```

Pro Pro Ser Arg Asp Glu Leu Thr Lys Asn Gln Val Ser Leu Ser Cys
            355                 360                 365

Ala Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn Ala Tyr Thr Gln Lys Ser Leu Ser Leu Ser Pro
            435                 440                 445

<210> SEQ ID NO 139
<211> LENGTH: 211
<212> TYPE: PRT
<213> ORGANISM: Artificial Sequence
<220> FEATURE:
<223> OTHER INFORMATION: huH34-2 LC non-cross for CH1Ck

<400> SEQUENCE: 139

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
            20                  25                  30

His Trp Ser Gln Gln Lys Pro Gly Gln Ala Pro Arg Leu Leu Ile Tyr
        35                  40                  45

Ser Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys His Gln Trp Ser Asn Tyr Tyr Thr Phe
                85                  90                  95

Gly Gln Gly Thr Lys Leu Glu Ile Lys Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
    130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
    210

<210> SEQ ID NO 140
<211> LENGTH: 129
<212> TYPE: PRT
<213> ORGANISM: Artificial sequence
<220> FEATURE:
<223> OTHER INFORMATION: Ang2 LC10 wt + G114A, S360P, T28N, T30A (HC) +
      D50T (LC) VH

<400> SEQUENCE: 140

| | | | | | | | | | | | | | | |
|---|---|---|---|---|---|---|---|---|---|---|---|---|---|---|
|Gln|Val|Gln|Leu|Val|Gln|Ser|Gly|Ala|Glu|Val|Lys|Lys|Pro|Gly|Ala|
|1| | | |5| | | | |10| | | | |15|

Ser Val Lys Val Ser Cys Lys Ala Ser Gly Tyr Asn Phe Ala Gly Tyr
            20            25            30

Tyr Met His Trp Val Arg Gln Ala Pro Gly Gln Gly Leu Glu Trp Met
      35            40            45

Gly Trp Ile Asn Pro Asn Ser Gly Gly Thr Asn Tyr Ala Gln Lys Phe
50            55            60

Gln Gly Arg Val Thr Met Thr Arg Asp Thr Ser Ile Ser Thr Ala Tyr
65            70            75            80

Met Glu Leu Ser Arg Leu Arg Ser Asp Asp Thr Ala Val Tyr Tyr Cys
      85            90            95

Ala Arg Ser Pro Asn Pro Tyr Tyr Tyr Asp Ser Pro Gly Tyr Tyr Tyr
          100           105          110

Pro Ala Ala Phe Asp Ile Trp Gly Gln Gly Thr Met Val Thr Val Ser
        115           120          125

Ser

<210> SEQ ID NO 141
<211> LENGTH: 110
<212> TYPE: PRT
<213> ORGANISM: Artificial sequence
<220> FEATURE:
<223> OTHER INFORMATION: Ang2 LC10 wt + G114A, S360P, T28N, T30A (HC) +
     D50T (LC) VL

<400> SEQUENCE: 141

Ser Tyr Val Leu Thr Gln Pro Pro Ser Val Ser Val Ala Pro Gly Gln
1            5            10            15

Thr Ala Arg Ile Thr Cys Gly Gly Asn Asn Ile Gly Ser Lys Ser Val
          20           25          30

His Trp Tyr Gln Gln Lys Pro Gly Gln Ala Pro Val Leu Val Val Tyr
      35            40            45

Asp Thr Ser Asp Arg Pro Ser Gly Ile Pro Glu Arg Phe Ser Gly Ser
50            55            60

Asn Ser Gly Asn Thr Ala Thr Leu Thr Ile Ser Arg Val Glu Ala Gly
65            70            75            80

Asp Glu Ala Asp Tyr Tyr Cys Gln Val Trp Asp Ser Ser Ser Asp His
      85            90            95

Trp Val Phe Gly Gly Gly Thr Lys Leu Thr Val Leu Ser Ser
        100           105          110

<210> SEQ ID NO 142
<211> LENGTH: 123
<212> TYPE: PRT
<213> ORGANISM: Artificial sequence
<220> FEATURE:
<223> OTHER INFORMATION: VEGF_LC VHVL cross LC kappa

<400> SEQUENCE: 142

Glu Val Gln Leu Val Glu Ser Gly Gly Gly Leu Val Gln Pro Gly Gly
1            5            10            15

Ser Leu Arg Leu Ser Cys Ala Ala Ser Gly Tyr Asp Phe Thr His Tyr
          20           25          30

Gly Met Asn Trp Val Arg Gln Ala Pro Gly Lys Gly Leu Glu Trp Val
      35            40            45

Gly Trp Ile Asn Thr Tyr Thr Gly Glu Pro Thr Tyr Ala Ala Asp Phe
            50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
                100                 105                 110

Trp Gly Gln Gly Thr Leu Val Thr Val Ser Ser
            115                 120

<210> SEQ ID NO 143
<211> LENGTH: 107
<212> TYPE: PRT
<213> ORGANISM: Artificial sequence
<220> FEATURE:
<223> OTHER INFORMATION: VEGF_LC10 VHVL cross IgG HC LALAPGAAA knob

<400> SEQUENCE: 143

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
                20                  25                  30

Leu Asn Trp Tyr Gln Gln Lys Pro Gly Lys Ala Pro Lys Val Leu Ile
            35                  40                  45

Tyr Phe Thr Ser Ser Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys
                100                 105

<210> SEQ ID NO 144
<211> LENGTH: 116
<212> TYPE: PRT
<213> ORGANISM: Artificial Sequence
<220> FEATURE:
<223> OTHER INFORMATION: PDGFang2-0044 VH

<400> SEQUENCE: 144

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Tyr
                20                  25                  30

Trp Ile Glu Trp Val Lys Gln Arg Pro Gly His Gly Leu Glu Trp Ile
            35                  40                  45

Gly Glu Ile Leu Pro Gly Ser Gly Ser Thr Asn Tyr Asn Glu Lys Phe
        50                  55                  60

Lys Val Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Gln Thr Thr Gln Asp Phe Asp Ser Trp Gly Gln Gly Thr Thr Leu
                100                 105                 110

Thr Val Ser Ser
            115

<210> SEQ ID NO 145
<211> LENGTH: 112
<212> TYPE: PRT
<213> ORGANISM: Artificial Sequence
<220> FEATURE:
<223> OTHER INFORMATION: PDGFang2-0044 VL

<400> SEQUENCE: 145

Asp Ile Val Leu Thr Gln Ser Pro Gly Ser Leu Ala Val Ser Leu Gly
1               5                   10                  15

Gln Arg Ala Thr Ile Ser Cys Arg Ala Ser Glu Ser Val Asp Ile Tyr
            20                  25                  30

Gly Tyr Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Arg Thr Phe Gly Gly Gly Thr Lys Leu Glu Ile Lys Arg
            100                 105                 110

<210> SEQ ID NO 146
<211> LENGTH: 440
<212> TYPE: PRT
<213> ORGANISM: Artificial Sequence
<220> FEATURE:
<223> OTHER INFORMATION: CrossMab Ang2 wt-PDGF-0044 HC1

<400> SEQUENCE: 146

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val

```
                195                 200                 205
Glu Pro Lys Ser Cys Asp Lys Thr His Thr Cys Pro Pro Cys Pro Ala
    210                 215                 220

Pro Glu Ala Ala Gly Gly Pro Ser Val Phe Leu Phe Pro Pro Lys Pro
225                 230                 235                 240

Lys Asp Thr Leu Met Ala Ser Arg Thr Pro Glu Val Thr Cys Val Val
                245                 250                 255

Val Asp Val Ser His Glu Asp Pro Glu Val Lys Phe Asn Trp Tyr Val
            260                 265                 270

Asp Gly Val Glu Val His Asn Ala Lys Thr Lys Pro Arg Glu Glu Gln
        275                 280                 285

Tyr Asn Ser Thr Tyr Arg Val Val Ser Val Leu Thr Val Leu Ala Gln
    290                 295                 300

Asp Trp Leu Asn Gly Lys Glu Tyr Lys Cys Lys Val Ser Asn Lys Ala
305                 310                 315                 320

Leu Gly Ala Pro Ile Glu Lys Thr Ile Ser Lys Ala Lys Gly Gln Pro
                325                 330                 335

Arg Glu Pro Gln Val Tyr Thr Leu Pro Pro Cys Arg Asp Glu Leu Thr
            340                 345                 350

Lys Asn Gln Val Ser Leu Trp Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
                405                 410                 415

Ser Cys Ser Val Met His Glu Ala Leu His Asn Ala Tyr Thr Gln Lys
            420                 425                 430

Ser Leu Ser Leu Ser Pro Gly Lys
        435                 440

<210> SEQ ID NO 147
<211> LENGTH: 446
<212> TYPE: PRT
<213> ORGANISM: Artificial Sequence
<220> FEATURE:
<223> OTHER INFORMATION: CrossMab Ang2 wt-PDGF-0044 HC2

<400> SEQUENCE: 147

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Ser Thr Asn Tyr Asn Glu Lys Phe
    50                  55                  60

Lys Val Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Gln Thr Thr Gln Asp Phe Asp Ser Trp Gly Gln Gly Thr Thr Leu
            100                 105                 110

Thr Val Ser Ser Ala Ser Thr Lys Gly Pro Ser Val Phe Pro Leu Ala
```

```
             115                 120                 125
Pro Ser Ser Lys Ser Thr Ser Gly Gly Thr Ala Ala Leu Gly Cys Leu
        130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Glu Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ala Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu Ala Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Cys Thr Leu Pro Pro
            340                 345                 350

Ser Arg Asp Glu Leu Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn Ala Tyr Thr Gln Lys Ser Leu Ser Leu Ser Pro Gly Lys
        435                 440                 445

<210> SEQ ID NO 148
<211> LENGTH: 236
<212> TYPE: PRT
<213> ORGANISM: Artificial Sequence
<220> FEATURE:
<223> OTHER INFORMATION: CrossMab Ang2 wt-PDGF-0044 LC1

<400> SEQUENCE: 148

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
```

```
                35                  40                  45
Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Ser Pro Asn Pro Tyr Tyr Tyr Asp Ser Ser Gly Tyr Tyr Tyr
                100                 105                 110

Pro Gly Ala Phe Asp Ile Trp Gly Gln Gly Thr Met Val Thr Val Ser
                115                 120                 125

Ser Ala Ser Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
                195                 200                 205

Glu Lys His Lys Val Tyr Ala Cys Glu Val Thr His Gln Gly Leu Ser
                210                 215                 220

Ser Pro Val Thr Lys Ser Phe Asn Arg Gly Glu Cys
225                 230                 235

<210> SEQ ID NO 149
<211> LENGTH: 218
<212> TYPE: PRT
<213> ORGANISM: Artificial Sequence
<220> FEATURE:
<223> OTHER INFORMATION: CrossMab Ang2 wt-PDGF-0044 LC2

<400> SEQUENCE: 149

Asp Ile Val Leu Thr Gln Ser Pro Gly Ser Leu Ala Val Ser Leu Gly
 1               5                  10                  15

Gln Arg Ala Thr Ile Ser Cys Arg Ala Ser Glu Ser Val Asp Ile Tyr
                20                  25                  30

Gly Tyr Ser Phe Met His Trp Tyr Gln Gln Lys Pro Gly Gln Pro Pro
                35                  40                  45

Lys Leu Leu Ile Tyr Arg Ala Ser Asn Leu Glu Ser Gly Ile Pro Ala
 50                  55                  60

Arg Phe Ser Gly Ser Gly Ser Arg Thr Asp Phe Thr Leu Thr Ile Asn
 65                  70                  75                  80

Pro Val Glu Ala Asp Asp Val Ala Thr Tyr Tyr Cys Gln Gln Ser Asn
                 85                  90                  95

Glu Asp Pro Arg Thr Phe Gly Gly Gly Thr Lys Leu Glu Ile Lys Arg
                100                 105                 110

Thr Val Ala Ala Pro Ser Val Phe Ile Phe Pro Pro Ser Asp Arg Lys
                115                 120                 125

Leu Lys Ser Gly Thr Ala Ser Val Val Cys Leu Leu Asn Asn Phe Tyr
                130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
```

165                 170                 175
Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
        210                 215

<210> SEQ ID NO 150
<211> LENGTH: 440
<212> TYPE: PRT
<213> ORGANISM: Artificial Sequence
<220> FEATURE:
<223> OTHER INFORMATION: CrossMab Ang2 wt-PDGF-0085 HC1

<400> SEQUENCE: 150

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys Asp Lys Thr His Thr Cys Pro Pro Cys Pro Ala
    210                 215                 220

Pro Glu Ala Ala Gly Gly Pro Ser Val Phe Leu Phe Pro Pro Lys Pro
225                 230                 235                 240

Lys Asp Thr Leu Met Ala Ser Arg Thr Pro Glu Val Thr Cys Val Val
                245                 250                 255

Val Asp Val Ser His Glu Asp Pro Glu Val Lys Phe Asn Trp Tyr Val
            260                 265                 270

Asp Gly Val Glu Val His Asn Ala Lys Thr Lys Pro Arg Glu Glu Gln
        275                 280                 285

Tyr Asn Ser Thr Tyr Arg Val Val Ser Val Leu Thr Val Leu Ala Gln
    290                 295                 300

Asp Trp Leu Asn Gly Lys Glu Tyr Lys Cys Lys Val Ser Asn Lys Ala

```
305                 310                 315                 320
Leu Gly Ala Pro Ile Glu Lys Thr Ile Ser Lys Ala Lys Gly Gln Pro
                325                 330                 335
Arg Glu Pro Gln Val Tyr Thr Leu Pro Pro Cys Arg Asp Glu Leu Thr
                340                 345                 350
Lys Asn Gln Val Ser Leu Trp Cys Leu Val Lys Gly Phe Tyr Pro Ser
                355                 360                 365
Asp Ile Ala Val Glu Trp Glu Ser Asn Gly Gln Pro Glu Asn Asn Tyr
            370                 375                 380
Lys Thr Thr Pro Pro Val Leu Asp Ser Asp Gly Ser Phe Phe Leu Tyr
385                 390                 395                 400
Ser Lys Leu Thr Val Asp Lys Ser Arg Trp Gln Gln Gly Asn Val Phe
                405                 410                 415
Ser Cys Ser Val Met His Glu Ala Leu His Asn Ala Tyr Thr Gln Lys
                420                 425                 430
Ser Leu Ser Leu Ser Pro Gly Lys
                435                 440

<210> SEQ ID NO 151
<211> LENGTH: 450
<212> TYPE: PRT
<213> ORGANISM: Artificial Sequence
<220> FEATURE:
<223> OTHER INFORMATION: CrossMab Ang2 wt-PDGF-0085 HC2

<400> SEQUENCE: 151

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
                20                  25                  30
Trp Met Ser Trp Val Arg Gln Ala Pro Glu Lys Gly Leu Glu Trp Val
            35                  40                  45
Ser Thr Ile Ser Asp Gly Gly Leu Thr Tyr Tyr Ala Asp Ser Val
        50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Glu Ser Gly Gly Tyr Thr Asp Trp Leu Phe Gly Tyr Trp Gly Gln
                100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
            130                 135                 140
Leu Gly Cys Leu Val Glu Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
            195                 200                 205
Pro Ser Asn Thr Lys Val Asp Glu Lys Val Glu Pro Lys Ser Cys Asp
        210                 215                 220
Lys Thr His Thr Cys Pro Pro Cys Pro Ala Pro Glu Ala Ala Gly Gly
```

```
              225                 230                 235                 240
Pro Ser Val Phe Leu Phe Pro Lys Pro Lys Asp Thr Leu Met Ala
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
                275                 280                 285
Asn Ala Lys Thr Lys Pro Arg Glu Glu Gln Tyr Asn Ser Thr Tyr Arg
            290                 295                 300
Val Val Ser Val Leu Thr Val Leu Ala Gln Asp Trp Leu Asn Gly Lys
305                 310                 315                 320
Glu Tyr Lys Cys Lys Val Ser Asn Lys Ala Leu Gly Ala Pro Ile Glu
                325                 330                 335
Lys Thr Ile Ser Lys Ala Lys Gly Gln Pro Arg Glu Pro Gln Val Cys
                340                 345                 350
Thr Leu Pro Pro Ser Arg Asp Glu Leu Thr Lys Asn Gln Val Ser Leu
            355                 360                 365
Ser Cys Ala Val Lys Gly Phe Tyr Pro Ser Asp Ile Ala Val Glu Trp
        370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Val Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn Ala Tyr Thr Gln Lys Ser Leu Ser Leu Ser Pro
            435                 440                 445
Gly Lys
    450

<210> SEQ ID NO 152
<211> LENGTH: 236
<212> TYPE: PRT
<213> ORGANISM: Artificial Sequence
<220> FEATURE:
<223> OTHER INFORMATION: CrossMab Ang2 wt-PDGF-0085 LC1

<400> SEQUENCE: 152

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
                20                  25                  30
Tyr Met His Trp Val Arg Gln Ala Pro Gly Gln Gly Leu Glu Trp Met
            35                  40                  45
Gly Trp Ile Asn Pro Asn Ser Gly Gly Thr Asn Tyr Ala Gln Lys Phe
    50                  55                  60
Gln Gly Arg Val Thr Met Thr Arg Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Ser Pro Asn Pro Tyr Tyr Tyr Asp Ser Ser Gly Tyr Tyr Tyr
                100                 105                 110
Pro Gly Ala Phe Asp Ile Trp Gly Gln Gly Thr Met Val Thr Val Ser
            115                 120                 125
Ser Ala Ser Val Ala Ala Pro Ser Val Phe Ile Phe Pro Pro Ser Asp
```

```
            130                 135                 140
Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 153
<211> LENGTH: 214
<212> TYPE: PRT
<213> ORGANISM: Artificial Sequence
<220> FEATURE:
<223> OTHER INFORMATION: CrossMab Ang2 wt-PDGF-0085 LC2

<400> SEQUENCE: 153

Asp Ile Gln Met Thr Gln Ser Pro Ser Ser Leu Ser Ala Ser Val Gly
1               5                   10                  15

Asp Arg Val Ala Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Arg Lys Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 154
<211> LENGTH: 440
<212> TYPE: PRT
<213> ORGANISM: Artificial Sequence
<220> FEATURE:
<223> OTHER INFORMATION: CrossMab Ang2 wt-PDGF-0086 HC1
```

<400> SEQUENCE: 154

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65              70                  75                  80

Asp Glu Ala Asp Tyr Tyr Cys Gln Val Trp Asp Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
            115                 120                 125

Ser Gly Gly Thr Ala Ala Leu Gly Cys Leu Val Lys Asp Tyr Phe Pro
        130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys Asp Lys Thr His Thr Cys Pro Pro Cys Pro Ala
    210                 215                 220

Pro Glu Ala Ala Gly Gly Pro Ser Val Phe Leu Phe Pro Pro Lys Pro
225                 230                 235                 240

Lys Asp Thr Leu Met Ala Ser Arg Thr Pro Glu Val Thr Cys Val Val
                245                 250                 255

Val Asp Val Ser His Glu Asp Pro Glu Val Lys Phe Asn Trp Tyr Val
            260                 265                 270

Asp Gly Val Glu Val His Asn Ala Lys Thr Lys Pro Arg Glu Glu Gln
        275                 280                 285

Tyr Asn Ser Thr Tyr Arg Val Val Ser Val Leu Thr Val Leu Ala Gln
    290                 295                 300

Asp Trp Leu Asn Gly Lys Glu Tyr Lys Cys Lys Val Ser Asn Lys Ala
305                 310                 315                 320

Leu Gly Ala Pro Ile Glu Lys Thr Ile Ser Lys Ala Lys Gly Gln Pro
                325                 330                 335

Arg Glu Pro Gln Val Tyr Thr Leu Pro Pro Cys Arg Asp Glu Leu Thr
            340                 345                 350

Lys Asn Gln Val Ser Leu Trp Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asn Val Phe

```
                       405                 410                 415

Ser Cys Ser Val Met His Glu Ala Leu His Asn Ala Tyr Thr Gln Lys
            420                 425                 430

Ser Leu Ser Leu Ser Pro Gly Lys
        435                 440

<210> SEQ ID NO 155
<211> LENGTH: 450
<212> TYPE: PRT
<213> ORGANISM: Artificial Sequence
<220> FEATURE:
<223> OTHER INFORMATION: CrossMab Ang2 wt-PDGF-0086 HC2

<400> SEQUENCE: 155

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ser Thr Ile Ser Asp Gly Gly Leu Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Glu Ser Gly Gly Tyr Thr Asp Trp Leu Phe Gly Tyr Trp Gly Gln
            100                 105                 110

Gly Thr Leu Val Thr Val Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Glu Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Glu Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ala
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu Ala Gln Asp Trp Leu Asn Gly Lys
305                 310                 315                 320

Glu Tyr Lys Cys Lys Val Ser Asn Lys Ala Leu Gly Ala Pro Ile Glu
```

```
                    325                 330                 335
Lys Thr Ile Ser Lys Ala Lys Gly Gln Pro Arg Glu Pro Gln Val Cys
                340                 345                 350
Thr Leu Pro Pro Ser Arg Asp Glu Leu Thr Lys Asn Gln Val Ser Leu
            355                 360                 365
Ser Cys Ala Val Lys Gly Phe Tyr Pro Ser Asp Ile Ala Val Glu Trp
        370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Val Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn Ala Tyr Thr Gln Lys Ser Leu Ser Leu Ser Pro
            435                 440                 445
Gly Lys
    450

<210> SEQ ID NO 156
<211> LENGTH: 236
<212> TYPE: PRT
<213> ORGANISM: Artificial Sequence
<220> FEATURE:
<223> OTHER INFORMATION: CrossMab Ang2 wt-PDGF-0086 LC1

<400> SEQUENCE: 156

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
            20                  25                  30
Tyr Met His Trp Val Arg Gln Ala Pro Gly Gln Gly Leu Glu Trp Met
        35                  40                  45
Gly Trp Ile Asn Pro Asn Ser Gly Gly Thr Asn Tyr Ala Gln Lys Phe
    50                  55                  60
Gln Gly Arg Val Thr Met Thr Arg Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Ser Pro Asn Pro Tyr Tyr Tyr Asp Ser Ser Gly Tyr Tyr Tyr
            100                 105                 110
Pro Gly Ala Phe Asp Ile Trp Gly Gln Gly Thr Met Val Thr Val Ser
        115                 120                 125
Ser Ala Ser Val Ala Ala Pro Ser Val Phe Ile Phe Pro Pro Ser Asp
    130                 135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
                165                 170                 175
Gln Ser Gly Asn Ser Gln Glu Ser Val Thr Glu Gln Asp Ser Lys Asp
            180                 185                 190
Ser Thr Tyr Ser Leu Ser Ser Thr Leu Thr Leu Ser Lys Ala Asp Tyr
        195                 200                 205
Glu Lys His Lys Val Tyr Ala Cys Glu Val Thr His Gln Gly Leu Ser
    210                 215                 220
Ser Pro Val Thr Lys Ser Phe Asn Arg Gly Glu Cys
```

<210> SEQ ID NO 157
<211> LENGTH: 214
<212> TYPE: PRT
<213> ORGANISM: Artificial Sequence
<220> FEATURE:
<223> OTHER INFORMATION: CrossMab Ang2 wt-PDGF-0086 LC2

<400> SEQUENCE: 157

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Arg Lys Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 158
<211> LENGTH: 440
<212> TYPE: PRT
<213> ORGANISM: Artificial Sequence
<220> FEATURE:
<223> OTHER INFORMATION: Clone 146 HC1

<400> SEQUENCE: 158

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Thr Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys Asp Lys Thr His Thr Cys Pro Pro Cys Pro Ala
    210                 215                 220

Pro Glu Ala Ala Gly Gly Pro Ser Val Phe Leu Phe Pro Pro Lys Pro
225                 230                 235                 240

Lys Asp Thr Leu Met Ala Ser Arg Thr Pro Glu Val Thr Cys Val Val
                245                 250                 255

Val Asp Val Ser His Glu Asp Pro Glu Val Lys Phe Asn Trp Tyr Val
            260                 265                 270

Asp Gly Val Glu Val His Asn Ala Lys Thr Lys Pro Arg Glu Glu Gln
        275                 280                 285

Tyr Asn Ser Thr Tyr Arg Val Val Ser Val Leu Thr Val Leu Ala Gln
    290                 295                 300

Asp Trp Leu Asn Gly Lys Glu Tyr Lys Cys Lys Val Ser Asn Lys Ala
305                 310                 315                 320

Leu Gly Ala Pro Ile Glu Lys Thr Ile Ser Lys Ala Lys Gly Gln Pro
                325                 330                 335

Arg Glu Pro Gln Val Tyr Thr Leu Pro Pro Cys Arg Asp Glu Leu Thr
            340                 345                 350

Lys Asn Gln Val Ser Leu Trp Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
                405                 410                 415

Ser Cys Ser Val Met His Glu Ala Leu His Asn Ala Tyr Thr Gln Lys
            420                 425                 430

Ser Leu Ser Leu Ser Pro Gly Lys
        435                 440

<210> SEQ ID NO 159
<211> LENGTH: 446
<212> TYPE: PRT
<213> ORGANISM: Artificial Sequence
<220> FEATURE:
<223> OTHER INFORMATION: Clone 146 HC2

<400> SEQUENCE: 159

-continued

```
Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Ser Thr Asn Tyr Asn Glu Lys Phe
    50                  55                  60

Lys Val Lys Ala Thr Phe Thr Ala Asp Thr Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Gln Thr Thr Gln Asp Phe Asp Ser Trp Gly Gln Gly Thr Thr Leu
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
    195                 200                 205

Lys Val Asp Glu Lys Val Glu Pro Lys Ser Cys Asp Lys Thr His Thr
210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ala Ser Arg Thr Pro
            245                 250                 255

Glu Val Thr Cys Val Val Val Asp Val Ser His Glu Asp Pro Glu Val
        260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
290                 295                 300

Leu Thr Val Leu Ala Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
            325                 330                 335

Lys Ala Lys Gly Gln Pro Arg Glu Pro Gln Val Cys Thr Leu Pro Pro
        340                 345                 350

Ser Arg Asp Glu Leu Thr Lys Asn Gln Val Ser Leu Ser Cys Ala Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
            405                 410                 415

Gln Gln Gly Asn Val Phe Ser Cys Ser Val Met His Glu Ala Leu His
```

```
                420             425             430
Asn Ala Tyr Thr Gln Lys Ser Leu Ser Leu Ser Pro Gly Lys
        435             440             445
```

<210> SEQ ID NO 160
<211> LENGTH: 236
<212> TYPE: PRT
<213> ORGANISM: Artificial Sequence
<220> FEATURE:
<223> OTHER INFORMATION: Clone 146 LC1

<400> SEQUENCE: 160

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Asp Ser Pro Gly Tyr Tyr Tyr
            100                 105                 110

Pro Ala Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 161
<211> LENGTH: 218
<212> TYPE: PRT
<213> ORGANISM: Artificial Sequence
<220> FEATURE:
<223> OTHER INFORMATION: Clone 146 LC2

<400> SEQUENCE: 161

```
Asp Ile Val Leu Thr Gln Ser Pro Gly Ser Leu Ala Val Ser Leu Gly
1               5                   10                  15

Gln Arg Ala Thr Ile Ser Cys Arg Ala Ser Glu Ser Val Asp Ile Tyr
            20                  25                  30

Gly Tyr Ser Phe Met His Trp Tyr Gln Gln Lys Pro Gly Gln Pro Pro
        35                  40                  45
```

```
Lys Leu Leu Ile Tyr Arg Ala Ser Asn Leu Glu Ser Gly Ile Pro Ala
 50                  55                  60

Arg Phe Ser Gly Ser Gly Ser Arg Thr Asp Phe Thr Leu Thr Ile Asn
 65                  70                  75                  80

Pro Val Glu Ala Asp Asp Val Ala Thr Tyr Tyr Cys Gln Gln Ser Asn
                 85                  90                  95

Glu Asp Pro Arg Thr Phe Gly Gly Thr Lys Leu Glu Ile Lys Arg
                100                 105                 110

Thr Val Ala Ala Pro Ser Val Phe Ile Phe Pro Pro Ser Asp Arg Lys
                115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
210                 215

<210> SEQ ID NO 162
<211> LENGTH: 440
<212> TYPE: PRT
<213> ORGANISM: Artificial Sequence
<220> FEATURE:
<223> OTHER INFORMATION: Clone 144 HC1

<400> SEQUENCE: 162

Ser Tyr Val Leu Thr Gln Pro Pro Ser Val Ser Val Ala Pro Gly Gln
  1               5                  10                  15

Thr Ala Arg Ile Thr Cys Gly Gly Asn Asn Ile Gly Ser Lys Ser Val
                 20                  25                  30

His Trp Tyr Gln Gln Lys Pro Gly Gln Ala Pro Val Leu Val Val Tyr
             35                  40                  45

Asp Thr Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Trp Val Phe Gly Gly Gly Thr Lys Leu Thr Val Leu Ser Ser Ala Ser
                100                 105                 110

Thr Lys Gly Pro Ser Val Phe Pro Leu Ala Pro Ser Ser Lys Ser Thr
                115                 120                 125

Ser Gly Gly Thr Ala Ala Leu Gly Cys Leu Val Lys Asp Tyr Phe Pro
                130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
                180                 185                 190
```

Cys Asn Val Asn His Lys Pro Ser Asn Thr Lys Val Asp Lys Lys Val
            195                 200                 205

Glu Pro Lys Ser Cys Asp Lys Thr His Thr Cys Pro Pro Cys Pro Ala
    210                 215                 220

Pro Glu Ala Ala Gly Gly Pro Ser Val Phe Leu Phe Pro Pro Lys Pro
225                 230                 235                 240

Lys Asp Thr Leu Met Ala Ser Arg Thr Pro Glu Val Thr Cys Val Val
                245                 250                 255

Val Asp Val Ser His Glu Asp Pro Glu Val Lys Phe Asn Trp Tyr Val
            260                 265                 270

Asp Gly Val Glu Val His Asn Ala Lys Thr Lys Pro Arg Glu Glu Gln
        275                 280                 285

Tyr Asn Ser Thr Tyr Arg Val Val Ser Val Leu Thr Val Leu Ala Gln
    290                 295                 300

Asp Trp Leu Asn Gly Lys Glu Tyr Lys Cys Lys Val Ser Asn Lys Ala
305                 310                 315                 320

Leu Gly Ala Pro Ile Glu Lys Thr Ile Ser Lys Ala Lys Gly Gln Pro
                325                 330                 335

Arg Glu Pro Gln Val Tyr Thr Leu Pro Pro Cys Arg Asp Glu Leu Thr
            340                 345                 350

Lys Asn Gln Val Ser Leu Trp Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
                405                 410                 415

Ser Cys Ser Val Met His Glu Ala Leu His Asn Ala Tyr Thr Gln Lys
            420                 425                 430

Ser Leu Ser Leu Ser Pro Gly Lys
        435                 440

<210> SEQ ID NO 163
<211> LENGTH: 450
<212> TYPE: PRT
<213> ORGANISM: Artificial Sequence
<220> FEATURE:
<223> OTHER INFORMATION: Clone 144 HC2

<400> SEQUENCE: 163

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ser Thr Ile Ser Asp Gly Gly Leu Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Glu Ser Gly Gly Tyr Thr Asp Trp Leu Phe Gly Tyr Trp Gly Gln
            100                 105                 110

Gly Thr Leu Val Thr Val Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Glu Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Glu Lys Val Glu Pro Lys Ser Cys Asp
210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ala
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu Ala Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
            355                 360                 365

Ser Cys Ala Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn Ala Tyr Thr Gln Lys Ser Leu Ser Leu Ser Pro
            435                 440                 445

Gly Lys
450

<210> SEQ ID NO 164
<211> LENGTH: 236
<212> TYPE: PRT
<213> ORGANISM: Artificial Sequence
<220> FEATURE:
<223> OTHER INFORMATION: Clone 144 LC1

<400> SEQUENCE: 164

Gln Val Gln Leu Val Gln Ser Gly Ala Glu Val Lys Lys Pro Gly Ala
1               5                   10                  15

```
Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Pro Gly Tyr Tyr Tyr
            100                 105                 110

Pro Ala Ala Phe Asp Ile Trp Gly Gln Gly Thr Met Val Thr Val Ser
            115                 120                 125

Ser Ala Ser Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 165
<211> LENGTH: 214
<212> TYPE: PRT
<213> ORGANISM: Artificial Sequence
<220> FEATURE:
<223> OTHER INFORMATION: Clone 144 LC2

<400> SEQUENCE: 165

Asp Ile Gln Met Thr Gln Ser Pro Ser Ser Leu Ser Ala Ser Val Gly
1               5                   10                  15

Asp Arg Val Ala Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Arg Lys Leu Lys Ser Gly
            115                 120                 125

Thr Ala Ser Val Val Cys Leu Leu Asn Asn Phe Tyr Pro Arg Glu Ala
130                 135                 140
```

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 166
<211> LENGTH: 440
<212> TYPE: PRT
<213> ORGANISM: Artificial Sequence
<220> FEATURE:
<223> OTHER INFORMATION: Clone 145 HC1

<400> SEQUENCE: 166

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Thr Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys Asp Lys Thr His Thr Cys Pro Pro Cys Pro Ala
    210                 215                 220

Pro Glu Ala Ala Gly Gly Pro Ser Val Phe Leu Phe Pro Pro Lys Pro
225                 230                 235                 240

Lys Asp Thr Leu Met Ala Ser Arg Thr Pro Glu Val Thr Cys Val Val
                245                 250                 255

Val Asp Val Ser His Glu Asp Pro Glu Val Lys Phe Asn Trp Tyr Val
            260                 265                 270

Asp Gly Val Glu Val His Asn Ala Lys Thr Lys Pro Arg Glu Glu Gln
        275                 280                 285

```
Tyr Asn Ser Thr Tyr Arg Val Val Ser Val Leu Thr Val Leu Ala Gln
            290                 295                 300

Asp Trp Leu Asn Gly Lys Glu Tyr Lys Cys Lys Val Ser Asn Lys Ala
305                 310                 315                 320

Leu Gly Ala Pro Ile Glu Lys Thr Ile Ser Lys Ala Lys Gly Gln Pro
                325                 330                 335

Arg Glu Pro Gln Val Tyr Thr Leu Pro Pro Cys Arg Asp Glu Leu Thr
                340                 345                 350

Lys Asn Gln Val Ser Leu Trp Cys Leu Val Lys Gly Phe Tyr Pro Ser
            355                 360                 365

Asp Ile Ala Val Glu Trp Glu Ser Asn Gly Gln Pro Glu Asn Asn Tyr
            370                 375                 380

Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
                405                 410                 415

Ser Cys Ser Val Met His Glu Ala Leu His Asn Ala Tyr Thr Gln Lys
            420                 425                 430

Ser Leu Ser Leu Ser Pro Gly Lys
            435                 440
```

<210> SEQ ID NO 167
<211> LENGTH: 450
<212> TYPE: PRT
<213> ORGANISM: Artificial Sequence
<220> FEATURE:
<223> OTHER INFORMATION: Clone 145 HC2

<400> SEQUENCE: 167

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Glu Lys Gly Leu Glu Trp Val
            35                  40                  45

Ser Thr Ile Ser Asp Gly Gly Leu Thr Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Glu Ser Gly Gly Tyr Thr Asp Trp Leu Phe Gly Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Glu Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205
```

Pro Ser Asn Thr Lys Val Asp Glu Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ala
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu Ala Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn Ala Tyr Thr Gln Lys Ser Leu Ser Leu Ser Pro
        435                 440                 445

Gly Lys
    450

<210> SEQ ID NO 168
<211> LENGTH: 236
<212> TYPE: PRT
<213> ORGANISM: Artificial Sequence
<220> FEATURE:
<223> OTHER INFORMATION: Clone 145 LC1

<400> SEQUENCE: 168

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Ser Pro Asn Pro Tyr Tyr Tyr Asp Ser Pro Gly Tyr Tyr Tyr
            100                 105                 110

```
Pro Ala Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 169
<211> LENGTH: 214
<212> TYPE: PRT
<213> ORGANISM: Artificial Sequence
<220> FEATURE:
<223> OTHER INFORMATION: Clone 145 LC2

<400> SEQUENCE: 169

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Arg Lys Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 170
<211> LENGTH: 440
```

<212> TYPE: PRT
<213> ORGANISM: Artificial Sequence
<220> FEATURE:
<223> OTHER INFORMATION: CrossMab Ang2 mut-PDGF-0044 HC1

<400> SEQUENCE: 170

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Thr Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys Asp Lys Thr His Thr Cys Pro Pro Cys Pro Ala
    210                 215                 220

Pro Glu Ala Ala Gly Gly Pro Ser Val Phe Leu Phe Pro Pro Lys Pro
225                 230                 235                 240

Lys Asp Thr Leu Met Ala Ser Arg Thr Pro Glu Val Thr Cys Val Val
                245                 250                 255

Val Asp Val Ser His Glu Asp Pro Glu Val Lys Phe Asn Trp Tyr Val
            260                 265                 270

Asp Gly Val Glu Val His Asn Ala Lys Thr Lys Pro Arg Glu Glu Gln
        275                 280                 285

Tyr Asn Ser Thr Tyr Arg Val Val Ser Val Leu Thr Val Leu Ala Gln
    290                 295                 300

Asp Trp Leu Asn Gly Lys Glu Tyr Lys Cys Lys Val Ser Asn Lys Ala
305                 310                 315                 320

Leu Gly Ala Pro Ile Glu Lys Thr Ile Ser Lys Ala Lys Gly Gln Pro
                325                 330                 335

Arg Glu Pro Gln Val Tyr Thr Leu Pro Pro Cys Arg Asp Glu Leu Thr
            340                 345                 350

Lys Asn Gln Val Ser Leu Trp Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380
```

-continued

```
Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
            405                 410                 415

Ser Cys Ser Val Met His Glu Ala Leu His Asn Ala Tyr Thr Gln Lys
        420                 425                 430

Ser Leu Ser Leu Ser Pro Gly Lys
    435                 440

<210> SEQ ID NO 171
<211> LENGTH: 446
<212> TYPE: PRT
<213> ORGANISM: Artificial Sequence
<220> FEATURE:
<223> OTHER INFORMATION: CrossMab Ang2 mut-PDGF-0044 HC2

<400> SEQUENCE: 171

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Ser Thr Asn Tyr Asn Glu Lys Phe
    50                  55                  60

Lys Val Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Gln Thr Thr Gln Asp Phe Asp Ser Trp Gly Gln Gly Thr Thr Leu
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Glu Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ala Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300
```

Leu Thr Val Leu Ala Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
            325                 330                 335

Lys Ala Lys Gly Gln Pro Arg Glu Pro Gln Val Cys Thr Leu Pro Pro
        340                 345                 350

Ser Arg Asp Glu Leu Thr Lys Asn Gln Val Ser Leu Ser Cys Ala Val
    355                 360                 365

Lys Gly Phe Tyr Pro Ser Asp Ile Ala Val Glu Trp Glu Ser Asn Gly
370                 375                 380

Gln Pro Glu Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn Ala Tyr Thr Gln Lys Ser Leu Ser Leu Ser Pro Gly Lys
    435                 440                 445

<210> SEQ ID NO 172
<211> LENGTH: 236
<212> TYPE: PRT
<213> ORGANISM: Artificial Sequence
<220> FEATURE:
<223> OTHER INFORMATION: CrossMab Ang2 mut-PDGF-0044 LC1

<400> SEQUENCE: 172

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Ser Ser Pro Gly Tyr Tyr Tyr
            100                 105                 110

Pro Ala Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 173
<211> LENGTH: 218
<212> TYPE: PRT
<213> ORGANISM: Artificial Sequence
<220> FEATURE:
<223> OTHER INFORMATION: CrossMab Ang2 mut-PDGF-0044 LC2

<400> SEQUENCE: 173

Asp Ile Val Leu Thr Gln Ser Pro Gly Ser Leu Ala Val Ser Leu Gly
1               5                   10                  15

Gln Arg Ala Thr Ile Ser Cys Arg Ala Ser Glu Ser Val Asp Ile Tyr
            20                  25                  30

Gly Tyr Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Arg Thr Phe Gly Gly Gly Thr Lys Leu Glu Ile Lys Arg
            100                 105                 110

Thr Val Ala Ala Pro Ser Val Phe Ile Phe Pro Pro Ser Asp Arg Lys
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 174
<211> LENGTH: 440
<212> TYPE: PRT
<213> ORGANISM: Artificial Sequence
<220> FEATURE:
<223> OTHER INFORMATION: CrossMab Ang2 mut5-PDGF-0085 HC1

<400> SEQUENCE: 174

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Thr Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

Trp Val Phe Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
            165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
            195                 200                 205

Glu Pro Lys Ser Cys Asp Lys Thr His Thr Cys Pro Pro Cys Pro Ala
210                 215                 220

Pro Glu Ala Ala Gly Gly Pro Ser Val Phe Leu Phe Pro Pro Lys Pro
225                 230                 235                 240

Lys Asp Thr Leu Met Ala Ser Arg Thr Pro Glu Val Thr Cys Val Val
            245                 250                 255

Val Asp Val Ser His Glu Asp Pro Glu Val Lys Phe Asn Trp Tyr Val
            260                 265                 270

Asp Gly Val Glu Val His Asn Ala Lys Thr Lys Pro Arg Glu Glu Gln
            275                 280                 285

Tyr Asn Ser Thr Tyr Arg Val Val Ser Val Leu Thr Val Leu Ala Gln
290                 295                 300

Asp Trp Leu Asn Gly Lys Glu Tyr Lys Cys Lys Val Ser Asn Lys Ala
305                 310                 315                 320

Leu Gly Ala Pro Ile Glu Lys Thr Ile Ser Lys Ala Lys Gly Gln Pro
            325                 330                 335

Arg Glu Pro Gln Val Tyr Thr Leu Pro Pro Cys Arg Asp Glu Leu Thr
            340                 345                 350

Lys Asn Gln Val Ser Leu Trp Cys Leu Val Lys Gly Phe Tyr Pro Ser
            355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
            405                 410                 415

Ser Cys Ser Val Met His Glu Ala Leu His Asn Ala Tyr Thr Gln Lys
            420                 425                 430

Ser Leu Ser Leu Ser Pro Gly Lys
            435                 440

<210> SEQ ID NO 175
<211> LENGTH: 450
<212> TYPE: PRT
<213> ORGANISM: Artificial Sequence
<220> FEATURE:
<223> OTHER INFORMATION: CrossMab Ang2 mut5-PDGF-0085 HC2

<400> SEQUENCE: 175

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ser Thr Ile Ser Asp Gly Gly Leu Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Glu Ser Gly Gly Tyr Thr Asp Trp Leu Phe Gly Tyr Trp Gly Gln
                100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
        130                 135                 140

Leu Gly Cys Leu Val Glu Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Glu Lys Val Glu Pro Lys Ser Cys Asp
210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ala
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu Ala Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
            355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415
```

Lys Ser Arg Trp Gln Gln Gly Asn Val Phe Ser Cys Ser Val Met His
            420                 425                 430

Glu Ala Leu His Asn Ala Tyr Thr Gln Lys Ser Leu Ser Leu Ser Pro
        435                 440                 445

Gly Lys
    450

<210> SEQ ID NO 176
<211> LENGTH: 236
<212> TYPE: PRT
<213> ORGANISM: Artificial Sequence
<220> FEATURE:
<223> OTHER INFORMATION: CrossMab Ang2 mut5-PDGF-0085 LC1

<400> SEQUENCE: 176

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Ser Ser Pro Gly Tyr Tyr Tyr
            100                 105                 110

Pro Ala Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 177
<211> LENGTH: 214
<212> TYPE: PRT
<213> ORGANISM: Artificial Sequence
<220> FEATURE:
<223> OTHER INFORMATION: CrossMab Ang2 mut5-PDGF-0085 LC2

<400> SEQUENCE: 177

Asp Ile Gln Met Thr Gln Ser Pro Ser Ser Leu Ser Ala Ser Val Gly
1               5                   10                  15

Asp Arg Val Ala Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
                35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Arg Lys Leu Lys Ser Gly
                115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 178
<211> LENGTH: 440
<212> TYPE: PRT
<213> ORGANISM: Artificial Sequence
<220> FEATURE:
<223> OTHER INFORMATION: CrossMab Ang2 mut5-PDGF-0086 HC1

<400> SEQUENCE: 178

Ser Tyr Val Leu Thr Gln Pro Pro Ser Val Ser Val Ala Pro Gly Gln
 1               5                  10                  15

Thr Ala Arg Ile Thr Cys Gly Gly Asn Asn Ile Gly Ser Lys Ser Val
                 20                  25                  30

His Trp Tyr Gln Gln Lys Pro Gly Gln Ala Pro Val Leu Val Val Tyr
                 35                  40                  45

Asp Thr Ser Asp Arg Pro Ser Gly Ile Pro Glu Arg Phe Ser Gly Ser
         50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Trp Val Phe Gly Gly Gly Thr Lys Leu Thr Val Leu Ser Ser Ala Ser
                100                 105                 110

Thr Lys Gly Pro Ser Val Phe Pro Leu Ala Pro Ser Ser Lys Ser Thr
            115                 120                 125

Ser Gly Gly Thr Ala Ala Leu Gly Cys Leu Val Lys Asp Tyr Phe Pro
        130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

```
Ser Val Val Thr Val Pro Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys Asp Lys Thr His Thr Cys Pro Pro Cys Pro Ala
210                 215                 220

Pro Glu Ala Ala Gly Gly Pro Ser Val Phe Leu Phe Pro Pro Lys Pro
225                 230                 235                 240

Lys Asp Thr Leu Met Ala Ser Arg Thr Pro Glu Val Thr Cys Val Val
                245                 250                 255

Val Asp Val Ser His Glu Asp Pro Glu Val Lys Phe Asn Trp Tyr Val
                260                 265                 270

Asp Gly Val Glu Val His Asn Ala Lys Thr Lys Pro Arg Glu Glu Gln
            275                 280                 285

Tyr Asn Ser Thr Tyr Arg Val Val Ser Val Leu Thr Val Leu Ala Gln
        290                 295                 300

Asp Trp Leu Asn Gly Lys Glu Tyr Lys Cys Lys Val Ser Asn Lys Ala
305                 310                 315                 320

Leu Gly Ala Pro Ile Glu Lys Thr Ile Ser Lys Ala Lys Gly Gln Pro
                325                 330                 335

Arg Glu Pro Gln Val Tyr Thr Leu Pro Pro Cys Arg Asp Glu Leu Thr
                340                 345                 350

Lys Asn Gln Val Ser Leu Trp Cys Leu Val Lys Gly Phe Tyr Pro Ser
            355                 360                 365

Asp Ile Ala Val Glu Trp Glu Ser Asn Gly Gln Pro Glu Asn Asn Tyr
        370                 375                 380

Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
                405                 410                 415

Ser Cys Ser Val Met His Glu Ala Leu His Asn Ala Tyr Thr Gln Lys
                420                 425                 430

Ser Leu Ser Leu Ser Pro Gly Lys
            435                 440

<210> SEQ ID NO 179
<211> LENGTH: 450
<212> TYPE: PRT
<213> ORGANISM: Artificial Sequence
<220> FEATURE:
<223> OTHER INFORMATION: CrossMab Ang2 mut5-PDGF-0086 HC2

<400> SEQUENCE: 179

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Glu Lys Gly Leu Glu Trp Val
        35                  40                  45

Ser Thr Ile Ser Asp Gly Gly Leu Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

Ala Glu Ser Gly Gly Tyr Thr Asp Trp Leu Phe Gly Tyr Trp Gly Gln
            100                 105                 110

Gly Thr Leu Val Thr Val Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Glu Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Glu Lys Val Glu Pro Lys Ser Cys Asp
210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ala
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu Ala Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn Ala Tyr Thr Gln Lys Ser Leu Ser Leu Ser Pro
        435                 440                 445

Gly Lys
    450

<210> SEQ ID NO 180
<211> LENGTH: 236
<212> TYPE: PRT
<213> ORGANISM: Artificial Sequence
<220> FEATURE:
<223> OTHER INFORMATION: CrossMab Ang2 mut5-PDGF-0086 LC1

<400> SEQUENCE: 180

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Ser Ser Pro Gly Tyr Tyr Tyr
            100                 105                 110

Pro Ala Ala Phe Asp Ile Trp Gly Gln Gly Thr Met Val Thr Val Ser
            115                 120                 125

Ser Ala Ser Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 181
<211> LENGTH: 214
<212> TYPE: PRT
<213> ORGANISM: Artificial Sequence
<220> FEATURE:
<223> OTHER INFORMATION: CrossMab Ang2 mut5-PDGF-0086 LC2

<400> SEQUENCE: 181

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Arg Lys Leu Lys Ser Gly
            115                 120                 125

```
Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 182
<211> LENGTH: 440
<212> TYPE: PRT
<213> ORGANISM: Artificial Sequence
<220> FEATURE:
<223> OTHER INFORMATION: CrossMab Ang2mut4 + huH34-2 HC1

<400> SEQUENCE: 182

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Thr Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys Asp Lys Thr His Thr Cys Pro Pro Cys Pro Ala
210                 215                 220

Pro Glu Ala Ala Gly Gly Pro Ser Val Phe Leu Phe Pro Pro Lys Pro
225                 230                 235                 240

Lys Asp Thr Leu Met Ala Ser Arg Thr Pro Glu Val Thr Cys Val Val
                245                 250                 255

Val Asp Val Ser His Glu Asp Pro Glu Val Lys Phe Asn Trp Tyr Val
            260                 265                 270
```

```
Asp Gly Val Glu Val His Asn Ala Lys Thr Lys Pro Arg Glu Glu Gln
            275                 280                 285

Tyr Asn Ser Thr Tyr Arg Val Val Ser Val Leu Thr Val Leu Ala Gln
        290                 295                 300

Asp Trp Leu Asn Gly Lys Glu Tyr Lys Cys Lys Val Ser Asn Lys Ala
305                 310                 315                 320

Leu Gly Ala Pro Ile Glu Lys Thr Ile Ser Lys Ala Lys Gly Gln Pro
                325                 330                 335

Arg Glu Pro Gln Val Tyr Thr Leu Pro Pro Cys Arg Asp Glu Leu Thr
            340                 345                 350

Lys Asn Gln Val Ser Leu Trp Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
                405                 410                 415

Ser Cys Ser Val Met His Glu Ala Leu His Asn Ala Tyr Thr Gln Lys
            420                 425                 430

Ser Leu Ser Leu Ser Pro Gly Lys
        435                 440

<210> SEQ ID NO 183
<211> LENGTH: 448
<212> TYPE: PRT
<213> ORGANISM: Artificial Sequence
<220> FEATURE:
<223> OTHER INFORMATION: CrossMab Ang2mut4 + huH34-2 HC2

<400> SEQUENCE: 183

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Ile
        35                  40                  45

Gly Tyr Ile Ser Ser Tyr Asn Ala Phe Thr Thr Tyr Asn Gln Lys Phe
    50                  55                  60

Arg Gly Arg Ala Thr Phe Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Val Arg Ser Asp Tyr Tyr Gly Thr Ser Leu Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Glu Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190
```

```
Ser Leu Gly Thr Gln Thr Tyr Ile Cys Asn Val Asn His Lys Pro Ser
        195                 200                 205

Asn Thr Lys Val Asp Glu Lys Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ala Ser Arg
            245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu Ala Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn Ala Tyr Thr Gln Lys Ser Leu Ser Leu Ser Pro Gly Lys
        435                 440                 445

<210> SEQ ID NO 184
<211> LENGTH: 236
<212> TYPE: PRT
<213> ORGANISM: Artificial Sequence
<220> FEATURE:
<223> OTHER INFORMATION: CrossMab Ang2mut4 + huH34-2 LC1

<400> SEQUENCE: 184

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Pro Gly Tyr Tyr Tyr
            100                 105                 110
```

```
Pro Ala Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
                195                 200                 205

Glu Lys His Lys Val Tyr Ala Cys Glu Val Thr His Gln Gly Leu Ser
                210                 215                 220

Ser Pro Val Thr Lys Ser Phe Asn Arg Gly Glu Cys
225                 230                 235
```

<210> SEQ ID NO 185
<211> LENGTH: 212
<212> TYPE: PRT
<213> ORGANISM: Artificial Sequence
<220> FEATURE:
<223> OTHER INFORMATION: CrossMab Ang2mut4 + huH34-2 LC2

<400> SEQUENCE: 185

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
                20                  25                  30

His Trp Ser Gln Gln Lys Pro Gly Gln Ala Pro Arg Leu Leu Ile Tyr
            35                  40                  45

Ser Thr Ser Asn Leu Ala Ser Gly Ile Pro Ala Arg Phe Ser Gly Ser
        50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys His Gln Trp Ser Asn Tyr Tyr Thr Phe
                85                  90                  95

Gly Gln Gly Thr Lys Leu Glu Ile Lys Arg Thr Val Ala Ala Pro Ser
                100                 105                 110

Val Phe Ile Phe Pro Pro Ser Asp Arg Lys Leu Lys Ser Gly Thr Ala
            115                 120                 125

Ser Val Val Cys Leu Leu Asn Asn Phe Tyr Pro Arg Glu Ala Lys Val
        130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
                180                 185                 190

Glu Val Thr His Gln Gly Leu Ser Ser Pro Val Thr Lys Ser Phe Asn
                195                 200                 205

Arg Gly Glu Cys
    210
```

<210> SEQ ID NO 186

```
<211> LENGTH: 440
<212> TYPE: PRT
<213> ORGANISM: Artificial Sequence
<220> FEATURE:
<223> OTHER INFORMATION: CrossMab Ang2mut5 + huH34-2 HC1

<400> SEQUENCE: 186
```

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Thr Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys Asp Lys Thr His Thr Cys Pro Pro Cys Pro Ala
    210                 215                 220

Pro Glu Ala Ala Gly Gly Pro Ser Val Phe Leu Phe Pro Pro Lys Pro
225                 230                 235                 240

Lys Asp Thr Leu Met Ala Ser Arg Thr Pro Glu Val Thr Cys Val Val
                245                 250                 255

Val Asp Val Ser His Glu Asp Pro Glu Val Lys Phe Asn Trp Tyr Val
            260                 265                 270

Asp Gly Val Glu Val His Asn Ala Lys Thr Lys Pro Arg Glu Glu Gln
        275                 280                 285

Tyr Asn Ser Thr Tyr Arg Val Val Ser Val Leu Thr Val Leu Ala Gln
    290                 295                 300

Asp Trp Leu Asn Gly Lys Glu Tyr Lys Cys Lys Val Ser Asn Lys Ala
305                 310                 315                 320

Leu Gly Ala Pro Ile Glu Lys Thr Ile Ser Lys Ala Lys Gly Gln Pro
                325                 330                 335

Arg Glu Pro Gln Val Tyr Thr Leu Pro Pro Cys Arg Asp Glu Leu Thr
            340                 345                 350

Lys Asn Gln Val Ser Leu Trp Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380
```

```
Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
            405                 410                 415

Ser Cys Ser Val Met His Glu Ala Leu His Asn Ala Tyr Thr Gln Lys
        420                 425                 430

Ser Leu Ser Leu Ser Pro Gly Lys
        435                 440

<210> SEQ ID NO 187
<211> LENGTH: 448
<212> TYPE: PRT
<213> ORGANISM: Artificial Sequence
<220> FEATURE:
<223> OTHER INFORMATION: CrossMab Ang2mut5 + huH34-2 HC2

<400> SEQUENCE: 187

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Ile
        35                  40                  45

Gly Tyr Ile Ser Ser Tyr Asn Ala Phe Thr Thr Tyr Asn Gln Lys Phe
    50                  55                  60

Arg Gly Arg Ala Thr Phe Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Val Arg Ser Asp Tyr Tyr Gly Thr Ser Leu Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Glu Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Glu Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ala Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300
```

```
Ser Val Leu Thr Val Leu Ala Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn Ala Tyr Thr Gln Lys Ser Leu Ser Leu Ser Pro Gly Lys
        435                 440                 445

<210> SEQ ID NO 188
<211> LENGTH: 236
<212> TYPE: PRT
<213> ORGANISM: Artificial Sequence
<220> FEATURE:
<223> OTHER INFORMATION: CrossMab Ang2mut5 + huH34-2 LC1

<400> SEQUENCE: 188

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Ser Ser Pro Gly Tyr Tyr Tyr
            100                 105                 110

Pro Ala Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220
```

```
Ser Pro Val Thr Lys Ser Phe Asn Arg Gly Glu Cys
225                 230                 235

<210> SEQ ID NO 189
<211> LENGTH: 212
<212> TYPE: PRT
<213> ORGANISM: Artificial Sequence
<220> FEATURE:
<223> OTHER INFORMATION: CrossMab Ang2mut5 + huH34-2 LC2

<400> SEQUENCE: 189

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
            20                  25                  30

His Trp Ser Gln Gln Lys Pro Gly Gln Ala Pro Arg Leu Leu Ile Tyr
        35                  40                  45

Ser Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys His Gln Trp Ser Asn Tyr Tyr Thr Phe
                85                  90                  95

Gly Gln Gly Thr Lys Leu Glu Ile Lys Arg Thr Val Ala Ala Pro Ser
            100                 105                 110

Val Phe Ile Phe Pro Pro Ser Asp Arg Lys Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210
```

BISPECIFIC ANTIBODIES AND METHODS OF USE IN OPHTHALMOLOGY

CROSS REFERENCE TO RELATED APPLICATIONS

This application is a continuation of International Patent Application No. PCT/EP2015/075879 having an international filing date of Nov. 6, 2015, the entire contents of which are incorporated herein by reference, and which claims benefit under 35 U.S.C. 119 to European Patent Application No. 14192517.2 filed Nov. 10, 2014.

SEQUENCE LISTING

The instant application contains a Sequence Listing which has been submitted electronically in ASCII format and is hereby incorporated by reference in its entirety. Said ASCII copy, created on May 1, 2017, is named P32416_US_Sequence_Listing.txt and is 298,606 bytes in size.

FIELD OF THE INVENTION

The present invention relates to bispecific antibodies and methods of using the same, for example in ophthalmology.

BACKGROUND OF THE INVENTION

Ocular vascular diseases such as age related macular degeneration (AMD) and diabetic retinopathy (DR) are due to abnormal choroidal or retinal neovascularization, respectively. They are the leading causes of visual loss in industrialized nations. Since the retina consists of well-defined layers of neuronal, glial, and vascular elements, relatively small disturbances such as those seen in vascular proliferation or edema can lead to significant loss of visual function. Inherited retinal degenerations, such as Retinitis Pigmentosa (RP), are also associated with vascular abnormalities, such as arteriolar narrowing and vascular atrophy. They affect as many as 1 in 3,500 individuals and are characterized by progressive night blindness, visual field loss, optic nerve atrophy, arteriolar attenuation, and central loss of vision often progressing to complete blindness.

Ischemic retinopathies are characterized by loss or dysfunction of the retinal vasculature which results in a reduction of blood flow and hypoxia. The retina responds to hypoxia by generating signals to grow new blood vessels, but these new vessels are usually fragile and disorganized. It is the growth of these abnormal new vessels that creates most of the threat to vision since they can leak, lead to hemorrhage or lead to scarring that may end in retinal detachment. Current treatments for ischemic retinopathies seek to halt the growth of the pathological vessels but do not address the underlying ischemia that drives their growth. Furthermore, standard treatment for diabetic retinopathy, an ischemic retinopathy that affects millions, involves destruction of a portion of the retina with a laser in an attempt to stop new vessel growth and preserve central vision. Strategies have been employed to block the function of vascular endothelial growth factor (VEGF), a major promoter of vessel growth. In the short term, anti-VEGF therapy can improve vision, but it does not address the underlying ischemia and in fact may exacerbate this condition as it inhibits all vessel growth, including beneficial collaterals. There is also the serious concern of systemic exposure of these drugs in elderly and/or diabetic patients where new vessel growth may be required in ischemic brains, hearts or limbs.

Typically for ocular diseases via intravitreal application smaller antibody fragments like Fab or $Fab_2$ are often used as they have a low serum half-life and the risk of systemic toxicities is lower.

However this smaller fragments typically have also lower intravitreal half-lives (e.g. due to the faster diffusion into serum) and have to be dosed typically more often.

Multispecific antibodies with a domain replacement/exchange in one binding arm (CrossMabVH-VL) are described in detail in WO 2009/080252 and Schaefer, W. et al, Proc. Natl. Acad. Sci. USA, 108 (2011) 11187-11191 (which are incorporated as reference herein). They clearly reduce the byproducts caused by the mismatch of a light chain against a first antigen with the wrong heavy chain against the second antigen (compared to approaches without such domain exchange). However their preparation is not completely free of side products. The main side product is based on a Bence-Jones-type interaction. See also Schaefer, W. et al, Proc. Natl. Acad. Sci. USA, 108 (2011) 11187-11191; in FIG. S11 of the Supplement).

In WO 2011/117329 bispecific, bivalent anti-VEGF/anti-ANG2 antibodies are reported. Human FcRn-binding modified antibodies and methods of use are reported in WO 2014/177460. Kienast, Y., et al. (Clin. Canc. Res. 19 (2013) 6730-6740) reported Ang-2-VEGF-A CrossMab as a novel bispecific human IgG1 antibody blocking VEGF-A and Ang-2 functions simultaneously, mediates potent antitumor, antiangiogenic, and anti-metastatic efficacy.

SUMMARY OF THE INVENTION

The invention provides novel bispecific antibodies and methods of using the same. Herein is reported a bispecific antibody that specifically binds to two different antigens selected from the group consisting of human ANG2, human VEGF, human IL-1beta and human PDGF-B.

In one embodiment the antibody is not an anti-ANG2/VEGF antibody.

In one embodiment the antibody specifically binds to human IL-1beta and comprises
  a) a heavy chain variable domain comprising
    (a) a HVR-H1 comprising the amino acid sequence of SEQ ID NO: 02, (b) a HVR-H2 comprising the amino acid sequence of SEQ ID NO: 04, and (c) a HVR-H3 comprising the amino acid sequence of SEQ ID NO: 05, or
    (a) a HVR-H1 comprising the amino acid sequence of SEQ ID NO: 07, (b) a HVR-H2 comprising the amino acid sequence of SEQ ID NO: 08, and (c) a HVR-H3 comprising the amino acid sequence of SEQ ID NO: 10, or
    (a) a HVR-H1 comprising the amino acid sequence of SEQ ID NO: 12, (b) a HVR-H2 comprising the amino acid sequence of SEQ ID NO: 13, and (c) a HVR-H3 comprising the amino acid sequence of SEQ ID NO: 15,
    and
    a light chain variable domain comprising (a) a HVR-L1 comprising the amino acid sequence of SEQ ID NO: 17; (b) a HVR-L2 comprising the amino acid sequence of SEQ ID NO: 18; and (c) HVR-L3 comprising the amino acid sequence of SEQ ID NO: 19,
    or a) a heavy chain variable domain comprising a HVR-H1 comprising the amino acid sequence of SEQ ID NO: 21, (b) a HVR-H2 comprising the amino acid sequence of SEQ ID NO: 22, and (c) a HVR-H3 comprising the amino acid sequence of SEQ ID NO: 24, and a light chain variable domain comprising (a) a HVR-L1 comprising the amino acid sequence of SEQ ID NO: 26; (b) a HVR-L2 comprising the amino acid sequence of SEQ ID NO: 27; and (c) HVR-L3 comprising the amino acid sequence of SEQ ID NO: 28.

In one embodiment the antibody specifically binds to human PDGF-B and comprises a) a heavy chain variable domain comprising (a) a HVR-H1 comprising the amino acid sequence of SEQ ID NO: 30, (b) a HVR-H2 comprising the amino acid sequence of SEQ ID NO: 31, and (c) a HVR-H3 comprising the amino acid sequence of SEQ ID NO: 33, and a light chain variable domain comprising (a) a HVR-L1 comprising the amino acid sequence of SEQ ID NO: 35; (b) a HVR-L2 comprising the amino acid sequence of SEQ ID NO: 36; and (c) HVR-L3 comprising the amino acid sequence of SEQ ID NO: 37, or b) a heavy chain variable domain comprising (a) a HVR-H1 comprising the amino acid sequence of SEQ ID NO: 39, (b) a HVR-H2 comprising the amino acid sequence of SEQ ID NO: 40, and (c) a HVR-H3 comprising the amino acid sequence of SEQ ID NO: 42, and a light chain variable domain comprising (a) a HVR-L1 comprising the amino acid sequence of SEQ ID NO: 44; (b) a HVR-L2 comprising the amino acid sequence of SEQ ID NO: 45; and (c) HVR-L3 comprising the amino acid sequence of SEQ ID NO: 46, or c) a heavy chain variable domain comprising (a) a HVR-H1 comprising the amino acid sequence of SEQ ID NO: 48, (b) a HVR-H2 comprising the amino acid sequence of SEQ ID NO: 49, and (c) a HVR-H3 comprising the amino acid sequence of SEQ ID NO: 51, and a light chain variable domain comprising (a) a HVR-L1 comprising the amino acid sequence of SEQ ID NO: 53; (b) a HVR-L2 comprising the amino acid sequence of SEQ ID NO: 54; and (c) HVR-L3 comprising the amino acid sequence of SEQ ID NO: 55.

In one embodiment the antibody specifically binds to human ANG2 and comprises a) a heavy chain variable domain comprising (a) a HVR-H1 comprising the amino acid sequence of SEQ ID NO: 57, (b) a HVR-H2 comprising the amino acid sequence of SEQ ID NO: 58, and (c) a HVR-H3 comprising the amino acid sequence of SEQ ID NO: 60, and a light chain variable domain comprising (a) a HVR-L1 comprising the amino acid sequence of SEQ ID NO: 62; (b) a HVR-L2 comprising the amino acid sequence of SEQ ID NO: 63; and (c) HVR-L3 comprising the amino acid sequence of SEQ ID NO: 64, or b) a heavy chain variable domain comprising (a) a HVR-H1 comprising the amino acid sequence of SEQ ID NO: 66, (b) a HVR-H2 comprising the amino acid sequence of SEQ ID NO: 67, and (c) a HVR-H3 comprising the amino acid sequence of SEQ ID NO: 69, and a light chain variable domain comprising (a) a HVR-L1 comprising the amino acid sequence of SEQ ID NO: 71; (b) a HVR-L2 comprising the amino acid sequence of SEQ ID NO: 72; and (c) HVR-L3 comprising the amino acid sequence of SEQ ID NO: 73, or c) a heavy chain variable domain comprising (a) a HVR-H1 comprising the amino acid sequence of SEQ ID NO: 75, (b) a HVR-H2 comprising the amino acid sequence of SEQ ID NO: 76, and (c) a HVR-H3 comprising the amino acid sequence of SEQ ID NO: 78, and a light chain variable domain comprising (a) a HVR-L1 comprising the amino acid sequence of SEQ ID NO: 80; (b) a HVR-L2 comprising the amino acid sequence of SEQ ID NO: 81; and (c) HVR-L3 comprising the amino acid sequence of SEQ ID NO: 82, or d) a heavy chain variable domain comprising (a) a HVR-H1 comprising the amino acid sequence of SEQ ID NO: 84, (b) a HVR-H2 comprising the amino acid sequence of SEQ ID NO: 85, and (c) a HVR-H3 comprising the amino acid sequence of SEQ ID NO: 87, and a light chain variable domain comprising (a) a HVR-L1 comprising the amino acid sequence of SEQ ID NO: 89; (b) a HVR-L2 comprising the amino acid sequence of SEQ ID NO: 90; and (c) HVR-L3 comprising the amino acid sequence of SEQ ID NO: 91.

In one embodiment the antibody specifically binds to human VEGF and comprises a) a heavy chain variable domain comprising (a) a HVR-H1 comprising the amino acid sequence of SEQ ID NO: 93, (b) a HVR-H2 comprising the amino acid sequence of SEQ ID NO: 94, and (c) a HVR-H3 comprising the amino acid sequence of SEQ ID NO: 96, and a light chain variable domain comprising (a) a HVR-L1 comprising the amino acid sequence of SEQ ID NO: 97; (b) a HVR-L2 comprising the amino acid sequence of SEQ ID NO: 98; and (c) HVR-L3 comprising the amino acid sequence of SEQ ID NO: 99, or b) a heavy chain variable domain comprising (a) a HVR-H1 comprising the amino acid sequence of SEQ ID NO: 101, (b) a HVR-H2 comprising the amino acid sequence of SEQ ID NO: 102, and (c) a HVR-H3 comprising the amino acid sequence of SEQ ID NO: 104, and a light chain variable domain comprising (a) a HVR-L1 comprising the amino acid sequence of SEQ ID NO: 106; (b) a HVR-L2 comprising the amino acid sequence of SEQ ID NO: 107; and (c) HVR-L3 comprising the amino acid sequence of SEQ ID NO: 108.

In one embodiment the antibody is a bivalent, bispecific antibody comprising a) a first light chain and a first heavy chain of an antibody specifically binding to a first antigen, and b) a second light chain and a second heavy chain of an antibody specifically binding to a second antigen, wherein the variable domains VL and VH of the second light chain and the second heavy chain are replaced by each other.

In one preferred embodiment the antibody comprises i) in the constant domain CL of the first light chain under a) the amino acid at position 124 is substituted independently by lysine (K), arginine (R) or histidine (H) (numbering according to Kabat) (in one preferred embodiment independently by lysine (K) or arginine (R)), and wherein in the constant domain CH1 of the first heavy chain under a) the amino acid at position 147 or the amino acid at position 213 is substituted independently by glutamic acid (E) or aspartic acid (D) (numbering according to Kabat EU index), or ii) in the constant domain CL of the second light chain under b) the amino acid at position 124 is substituted independently by lysine (K), arginine (R) or histidine (H) (numbering according to Kabat) (in one preferred embodiment independently by lysine (K) or arginine (R)), and wherein in the constant domain CH1 of the second heavy chain under b) the amino acid at position 147 or the amino acid at position 213 is substituted independently by glutamic acid (E) or aspartic acid (D) (numbering according to Kabat EU index).

In one embodiment the antibody is a bivalent, bispecific antibody, comprising
   a) a first light chain and a first heavy chain of an antibody specifically binding to a first antigen, and
   b) a second light chain and a second heavy chain of an antibody specifically binding to a second antigen, wherein the constant domains CL and CH1 of the second light chain and the second heavy chain are replaced by each other.

In one embodiment the antibody comprises a first Fc-region polypeptide and a second Fc-region polypeptide, and wherein
   i) the first Fc-region polypeptide is a human IgG1 Fc-region polypeptide and the second Fc-region polypeptide is a human IgG1 Fc-region polypeptide, or
   ii) the first Fc-region polypeptide is a human IgG1 Fc-region polypeptide with the mutations L234A, L235A and the second Fc-region polypeptide is a human IgG1 Fc-region polypeptide with the mutations L234A, L235A, or
   iii) the first Fc-region polypeptide is a human IgG1 Fc-region polypeptide with the mutations L234A, L235A, P329G and the second Fc-region polypeptide is a human IgG1 Fc-region polypeptide with the mutations L234A, L235A, P329G, or
   iv) the first Fc-region polypeptide is a human IgG1 Fc-region polypeptide with the mutations L234A, L235A, S354C, T366W and the second Fc-region polypeptide is a human IgG1 Fc-region polypeptide with the mutations L234A, L235A, Y349C, T366S, L368A, Y407V, or
   v) the first Fc-region polypeptide is a human IgG1 Fc-region polypeptide with the mutations L234A, L235A, P329G, S354C, T366W and the second Fc-region polypeptide is a human IgG1 Fc-region polypeptide with the mutations L234A, L235A, P329G, Y349C, T366S, L368A, Y407V, or
   vi) the first Fc-region polypeptide is a human IgG4 Fc-region polypeptide and the second Fc-region polypeptide is a human IgG4 Fc-region polypeptide, or
   vii) the first Fc-region polypeptide is a human IgG4 Fc-region polypeptide with the mutations S228P, L235E and the second Fc-region polypeptide is a human IgG4 Fc-region polypeptide with the mutations S228P, L235E, or
   viii) the first Fc-region polypeptide is a human IgG4 Fc-region polypeptide with the mutations S228P, L235E, P329G and the second Fc-region polypeptide is a human IgG4 Fc-region polypeptide with the mutations S228P, L235E, P329G, or
   ix) the first Fc-region polypeptide is a human IgG4 Fc-region polypeptide with the mutations S228P, L235E, S354C, T366W and the second Fc-region polypeptide is a human IgG4 Fc-region polypeptide with the mutations S228P, L235E, Y349C, T366S, L368A, Y407V, or
   x) the first Fc-region polypeptide is a human IgG4 Fc-region polypeptide with the mutations S228P, L235E, P329G, S354C, T366W and the second Fc-region polypeptide is a human IgG4 Fc-region polypeptide with the mutations S228P, L235E, P329G, Y349C, T366S, L368A, Y407V.

In one embodiment the antibody comprises a first Fc-region polypeptide and a second Fc-region polypeptide, and wherein the antibody comprises the combination of mutations
   i) I253A, H310A, and H435A, or
   ii) H310A, H433A, and Y436A, or
   iii) L251D, L314D, and L432D, or
   iv) combinations of i) to iii)
   in the first Fc-region polypeptide and in the second Fc-region polypeptide.

One aspect as reported herein is a pharmaceutical formulation comprising an antibody as reported herein and optionally a pharmaceutically acceptable carrier.

One aspect as reported herein is the antibody as reported herein for use as a medicament.

One aspect as reported herein is the use of the antibody as reported herein in the manufacture of a medicament.

In one embodiment the medicament is for the treatment of an ocular vascular disease, preferably for the treatment of macular degeneration.

DETAILED DESCRIPTION OF EMBODIMENTS OF THE INVENTION

I. Definitions

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($k_d$). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-IL-1beta antibody" and "an antibody that binds to IL-1beta" refer to an antibody that is capable of binding IL-1beta with sufficient affinity such that the antibody is useful as a diagnostic and/or therapeutic agent in targeting IL-1beta. In one embodiment, the extent of binding of an anti-IL-1beta antibody to an unrelated, non-IL-1beta protein is less than about 10% of the binding of the antibody to IL-1beta as measured, e.g., by ELISA or surface plasmon resonance. In certain embodiments, an antibody that binds to IL-1beta has a dissociation constant (KD) of ≤1 µM, ≤100 nM, ≤10 nM, ≤1 nM, or ≤0.1 nM (e.g. $10^{-8}$M or less, e.g. from $10^{-8}$M to $10^{-10}$M, e.g., from $10^{-9}$M to $10^{-10}$ M). In certain embodiments, an anti-IL-1beta antibody binds to an epitope of IL-1beta that is conserved among IL-1beta from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that has interactions with at least the same amino acid residues as the reference antibody. These interactions are e.g. ionic interactions between charged amino acid residues or hydrophobic interactions between hydrophobic amino acid residues.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and µ, respectively.

The term "immunoconjugate" denotes a covalent conjugate between an antibody and a non-antibody moiety. Such a non-antibody moiety can be a detectable label, an effector molecule or a cytotoxic agent.

The term "cytotoxic agent" as used herein refers to a substance that inhibits or prevents a cellular function and/or causes cell death or destruction. Cytotoxic agents include, but are not limited to, radioactive isotopes (e.g., At$^{211}$, I$^{131}$, I$^{125}$, Y$^{90}$, Re$^{186}$, Re$^{188}$, Sm$^{153}$, Bi$^{212}$, P$^{32}$, Pb$^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc-region of an antibody, which vary with the antibody class. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc-region" herein is used to define a C-terminal region of an immunoglobulin heavy chain that contains at least a portion of the constant region. The term includes native sequence Fc-regions and variant Fc-regions. In one embodiment, a human IgG heavy chain Fc-region extends from Cys226, or from Pro230, to the carboxyl-terminus of the heavy chain. However, the C-terminal lysine (Lys447) or the C-terminal glycyl-lysine dipeptide (Gly446Lys447) of the Fc-region may or may not be present. Unless otherwise specified herein, numbering of amino acid residues in the Fc-region or constant region is according to the EU numbering system, also called the EU index, as described in Kabat, E. A. et al., Sequences of Proteins of Immunological Interest, 5th ed., Public Health Service, National Institutes of Health, Bethesda, Md. (1991), NIH Publication 91-3242.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody", "intact antibody," and "whole antibody" are used herein interchangeably to refer to an antibody having a structure substantially similar to a native antibody structure or having heavy chains that contain an Fc-region as defined herein.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, E. A. et al., Sequences of Proteins of Immunological Interest, 5th ed., Bethesda Md. (1991), NIH Publication 91-3242, Vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain which are hypervariable in sequence ("complementarity determining regions" or "CDRs") and/or form structurally defined loops ("hypervariable loops"), and/or contain the antigen-contacting residues ("antigen contacts"). Generally, antibodies comprise six HVRs; three in the VH (H1, H2, H3), and three in the VL (L1, L2, L3).

HVRs herein include
(a) hypervariable loops occurring at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917);
(b) CDRs occurring at amino acid residues 24-34 (L1), 50-56 (L2), 89-97 (L3), 31-35b (H1), 50-65 (H2), and 95-102 (H3) (Kabat, E. A. et al., Sequences of Proteins of Immunological Interest, 5th ed. Public Health Service, National Institutes of Health, Bethesda, Md. (1991), NIH Publication 91-3242.);
(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and
(d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s).

An "individual" or "subject" is a mammal. Mammals include, but are not limited to, domesticated animals (e.g. cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman, S. et al., J. Chromatogr. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-IL-1beta antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "IL-1beta" as used herein, refers to human IL-1beta. The term encompasses "full-length," unprocessed IL-1beta as well as any form of IL-1beta that results from processing in the cell. The term also encompasses naturally occurring variants of IL-1beta, e.g., splice variants or allelic variants. The amino acid sequence of human IL-1beta is shown in SEQ ID NO: 92.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt, T. J. et al. Kuby Immunology, 6th ed., W. H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (see, e.g., Portolano, S. et al., J. Immunol. 150 (1993) 880-887; Clackson, T. et al., Nature 352 (1991) 624-628).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

II. Compositions and Methods

Herein are reported novel bispecific antibodies specifically binding to different antigens selected from the group consisting of (human) ANG2, (human) VEGF, (human) IL-1beta and (human PDGF-B), wherein the antibody is not an anti-ANG2/VEGF bispecific antibody. Antibodies of the invention are useful, e.g., for the treatment of ocular vascular diseases, such as macular degeneration.

A. Exemplary Antibodies

A.1 Anti-IL1beta Antibodies from which the Anti-IL-1beta Binding Site of the Bispecific Antibody as Reported herein can be Derived Herein four novel anti-human IL-1beta antibodies are provided.

The first anti-IL-1beta antibody is a novel murine anti-human IL-1beta antibody with a VH of SEQ ID NO: 20 and a VL of SEQ ID NO: 25. This antibody is termed IL-1beta-mumAb in the following. This antibody binds to human, cynomolgus, rabbit, rat and murine IL-1beta and inhibits the interaction between IL-1beta and the human IL-1 receptors I and II.

The antibody has the following properties:

TABLE 1

| binding to human IL-1beta | ka<br>[1/Ms * $10^6$] | kd<br>[1/s * $10^{-4}$] | KD<br>[nM] |
|---|---|---|---|
| IL-1beta-mumAb | 1.12 | 0.75 | 0.07 |

TABLE 2

| binding to cynomolgus IL-1beta | ka<br>[1/Ms * $10^6$] | kd<br>[1/s * $10^{-4}$] | KD<br>[nM] |
|---|---|---|---|
| IL-1beta-mumAb | 1.15 | 0.95 | 0.08 |

TABLE 3

| binding to murine IL-1beta | ka [1/Ms * $10^6$] | kd [1/s * $10^{-4}$] | KD [nM] |
|---|---|---|---|
| IL-1beta-mumAb | 2.47 | 12.2 | 0.49 |
| Gevokizumab | 2.48 | 5.35 | 0.22 |

TABLE 4

| binding to rat IL-1beta | ka [1/Ms * $10^6$] | kd [1/s * $10^{-4}$] | KD [nM] |
|---|---|---|---|
| IL-1beta-mumAb | 2.04 | 6.36 | 0.31 |
| Gevokizumab | 2.79 | 0.20 | 0.007 |

TABLE 5

| binding to rabbit IL-1beta | KD [nM] |
|---|---|
| mumAb (SEQ ID NO: 9 and 10) | 1.4 |
| Gevokizumab | n.a. |

The above data was determined by BIAcore.

TABLE 6

| origin of IL-1beta | $EC_{50}$ [ng/mL] | $EC_{50}$ (based on MWC 150 kDa) [$10^{-10}$ M] | example |
|---|---|---|---|
| human 1 | 34.02 | 2.27 | 4 variant 1 |
| human 2 | 15.16 | 1.01 | 4 variant 2 |
| murine | 23.07 | 1.54 | 6 |
| cynomolgus | 21.27 | 1.42 | 5 |

The above data was determined by ELISA.

Inhibition of binding of IL-1beta to IL-1 receptor I and II:

TABLE 7

| | $IC_{50}$ [ng/mL] | $IC_{50}$ (based on MWC 150 kDa) [$10^{-9}$ M] | example |
|---|---|---|---|
| IL-1beta receptor I | 230.9 | 1.54 | 7 |
| IL-1beta receptor II | 132.4 | 0.88 | 8 |

The above data was determined by ELISA.

In a stimulation experiment it could be shown that the murine antibody as reported herein can inhibit ICAM-1 expression upon IL-1β stimulation of A549 cells (see Table 8 below).

TABLE 8

| antibody | $IC_{50}$ [nM] |
|---|---|
| IL-1beta-mumAb | 0.7 |

In the following Table the $IC_{50}$ value for inhibition of ICAM-1 expression upon IL-1beta stimulation of HUVEC cells is shown.

TABLE 9

| antibody | $IC_{50}$ [nM] |
|---|---|
| IL-1beta-mumAb | 16.50 |

In stimulation experiments it could be shown that the humanized antibodies as reported herein reduce IL-6 expression upon IL-1beta stimulation of A549 cells (see Table 10 below).

TABLE 10

| antibody | $EC_{50}$ [nM] |
|---|---|
| IL-1beta-mumAb | 1.09 |

In addition, the murine antibody showed stability in stress tests. The binding activity has been determined using surface plasmon resonance (see Table 11 below).

TABLE 11

| | relative binding activity | |
|---|---|---|
| antibody | 2 weeks at 37° C. pH 7.5 | 2 weeks at 40° C. pH 6.0 |
| IL-1beta-mumAb | 103% | 102% |

100% = sample stored at −80° C.

The same stability can be seen when the high molecular weight content is determined (see Table 12 below).

TABLE 12

| | | high molecular weight fraction | |
|---|---|---|---|
| antibody | start | 2 weeks at 37° C. pH 7.4 | 2 weeks at 40° C. pH 6.0 |
| IL-1beta-mumAb | 0.97% | 1.24% | 1.00% |

The same stability can be seen in the CE-SDS analysis (see Table 13 below).

TABLE 13

| | | relative area % | |
|---|---|---|---|
| antibody | start | 2 weeks at 37° C. pH 7.4 | 2 weeks at 40° C. pH 6.0 |
| IL-1beta-mumAb | 91.9% | 86.5% | 90.0% |

The thermal stability of the murine antibody has been evaluated by determining the aggregation onset temperature (Tagg) and the melting temperature (Tm) (see Table 14 below).

TABLE 14

| antibody | Tagg [° C.] | Tm [° C.] |
|---|---|---|
| IL-1beta-mumAb | approx. 60 | approx. 64 |

The other three antibodies are humanized variants of the murine anti-IL1-beta antibody H34: huH34-1 (SEQ ID NO: 01 to 05, and 16), huH34-2 (SEQ ID NO: 06 to 10, and 16) and huH34-3 (SEQ ID NO: 11 to 16).

Herein is reported a humanized anti-IL-1beta antibody. This antibody is derived from the murine anti-IL-1beta antibody H34.

Based upon the amino acid sequence of the murine H34 antibody, a corresponding humanized anti-IL-1β antibody was generated (huH34-2). The humanized variant VH is based on the human VBase_VH1_1 and the J-element of the human IGHJ4-01-3 germline (huH34-1). In order to restore affinity one backmutation was introduced at position 48 of framework region 2 (M48I). In framework region 3, 4 positions were backmutated: V67A, M69F, R71V and A93V. In addition, the cysteine in position 52a of HVR-H2 was replaced by a serine. For VL, the humanized variant is based on the human IMGT_hVK_3_11 germline with an IGKJ2-01 J-element. One backmutation was introduced at positions 36 of framework region 2 (Y36S). The amino acid sequence of the humanized VH is shown in SEQ ID NO: 04 and the amino acid sequence of the humanized VL is shown in SEQ ID NO: 06.

Murine anti-IL-1beta antibody H34 contains a cysteine in HVR-H2 (C52a, Kabat numbering) that needs to be removed for development as a therapeutic candidate that can be produced at large scale. Removing this Cys by a C52aS mutation in the murine antibody results in a reduced affinity for IL-1beta by a factor of about 6 to 7 (see Tables below).

TABLE 15

| | ka [1/Ms * $10^6$] | kd [1/s * $10^{-4}$] | KD [nM] |
|---|---|---|---|
| binding to human IL-1beta antibody | | | |
| H34 | 1.85 | 1.27 | 0.07 |
| H34 + C52aS mutations | 1.60 | 6.45 | 0.40 |
| binding to cynomolgus IL-1beta antibody | | | |
| H34 | 1.99 | 0.98 | 0.05 |
| H34 + C52aS mutations | 1.43 | 7.28 | 0.51 |

The above data was determined by BIAcore.

For the humanized version of H34 (huH34-2) the loss of affinity upon C52aS mutation is compensated and this antibody has a comparable affinity (and comparable functional potency in cellular assays) as the murine parental antibody H34.

This compensation effect is accountable to the germline sequence that was chosen for humanization and the choice of backmutations within framework IGHJ4-01-3 and IMGT_hVK_3_11. An additional variant was designed based on the same human germline for VH (IGHJ4-01-3) and VL (IMGT_hVK_3_11), respectively. Backmutations described for huH34-2 were omitted from the VH and VL sequence (SEQ ID NO: 7 and 8).

TABLE 16

| | ka [1/Ms * $10^6$] | kd [1/s * $10^{-4}$] | KD [nM] |
|---|---|---|---|
| binding to human IL-1beta antibody | | | |
| H34 | 1.85 | 1.27 | 0.07 |
| H34 + C52aS mutations | 1.60 | 6.45 | 0.40 |
| huH34-1 | 1.49 | 15.1 | 1.02 |
| huH34-2 | 1.93 | 1.10 | 0.06 |
| huH34-2 FAB | 1.81 | 1.11 | 0.06 |
| huH34-3 | 1.97 | 3.02 | 0.15 |

TABLE 16-continued

| | ka [1/Ms * $10^6$] | kd [1/s * $10^{-4}$] | KD [nM] |
|---|---|---|---|
| Gevokizumab | 3.01 | 0.52 | 0.02 |
| Canakinumab | 2.78 | 0.52 | 0.02 |
| binding to cynomolgus IL-1beta antibody | | | |
| H34 | 1.99 | 0.98 | 0.05 |
| H34 + C52aS mutations | 1.43 | 7.28 | 0.51 |
| huH34-1 | 1.61 | 21.2 | 1.31 |
| huH34-2 | 2.20 | 1.18 | 0.05 |
| huH34-3 | 2.21 | 4.91 | 0.22 |
| Gevokizumab | 3.21 | 0.67 | 0.02 |
| Canakinumab | 2.15 | 284 | 13.2 |

The above data was determined by BIAcore.

In one embodiment the humanized anti-IL-1beta antibody binds to human and cynomolgus IL-1beta.

In the presence of human IL-1beta the binding signal in a surface plasmon resonance experiment increased from Gevokizumab. Thus, antibody-bound IL-1b still binds to IL-1 receptor I. Therefore, the mode of action for Gevokizumab is allosteric inhibition of IL-1RAc binding (allosteric antibody).

For Canakinumab, H34 and mumAb IL-1beta binding to IL-1 receptor I is prevented after antibody binding. Thus, mode of action is receptor blocking for Canakinumab, H34 and mumAb (competitive antibody).

TABLE 17

| antibody | $IC_{50}$ in the presence of @ 10 nM IL-1beta [nM] |
|---|---|
| Canakinumab | 1.6 |
| mumAb | 2.5 |
| H34 | 3.5 |

In stimulation experiments it could be shown that the humanized antibodies as reported herein have the same activity as the murine parental antibody. In the following Table the $IC_{50}$ values for inhibition of ICAM-1 expression upon IL-1beta stimulation of A549 cells are shown for different antibodies.

TABLE 18

| antibody | $IC_{50}$ [nM] |
|---|---|
| H34 | 0.18 |
| huH34-1 | >7 |
| huH34-2 | 0.23 |
| huH34-3 | 2.23 |
| Gevokizumab | 0.94 |
| Canakinumab | 0.31 |

In the following Table the $IC_{50}$ value for inhibition of ICAM-1 expression upon IL-1beta stimulation of HUVEC cells is shown.

TABLE 19

| antibody | $IC_{50}$ [nM] |
|---|---|
| H34 | 0.24 |
| huH34-2 | 0.30 |
| Canakinumab | 9.02 |

In stimulation experiments it could be shown that the humanized antibodies as reported herein reduce IL-6 expression upon IL-1beta stimulation of A549 cells (see Table 20 below).

TABLE 20

| antibody | $EC_{50}$ [nM] |
|---|---|
| huH34-1 | 5.52 |
| huH34-2 | 0.11 |
| huH34-3 | 1.09 |
| Gevokizumab | 0.11 |
| Canakinumab | 0.12 |

In proliferation inhibition experiments it could be shown that the humanized antibody as reported herein inhibits proliferation of D10 cells (see Table below).

TABLE 21

| antibody | $IC_{50}$ [nM] |
|---|---|
| huH34-2 | 0.83 |
| Gevokizumab | 3.36 |
| Canakinumab | 1.99 |

In the following Table the $IC_{50}$ values for inhibition of TNFalpha expression upon MSU stimulation of THP1 cells are shown for different antibodies.

TABLE 22

| antibody | $IC_{50}$ [nM] |
|---|---|
| H34 | 0.43 |
| huH34-2 | 2.38 |
| Canakinumab | 0.41 |

In addition, the humanized antibodies show improved stability compared to the murine H34 parent antibody in stress tests. The binding activity has been determined using surface plasmon resonance (see Table 23 below).

TABLE 23

| | relative binding activity | |
|---|---|---|
| antibody | 2 weeks at 37° C. pH 7.4 | 2 weeks at 40° C. pH 6.0 |
| H34 | 70% | 101% |
| huH34-1 | 96% | 99% |
| huH34-2 | 94% | 99% |
| huH34-3 | 96% | 100% |

100% = sample stored at −80° C.

The same stability can be seen when the high molecular weight content is determined (see Table 24 below).

TABLE 24

| | high molecular weight fraction | | |
|---|---|---|---|
| antibody | start | 2 weeks at 37° C. pH 7.4 | 2 weeks at 40° C. pH 6.0 |
| huH34-1 | 4.57% | 4.13% | 4.39% |
| huH34-2 | 0.21% | 0.15% | 0.13% |
| huH34-3 | 0.19% | 0.17% | 0.13% |

The same stability can be seen in the CE-SDS analysis (see Table 25 below).

TABLE 25

| | relative area % | | |
|---|---|---|---|
| antibody | start | 2 weeks at 37° C. pH 7.4 | 2 weeks at 40° C. pH 6.0 |
| huH34-1 | 96.1% | 92.9% | 93.8% |
| huH34-2 | 96.4% | 92.5% | 95.2% |
| huH34-3 | 96.0% | 92.1% | 95.1% |

The thermal stability of the different humanized antibodies has been evaluated by determining the aggregation onset temperature (Tagg) and the melting temperature (Tm) (see Table 26 below).

TABLE 26

| antibody | Tagg [° C.] | Tm [° C.] |
|---|---|---|
| huH34-1 | 61.5 | 69.1 |
| huH34-2 | 63.0 | 72.0 |
| huH34-3 | 63.0 | 70.6 |

The high-resolution crystal structure of the huH34-2 Fab-fragment bound to human IL-1 beta showed detailed information on the functional epitope of this antibody. The structure was compared to the structure of the ternary Th-1b signaling complex (human IL-1b bound to the IL-1 receptor 1, IL-1R1, and the IL-1 accessory protein, IL-1RAcP, PDB code 4DEP). It has been found that the epitope of huH34 overlaps with the interaction sites of both IL-1R1 and IL-1RAcP. Thus, the antibody blocks the formation of the IL-1 beta signaling complex at the first step of its assembly, which is the association of IL-1 beta and the IL-IR1.

Antibody 0031 is a bispecific anti-ANG2/IL-beta antibody comprising as the IL-1beta binding specificity the VE1 and VL domain of huH34-2.

Antibody 0032 is a bispecific anti-VEGF/IL-1beta antibody comprising as the IL-1beta binding specificity the VE1 and VL domain of huH34-2.

For the determination of the kinetic binding values the assay as reported in Example 52 was used.

TABLE 27

| ANG2 | ka [1/Ms] | kd [1/s] | KD* [nM] | t½ [s] |
|---|---|---|---|---|
| antibody-0031 | 1.45E+05 | 1.15E−03 | 8 | 604 |

TABLE 28

| VEGF | ka [1/Ms] | kd [1/s] | KD* [nM] | t½ [s] |
|---|---|---|---|---|
| antibody-0032 | 2.77E+04 | <1E−06 | <0.1 | — |

TABLE 29

| IL-1beta | ka [1/Ms] | kd [1/s] | KD* [nM] | $t^{1/2+12}$[s] |
|---|---|---|---|---|
| huH34-2 bivalent | 2.43E+06 | 1.15E−04 | 0.05 | 101 |
| antibody-0031 | 2.56E+06 | 3.02E−04 | 0.12 | 38 |
| antibody-0032 | 2.49E+06 | 3.05E−04 | 0.12 | 38 |

It has been shown by SPR analysis that all bispecific antibodies have the property of binding to both its antigens simultaneously.

In an ANG2 specific pTie2-ELISA the antibody 0031, is 6 times more active than the anti-ANG2/VEGF antibody reported in WO 2014/09465.

In one embodiment the humanized anti-IL-1beta antibody binds to human and cynomolgus IL-1beta.

In the following Table the $IC_{50}$ value for inhibition of ICAM-1 expression upon IL-1beta stimulation of A549 cells is shown.

TABLE 30

| antibody | $IC_{50}$ [ng/mL] |
|---|---|
| antibody 0031 | 103.9 |
| Gevokizumab | 204.4 |

In the following Table the $IC_{50}$ value for inhibition of ICAM-1 expression upon IL-1beta stimulation of HUVEC cells is shown.

TABLE 31

| antibody | $IC_{50}$ [ng/mL] |
|---|---|
| huH34-2 | 1.2-0.9 |
| huH34-2 Fab | 1.1-2.5 |
| antibody 0031 | 2.0-5.5 |
| antibody 0032 | 3.5-6.3 |

In stimulation experiments it could be shown that the humanized antibodies as reported herein reduce IL-6 expression upon IL-1beta stimulation of A549 cells (see Table 32 below).

TABLE 32

| antibody | $EC_{50}$ [ng/mL] |
|---|---|
| antibody 0031 | 17.0 |
| antibody 0032 | 38.7 |
| Gevokizumab | 62.0 |
| Canakinumab | 86.4 |

The thermal stability of the different bispecific antibodies has been evaluated by determining the aggregation onset temperature (Tagg) and the melting temperature (Tm) (see Table 33 below).

TABLE 33

| antibody | Tagg [° C.] | Tm [° C.] |
|---|---|---|
| 0031 | 61 | 67.5 |
| 0032 | 55 | 62.5 |

Antibody huH34-2 is described with the sequences of SEQ ID NO: 06 to 10 and 16 (binding sites, HVRs, VL). The bispecific formats of antibody huH34-2 are described in sequences SEQ ID NO: 102 to 103 and 182 to 189. All of these sequences constitute alone and in combination aspects of the current invention.

In one preferred embodiment the a -IL-1beta antibody comprises (a) a HVR-H1 comprising the amino acid sequence of SEQ ID NO: 07; (b) a HVR-H2 comprising the amino acid sequence of SEQ ID NO: 08; and (c) a HVR-H3 comprising the amino acid sequence of SEQ ID NO: 10. In one embodiment the antibody further comprises (d) a HVR-L1 comprising the amino acid sequence of SEQ ID NO: 17; (e) a HVR-L2 comprising the amino acid sequence of SEQ ID NO: 18; and (f) a HVR-L3 comprising the amino acid sequence of SEQ ID NO: 19.

In one preferred embodiment, the antibody comprises the VH and VL sequences in SEQ ID NO: 06 and SEQ ID NO: 16, respectively, including post-translational modifications of those sequences.

In one preferred embodiment the anti-human IL-1beta antibody specifically binds to human and cynomolgus IL-1beta and comprises (a) a HVR-H1 comprising the amino acid sequence of SEQ ID NO: 07, (b) a HVR-H2 comprising the amino acid sequence of SEQ ID NO: 08, (c) a HVR-H3 comprising the amino acid sequence of SEQ ID NO: 10, (d) a HVR-L1 comprising the amino acid sequence of SEQ ID NO: 17, (e) a HVR-L2 comprising the amino acid sequence of SEQ ID NO: 18, and (f) a HVR-L3 comprising the amino acid sequence of SEQ ID NO: 19. In one preferred embodiment the anti-human IL-1beta antibody has a heavy chain variable domain that has the amino acid sequence of SEQ ID NO: 06 and a light chain variable domain that has the amino acid sequence of SEQ ID NO: 16.

A.2 Anti-PDGF-B Antibodies from which the Anti-PDGF-B Binding Site of the Bispecific Antibody as Reported herein can be Derived Herein different novel anti-human PDGF-B antibodies are provided.

The first anti-PDGF-B antibody is a novel murine anti-human PDGF-B antibody with a VH of SEQ ID NO: 29 and a VL of SEQ ID NO: 34. This antibody is termed PDGF-B-mumAb in the following. This antibody binds to human, cynomolgus, rat and murine PDGF-B and inhibits the interaction between PDGF-B and its receptor.

The antibody has the following properties as listed in the Tables below.

TABLE 34

|  | huPDGF-BB (EC50) [ng/mL] | muPDGF-BB (EC50) [ng/mL] | ratPDGF-BB (EC50) [ng/mL] | huPDGF-AA (EC50) [ng/mL] |
|---|---|---|---|---|
| PDGF-B-mumAb | 16.3 | 8.8 | 5.124 | 2.04 |

TABLE 35

| | PPII huPDGF-BB::huPDGF-Rβ IC50 [ng/ml] |
|---|---|
| PDGF-B-mumAb | 12.16 |

TABLE 36

| | yield [mg] | scale [l] | yield [mg/L supernatant] | monomer (analytical SEC) [%] | main peak (CE-SDS/SDS PAGE) [%] |
|---|---|---|---|---|---|
| PDGF-B-mumAb | 6.4 | 0.2 | 32 | 99 | 98 |

TABLE 37

| | $IC_{50}$ Phospho-Inhibition | $IC_{50}$ Proliferation 3T3 |
|---|---|---|
| PDGF-B-mumAb | 1.7 ng/ml | 55.1 ng/ml |

TABLE 37

| | $IC_{50}$ Phospho-Inhibition | $IC_{50}$ Proliferation 3T3 |
|---|---|---|
| PDGF-B-mumAb | 1.7 ng/ml | 55.1 ng/ml |

TABLE 39

| | Pericytes | | Balb-C3T3 |
|---|---|---|---|
| | Fab Migration [nM] | Fab Proliferation [nM] | Fab Proliferation [nM] |
| PDGF-B-mumAb | 0.24 | 2.17 | 2.3 |

TABLE 40

| | kd [1/s] | t½ [min] |
|---|---|---|
| PDGF-B-mumAb | 4.50E−04 | 26 |

TABLE 41

| Fab | ka [1/Ms] | kd [1/s] | KD [nM] | t½ [s] |
|---|---|---|---|---|
| PDGF-B-mumAb Fab | 4.39E+05 | 2.01E−03 | 5 | 345 |

TABLE 42

| | App. KD [nM] | T½ [s] | | App. KD** [nM] | T½ (s) |
|---|---|---|---|---|---|
| PDGF-B-mumAb FAB | 5 | 345 | mumAb | 0.042 | 2867 |

The storage stability of the antibody is shown in the Table below (active concentration with reference surface).

TABLE 43

| | 2 w/40° C. pH 6.0 with reference [%] | 2 w/37° C. pH 7.4 with reference [%] |
|---|---|---|
| PDGF-B-mumAb | 103 | 103 |

The thermal stability of the antibody has been evaluated by determining the aggregation onset temperature (Tagg) and the melting temperature (Tm) (see Table 44 below).

TABLE 44

| antibody | Tagg [° C.] | Tm [° C.] |
|---|---|---|
| PDGF-B-mumAb | 57 | 62-63.5 |

The other antibodies are human antibodies obtained from a human Ig locus transgenic rabbit. The antibodies have the binding properties as listed in the Table below.

Antibody 0085 is an anti-PDGF-B antibody comprising a VH of SEQ ID NO: 38 and a VL of SEQ ID NO: 43. Antibody 0086 is an anti-PDGF-B antibody comprising a VH of SEQ ID NO: 47 and a VL of SEQ ID NO: 52.

TABLE 45

| | huPDGF-BB [EC50] [ng/mL] | muPDGF-BB [EC50] [ng/mL] | ratPDGF-BB [EC50] [ng/mL] | cynPDGF-BB [EC50] [ng/mL] | huPDGF-AA [EC50] [ng/mL] | huPDGF-CC [EC50] [ng/mL] |
|---|---|---|---|---|---|---|
| antibody 0085 | 7.55 | 24.96 | 15.96 | 15.33 | n.d. | n.d. |
| antibody 0086 | 12.04 | 14.08 | 10.57 | 16.19 | n.d. | n.d. |

| | huPDGF-BB - avidity by SPR [M] | huPDGF-BB - kon by SPR [M−1s−1] | huPDGF-BB - koff by SPR [s−1] | cynPDGF-BB - avidity by SPR [M] | cynPDGF-BB - kon by SPR [M−1s−1] | cynPDGF-BB - koff by SPR [s−1] |
|---|---|---|---|---|---|---|
| antibody 0085 | 4.76E−11 | 0.93E6 | 0.44E−4 | 4.78E−11 | 0.94E6 | 4.52E−5 |
| antibody 0086 | 2.18E−11 | 1.04E6 | 0.23E−4 | 1.78E−11 | 1.04E6 | 1.84E−5 |

TABLE 46

| | PPII huPDGF-BB::huPDGF-Rβ IC50 [ng/ml] |
|---|---|
| antibody 0085 | 17.76 |
| antibody 0086 | 11.73 |

In one embodiment the humanized anti-PDGF-B antibody binds to human, rat, mouse and cynomolgus PDGF-B.

TABLE 47

| | yield [mg] | scale [l] | yield [mg/l supernatant] | monomer (analytical SEC) [%] | main peak (CE-SDS/SDS PAGE) [%] |
|---|---|---|---|---|---|
| antibody 0085 | 22.5 | 0.25 | 90 | 99 | 96 |
| antibody 0086 | 20.8 | 0.25 | 83 | 99 | 96 |
| antibody 0106 | 12.0 | 0.3 | 40 | 98 | 99 |
| antibody 0107 | 10.5 | 0.3 | 35 | 98 | 99 |
| antibody 0144 | 37.7 | 1.5 | 25.1 | >98 | >95 |
| antibody 0117 | 46.3 | 1 | 46.3 | >98 | >95 |
| antibody 0145 | 21.5 | 1 | 21.5 | >98 | >95 |
| antibody 0146 | 14.6 | 0.5 | 29.2 | >98 | >95 |

TABLE 48

| | $IC_{50}$ Phospho-Inhibition | | $IC_{50}$ Proliferation 3T3 | |
|---|---|---|---|---|
| antibody 0085 | n.d. | n.d. | 31.8 | ng/ml |
| antibody 0086 | n.d. | n.d. | 56.0 | ng/ml |

In diverse activity assays the antibody show biological activity as can be seen from the data presented in the Tables below.

TABLE 49

| | Pericytes | | | | Balb-C3T3 | |
|---|---|---|---|---|---|---|
| | Migration EC50[nM] | | Proliferation EC50[nM] | | Proliferation EC50[nM] | |
| huPDGF-BB | 0.03/0.04 | | 0.02/0.03 | | 0.025/0.023 | |
| | IC50(nM) | % neutralization | IC50(nM) | % neutralization | IC50(nM) | % neutralization |
| R&D polyclonal Antibody | 0.56/0.32 | 100 | 0.36/0.41 | 100 | 0.69/0.65 | 100 |
| antibody 0085 | 0.15 | 90 | 0.11 | 100 | 0.06 | 100 |
| antibody 0086 | 0.09 | 100 | 0.09 | 100 | 0.11 | 100 |

TABLE 50

| | Fab Migration inhibition [nM] | Fab Proliferation inhibition [nM] | Fab Proliferation inhibition [nM] |
|---|---|---|---|
| antibody 0085 | 0.41 | 1.02 | 1.36 |
| antibody 0086 | 0.14 | 0.62 | 1.18 |

The kinetic binding properties of the different antibodies have been determined using surface plasmon resonance technology (see the following Tables).

TABLE 51

| | kd (1/s) | t½ [min] |
|---|---|---|
| antibody-0085 | 1.02E−04 | 114 |
| antibody-0086 | 7.93E−05 | 146 |

TABLE 52

| Fab | ka (1/Ms) | kd (1/s) | KD* (nM) | t½ (s) |
|---|---|---|---|---|
| antibody-0106 | 2.02E+05 | 3.74E−04 | 2 | 1853 |
| antibody-0107 | 1.95E+05 | 3.62E−04 | 2 | 1915 |

TABLE 53

| Fab | App. KD* (nM) | T½ (s) | IgG | App. KD** (nM) | T½ (s) |
|---|---|---|---|---|---|
| antibody-0106 | 2 | 1853 | antibody-0085 | 0.023 | 8739 |
| antibody-0107 | 2 | 1915 | antibody-0086 | 0.030 | 2461 |

The storage stability of the antibody 0086 is shown in the Table below (active concentration with reference surface).

TABLE 54

| | 2 w/40° C. pH 6.0 with reference (%) | 2 w/37° C. pH 7.4 with reference (%) |
|---|---|---|
| antibody-0086 | 99 | 98 |

The thermal stability of the antibodies has been evaluated by determining the aggregation onset temperature (Tagg) and the melting temperature (Tm) (see Table 55 below).

TABLE 55

| | Tagg [° C.] | Tm [° C.] |
|---|---|---|
| antibody-0086 | 64 | 64.5-68 |

Antibody 0144 is a bispecific anti-ANG2/PDGF-B antibody comprising as the PDGF-B binding specificity the VH and VL domain of antibody 0085.

Antibody 0117 is a bispecific anti-VEGF/PDGF-B antibody comprising as the PDGF-B binding specificity the VH and VL domain of antibody 0085.

For the determination of the kinetic binding values the assay as reported in Example 52 was used.

TABLE 56

| ANG2 | ka [1/Ms] | kd [1/s] | KD* [nM] | t½ [s] |
|---|---|---|---|---|
| antibody 0144 | 9.06E+04 | 1.55E−03 | 17 | 446 |

TABLE 57

| VEGF | ka [1/Ms] | kd [1/s] | KD* [nM] | t½+12[s] |
|---|---|---|---|---|
| antibody 0117 | 2.46E+04 | <1E−06 | <0.1 | — |

TABLE 58

| PDGF-BB | ka [1/Ms] | kd [1/s] | KD* [nM] | t½ [s] |
|---|---|---|---|---|
| antibody 0106 | 2.94E+05 | 2.91E−04 | 1 | 40 |
| antibody 0117 | 7.67E+04 | 2.45E−04 | 3 | 47 |
| antibody 0144 | 8.31E+04 | 2.15E−04 | 3 | 53 |

It has been shown by SPR analysis that all bispecific antibodies have the property binding to both its antigens simultaneously.

The bispecific antibodies show binding and biological activity in cell based assays.

TABLE 59

| | $IC_{50}$ Proliferation human pericytes | | $IC_{50}$ Proliferation 3T3 | |
|---|---|---|---|---|
| antibody 0117 | 0.016 | nM | 0.019 | nM |
| antibody 0144 | 0.030 | nM | 0.020 | nM |
| antibody 0085 FAB | 0.012 | nM | not det. | |

TABLE 60

| | $IC_{50}$ Phospho-Inhibition human pericytes | | $IC_{50}$ Migration-Inhibition human pericytes | |
|---|---|---|---|---|
| antibody 0117 | 0.055 | nM | 0.06 | nM |
| antibody 0144 | 0.055 | nM | 0.06 | nM |
| antibody 0085 FAB | not det. | | 0.27 | nM |

In an ANG2 specific pTie2-ELISA the antibody 0144, is 6 times more active than the anti-ANG2/VEGF antibody reported in WO 2014/09465.

In a VEGF specific reporter assay the antibody 0117 has a similar activity than the anti-ANG2/VEGF antibody reported in WO 2014/09465.

Antibody 0085 is described with the sequences of SEQ ID NO: 38 to 46 (binding sites, HVRs, VH, VL). The bispecific formats of antibody 0085 are described in sequences SEQ II) NO: 129 to 130, 150 to 153, 162 to 165, and 174 to 177. All of these sequences constitute alone and in combination aspects of the current invention.

Antibody 0086 is described with the sequences of SEQ ID NO: 47 to 55 (binding sites, HVRs, VH, VL). The bispecific formats of antibody 0086 are described in sequences SEQ ID NO: 131, 154 to 157, 166 to 169, and 178 to 181. All of these sequences constitute alone and in combination aspects of the current invention.

Antibody 0144 is described with the sequences of SEQ ID NO: 162 to 165 (CrossMab format, 2 heavy chains, 2 light chains).

Antibody 0144 and 0145 were incubated at different pH values for 2 weeks and thereafter their binding to PDGF-BB and ANG2, respectively, have been determined.

TABLE 61

| antibody 0144 | binding to | rel. binding [%] | SD |
|---|---|---|---|
| reference value at start | PDGF-BB | 100 | |
| incubation at pH 6 | | 101 | 4 |
| incubation at pH 7.4 | | 94 | 6 |
| reference value at start | ANG2 | 100 | |
| incubation at pH 6 | | 100 | 1 |
| incubation at pH 7.4 | | 91 | 4 |

TABLE 62

| antibody 0145 | binding to | rel. binding [%] | SD |
|---|---|---|---|
| reference value at start | PDGF-BB | 100 | |
| incubation at pH 6 | | 99 | 1 |
| incubation at pH 7.4 | | 95 | 2 |
| reference value at start | ANG2 | 100 | |
| incubation at pH 6 | | 99 | 2 |
| incubation at pH 7.4 | | 94 | 0 |

In one preferred embodiment the anti-PDGF-B antibody comprises (a) a HVR-H1 comprising the amino acid sequence of SEQ ID NO: 30; (b) a HVR-H2 comprising the amino acid sequence of SEQ ID NO: 31; and (c) a HVR-H3 comprising the amino acid sequence of SEQ ID NO: 33. In one embodiment the antibody further comprises (d) a HVR-L1 comprising the amino acid sequence of SEQ ID NO: 35; (e) a HVR-L2 comprising the amino acid sequence of SEQ ID NO: 36; and (f) a HVR-L3 comprising the amino acid sequence of SEQ ID NO: 37.

In one embodiment, the antibody comprises to humanized variant of the VH and VL sequences in SEQ ID NO: 29 and SEQ ID NO: 34, respectively, including post-translational modifications of those sequences.

In one preferred embodiment thy: anti-PDGF-B antibody comprises (a) a HVR-H1 comprising the amino acid sequence of SEQ ID NO: 39; (b) a HVR-H2 comprising the amino acid sequence of SEQ ID NO: 40; and (c) a HVR-H3 comprising the amino acid sequence of SEQ ID NO: 42. In one embodiment the antibody further comprises (d) a HVR-L1 comprising the amino acid sequence of SEQ ID NO: 44; (e) a HVR-L2 comprising the amino acid sequence of SEQ ID NO: 45; and (f) a HVR-L3 comprising the amino acid sequence of SEQ ID NO: 46.

In one preferred embodiment the anti-PDGF-B antibody as reported herein comprises (a) a HVR-H1 comprising the amino acid sequence of SEQ ID NO: 39; (b) a HVR-H2 comprising the amino acid sequence of SEQ ID NO: 40; (c) a HVR-H3 comprising the amino acid sequence of SEQ ID NO: 41; (d) a HVR-L1 comprising the amino acid sequence of SEQ ID NO: 43; (e) a HVR-L2 comprising the amino acid sequence of SEQ ID NO: 44; and (f) a HVR-L3 comprising the amino acid sequence of SEQ ID NO: 45. In also one preferred embodiment the anti-PDGF-B antibody as reported herein comprises a VH that has the amino acid sequence of SEQ ID NO: 38 and a VL that has the amino acid sequence of SEQ ID NO: 43. In also one preferred embodiment the anti-PDGF-B antibody is a bispecific antibody.

In one embodiment, the antibody comprises the VH and VL sequences in SEQ ID NO: 38 and SEQ ID NO: 43, respectively, including post-translational modifications of those sequences.

In one preferred embodiment the anti-PDGF-B antibody comprises (a) a HVR-H1 comprising the amino acid sequence of SEQ ID NO: 48; (b) a HVR-H2 comprising the amino acid sequence of SEQ ID NO: 49; and (c) a HVR-H3 comprising the amino acid sequence of SEQ ID NO: 51. In one embodiment the antibody further comprises (d) a HVR-L1 comprising the amino acid sequence of SEQ ID NO: 53; (e) a HVR-L2 comprising the amino acid sequence of SEQ ID NO: 54; and (f) a HVR-L3 comprising the amino acid sequence of SEQ ID NO: 55.

In one preferred embodiment the anti-PDGF-B antibody comprises (a) a HVR-H1 comprising the amino acid sequence of SEQ ID NO: 48; (b) a HVR-H2 comprising the amino acid sequence of SEQ ID NO: 50; (c) a HVR-H3 comprising the amino acid sequence of SEQ ID NO: 51; (d) a HVR-L1 comprising the amino acid sequence of SEQ ID NO: 53; (e) a HVR-L2 comprising the amino acid sequence of SEQ ID NO: 54; and (f) a HVR-L3 comprising the amino acid sequence of SEQ ID NO: 55. In also one preferred embodiment the anti-PDGF-B antibody as reported herein comprises a VH that has the amino acid sequence of SEQ ID NO: 47 and a VL that has the amino acid sequence of SEQ ID NO: 52. In also one preferred embodiment the anti-PDGF-B antibody is a bispecific antibody.

In one embodiment, the antibody comprises the VH and VL sequences in SEQ ID NO: 47 and SEQ ID NO: 52, respectively, including post-translational modifications of those sequences.

A.3 Anti-ANG2 Antibodies from which the Anti-ANG2 Binding Site of the Bispecific Antibody as Reported Herein can be Derived Human ANG2 binding kinetics:

TABLE 63

| molecule | $k_a$ (1/Ms) | $k_d$ (1/s) | $K_D$ (nM)* | t½ (s) |
|---|---|---|---|---|
| 0009 | 1.92E+06 | 0.07565 | 39 | 9 |
| 0041 | 3.85E+06 | 3.17E-03 | 1 | 219 |
| 0075 | 2.22E+06 | 3.10E-02 | 14 | 22 |
| 0090 | 2.16E+06 | 2.53E-03 | 1 | 274 |
| 0098 | 1.56E+07 | 1.58E-04 | 10* | |
| 0099 | 2.61E+07 | 1.10E-04 | 4* | |
| 0100 | 2.06E+07 | 1.67E-04 | 8* | |
| 0101 | 1.83E+07 | 1.20E-04 | 7* | |

*Avidity.

Cynomolgus ANG2 binding kinetics:

TABLE 64

| molecule | $k_a$ (1/Ms) | $k_d$ (1/s) | $K_D$ (nM)* | t½ (s) |
|---|---|---|---|---|
| 0009 | 1.45E+06 | 8.81E-02 | 61 | 8 |
| 0041 | 2.14E+06 | 3.60E-03 | 2 | 193 |
| 0075 | 1.34E+06 | 3.25E-02 | 24 | 21 |
| 0090 | 2.02E+06 | 3.08E-03 | 2 | 225 |

The relative biological activities of the antibodies as reported herein are given in the Table 65 below.

TABLE 65

| molecule | relative biological activity (nM) |
|---|---|
| 0009 | 72 |
| 0041 | 838 |

TABLE 65-continued

| molecule | relative biological activity (nM) |
|---|---|
| 0075 | 128 |
| 0090 | 706 |
| 0098 | 100 |

The thermal stability of the different antibodies has been evaluated by determining the aggregation onset temperature (Tagg) and the melting temperature (Tm) (see Table 66 below).

TABLE 66

| molecule | Tagg [° C.] | Tm [° C.] |
|---|---|---|
| 0009 | 62.2 | 65.9 |
| 0041 | 63.1 | 66.0 |
| 0075 | 63.6 | 67.0 |
| 0090 | 64.0 | 67.4 |

In addition, the antibodies show good stability in stress tests. The binding activity has been determined using surface plasmon resonance (see Table 67 below).

TABLE 67

| | relative binding activity | |
|---|---|---|
| molecule | 2 weeks at 37° C. pH 7.4 | 2 weeks at 40° C. pH 6.0 |
| 0009 | 99% | 91% |
| 0041 | 100% | 101% |
| 0075 | 101% | 105% |
| 0090 | 112% | 100% |

100% = sample stored at −80° C.

The same stability can be seen in the CE-SDS analysis (see Table 68 below).

TABLE 68

| | | relative area % | |
|---|---|---|---|
| molecule | start | 2 weeks at 37° C. pH 7.4 | 2 weeks at 40° C. pH 6.0 |
| 0009 | 98.9 | 98.5 | 98.8 |
| 0041 | 98.9 | 98.6 | 98.6 |
| 0090 | 99.2 | 98.5 | 98.2 |

In one preferred embodiment the anti-ANG2 antibody comprises (a) a HVR-H1 comprising the amino acid sequence of SEQ ID NO: 75; (b) a HVR-H2 comprising the amino acid sequence of SEQ ID NO: 76; and (c) a HVR-H3 comprising the amino acid sequence of SEQ ID NO: 78. In one embodiment the antibody further comprises (d) a HVR-L1 comprising the amino acid sequence of SEQ ID NO: 80; (e) a HVR-L2 comprising the amino acid sequence of SEQ ID NO: 81; and (f) a HVR-L3 comprising the amino acid sequence of SEQ ID NO: 82.

In one embodiment, the antibody comprises the VH and VL sequences in SEQ ID NO: 74 and SEQ ID NO: 79, respectively, including post-translational modifications of those sequences.

A.4 Anti-VEGF Antibodies from which the Anti-VEGF Binding Site of the Bispecific Antibody as Reported Herein can be Derived In one preferred embodiment the anti-VEGF antibody comprises the HVR-H1, HVR-H2 and HVR-H3 as contained in the heavy chain variable domain of SEQ ID NO: 107. The HVRs comprise the CDRs according to Kabat. In one embodiment the antibody further comprises the HVR-L1, HVR-L2 and HVR-L3 as contained in the heavy chain variable domain of SEQ ID NO: 108. The HVRs comprise the CDRs according to Kabat.

In one embodiment, the antibody comprises the HC and LC sequences in SEQ ID NO: 107 and SEQ ID NO: 108, respectively, including post-translational modifications of those sequences.

In one preferred embodiment the anti-VEGF antibody comprises the HVR-H1, HVR-H2 and HVR-H3 as contained in the heavy chain variable domain of SEQ ID NO: 109. The HVRs comprise the CDRs according to Kabat. In one embodiment the antibody further comprises the HVR-L1, HVR-L2 and HVR-L3 as contained in the heavy chain variable domain of SEQ ID NO: 110. The HVRs comprise the CDRs according to Kabat.

In one embodiment, the antibody comprises the HC and LC sequences in SEQ ID NO: 109 and SEQ ID NO: 110, respectively, including post-translational modifications of those sequences.

A.5 Bispecific Antibodies

One aspect as reported herein is a bivalent, bispecific antibody comprising
  a) a first light chain and a first heavy chain of an antibody specifically binding to a first antigen, and
  b) a second light chain and a second heavy chain of an antibody specifically binding to a second antigen, wherein the variable domains VL and VH of the second light chain and the second heavy chain are replaced by each other,
  wherein the first and the second antigen are different antigens selected from the group consisting of (human) ANG2, (human) VEGF, (human) IL-1beta and (human) PDGF-B.

The antibody under a) does not contain a modification as reported under b) and the heavy chain and the light chain under a) are isolated chains.

In the antibody under b)
  within the light chain
    the variable light chain domain VL is replaced by the variable heavy chain domain VH of said antibody,
  and
  within the heavy chain
    the variable heavy chain domain VH is replaced by the variable light chain domain VL of said antibody.

In one embodiment
  i) in the constant domain CL of the first light chain under a) the amino acid at position 124 (numbering according to Kabat) is substituted by a positively charged amino acid, and wherein in the constant domain CH1 of the first heavy chain under a) the amino acid at position 147 or the amino acid at position 213 (numbering according to Kabat EU index) is substituted by a negatively charged amino acid,
  or
  ii) in the constant domain CL of the second light chain under b) the amino acid at position 124 (numbering according to Kabat) is substituted by a positively charged amino acid, and wherein in the constant domain CH1 of the second heavy chain under b) the amino acid at position 147 or the amino acid at position 213 (numbering according to Kabat EU index) is substituted by a negatively charged amino acid.

In one preferred embodiment
  i) in the constant domain CL of the first light chain under a) the amino acid at position 124 is substituted independently by lysine (K), arginine (R) or histidine (H) (numbering according to Kabat) (in one preferred embodiment independently by lysine (K) or arginine (R)), and wherein in the constant domain CH1 of the first heavy chain under a) the amino acid at position 147 or the amino acid at position 213 is substituted independently by glutamic acid (E) or aspartic acid (D) (numbering according to Kabat EU index),
  or
  ii) in the constant domain CL of the second light chain under b) the amino acid at position 124 is substituted independently by lysine (K), arginine (R) or histidine (H) (numbering according to Kabat) (in one preferred embodiment independently by lysine (K) or arginine (R)), and wherein in the constant domain CH1 of the second heavy chain under b) the amino acid at position 147 or the amino acid at position 213 is substituted independently by glutamic acid (E) or aspartic acid (D) (numbering according to Kabat EU index).

In one embodiment in the constant domain CL of the second heavy chain the amino acids at position 124 and 123 are substituted by K (numbering according to Kabat EU index).

In one embodiment in the constant domain CH1 of the second light chain the amino acids at position 147 and 213 are substituted by E (numbering according to EU index of Kabat).

In one preferred embodiment in the constant domain CL of the first light chain the amino acids at position 124 and 123 are substituted by K, and in the constant domain CH1 of the first heavy chain the amino acids at position 147 and 213 are substituted by E (numbering according to Kabat EU index).

In one embodiment in the constant domain CL of the second heavy chain the amino acids at position 124 and 123 are substituted by K, and wherein in the constant domain CH1 of the second light chain the amino acids at position 147 and 213 are substituted by E, and in the variable domain VL of the first light chain the amino acid at position 38 is substituted by K, in the variable domain VH of the first heavy chain the amino acid at position 39 is substituted by E, in the variable domain VL of the second heavy chain the amino acid at position 38 is substituted by K, and in the variable domain VH of the second light chain the amino acid at position 39 is substituted by E (numbering according to Kabat EU index).

One aspect as reported herein is a bivalent, bispecific antibody comprising
  a) a first light chain and a first heavy chain of an antibody specifically binding to a first antigen, and
  b) a second light chain and a second heavy chain of an antibody specifically binding to a second antigen, wherein the variable domains VL and VH of the second light chain and the second heavy chain are replaced by each other, and wherein the constant domains CL and CH1 of the second light chain and the second heavy chain are replaced by each other,
  wherein the first and the second antigen are different antigens selected from the group consisting of (human) ANG2, (human) VEGF, (human) IL-1beta and (human) PDGF-B.

The antibody under a) does not contain a modification as reported under b) and the heavy chain and the light chain and a) are isolated chains.

In the antibody under b)
within the light chain
the variable light chain domain VL is replaced by the variable heavy chain domain VH of said antibody, and the constant light chain domain CL is replaced by the constant heavy chain domain CH1 of said antibody;
and
within the heavy chain
the variable heavy chain domain VH is replaced by the variable light chain domain VL of said antibody, and the constant heavy chain domain CH1 is replaced by the constant light chain domain CL of said antibody.

One aspect as reported herein is a bivalent, bispecific antibody comprising
a) a first light chain and a first heavy chain of an antibody specifically binding to a first antigen, and
b) a second light chain and a second heavy chain of an antibody specifically binding to a second antigen, wherein the constant domains CL and CH1 of the second light chain and the second heavy chain are replaced by each other,
wherein the first and the second antigen are different antigens selected from the group consisting of (human) ANG2, (human) VEGF, (human) IL-1beta and (human) PDGF-B.

The antibody under a) does not contain a modification as reported under b) and the heavy chain and the light chain under a) are isolated chains.

In the antibody under b)
within the light chain
the constant light chain domain CL is replaced by the constant heavy chain domain CH1 of said antibody;
and within the heavy chain
the constant heavy chain domain CH1 is replaced by the constant light chain domain CL of said antibody.

One aspect as reported herein is a multispecific antibody comprising
a) a full length antibody specifically binding to a first antigen and consisting of two antibody heavy chains and two antibody light chains, and
b) one, two, three or four single chain Fab fragments specifically binding to one to four further antigens (i.e. a second and/or third and/or fourth and/or fifth antigen, preferably specifically binding to one further antigen, i.e. a second antigen),
wherein said single chain Fab fragments under b) are fused to said full length antibody under a) via a peptidic linker at the C- or N-terminus of the heavy or light chain of said full length antibody,
wherein the first and the second antigen are different antigens selected from the group consisting of (human) ANG2, (human) VEGF, (human) IL-1beta and (human) PDGF-B.

In one embodiment one or two identical single chain Fab fragments binding to a second antigen are fused to said full length antibody via a peptidic linker at the C-terminus of the heavy or light chains of said full length antibody.

In one embodiment one or two identical single chain Fab fragments binding to a second antigen are fused to said full length antibody via a peptidic linker at the C-terminus of the heavy chains of said full length antibody.

In one embodiment one or two identical single chain Fab fragments binding to a second antigen are fused to said full length antibody via a peptidic linker at the C-terminus of the light chains of said full length antibody.

In one embodiment two identical single chain Fab fragments binding to a second antigen are fused to said full length antibody via a peptidic linker at the C-terminus of each heavy or light chain of said full length antibody.

In one embodiment two identical single chain Fab fragments binding to a second antigen are fused to said full length antibody via a peptidic linker at the C-terminus of each heavy chain of said full length antibody.

In one embodiment two identical single chain Fab fragments binding to a second antigen are fused to said full length antibody via a peptidic linker at the C-terminus of each light chain of said full length antibody.

One aspect as reported herein is a trivalent, bispecific antibody comprising
a) a full length antibody specifically binding to a first antigen and consisting of two antibody heavy chains and two antibody light chains,
b) a first polypeptide consisting of
ba) an antibody heavy chain variable domain (VH), or
bb) an antibody heavy chain variable domain (VH) and an antibody constant domain 1 (CH1),
wherein said first polypeptide is fused with the N-terminus of its VH domain via a peptidic linker to the C-terminus of one of the two heavy chains of said full length antibody,
c) a second polypeptide consisting of
ca) an antibody light chain variable domain (VL), or
cb) an antibody light chain variable domain (VL) and an antibody light chain constant domain (CL),
wherein said second polypeptide is fused with the N-terminus of the VL domain via a peptidic linker to the C-terminus of the other of the two heavy chains of said full length antibody,
and
wherein the antibody heavy chain variable domain (VH) of the first polypeptide and the antibody light chain variable domain (VL) of the second polypeptide together form an antigen-binding site specifically binding to a second antigen,
and
wherein the first and the second antigen are different antigens selected from the group consisting of (human) ANG2, (human) VEGF, (human) IL-1beta and (human) PDGF-B.

In one embodiment the antibody heavy chain variable domain (VH) of the polypeptide under b) and the antibody light chain variable domain (VL) of the polypeptide under c) are linked and stabilized via an interchain disulfide bridge by introduction of a disulfide bond between the following positions:
i) heavy chain variable domain position 44 to light chain variable domain position 100, or
ii) heavy chain variable domain position 105 to light chain variable domain position 43, or
iii) heavy chain variable domain position 101 to light chain variable domain position 100 (numbering always according to Kabat EU index).

Techniques to introduce unnatural disulfide bridges for stabilization are described e.g. in WO 94/029350, Rajagopal, V., et al., Prot. Eng. (1997) 1453-59; Kobayashi, H., et al., Nuclear Medicine & Biology, Vol. 25, (1998) 387-393; or Schmidt, M., et al., Oncogene (1999) 18 1711-1721. In one embodiment the optional disulfide bond between the variable domains of the polypeptides under b) and c) is between heavy chain variable domain position 44 and light chain variable domain position 100. In one embodiment the optional disulfide bond between the variable domains of the polypeptides under b) and c) is between heavy chain variable domain position 105 and light chain variable domain position 43. (numbering always according to EU index of Kabat) In one embodiment a trivalent, bispecific antibody without said optional disulfide stabilization between the variable domains VH and VL of the single chain Fab fragments is preferred.

One aspect as reported herein is a tri specific or tetraspecific antibody, comprising
- a) a first light chain and a first heavy chain of a full length antibody which specifically binds to a first antigen, and
- b) a second (modified) light chain and a second (modified) heavy chain of a full length antibody which specifically binds to a second antigen, wherein the variable domains VL and VH are replaced by each other, and/or wherein the constant domains CL and CH1 are replaced by each other, and
- c) wherein one to four antigen binding peptides which specifically bind to one or two further antigens (i.e. to a third and/or fourth antigen) are fused via a peptidic linker to the C- or N-terminus of the light chains or heavy chains of a) and/or b),
  wherein the first and the second antigen are different antigens selected from the group consisting of (human) ANG2, (human) VEGF, (human) IL-1beta and (human) PDGF-B.

The antibody under a) does not contain a modification as reported under b) and the heavy chain and the light chain and a) are isolated chains.

In one embodiment the trispecific or tetraspecific antibody comprises under c) one or two antigen binding peptides which specifically bind to one or two further antigens.

In one embodiment the antigen binding peptides are selected from the group of a scFv fragment and a scFab fragment.

In one embodiment the antigen binding peptides are scFv fragments.

In one embodiment the antigen binding peptides are scFab fragments.

In one embodiment the antigen binding peptides are fused to the C-terminus of the heavy chains of a) and/or b).

In one embodiment the trispecific or tetraspecific antibody comprises under c) one or two antigen binding peptides which specifically bind to one further antigen.

In one embodiment the trispecific or tetraspecific antibody comprises under c) two identical antigen binding peptides which specifically bind to a third antigen. In one preferred embodiment such two identical antigen binding peptides are fused both via the same peptidic linker to the C-terminus of the heavy chains of a) and b). In one preferred embodiment the two identical antigen binding peptides are either a scFv fragment or a scFab fragment.

In one embodiment the trispecific or tetraspecific antibody comprises under c) two antigen binding peptides which specifically bind to a third and a fourth antigen. In one embodiment said two antigen binding peptides are fused both via the same peptide connector to the C-terminus of the heavy chains of a) and b). In one preferred embodiment said two antigen binding peptides are either a scFv fragment or a scFab fragment.

One aspect as reported herein is a bispecific, tetravalent antibody comprising
- a) two light chains and two heavy chains of an antibody, which specifically bind to a first antigen (and comprise two Fab fragments),
- b) two additional Fab fragments of an antibody, which specifically bind to a second antigen, wherein said additional Fab fragments are fused both via a peptidic linker either to the C- or N-termini of the heavy chains of a), and
wherein in the Fab fragments the following modifications were performed
  i) in both Fab fragments of a), or in both Fab fragments of b), the variable domains VL and VH are replaced by each other, and/or the constant domains CL and CH1 are replaced by each other,
  or
  ii) in both Fab fragments of a) the variable domains VL and VH are replaced by each other, and the constant domains CL and CH1 are replaced by each other, and
    in both Fab fragments of b) the variable domains VL and VH are replaced by each other, or the constant domains CL and CH1 are replaced by each other,
  or
  iii) in both Fab fragments of a) the variable domains VL and VH are replaced by each other, or the constant domains CL and CH1 are replaced by each other, and
    in both Fab fragments of b) the variable domains VL and VH are replaced by each other, and the constant domains CL and CH1 are replaced by each other,
  or
  iv) in both Fab fragments of a) the variable domains VL and VH are replaced by each other, and in both Fab fragments of b) the constant domains CL and CH1 are replaced by each other,
  or
  v) in both Fab fragments of a) the constant domains CL and CH1 are replaced by each other, and in both Fab fragments of b) the variable domains VL and VH are replaced by each other,
wherein the first and the second antigen are different antigens selected from the group consisting of (human) ANG2, (human) VEGF, (human) IL-1beta and (human) PDGF-B.

In one embodiment said additional Fab fragments are fused both via a peptidic linker either to the C-termini of the heavy chains of a), or to the N-termini of the heavy chains of a).

In one embodiment said additional Fab fragments are fused both via a peptidic linker either to the C-termini of the heavy chains of a).

In one embodiment said additional Fab fragments are fused both via a peptide connector to the N-termini of the heavy chains of a).

In one embodiment in the Fab fragments the following modifications are performed:
  i) in both Fab fragments of a), or in both Fab fragments of b), the variable domains VL and VH are replaced by each other,
  and/or
    the constant domains CL and CH1 are replaced by each other.

In one embodiment in the Fab fragments the following modifications are performed:
  i) in both Fab fragments of a) the variable domains VL and VH are replaced by each other,
  and/or the constant domains CL and CH1 are replaced by each other.

In one embodiment in the Fab fragments the following modifications are performed:
  i) in both Fab fragments of a) the constant domains CL and CH1 are replaced by each other.

In one embodiment in the Fab fragments the following modifications are performed:
  i) in both Fab fragments of b) the variable domains VL and VH are replaced by each other,
  and/or
  the constant domains CL and CH1 are replaced by each other.

In one embodiment in the Fab fragments the following modifications are performed:
  i) in both Fab fragments of b) the constant domains CL and CH1 are replaced by each other.

One aspect as reported herein is a bispecific, tetravalent antibody comprising:
  a) a (modified) heavy chain of a first antibody, which specifically binds to a first antigen and comprises a first VH-CH1 domain pair, wherein to the C-terminus of said heavy chain the N-terminus of a second VH-CH1 domain pair of said first antibody is fused via a peptidic linker,
  b) two light chains of said first antibody of a),
  c) a (modified) heavy chain of a second antibody, which specifically binds to a second antigen and comprises a first VH-CL domain pair, wherein to the C-terminus of said heavy chain the N-terminus of a second VH-CL domain pair of said second antibody is fused via a peptidic linker, and
  d) two (modified) light chains of said second antibody of c), each comprising a CL-CH1 domain pair,
  wherein the first and the second antigen are different antigens selected from the group consisting of (human) ANG2, (human) VEGF, (human) IL-1beta and (human) PDGF-B.

One aspect as reported herein is a bispecific antibody comprising
  a) the heavy chain and the light chain of a first full length antibody that specifically binds to a first antigen, and
  b) the heavy chain and the light chain of a second full length antibody that specifically binds to a second antigen, wherein the N-terminus of the heavy chain is connected to the C-terminus of the light chain via a peptidic linker,
  wherein the first and the second antigen are different antigens selected from the group consisting of (human) ANG2, (human) VEGF, (human) IL-1beta and (human) PDGF-B.

The antibody under a) does not contain a modification as reported under b) and the heavy chain and the light chain are isolated chains.

One aspect as reported herein is a bispecific antibody comprising
  a) a full length antibody specifically binding to a first antigen and consisting of two antibody heavy chains and two antibody light chains, and
  b) an Fv fragment specifically binding to a second antigen comprising a $VH^2$ domain and a $VL^2$ domain, wherein both domains are connected to each other via a disulfide bridge,
  wherein only either the $VH^2$ domain or the $VL^2$ domain is fused via a peptide linker to the heavy or light chain of the full length antibody specifically binding to a first antigen,
  wherein the first and the second antigen are different antigens selected from the group consisting of (human) ANG2, (human) VEGF, (human) IL-1beta and (human) PDGF-B.

In the bispecific the heavy chains and the light chains under a) are isolated chains.

In one embodiment the other of the $VH^2$ domain or the $VL^2$ domain is not fused via a peptide linker to the heavy or light chain of the full length antibody specifically binding to a first antigen.

In all aspects as reported herein the first light chain comprises a VL domain and a CL domain and the first heavy chain comprises a VH domain, a CH1 domain, a hinge region, a CH2 domain and a CH3 domain.

In one embodiment of all aspects the antibody as reported herein is a multispecific antibody, which requires heterodimerization of at least two heavy chain polypeptides, and wherein the antibody specifically binds to human IL-1beta and a second non-human IL-1beta antigen.

Several approaches for CH3-modifications in order to support heterodimerization have been described, for example in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291, which are herein included by reference. Typically, in the approaches known in the art, the CH3 domain of the first heavy chain and the CH3 domain of the second heavy chain are both engineered in a complementary manner so that the heavy chain comprising one engineered CH3 domain can no longer homodimerize with another heavy chain of the same structure (e.g. a CH3-engineered first heavy chain can no longer homodimerize with another CH3-engineered first heavy chain; and a CH3-engineered second heavy chain can no longer homodimerize with another CH3-engineered second heavy chain). Thereby the heavy chain comprising one engineered CH3 domain is forced to heterodimerize with another heavy chain comprising the CH3 domain, which is engineered in a complementary manner. For this embodiment of the invention, the CH3 domain of the first heavy chain and the CH3 domain of the second heavy chain are engineered in a complementary manner by amino acid substitutions, such that the first heavy chain and the second heavy chain are forced to heterodimerize, whereas the first heavy chain and the second heavy chain can no longer homodimerize (e.g. for steric reasons).

The different approaches for supporting heavy chain heterodimerization known in the art, that were cited and included above, are contemplated as different alternatives used in a multispecific antibody according to the invention, which comprises a "non-crossed Fab region" derived from a first antibody, which specifically binds to a first antigen, and a "crossed Fab region" derived from a second antibody, which specifically binds to a second antigen, in combination with the particular amino acid substitutions described above for the invention.

The CH3 domains of the multispecific antibody as reported herein can be altered by the "knob-into-holes" technology which is described in detail with several examples in e.g. WO 96/027011, Ridgway, J. B., et al., Protein Eng. 9 (1996) 617-621; and Merchant, A. M., et al., Nat. Biotechnol. 16 (1998) 677-681. In this method the interaction surfaces of the two CH3 domains are altered to increase the heterodimerization of both heavy chains containing these two CH3 domains. Each of the two CH3 domains (of the two heavy chains) can be the "knob", while the other is the "hole". The introduction of a disulfide bridge further stabilizes the heterodimers (Merchant, A. M., et al., Nature Biotech. 16 (1998) 677-681; Atwell, S., et al., J. Mol. Biol. 270 (1997) 26-35) and increases the yield.

In one preferred embodiment the multispecific antibody as reported herein comprises a T366W mutation in the CH3 domain of the "knobs chain" and T366S, L368A, Y407V mutations in the CH3 domain of the "hole-chain" (numbering according to Kabat EU index). An additional interchain disulfide bridge between the CH3 domains can also be used (Merchant, A. M., et al., Nature Biotech. 16 (1998) 677-681) e.g. by introducing a Y349C mutation into the CH3 domain of the "knobs chain" and a E356C mutation or a S354C mutation into the CH3 domain of the "hole chain". Thus in a another preferred embodiment, the multispecific antibody as reported herein comprises the Y349C and T366W mutations in one of the two CH3 domains and the E356C, T366S, L368A and Y407V mutations in the other of the two CH3 domains or the multispecific antibody as reported herein comprises the Y349C and T366W mutations in one of the two CH3 domains and the S354C, T366S, L368A and Y407V mutations in the other of the two CH3 domains (the additional Y349C mutation in one CH3 domain and the additional E356C or S354C mutation in the other CH3 domain forming a interchain disulfide bridge) (numbering according to Kabat EU index).

But also other knobs-in-holes technologies as described by EP 1 870 459A1, can be used alternatively or additionally. In one embodiment the multispecific antibody as reported herein comprises the R409D and K370E mutations in the CH3 domain of the "knobs chain" and the D399K and E357K mutations in the CH3 domain of the "hole-chain" (numbering according to Kabat EU index).

In one embodiment the multispecific antibody as reported herein comprises a T366W mutation in the CH3 domain of the "knobs chain" and the T366S, L368A and Y407V mutations in the CH3 domain of the "hole chain" and additionally the R409D and K370E mutations in the CH3 domain of the "knobs chain" and the D399K and E357K mutations in the CH3 domain of the "hole chain" (numbering according to the Kabat EU index).

In one embodiment the multispecific antibody as reported herein comprises the Y349C and T366W mutations in one of the two CH3 domains and the S354C, T366S, L368A and Y407V mutations in the other of the two CH3 domains, or the multispecific antibody as reported herein comprises the Y349C and T366W mutations in one of the two CH3 domains and the S354C, T366S, L368A and Y407V mutations in the other of the two CH3 domains and additionally the R409D and K370E mutations in the CH3 domain of the "knobs chain" and the D399K and E357K mutations in the CH3 domain of the "hole chain" (numbering according to the Kabat EU index).

Apart from the "knob-into-hole technology" other techniques for modifying the CH3 domains of the heavy chains of a multispecific antibody to enforce heterodimerization are known in the art. These technologies, especially the ones described in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954 and WO 2013/096291 are contemplated herein as alternatives to the "knob-into-hole technology" in combination with a multispecific antibody as reported herein.

In one embodiment of a multispecific antibody as reported herein the approach described in EP 1870459 is used to support heterodimerization of the first heavy chain and the second heavy chain of the multispecific antibody. This approach is based on the introduction of charged amino acids with opposite charges at specific amino acid positions in the CH3/CH3-domain-interface between both, the first and the second heavy chain.

Accordingly, this embodiment relates to a multispecific antibody as reported herein, wherein in the tertiary structure of the antibody the CH3 domain of the first heavy chain and the CH3 domain of the second heavy chain form an interface that is located between the respective antibody CH3 domains, wherein the respective amino acid sequences of the CH3 domain of the first heavy chain and the CH3 domain of the second heavy chain each comprise a set of amino acids that is located within said interface in the tertiary structure of the antibody, wherein from the set of amino acids that is located in the interface in the CH3 domain of one heavy chain a first amino acid is substituted by a positively charged amino acid and from the set of amino acids that is located in the interface in the CH3 domain of the other heavy chain a second amino acid is substituted by a negatively charged amino acid. The multispecific antibody according to this embodiment is herein also referred to as "CH3(+/−)-engineered multispecific antibody" (wherein the abbreviation "+/−" stands for the oppositely charged amino acids that were introduced in the respective CH3 domains).

In one embodiment of said CH3(+/−)-engineered multispecific antibody as reported herein the positively charged amino acid is selected from K, R and H, and the negatively charged amino acid is selected from E or D.

In one embodiment of said CH3(+/−)-engineered multispecific antibody as reported herein the positively charged amino acid is selected from K and R, and the negatively charged amino acid is selected from E or D.

In one embodiment of said CH3(+/−)-engineered multispecific antibody as reported herein the positively charged amino acid is K, and the negatively charged amino acid is E.

In one embodiment of said CH3(+/−)-engineered multispecific antibody as reported herein in the CH3 domain of one heavy chain the amino acid R at position 409 is substituted by D and the amino acid K at position is substituted by E, and in the CH3 domain of the other heavy chain the amino acid D at position 399 is substituted by K and the amino acid E at position 357 is substituted by K (numbering according to Kabat EU index).

In one embodiment of a multispecific antibody as reported herein the approach described in WO2013/157953 is used to support heterodimerization of the first heavy chain and the second heavy chain of the multispecific antibody. In one embodiment of said multispecific antibody as reported herein, in the CH3 domain of one heavy chain the amino acid T at position 366 is substituted by K, and in the CH3 domain of the other heavy chain the amino acid L at position 351 is substituted by D (numbering according to Kabat EU index). In another embodiment of said multispecific antibody as reported herein, in the CH3 domain of one heavy chain the amino acid T at position 366 is substituted by K and the amino acid L at position 351 is substituted by K, and in the CH3 domain of the other heavy chain the amino acid L at position 351 is substituted by D (numbering according to Kabat EU index).

In another embodiment of said multispecific antibody as reported herein, in the CH3 domain of one heavy chain the amino acid T at position 366 is substituted by K and the amino acid L at position 351 is substituted by K, and in the CH3 domain of the other heavy chain the amino acid L at position 351 is substituted by D (numbering according to Kabat EU index). Additionally at least one of the following substitutions is comprised in the CH3 domain of the other heavy chain: the amino acid Y at position 349 is substituted by E, the amino acid Y at position 349 is substituted by D and the amino acid L at position 368 is substituted by E (numbering according to Kabat EU index). In one embodiment the amino acid L at position 368 is substituted by E (numbering according to Kabat EU index).

In one embodiment of a multispecific antibody as reported herein the approach described in WO2012/058768 is used to support heterodimerization of the first heavy chain and the second heavy chain of the multispecific antibody. In one embodiment of said multispecific antibody as reported herein, in the CH3 domain of one heavy chain the amino acid L at position 351 is substituted by Y and the amino acid Y at position 407 is substituted by A, and in the CH3 domain of the other heavy chain the amino acid T at position 366 is substituted by A and the amino acid K at position 409 is substituted by F (numbering according to Kabat EU index). In another embodiment, in addition to the aforementioned substitutions, in the CH3 domain of the other heavy chain at least one of the amino acids at positions 411 (originally T), 399 (originally D), 400 (originally S), 405 (originally F), 390 (originally N) and 392 (originally K) is substituted (numbering according to Kabat EU index). Preferred substitutions are:
  substituting the amino acid T at position 411 by an amino acid selected from N, R, Q, K, D, E and W (numbering according to Kabat EU index),
  substituting the amino acid D at position 399 by an amino acid selected from R, W, Y, and K (numbering according to Kabat EU index),
  substituting the amino acid S at position 400 by an amino acid selected from E, D, R and K (numbering according to Kabat EU index),
  substituting the amino acid F at position 405 by an amino acid selected from I, M, T, S, V and W (numbering according to Kabat EU index;
  substituting the amino acid N at position 390 by an amino acid selected from R, K and D (numbering according to Kabat EU index; and
  substituting the amino acid K at position 392 by an amino acid selected from V, M, R, L, F and E (numbering according to Kabat EU index).

In another embodiment of said multispecific antibody as reported herein (engineered according to WO2012/058768), in the CH3 domain of one heavy chain the amino acid L at position 351 is substituted by Y and the amino acid Y at position 407 is substituted by A, and in the CH3 domain of the other heavy chain the amino acid T at position 366 is substituted by V and the amino acid K at position 409 is substituted by F (numbering according to Kabat EU index). In another embodiment of said multispecific antibody as reported herein, in the CH3 domain of one heavy chain the amino acid Y at position 407 is substituted by A, and in the CH3 domain of the other heavy chain the amino acid T at position 366 is substituted by A and the amino acid K at position 409 is substituted by F (numbering according to Kabat EU index). In said last aforementioned embodiment, in the CH3 domain of said other heavy chain the amino acid K at position 392 is substituted by E, the amino acid T at position 411 is substituted by E, the amino acid D at position 399 is substituted by R and the amino acid S at position 400 is substituted by R (numbering according to Kabat EU index).

In one embodiment of a multispecific antibody as reported herein the approach described in WO 2011/143545 is used to support heterodimerization of the first heavy chain and the second heavy chain of the multispecific antibody. In one embodiment of said multispecific antibody as reported herein, amino acid modifications in the CH3 domains of both heavy chains are introduced at positions 368 and/or 409 (numbering according to Kabat EU index).

In one embodiment of a multispecific antibody as reported herein the approach described in WO 2011/090762 is used to support heterodimerization of the first heavy chain and the second heavy chain of the multispecific antibody. WO 2011/090762 relates to amino acid modifications according to the "knob-into-hole" technology. In one embodiment of said CH3(KiH)-engineered multispecific antibody as reported herein, in the CH3 domain of one heavy chain the amino acid T at position 366 is substituted by W, and in the CH3 domain of the other heavy chain the amino acid Y at position 407 is substituted by A (numbering according to Kabat EU index). In another embodiment of said CH3 (KiH)-engineered multispecific antibody as reported herein, in the CH3 domain of one heavy chain the amino acid T at position 366 is substituted by Y, and in the CH3 domain of the other heavy chain the amino acid Y at position 407 is substituted by T (numbering according to Kabat EU index).

In one embodiment of a multispecific antibody as reported herein, which is of IgG2 isotype, the approach described in WO 2011/090762 is used to support heterodimerization of the first heavy chain and the second heavy chain of the multispecific antibody.

In one embodiment of a multispecific antibody as reported herein, the approach described in WO 2009/089004 is used to support heterodimerization of the first heavy chain and the second heavy chain of the multispecific antibody. In one embodiment of said multispecific antibody as reported herein, in the CH3 domain of one heavy chain the amino acid K or N at position 392 is substituted by a negatively charged amino acid (in one preferred embodiment by E or D, in one preferred embodiment by D), and in the CH3 domain of the other heavy chain the amino acid D at position 399 the amino acid E or D at position 356 or the amino acid E at position 357 is substituted by a positively charged amino acid (in one preferred embodiment K or R, in one preferred embodiment by K, in one preferred embodiment the amino acids at positions 399 or 356 are substituted by K) (numbering according to Kabat EU index). In one further embodiment, in addition to the aforementioned substitutions, in the CH3 domain of the one heavy chain the amino acid K or R at position 409 is substituted by a negatively charged amino acid (in one preferred embodiment by E or D, in one preferred embodiment by D) (numbering according to Kabat EU index). In one even further embodiment, in addition to or alternatively to the aforementioned substitutions, in the CH3 domain of the one heavy chain the amino acid K at position 439 and/or the amino acid K at position 370 is substituted independently from each other by a negatively charged amino acid (in one preferred embodiment by E or D, in one preferred embodiment by D) (numbering according to Kabat EU index).

In one embodiment of a multispecific antibody as reported herein, the approach described in WO 2007/147901 is used to support heterodimerization of the first heavy chain and the second heavy chain of the multispecific antibody. In one embodiment of said multispecific antibody as reported herein, in the CH3 domain of one heavy chain the amino acid K at position 253 is substituted by E, the amino acid D at position 282 is substituted by K and the amino acid K at position 322 is substituted by D, and in the CH3 domain of the other heavy chain the amino acid D at position 239 is substituted by K, the amino acid E at position 240 is substituted by K and the amino acid K at position 292 is substituted by D (numbering according to Kabat EU index).

In one embodiment of a multispecific antibody as reported herein, the approach described in WO 2007/110205 is used to support heterodimerization of the first heavy chain and the second heavy chain of the multispecific antibody In one embodiment of all aspects and embodiments as reported herein the multispecific antibody is a bispecific antibody or a trispecific antibody. In one preferred embodiment of the invention the multispecific antibody is a bispecific antibody.

In one embodiment of all aspects as reported herein, the antibody is a bivalent or trivalent antibody. In one embodiment the antibody is a bivalent antibody.

In one embodiment of all aspects as reported herein, the multispecific antibody has a constant domain structure of an IgG type antibody. In one further embodiment of all aspects as reported herein, the multispecific antibody is characterized in that said multispecific antibody is of human subclass IgG1, or of human subclass IgG1 with the mutations L234A and L235A. In one further embodiment of all aspects as reported herein, the multispecific antibody is characterized in that said multispecific antibody is of human subclass IgG2. In one further embodiment of all aspects as reported herein, the multispecific antibody is characterized in that said multispecific antibody is of human subclass IgG3. In one further embodiment of all aspects as reported herein, the multispecific antibody is characterized in that said multispecific antibody is of human subclass IgG4 or, of human subclass IgG4 with the additional mutation S228P. In one further embodiment of all aspects as reported herein, the multispecific antibody is characterized in that said multispecific antibody is of human subclass IgG1 or human subclass IgG4. In one further embodiment of all aspects as reported herein, the multispecific antibody is characterized in that said multispecific antibody is of human subclass IgG1 with the mutations L234A and L235A (numbering according to Kabat EU index). In one further embodiment of all aspects as reported herein, the multispecific antibody is characterized in that said multispecific antibody is of human subclass IgG1 with the mutations L234A, L235A and P329G (numbering according to Kabat EU index). In one further embodiment of all aspects as reported herein, the multispecific antibody is characterized in that said multispecific antibody is of human subclass IgG4 with the mutations S228P and L235E (numbering according to Kabat EU index). In one further embodiment of all aspects as reported herein, the multispecific antibody is characterized in that said multispecific antibody is of human subclass IgG4 with the mutations S228P, L235E and P329G (numbering according to Kabat EU index).

In one embodiment of all aspects as reported herein, an antibody comprising a heavy chain including a CH3 domain as specified herein, comprises an additional C-terminal glycine-lysine dipeptide (G446 and K447, numbering according to Kabat EU index). In one embodiment of all aspects as reported herein, an antibody comprising a heavy chain including a CH3 domain, as specified herein, comprises an additional C-terminal glycine residue (G446, numbering according to Kabat EU index).

In one embodiment the antibody comprises a first Fc-region polypeptide and a second Fc-region polypeptide, and wherein
 i) the first Fc-region polypeptide is a human IgG1 Fc-region polypeptide and the second Fc-region polypeptide is a human IgG1 Fc-region polypeptide, or
 ii) the first Fc-region polypeptide is a human IgG1 Fc-region polypeptide with the mutations L234A, L235A and the second Fc-region polypeptide is a human IgG1 Fc-region polypeptide with the mutations L234A, L235A, or
 iii) the first Fc-region polypeptide is a human IgG1 Fc-region polypeptide with the mutations L234A, L235A, P329G and the second Fc-region polypeptide is a human IgG1 Fc-region polypeptide with the mutations L234A, L235A, P329G, or
 iv) the first Fc-region polypeptide is a human IgG1 Fc-region polypeptide with the mutations L234A, L235A, S354C, T366W and the second Fc-region polypeptide is a human IgG1 Fc-region polypeptide with the mutations L234A, L235A, Y349C, T366S, L368A, Y407V, or
 v) the first Fc-region polypeptide is a human IgG1 Fc-region polypeptide with the mutations L234A, L235A, P329G, S354C, T366W and the second Fc-region polypeptide is a human IgG1 Fc-region polypeptide with the mutations L234A, L235A, P329G, Y349C, T366S, L368A, Y407V, or
 vi) the first Fc-region polypeptide is a human IgG4 Fc-region polypeptide and the second Fc-region polypeptide is a human IgG4 Fc-region polypeptide, or
 vii) the first Fc-region polypeptide is a human IgG4 Fc-region polypeptide with the mutations S228P, L235E and the second Fc-region polypeptide is a human IgG4 Fc-region polypeptide with the mutations S228P, L235E, or
 viii) the first Fc-region polypeptide is a human IgG4 Fc-region polypeptide with the mutations S228P, L235E, P329G and the second Fc-region polypeptide is a human IgG4 Fc-region polypeptide with the mutations S228P, L235E, P329G, or
 ix) the first Fc-region polypeptide is a human IgG4 Fc-region polypeptide with the mutations S228P, L235E, S354C, T366W and the second Fc-region polypeptide is a human IgG4 Fc-region polypeptide with the mutations S228P, L235E, Y349C, T366S, L368A, Y407V, or
 x) the first Fc-region polypeptide is a human IgG4 Fc-region polypeptide with the mutations S228P, L235E, P329G, S354C, T366W and the second Fc-region polypeptide is a human IgG4 Fc-region polypeptide with the mutations S228P, L235E, P329G, Y349C, T366S, L368A, Y407V.

In one embodiment the antibody comprises a first Fc-region polypeptide and a second Fc-region polypeptide, and wherein the antibody comprises the combination of mutations
 i) I253A, H310A, and H435A, or
 ii) H310A, H433A, and Y436A, or
 iii) L251D, L314D, and L432D, or
 iv) combinations of i) to iii)
 in the first Fc-region polypeptide and in the second Fc-region polypeptide.

In one embodiment of all aspects as reported herein the antibody as reported herein is an effector silent antibody. In one embodiment of all aspects as reported herein the antibody is an effector silent antibody and does not bind to human FcRn. In one preferred embodiment of all aspects as reported herein is the antibody of the human subclass IgG1 and has the mutations L234A, L235A, P329G, I253A, H310A and H434A in both heavy chains (numbering according to the Kabat index).

In a further aspect, an anti-IL-1beta antibody according to any of the above embodiments may incorporate any of the features, singly or in combination, as described in Sections 1-4 below.

1. Antibody Affinity

Methods for the determination of the KD value are outlined in the Examples below.

When using a BIACORE® surface plasmon resonance assay the KD value can be measured alternatively as follows: An assay using a BIACORE®-2000 or a BIACORE®-3000 (BIAcore, Inc., Piscataway, N.J.) is performed at 25° C. with immobilized antigen CMS chips at ~10 response units (RU). In one embodiment, carboxymethylated dextran biosensor chips (CMS, BIACORE, Inc.) are activated with N-ethyl-N'-(3-dimethylaminopropyl)-carbodiimide hydrochloride (EDC) and N-hydroxysuccinimide (NETS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_a$) and dissociation rates ($k_d$) are calculated using a simple one-to-one Langmuir binding model (BIACORE® Evaluation Software version 3.2) by simultaneously fitting the association and dissociation sensorgrams. The equilibrium dissociation constant (KD) is calculated as the ratio $k_d/k_a$ (see, e.g., Chen, Y. et al., J. Mol. Biol. 293 (1999) 865-881). If the on-rate exceeds $10^6$ $M^{-1}$ $s^{-1}$ by the surface plasmon resonance assay above, then the association-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Chimeric and Humanized Antibodies

In certain embodiments, an antibody provided herein is a chimeric antibody. Certain chimeric antibodies are described, e.g., in U.S. Pat. No. 4,816,567; and Morrison, S. L. et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I. et al., Nature 332 (1988) 323-329; Queen, C. et al., Proc. Natl. Acad. Sci. USA 86 (1989) 10029-10033; U.S. Pat. Nos. 5,821,337, 7,527,791, 6,982,321, and 7,087,409; Kashmiri, S. V. et al., Methods 36 (2005) 25-34 (describing specificity determining region (SDR) grafting); Padlan, E. A., Mol. Immunol. 28 (1991) 489-498 (describing "resurfacing"); Dall'Acqua, W. F. et al., Methods 36 (2005) 43-60 (describing "FR shuffling"); and Osbourn, J. et al., Methods 36 (2005) 61-68 and Klimka, A. et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J. et al., J. Immunol. 151 (1993) 2296-2308; framework regions derived from the consensus sequence of human antibodies of a particular subgroup of light or heavy chain variable regions (see, e.g., Carter, P. et al., Proc. Natl. Acad. Sci. USA 89 (1992) 4285-4289; and Presta, L. G. et al., J. Immunol. 151 (1993) 2623-2632); human mature (somatically mutated) framework regions or human germline framework regions (see, e.g., Almagro, J. C. and Fransson, J., Front. Biosci. 13 (2008) 1619-1633); and framework regions derived from screening FR libraries (see, e.g., Baca, M. et al., J. Biol. Chem. 272 (1997) 10678-10684 and Rosok, M. J. et al., J. Biol. Chem. 271 (19969 22611-22618).

3. Multispecific Antibodies

An antibody provided herein is a multispecific antibody, e.g. a bispecific antibody. Multispecific antibodies are monoclonal antibodies that have binding specificities for at least two different sites. In certain embodiments, one of the binding specificities is for IL-1beta and the other is for any other antigen. In certain embodiments, bispecific antibodies may bind to two different epitopes of IL-1beta. Bispecific antibodies may also be used to localize cytotoxic agents to cells which express IL-1beta. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A. et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M. et al., Science 229 (1985) 81-83); using leucine zippers to produce bi-specific antibodies (see, e.g., Kostelny, S. A. et al., J. Immunol. 148 (1992) 1547-1553; using "diabody" technology for making bispecific antibody fragments (see, e.g., Holliger, P. et al., Proc. Natl. Acad. Sci. USA 90 (1993) 6444-6448); and using single-chain Fv (sFv) dimers (see, e.g. Gruber, M et al., J. Immunol. 152 (1994) 5368-5374); and preparing trispecific antibodies as described, e.g., in Tutt, A. et al., J. Immunol. 147 (1991) 60-69).

Engineered antibodies with three or more functional antigen binding sites, including "Octopus antibodies," are also included herein (see, e.g. US 2006/0025576).

The antibody or fragment herein also includes a "Dual Acting Fab" or "DAF" comprising an antigen binding site that binds to IL-1beta as well as another, different antigen (see, US 2008/0069820, for example).

The antibody or fragment herein also includes multispecific antibodies described in WO 2009/080251, WO 2009/080252, WO 2009/080253, WO 2009/080254, WO 2010/112193, WO 2010/115589, WO 2010/136172, WO 2010/145792, and WO 2010/145793.

4. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in the Table under the heading of "preferred substitutions". More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 69

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; norleucine | Leu |
| Leu (L) | norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; norleucine | Leu |

Amino acids may be grouped according to common side-chain properties:
(1) hydrophobic: norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, P. S., Methods Mol. Biol. 207 (2008) 179-196), and/or residues that contact antigen, with the resulting variant VH or VL being tested for binding affinity. Affinity maturation by constructing and reselecting from secondary libraries has been described, e.g., in Hoogenboom, H. R. et al. in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham, B. C. and Wells, J. A., Science 244 (1989) 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc-region, the carbohydrate attached thereto may be altered. Native antibodies produced by mammalian cells typically comprise a branched, biantennary oligosaccharide that is generally attached by an N-linkage to Asn297 of the CH2 domain of the Fc-region (see, e.g., Wright, A. and Morrison, S. L., TIBTECH 15 (1997) 26-32). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc-region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc-region (EU numbering of Fc-region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US 2003/0157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki, A. et al., J. Mol. Biol. 336 (2004) 1239-1249; Yamane-Ohnuki, N. et al., Biotech. Bioeng. 87 (2004) 614-622. Examples of cell lines capable of producing defucosylated antibodies include Lec13 CHO cells deficient in protein fucosylation (Ripka, J. et al., Arch. Biochem. Biophys. 249 (1986) 533-545; US 2003/0157108; and WO 2004/056312, especially at Example 11), and knockout cell lines, such as alpha-1,6-fucosyltransferase gene, FUT8, knockout CHO cells (see, e.g., Yamane-Ohnuki, N. et al., Biotech. Bioeng. 87 (2004) 614-622; Kanda, Y. et al., Biotechnol. Bioeng. 94 (2006) 680-688; and WO 2003/085107).

Antibodies variants are further provided with bisected oligosaccharides, e.g., in which a biantennary oligosaccharide attached to the Fc-region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc-region are also provided. Such antibody variants may have improved CDC function. Such antibody variants are described, e.g., in WO 1997/30087; WO 1998/58964; and WO 1999/22764.

c) Fc-Region Variants

In certain embodiments, one or more amino acid modifications may be introduced into the Fc-region of an antibody provided herein, thereby generating an Fc-region variant. The Fc-region variant may comprise a human Fc-region sequence (e.g., a human IgG1, IgG2, IgG3 or IgG4 Fc-region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII FcR expression on hematopoietic cells is summarized in Table 3 on page 464 of Ravetch, J. V. and Kinet, J. P., Annu. Rev. Immunol. 9 (1991) 457-492. Non-limiting examples of in vitro assays to assess ADCC activity of a molecule of interest is described in U.S. Pat. No. 5,500,362 (see, e.g. Hellstrom, I. et al., Proc. Natl. Acad. Sci. USA 83 (1986) 7059-7063; and Hellstrom, I. et al., Proc. Natl. Acad. Sci. USA 82 (1985) 1499-1502); U.S. Pat. No. 5,821,337 (see Bruggemann, M. et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R. et al., Proc. Natl. Acad. Sci. USA 95 (1998) 652-656. C1q binding assays may also be carried out to confirm that the antibody is unable to bind C1q and hence lacks CDC activity (see, e.g., C1q and C3c binding ELISA in WO 2006/029879 and WO 2005/100402). To assess complement activation, a CDC assay may be performed (see, for example, Gazzano-Santoro, H. et al., J. Immunol. Methods 202 (1996) 163-171; Cragg, M. S. et al., Blood 101 (2003) 1045-1052; and Cragg, M. S. and M. J. Glennie, Blood 103 (2004) 2738-2743). FcRn binding and in vivo clearance/half-life determinations can also be performed using methods known in the art (see, e.g., Petkova, S. B. et al., Int. Immunol. 18 (2006: 1759-1769).

Antibodies with reduced effector function include those with substitution of one or more of Fc-region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields, R. L. et al., J. Biol. Chem. 276 (2001) 6591-6604)

In certain embodiments, an antibody variant comprises an Fc-region with one or more amino acid substitutions which improve ADCC, e.g., substitutions at positions 298, 333, and/or 334 of the Fc-region (EU numbering of residues).

In some embodiments, alterations are made in the Fc-region that result in altered (i.e., either improved or diminished) C1q binding and/or Complement Dependent Cytotoxicity (CDC), e.g., as described in U.S. Pat. No. 6,194,551, WO 99/51642, and Idusogie, E. E. et al., J. Immunol. 164 (2000) 4178-4184.

Antibodies with increased half-lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc-region with one or more substitutions therein which improve binding of the Fc-region to FcRn. Such Fc variants include those with substitutions at one or more of Fc-region residues: 238, 256, 265, 272, 286, 303, 305, 307, 311, 312, 317, 340, 356, 360, 362, 376, 378, 380, 382, 413, 424 or 434, e.g., substitution of Fc-region residue 434 (U.S. Pat. No. 7,371,826).

See also Duncan, A. R. and Winter, G., Nature 322 (1988) 738-740; U.S. Pat. Nos. 5,648,260; 5,624,821; and WO 94/29351 concerning other examples of Fc-region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc-region. Cysteine engineered antibodies may be generated as described, e.g., in U.S. Pat. No. 7,521,541.

e) Antibody Derivatives

In certain embodiments, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an antibody as reported herein is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in *E. coli.*) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized", resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells.

Plant cell cultures can also be utilized as hosts (see, e.g., U.S. Pat. Nos. 5,959,177, 6,040,498, 6,420,548, 7,125,978, and 6,417,429 (describing PLANTIBODIES™ technology for producing antibodies in transgenic plants)).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P. et al., Annals N.Y. Acad. Sci. 383 (1982) 44-68; MRC 5 cells; and FS4 cells. Other useful mammalian host cell lines include Chinese hamster ovary (CHO) cells, including DHFR⁻ CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

C. Assays

Antibodies provided herein may be identified, screened for, or characterized for their physical/chemical properties and/or biological activities by various assays known in the art. Exemplary assays are reported in the Examples.

D. Immunoconjugates

The invention also provides immunoconjugates comprising an antibody as reported herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and EP 0 425 235 B1); an auristatin such as monomethyl auristatin drug moieties DE and DF (MMAE and MMAF) (see U.S. Pat. Nos. 5,635,483, 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman, L. M. et al., Cancer Res. 53 (1993) 3336-3342; and Lode, H. N. et al., Cancer Res. 58 (1998) 2925-2928); an anthracycline such as daunomycin or doxorubicin (see Kratz, F. et al., Curr. Med. Chem. 13 (2006) 477-523; Jeffrey, S. C., et al., Bioorg. Med. Chem. Lett. 16 (2006) 358-362; Torgov, M. Y., et al., Bioconjug. Chem. 16 (2005) 717-721; Nagy, A., et al., Proc. Natl. Acad. Sci. USA 97 (2000) 829-834; Dubowchik, G. M., et al., Bioorg. & Med. Chem. Letters 12 (2002) 1529-1532; King, H. D., et al., J. Med. Chem. 45 (2002) 4336-4343; and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, *sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example $TC^{99m}$ or $I^{123}$, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta, E. S. et al., Science 238 (1987) 1098-1104. Carbon-14-labeled 1-isothiocyanatobenzyl-3-methyldiethylene triamine pentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari, R. V. et al., Cancer Res. 52 (1992) 127-131; U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Pharmaceutical Formulations

Pharmaceutical formulations of a multispecific antibody as described herein are prepared by mixing such antibody having the desired degree of purity with one or more optional pharmaceutically acceptable carriers (Remington's Pharmaceutical Sciences, 16$^{th}$ edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US 2005/0260186 and US 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171, 586 and WO 2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide an anti-ANG2 antibody or an anti-VEGF antibody. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16$^{th}$ edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

F. Therapeutic Methods and Compositions

Any of the multispecific antibodies provided herein may be used in therapeutic methods.

In one aspect, a multispecific antibody for use as a medicament is provided. In further aspects, a multispecific antibody for use in treating an ocular vascular disease, preferably macular degeneration, is provided. In certain embodiments, a multispecific antibody for use in a method of treatment is provided. In certain embodiments, the invention provides a multispecific antibody for use in a method of treating an individual having an ocular vascular disease, preferably macular degeneration, comprising administering to the individual an effective amount of the multispecific antibody. In one such embodiment, the method further comprises administering to the individual an effective amount of at least one additional therapeutic agent, e.g., as described below. In further embodiments, the invention provides a multispecific antibody for use in inhibiting angiogenesis. In certain embodiments, the invention provides a multispecific antibody for use in a method of inhibiting angiogenesis in an individual comprising administering to the individual an effective of the multispecific antibody to inhibit angiogenesis. An "individual" according to any of the above embodiments is preferably a human.

In a further aspect, the invention provides for the use of a multispecific antibody in the manufacture or preparation of a medicament. In one embodiment, the medicament is for treatment of an ocular vascular disease, preferably macular degeneration. In a further embodiment, the medicament is for use in a method of treating an ocular vascular disease, preferably macular degeneration, comprising administering to an individual having an ocular vascular disease, preferably macular degeneration, an effective amount of the medicament. In one such embodiment, the method further comprises administering to the individual an effective amount of at least one additional therapeutic agent, e.g., as described below. In a further embodiment, the medicament is for inhibiting angiogenesis. In a further embodiment, the medicament is for use in a method of inhibiting angiogenesis in an individual comprising administering to the individual an amount effective of the medicament to inhibit angiogenesis. An "individual" according to any of the above embodiments may be a human.

In a further aspect, the invention provides a method for treating an ocular vascular disease, preferably macular degeneration. In one embodiment, the method comprises administering to an individual having such an ocular vascular disease, preferably macular degeneration, an effective amount of a multispecific antibody. In one such embodiment, the method further comprises administering to the individual an effective amount of at least one additional therapeutic agent, as described below. An "individual" according to any of the above embodiments may be a human.

In a further aspect, the invention provides a method for inhibiting angiogenesis in an individual. In one embodiment, the method comprises administering to the individual an effective amount of a multispecific antibody to inhibit angiogenesis. In one embodiment, an "individual" is a human.

In a further aspect, the invention provides pharmaceutical formulations comprising any of the multispecific antibodies provided herein, e.g., for use in any of the above therapeutic methods. In one embodiment, a pharmaceutical formulation comprises any of the multispecific antibodies provided herein and a pharmaceutically acceptable carrier. In another embodiment, a pharmaceutical formulation comprises any of the multispecific antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent. In certain embodiments, an additional therapeutic agent is an anti-VEGF antibody or an anti-ANG2 antibody.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the multispecific antibody and administration of an additional therapeutic agent occur within about one month, or within about one, two or three weeks, or within about one, two, three, four, five, or six days, of each other.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.5 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to a multispecific antibody.

III. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solu-

IV. Specific Embodiments

1. A bispecific antibody that specifically binds to two different antigens selected from the group consisting of human ANG2, human VEGF, human IL-1beta and human PDGF-B.
2. A bispecific antibody that specifically binds to i) human ANG2, and ii) human IL-1beta or human PDGF-B.
3. A bispecific antibody that specifically binds to two i) human VEGF, and ii) human IL-1beta or human PDGF-B.
4. A bispecific antibody that specifically binds to human IL-1beta and human PDGF-B.
5. The antibody according to any one of embodiments 1 to 4, wherein the antibody specifically binds to human IL-1beta and comprises
   a) a heavy chain variable domain comprising
      (a) a HVR-H1 comprising the amino acid sequence of SEQ ID NO: 02, (b) a HVR-H2 comprising the amino acid sequence of SEQ ID NO: 04, and (c) a HVR-H3 comprising the amino acid sequence of SEQ ID NO: 05, or
      (a) a HVR-H1 comprising the amino acid sequence of SEQ ID NO: 07, (b) a HVR-H2 comprising the amino acid sequence of SEQ ID NO: 08, and (c) a HVR-H3 comprising the amino acid sequence of SEQ ID NO: 10, or
      (a) a HVR-H1 comprising the amino acid sequence of SEQ ID NO: 12, (b) a HVR-H2 comprising the amino acid sequence of SEQ ID NO: 13, and (c) a HVR-H3 comprising the amino acid sequence of SEQ ID NO: 15,
      and
      a light chain variable domain comprising (a) a HVR-L1 comprising the amino acid sequence of SEQ ID NO: 17; (b) a HVR-L2 comprising the amino acid sequence of SEQ ID NO: 18; and (c) HVR-L3 comprising the amino acid sequence of SEQ ID NO: 19,
      or
   a) a heavy chain variable domain comprising a HVR-H1 comprising the amino acid sequence of SEQ ID NO: 21, (b) a HVR-H2 comprising the amino acid sequence of SEQ ID NO: 22, and (c) a HVR-H3 comprising the amino acid sequence of SEQ ID NO: 24, and a light chain variable domain comprising (a) a HVR-L1 comprising the amino acid sequence of SEQ ID NO: 26; (b) a HVR-L2 comprising the amino acid sequence of SEQ ID NO: 27; and (c) HVR-L3 comprising the amino acid sequence of SEQ ID NO: 28.
6. The antibody according to any one of embodiments 1 to 5, wherein the antibody specifically binds to human IL-1beta and comprises
   a) a heavy chain variable domain comprising (a) a HVR-H1 comprising the amino acid sequence of SEQ ID NO: 07, (b) a HVR-H2 comprising the amino acid sequence of SEQ ID NO: 08, and (c) a HVR-H3 comprising the amino acid sequence of SEQ ID NO: 10,
      and
      a light chain variable domain comprising (a) a HVR-L1 comprising the amino acid sequence of SEQ ID NO: 17; (b) a HVR-L2 comprising the amino acid sequence of SEQ ID NO: 18; and (c) HVR-L3 comprising the amino acid sequence of SEQ ID NO: 19.
7. The antibody according to any one of embodiments 1 to 6, wherein the antibody specifically binds to human PDGF-B and comprises
   a) a heavy chain variable domain comprising (a) a HVR-H1 comprising the amino acid sequence of SEQ ID NO: 30, (b) a HVR-H2 comprising the amino acid sequence of SEQ ID NO: 31, and (c) a HVR-H3 comprising the amino acid sequence of SEQ ID NO: 33, and a light chain variable domain comprising (a) a HVR-L1 comprising the amino acid sequence of SEQ ID NO: 35; (b) a HVR-L2 comprising the amino acid sequence of SEQ ID NO: 36; and (c) HVR-L3 comprising the amino acid sequence of SEQ ID NO: 37,
      or
   b) a heavy chain variable domain comprising (a) a HVR-H1 comprising the amino acid sequence of SEQ ID NO: 39, (b) a HVR-H2 comprising the amino acid sequence of SEQ ID NO: 40, and (c) a HVR-H3 comprising the amino acid sequence of SEQ ID NO: 42, and a light chain variable domain comprising (a) a HVR-L1 comprising the amino acid sequence of SEQ ID NO: 44; (b) a HVR-L2 comprising the amino acid sequence of SEQ ID NO: 45; and (c) HVR-L3 comprising the amino acid sequence of SEQ ID NO: 46,
      or
   c) a heavy chain variable domain comprising (a) a HVR-H1 comprising the amino acid sequence of SEQ ID NO: 48, (b) a HVR-H2 comprising the amino acid sequence of SEQ ID NO: 49, and (c) a HVR-H3 comprising the amino acid sequence of SEQ ID NO: 51, and a light chain variable domain comprising (a) a HVR-L1 comprising the amino acid sequence of SEQ ID NO: 53; (b) a HVR-L2 comprising the amino acid sequence of SEQ ID NO: 54; and (c) HVR-L3 comprising the amino acid sequence of SEQ ID NO: 55.
8. The antibody according to any one of embodiments 1 to 7, wherein the antibody specifically binds to human PDGF-B and comprises a heavy chain variable domain comprising (a) a HVR-H1 comprising the amino acid sequence of SEQ ID NO: 30, (b) a HVR-H2 comprising the amino acid sequence of SEQ ID NO: 31, and (c) a HVR-H3 comprising the amino acid sequence of SEQ ID NO: 33, and a light chain variable domain comprising (a) a HVR-L1 comprising the amino acid sequence of SEQ ID NO: 35; (b) a HVR-L2 comprising the amino acid sequence of SEQ ID NO: 36; and (c) HVR-L3 comprising the amino acid sequence of SEQ ID NO: 37.
9. The antibody according to any one of embodiments 1 to 7, wherein the antibody specifically binds to human PDGF-B and comprises a heavy chain variable domain comprising (a) a HVR-H1 comprising the amino acid sequence of SEQ ID NO: 39, (b) a HVR-H2 comprising the amino acid sequence of SEQ ID NO: 40, and (c) a HVR-H3 comprising the amino acid sequence of SEQ ID NO: 42, and a light chain variable domain comprising (a) a HVR-L1 comprising the amino acid sequence of SEQ ID NO: 44; (b) a HVR-L2 comprising the amino acid sequence of SEQ ID NO: 45; and (c) HVR-L3 comprising the amino acid sequence of SEQ ID NO: 46.
10. The antibody according to any one of embodiments 1 to 7, wherein the antibody specifically binds to human PDGF-B and comprises a heavy chain variable domain comprising (a) a HVR-H1 comprising the amino acid sequence of SEQ ID NO: 48, (b) a HVR-H2 comprising the amino acid sequence of SEQ ID NO: 49, and (c) a HVR-H3 comprising the amino acid sequence of SEQ ID NO: 51, and a light chain variable domain comprising (a) a HVR-L1 comprising the amino acid sequence of SEQ ID NO: 53; (b) a HVR-L2 comprising the amino acid sequence of SEQ ID NO: 54; and (c) HVR-L3 comprising the amino acid sequence of SEQ ID NO: 55.

11. The antibody according to any one of embodiments 1, 2 and 5 to 10, wherein the antibody specifically binds to human ANG2 and comprises
  a) a heavy chain variable domain comprising (a) a HVR-H1 comprising the amino acid sequence of SEQ ID NO: 57, (b) a HVR-H2 comprising the amino acid sequence of SEQ ID NO: 58, and (c) a HVR-H3 comprising the amino acid sequence of SEQ ID NO: 60, and a light chain variable domain comprising (a) a HVR-L1 comprising the amino acid sequence of SEQ ID NO: 62; (b) a HVR-L2 comprising the amino acid sequence of SEQ ID NO: 63; and (c) HVR-L3 comprising the amino acid sequence of SEQ ID NO: 64, or
  b) a heavy chain variable domain comprising (a) a HVR-H1 comprising the amino acid sequence of SEQ ID NO: 66, (b) a HVR-H2 comprising the amino acid sequence of SEQ ID NO: 67, and (c) a HVR-H3 comprising the amino acid sequence of SEQ ID NO: 69, and a light chain variable domain comprising (a) a HVR-L1 comprising the amino acid sequence of SEQ ID NO: 71; (b) a HVR-L2 comprising the amino acid sequence of SEQ ID NO: 72; and (c) HVR-L3 comprising the amino acid sequence of SEQ ID NO: 73, or
  c) a heavy chain variable domain comprising (a) a HVR-H1 comprising the amino acid sequence of SEQ ID NO: 75, (b) a HVR-H2 comprising the amino acid sequence of SEQ ID NO: 76, and (c) a HVR-H3 comprising the amino acid sequence of SEQ ID NO: 78, and a light chain variable domain comprising (a) a HVR-L1 comprising the amino acid sequence of SEQ ID NO: 80; (b) a HVR-L2 comprising the amino acid sequence of SEQ ID NO: 81; and (c) HVR-L3 comprising the amino acid sequence of SEQ ID NO: 82, or
  d) a heavy chain variable domain comprising (a) a HVR-H1 comprising the amino acid sequence of SEQ ID NO: 84, (b) a HVR-H2 comprising the amino acid sequence of SEQ ID NO: 85, and (c) a HVR-H3 comprising the amino acid sequence of SEQ ID NO: 87, and a light chain variable domain comprising (a) a HVR-L1 comprising the amino acid sequence of SEQ ID NO: 89; (b) a HVR-L2 comprising the amino acid sequence of SEQ ID NO: 90; and (c) HVR-L3 comprising the amino acid sequence of SEQ ID NO: 91.

12. The antibody according to any one of embodiments 1, 2 and 5 to 11, wherein the antibody specifically binds to human ANG2 and comprises a heavy chain variable domain comprising (a) a HVR-H1 comprising the amino acid sequence of SEQ ID NO: 75, (b) a HVR-H2 comprising the amino acid sequence of SEQ ID NO: 76, and (c) a HVR-H3 comprising the amino acid sequence of SEQ ID NO: 78, and a light chain variable domain comprising (a) a HVR-L1 comprising the amino acid sequence of SEQ ID NO: 80; (b) a HVR-L2 comprising the amino acid sequence of SEQ ID NO: 81; and (c) HVR-L3 comprising the amino acid sequence of SEQ ID NO: 82.

13. The antibody according to any one of embodiments 1, 3 and 5 to 12, wherein the antibody specifically binds to human VEGF and comprises
  a) the HVR-H1, HVR-H2 and HVR-H3 as contained in the heavy chain variable domain of SEQ ID NO: 107 and the HVR-L1, HVR-L2 and HVR-L3 as contained in the heavy chain variable domain of SEQ ID NO: 108,
  or
  b) the HVR-H1, HVR-H2 and HVR-H3 as contained in the heavy chain variable domain of SEQ ID NO: 109 and the HVR-L1, HVR-L2 and HVR-L3 as contained in the heavy chain variable domain of SEQ ID NO: 110.

14. The antibody according to any one of embodiments 1, 3 and 5 to 13, wherein the antibody specifically binds to human VEGF and comprises the HC and LC sequences in SEQ ID NO: 107 and SEQ ID NO: 108, respectively, including post-translational modifications of those sequences.

15. The antibody according to any one of embodiments 1, 3 and 5 to 13, wherein the antibody specifically binds to human VEGF and comprises the HC and LC sequences in SEQ ID NO: 109 and SEQ ID NO: 110, respectively, including post-translational modifications of those sequences.

16. The antibody according to any one of embodiments 1 to 15, wherein the antibody is of the human subclass IgG1 or the human subclass IgG4.

17. The antibody according to any one of embodiments 1 to 16, wherein the antibody is of the human subclass IgG1 with a kappa light chain.

18. The antibody according to any one of embodiments 1 to 17, wherein the antibody is a monoclonal antibody.

19. The antibody according to any one of embodiments 1 to 18, wherein the antibody is a bispecific antibody.

20. The antibody according to any one of embodiments 1 to 19, wherein the antibody is a bivalent, bispecific antibody comprising
  a) a first light chain and a first heavy chain of an antibody specifically binding to a first antigen, and
  b) a second light chain and a second heavy chain of an antibody specifically binding to a second antigen, wherein the variable domains VL and VH of the second light chain and the second heavy chain are replaced by each other.

21. The antibody according to embodiment 20, wherein the antibody comprises
  i) in the constant domain CL of the first light chain under a) the amino acid at position 124 is substituted independently by lysine (K), arginine (R) or histidine (H) (numbering according to Kabat) (in one preferred embodiment independently by lysine (K) or arginine (R)), and wherein in the constant domain CH1 of the first heavy chain under a) the amino acid at position 147 or the amino acid at position 213 is substituted independently by glutamic acid (E) or aspartic acid (D) (numbering according to Kabat EU index),
  or
  ii) in the constant domain CL of the second light chain under b) the amino acid at position 124 is substituted independently by lysine (K), arginine (R) or histidine (H) (numbering according to Kabat) (in one preferred embodiment independently by lysine (K) or arginine (R)), and wherein in the constant domain CH1 of the second heavy chain under b) the amino acid at position 147 or the amino acid at position 213 is substituted independently by glutamic acid (E) or aspartic acid (D) (numbering according to Kabat EU index).

22. The antibody according to any one of embodiment 20 to 21, wherein the antibody comprises in the constant domain CL of the second heavy chain the amino acids at position 124 and 123 are substituted by K (numbering according to Kabat EU index).

23. The antibody according to any one of embodiment 20 to 22, wherein the antibody comprises in the constant domain CH1 of the second light chain the amino acids at position 147 and 213 are substituted by E (numbering according to EU index of Kabat).

24. The antibody according to any one of embodiment 20 to 23, wherein the antibody comprises in the constant domain CL of the first light chain the amino acids at position 124 and 123 are substituted by K, and in the constant domain CH1 of the first heavy chain the amino acids at position 147 and 213 are substituted by E (numbering according to Kabat EU index).

25. The antibody according to any one of embodiment 20 to 24, wherein the antibody comprises in the constant domain CL of the second heavy chain the amino acids at position 124 and 123 are substituted by K, and wherein in the constant domain CH1 of the second light chain the amino acids at position 147 and 213 are substituted by E, and in the variable domain VL of the first light chain the amino acid at position 38 is substituted by K, in the variable domain VH of the first heavy chain the amino acid at position 39 is substituted by E, in the variable domain VL of the second heavy chain the amino acid at position 38 is substituted by K, and in the variable domain VH of the second light chain the amino acid at position 39 is substituted by E (numbering according to Kabat EU index).

26. The antibody according to any one of embodiments 1 to 19, wherein the antibody is a bivalent, bispecific antibody, comprising
    a) a first light chain and a first heavy chain of an antibody specifically binding to a first antigen, and
    b) a second light chain and a second heavy chain of an antibody specifically binding to a second antigen, wherein the variable domains VL and VH of the second light chain and the second heavy chain are replaced by each other, and wherein the constant domains CL and CH1 of the second light chain and the second heavy chain are replaced by each other.

27. The antibody according to any one of embodiments 1 to 19, wherein the antibody is a bivalent, bispecific antibody, comprising
    a) a first light chain and a first heavy chain of an antibody specifically binding to a first antigen, and
    b) a second light chain and a second heavy chain of an antibody specifically binding to a second antigen, wherein the constant domains CL and CH1 of the second light chain and the second heavy chain are replaced by each other.

28. The antibody according to any one of embodiments 1 to 19, wherein the antibody is a multispecific antibody comprising
    a) a full length antibody specifically binding to a first antigen and consisting of two antibody heavy chains and two antibody light chains, and
    b) one, two, three or four single chain Fab fragments specifically binding to one to four further antigens (i.e. a second and/or third and/or fourth and/or fifth antigen, preferably specifically binding to one further antigen, i.e. a second antigen),
    wherein said single chain Fab fragments under b) are fused to said full length antibody under a) via a peptidic linker at the C- or N-terminus of the heavy or light chain of said full length antibody.

29. The antibody according to any one of embodiments 1 to 19, wherein the antibody is a trivalent, bispecific antibody comprising
    a) a full length antibody specifically binding to a first antigen and consisting of two antibody heavy chains and two antibody light chains,
    b) a first polypeptide consisting of
       ba) an antibody heavy chain variable domain (VH),
       or
       bb) an antibody heavy chain variable domain (VH) and an antibody constant domain 1 (CH1),
       wherein said first polypeptide is fused with the N-terminus of its VH domain via a peptidic linker to the C-terminus of one of the two heavy chains of said full length antibody,
    c) a second polypeptide consisting of
       ca) an antibody light chain variable domain (VL),
       or
       cb) an antibody light chain variable domain (VL) and an antibody light chain constant domain (CL),
       wherein said second polypeptide is fused with the N-terminus of the VL domain via a peptidic linker to the C-terminus of the other of the two heavy chains of said full length antibody,
    and
    wherein the antibody heavy chain variable domain (VH) of the first polypeptide and the antibody light chain variable domain (VL) of the second polypeptide together form an antigen-binding site specifically binding to a second antigen.

30. The antibody according to embodiment 29, wherein the antibody heavy chain variable domain (VH) of the polypeptide under b) and the antibody light chain variable domain (VL) of the polypeptide under c) are linked and stabilized via an interchain disulfide bridge by introduction of a disulfide bond between the following positions:
    i) heavy chain variable domain position 44 to light chain variable domain position 100,
    or
    ii) heavy chain variable domain position 105 to light chain variable domain position 43,
    or
    iii) heavy chain variable domain position 101 to light chain variable domain position 100 (numbering always according to Kabat EU index).

31. The antibody according to any one of embodiments 1 to 19, wherein the antibody is a trispecific or tetraspecific antibody, comprising
    a) a first light chain and a first heavy chain of a full length antibody which specifically binds to a first antigen, and
    b) a second (modified) light chain and a second (modified) heavy chain of a full length antibody which specifically binds to a second antigen, wherein the variable domains VL and VH are replaced by each other, and/or wherein the constant domains CL and CH1 are replaced by each other, and
    c) wherein one to four antigen binding peptides which specifically bind to one or two further antigens (i.e. to a third and/or fourth antigen) are fused via a peptidic linker to the C- or N-terminus of the light chains or heavy chains of a) and/or b).

32. The antibody according to any one of embodiments 1 to 19, wherein the antibody is a bispecific, tetravalent antibody comprising
   a) two light chains and two heavy chains of an antibody, which specifically bind to a first antigen (and comprise two Fab fragments),
   b) two additional Fab fragments of an antibody, which specifically bind to a second antigen, wherein said additional Fab fragments are fused both via a peptidic linker either to the C- or N-termini of the heavy chains of a),
   and
      wherein in the Fab fragments the following modifications were performed
      i) in both Fab fragments of a), or in both Fab fragments of b), the variable domains VL and VH are replaced by each other, and/or the constant domains CL and CH1 are replaced by each other,
      or
      ii) in both Fab fragments of a) the variable domains VL and VH are replaced by each other, and the constant domains CL and CH1 are replaced by each other, and
         in both Fab fragments of b) the variable domains VL and VH are replaced by each other, or the constant domains CL and CH1 are replaced by each other,
      or
      iii) in both Fab fragments of a) the variable domains VL and VH are replaced by each other, or the constant domains CL and CH1 are replaced by each other, and
         in both Fab fragments of b) the variable domains VL and VH are replaced by each other, and the constant domains CL and CH1 are replaced by each other,
      or
      iv) in both Fab fragments of a) the variable domains VL and VH are replaced by each other, and in both Fab fragments of b) the constant domains CL and CH1 are replaced by each other,
      or
      v) in both Fab fragments of a) the constant domains CL and CH1 are replaced by each other, and in both Fab fragments of b) the variable domains VL and VH are replaced by each other.

33. The antibody according to any one of embodiments 1 to 19, wherein the antibody is a bispecific, tetravalent antibody comprising:
   a) a (modified) heavy chain of a first antibody, which specifically binds to a first antigen and comprises a first VH-CH1 domain pair, wherein to the C-terminus of said heavy chain the N-terminus of a second VH-CH1 domain pair of said first antibody is fused via a peptidic linker,
   b) two light chains of said first antibody of a),
   c) a (modified) heavy chain of a second antibody, which specifically binds to a second antigen and comprises a first VH-CL domain pair, wherein to the C-terminus of said heavy chain the N-terminus of a second VH-CL domain pair of said second antibody is fused via a peptidic linker, and
   d) two (modified) light chains of said second antibody of c), each comprising a CL-CH1 domain pair.

34. The antibody according to any one of embodiments 1 to 19, wherein the antibody is a bispecific antibody comprising
   a) the heavy chain and the light chain of a first full length antibody that specifically binds to a first antigen, and
   b) the heavy chain and the light chain of a second full length antibody that specifically binds to a second antigen, wherein the N-terminus of the heavy chain is connected to the C-terminus of the light chain via a peptidic linker.

35. The antibody according to any one of embodiments 1 to 19, wherein the antibody is a bispecific antibody comprising
   a) a full length antibody specifically binding to a first antigen and consisting of two antibody heavy chains and two antibody light chains, and
   b) an Fv fragment specifically binding to a second antigen comprising a $VH^2$ domain and a $VL^2$ domain, wherein both domains are connected to each other via a disulfide bridge,
   wherein only either the $VH^2$ domain or the $VL^2$ domain is fused via a peptidic linker to the heavy or light chain of the full length antibody specifically binding to a first antigen.

36. The antibody according to any one of embodiments 1 to 35, wherein the antibody comprises a first Fc-region polypeptide and a second Fc-region polypeptide, and wherein
   i) the first Fc-region polypeptide is selected from the group comprising
      human IgG1 Fc-region polypeptide,
      human IgG2 Fc-region polypeptide,
      human IgG3 Fc-region polypeptide,
      human IgG4 Fc-region polypeptide,
      human IgG1 Fc-region polypeptide with the mutations L234A, L235A,
      human IgG1 Fc-region polypeptide with the mutations Y349C, T366S, L368A, Y407V,
      human IgG1 Fc-region polypeptide with the mutations S354C, T366S, L368A, Y407V,
      human IgG1 Fc-region polypeptide with the mutations L234A, L235A, Y349C, T366S, L368A, Y407V,
      human IgG1 Fc-region polypeptide with the mutations L234A, L235A, S354C, T366S, L368A, Y407V,
      human IgG1 Fc-region polypeptide with the mutations P329G,
      human IgG1 Fc-region polypeptide with the mutations L234A, L235A, P329G,
      human IgG1 Fc-region polypeptide with the mutations P329G, Y349C, T366S, L368A, Y407V,
      human IgG1 Fc-region polypeptide with the mutations P329G, S354C, T366S, L368A, Y407V,
      human IgG1 Fc-region polypeptide with the mutations L234A, L235A, P329G, Y349C, T366S, L368A, Y407V,
      human IgG1 Fc-region polypeptide with the mutations L234A, L235A, P329G, S354C, T366S, L368A, Y407V,
      human IgG4 Fc-region polypeptide with the mutations S228P, L235E,
      human IgG4 Fc-region polypeptide with the mutations S228P, L235E, P329G,
      human IgG4 Fc-region polypeptide with the mutations Y349C, T366S, L368A, Y407V,
      human IgG4 Fc-region polypeptide with the mutations S354C, T366S, L368A, Y407V, human IgG4 Fc-region polypeptide with the mutations S228P, L235E, Y349C, T366S, L368A, Y407V,
human IgG4 Fc-region polypeptide with the mutations S228P, L235E, S354C, T366S, L368A, Y407V,
human IgG4 Fc-region polypeptide with the mutations P329G,
human IgG4 Fc-region polypeptide with the mutations P329G, Y349C, T366S, L368A, Y407V,
human IgG4 Fc-region polypeptide with the mutations P329G, S354C, T366S, L368A, Y407V,
human IgG4 Fc-region polypeptide with the mutations S228P, L235E, P329G, Y349C, T366S, L368A, Y407V,
human IgG4 Fc-region polypeptide with the mutations S228P, L235E, P329G, S354C, T366S, L368A, Y407V,
human IgG1, IgG2 or IgG4 with the mutations K392D, and
human IgG3 with the mutation N392D,
and
ii) the second Fc-region polypeptide is selected from the group comprising
human IgG1 Fc-region polypeptide,
human IgG2 Fc-region polypeptide,
human IgG3 Fc-region polypeptide,
human IgG4 Fc-region polypeptide,
human IgG1 Fc-region polypeptide with the mutations L234A, L235A,
human IgG1 Fc-region polypeptide with the mutations S354C, T366W,
human IgG1 Fc-region polypeptide with the mutations Y349C, T366W,
human IgG1 Fc-region polypeptide with the mutations L234A, L235A, S354C, T366W,
human IgG1 Fc-region polypeptide with the mutations L234A, L235A, Y349C, T366W,
human IgG1 Fc-region polypeptide with the mutations P329G,
human IgG1 Fc-region polypeptide with the mutations L234A, L235A, P329G,
human IgG1 Fc-region polypeptide with the mutations P329G, S354C, T366W,
human IgG1 Fc-region polypeptide with the mutations P329G, Y349C, T366W,
human IgG1 Fc-region polypeptide with the mutations L234A, L235A, P329G, S354C, T366W,
human IgG1 Fc-region polypeptide with the mutations L234A, L235A, P329G, Y349C, T366W,
human IgG4 Fc-region polypeptide with the mutations S228P, L235E,
human IgG4 Fc-region polypeptide with the mutations S228P, L235E, P329G,
human IgG4 Fc-region polypeptide with the mutations S354C, T366W,
human IgG4 Fc-region polypeptide with the mutations Y349C, T366W,
human IgG4 Fc-region polypeptide with the mutations S228P, L235E, S354C, T366W,
human IgG4 Fc-region polypeptide with the mutations S228P, L235E, Y349C, T366W,
human IgG4 Fc-region polypeptide with the mutations P329G,
human IgG4 Fc-region polypeptide with the mutations P329G, S354C, T366W,
human IgG4 Fc-region polypeptide with the mutations P329G, Y349C, T366W,
human IgG4 Fc-region polypeptide with the mutations S228P, L235E, P329G, S354C, T366W,
human IgG4 Fc-region polypeptide with the mutations S228P, L235E, P329G, Y349C, T366W,
human IgG1 with the mutations D399K, D356K, and/or E357K, and
human IgG2, IgG3 or IgG4 with the mutations D399K, E356K, and/or E357K.

37. The antibody according to any one of embodiments 1 to 35, wherein the antibody comprises a first Fc-region polypeptide and a second Fc-region polypeptide, and wherein
i) the first Fc-region polypeptide is a human IgG1 Fc-region polypeptide and the second Fc-region polypeptide is a human IgG1 Fc-region polypeptide, or
ii) the first Fc-region polypeptide is a human IgG1 Fc-region polypeptide with the mutations L234A, L235A and the second Fc-region polypeptide is a human IgG1 Fc-region polypeptide with the mutations L234A, L235A, or
iii) the first Fc-region polypeptide is a human IgG1 Fc-region polypeptide with the mutations L234A, L235A, P329G and the second Fc-region polypeptide is a human IgG1 Fc-region polypeptide with the mutations L234A, L235A, P329G, or
iv) the first Fc-region polypeptide is a human IgG1 Fc-region polypeptide with the mutations L234A, L235A, S354C, T366W and the second Fc-region polypeptide is a human IgG1 Fc-region polypeptide with the mutations L234A, L235A, Y349C, T366S, L368A, Y407V, or
v) the first Fc-region polypeptide is a human IgG1 Fc-region polypeptide with the mutations L234A, L235A, P329G, S354C, T366W and the second Fc-region polypeptide is a human IgG1 Fc-region polypeptide with the mutations L234A, L235A, P329G, Y349C, T366S, L368A, Y407V, or
vi) the first Fc-region polypeptide is a human IgG4 Fc-region polypeptide and the second Fc-region polypeptide is a human IgG4 Fc-region polypeptide, or
vii) the first Fc-region polypeptide is a human IgG4 Fc-region polypeptide with the mutations S228P, L235E and the second Fc-region polypeptide is a human IgG4 Fc-region polypeptide with the mutations S228P, L235E, or
viii) the first Fc-region polypeptide is a human IgG4 Fc-region polypeptide with the mutations S228P, L235E, P329G and the second Fc-region polypeptide is a human IgG4 Fc-region polypeptide with the mutations S228P, L235E, P329G, or
ix) the first Fc-region polypeptide is a human IgG4 Fc-region polypeptide with the mutations S228P, L235E, S354C, T366W and the second Fc-region polypeptide is a human IgG4 Fc-region polypeptide with the mutations S228P, L235E, Y349C, T366S, L368A, Y407V, or
x) the first Fc-region polypeptide is a human IgG4 Fc-region polypeptide with the mutations S228P, L235E, P329G, S354C, T366W and the second Fc-region polypeptide is a human IgG4 Fc-region polypeptide with the mutations S228P, L235E, P329G, Y349C, T366S, L368A, Y407V.

38. The antibody according to any one of embodiments 1 to 37, wherein the antibody comprises a first Fc-region polypeptide and a second Fc-region polypeptide, and wherein the antibody comprises the combination of mutations
 i) I253A, H310A, and H435A, or
 ii) H310A, H433A, and Y436A, or
 iii) L251D, L314D, and L432D, or
 iv) combinations of i) to iii)
 in the first Fc-region polypeptide and in the second Fc-region polypeptide.

39. The antibody according to any one of embodiments 1 to 37, wherein the antibody comprises a first Fc-region polypeptide and a second Fc-region polypeptide, and wherein
 a) the first and a second Fc-region polypeptide are both of human IgG1 or human IgG4 subclass (derived from human origin) and comprise one or two of the mutations selected from i) the group I253A, H310A and H435A, or ii) the group H310A, H433A and Y436A, or iii) the group L251D, L314D and L432D (numbering according to Kabat EU index numbering system) in the first Fc-region polypeptide and one or two of the mutations selected from the group comprising the mutations L251D, I253A, H310A, L314D, L432D, H433A, H435A and Y436A (numbering according to Kabat EU index numbering system) in the second Fc-region polypeptide so that all of the mutations in the first and the second Fc-region polypeptide when taken together result in that the mutations i) I253A, H310A and H435A, or ii) H310A, H433A and Y436A, or iii) L251D, L314D and L432D are comprised in the variant (human) IgG class Fc-region,
 or
 b) the first and a second Fc-region polypeptide both of human IgG1 or human IgG4 subclass (i.e. derived from human origin) and both comprise the mutations I253A/H310A/H435A or H310A/H433A/Y436A or L251D/L314D/L432D or combinations thereof in the Fc-region (numbering according to Kabat EU index numbering system), whereby either all mutations are in the first or the second Fc-region polypeptide, or one or two mutations are in the first Fc-region polypeptide and one or two mutations are in the second Fc-region polypeptide so that all of the mutations in the first and the second Fc-region polypeptide when taken together result in that the mutations i) I253A, H310A and H435A, or ii) H310A, H433A and Y436A, or iii) L251D, L314D and L432D are comprised in the Fc-region,
 or
 c) the first and a second Fc-region polypeptide both of human IgG1 or human IgG4 subclass (i.e. derived from human origin) and comprise the mutations I253A/H310A/H435A or H310A/H433A/Y436A or L251D/L314D/L432D in the first as well as in the second Fc-region polypeptide (numbering according to Kabat EU index numbering system), or comprises the combinations of the mutations I253A/H310A/H435A in the first Fc-region polypeptide and the combination of the mutations H310A/H433A/Y436A in the second Fc-region polypeptide (numbering according to Kabat EU index numbering system).

40. The antibody according to any one of embodiments 1 to 37, wherein the antibody comprises a first Fc-region polypeptide and a second Fc-region polypeptide, and wherein
 a) the first variant Fc-region polypeptide is derived from a first parent IgG class Fc-region polypeptide and the second variant Fc-region polypeptide is derived from a second parent IgG class Fc-region polypeptide, whereby the first parent IgG class Fc-region polypeptide is identical to or different from the second parent IgG class Fc-region polypeptide, and
 b) the first variant Fc-region polypeptide differs from the second variant Fc-region polypeptide in one or more amino acid residues other than those amino acid residues in which the first parent IgG class Fc-region polypeptide differs from the second parent IgG class Fc-region polypeptide, and
 c) the IgG class Fc-region comprising the first variant Fc-region polypeptide and the second variant Fc-region polypeptide has an affinity to a human Fc-receptor that is different than that of an IgG class Fc-region comprising the first parent IgG class Fc-region polypeptide of a) and the second parent IgG class Fc-region polypeptide of a),
 wherein either the first Fc-region polypeptide or the second Fc-region polypeptide or both Fc-region polypeptides comprise independently of each other one of the following mutations or combination of mutations:
 T307H, or
 Q311H, or
 E430 H, or
 N434H, or
 T307H and Q311H, or
 T307H and E430H, or
 T307H and N434A, or
 T307H and N434H, or
 T307Q and Q311H, or
 T307Q and E430H, or
 T307Q and N434H, or
 T307H and Q311H and E430H and N434A, or
 T307H and Q311H and E430H and N434H, or
 T307H and Q311H and E430H and N434Y, or
 T307Q and Q311H and E430H and N434A, or
 T307Q and Q311H and E430H and N434H, or
 T307Q and Q311H and E430H and N434Y, or
 T307Q and V308P and N434Y and Y436H, or
 T307H and M252Y and S254T and T256E, or
 T307Q and M252Y and S254T and T256E, or
 Q311H and M252Y and S254T and T256E, or
 E430 H and M252Y and S254T and T256E, or
 N434H and M252Y and S254T and T256E, or
 T307H and Q311H and M252Y and S254T and T256E, or
 T307H and E430H and M252Y and S254T and T256E, or
 T307H and N434A and M252Y and S254T and T256E, or
 T307H and N434H and M252Y and S254T and T256E, or
 T307Q and Q311H and M252Y and S254T and T256E, or
 T307Q and E430H and M252Y and S254T and T256E, or
 T307Q and N434H and M252Y and S254T and T256E, or
 T307H and Q311H and E430H and N434A and M252Y and S254T and T256E, or
 T307H and Q311H and E430H and N434H and M252Y and S254T and T256E, or
 T307H and Q311H and E430H and N434Y and M252Y and S254T and T256E, or
 T307Q and Q311H and E430H and N434A and M252Y and S254T and T256E, or T307Q and Q311H and E430H and N434H and M252Y and S254T and T256E, or T307Q and Q311H and E430H and N434Y and M252Y and S254T and T256E, or T307Q and V308P and N434Y and Y436H and M252Y and S254T and T256E.

41. The antibody according to any one of embodiments 1 to 37, wherein the antibody comprises a first Fc-region polypeptide and a second Fc-region polypeptide, and wherein the first Fc-region polypeptide comprises the mutations Y349C, T366S, L368A and Y407V (hole-chain) and the second Fc-region polypeptide comprises the mutations S354C and T366W (knob-chain), and wherein the first Fc-region polypeptide (hole-chain) comprises the mutations
  i) I253A or I253G, and
  ii) L314A or L314G or L314D, and wherein the first Fc-region polypeptide and the second Fc-region polypeptide are connected by one or more disulfide bridges, and wherein the CH3-domain of the first polypeptide and the CH3-domain of the second polypeptide both bind or both do not bind to protein A (numbering according to the Kabat EU index).

42. The antibody according to embodiment 41, wherein the antibody comprises the mutations
  i) I253A or I253G, and
  ii) L314A or L314G or L314D, and
  iii) T250Q, and/or
  iv) T256E or T256A.

43. The antibody according to any one of embodiments 41 to 42, wherein the antibody comprises the mutations
  i) I253A or I253G, and
  ii) L314A or L314G or L314D, and
  iii) optionally a) T250Q, and/or T256E or T256A, and.
  iv) a) L251A or L251G or L251D, and/or b) H310A or H310G.

44. The antibody according to any one of embodiments 41 to 43, wherein the antibody comprises the mutation
  i) I253A or I253G, and
  ii) L314A or L314G or L314D, and
  iii) a) T250Q, and/or T256E or T256A, and.
  iv) a) L251A or L251G or L251D, and/or b) H310A or H310G.
  v) optionally a) T307A or T307H or T307Q or T307P, and/or b) Q311H, and/or c) M252Y or d) S254T.

45. The antibody according to any one of embodiments 41 to 44, wherein the antibody comprises the mutation
  i) T250Q, and/or
  ii) M252Y, and/or
  iii) S254T, and/or
  iv) T256E or T256A, and/or
  v) T307A or T307H or T307Q or T307P, and/or
  vi) Q311H.

46. An antibody according to any one of embodiments 1 to 45 for use as a medicament.

47. An antibody according to any one of embodiments 1 to 45 for use in the treatment of an ocular vascular disease.

48. Use of an antibody according to any one of embodiments 1 to 45 for the treatment of eye diseases, especially of ocular vascular diseases.

49. An antibody according to any one of embodiments 1 to 45 for use in treating an eye disease.

50. An antibody according to any one of embodiments 1 to 45 for use in treating eye diseases, especially ocular vascular diseases.

51. A method of treating an individual having an ocular vascular disease comprising administering to the individual an effective amount of an antibody according to any one of embodiments 1 to 45.

52. A pharmaceutical formulation comprising the antibody according to any one of embodiments 1 to 45.

53. A pharmaceutical formulation comprising the antibody according to any one of embodiments 1 to 45 for use in the treatment of ocular vascular diseases.

54. Use of the antibody according to any one of embodiments 1 to 45 for the manufacture of a medicament for the treatment of ocular vascular diseases.

55. A method of treatment of patient suffering from ocular vascular diseases by administering the antibody according to any one of embodiments 1 to 45 to a patient in the need of such treatment.

56. The pharmaceutical formulation according to any one of embodiments 52 to 53, wherein the antibody is administered via intravitreal application.

57. The administering according to any one of embodiments 55 to 56, wherein the administering is an intravitreal application.

58. A nucleic acid encoding the antibody according to any one of embodiments 1 to 45.

59. A cell comprising one or more nucleic acids encoding the antibody according to any one of embodiments 1 to 45.

60. A method for producing an antibody according to any one of embodiments 1 to 45, wherein the method comprises the following steps:
  a) optionally transfecting a mammalian cell with one or more nucleic acids encoding the antibody according to any one of embodiments 1 to 45,
  b) cultivating the cell to express the antibody, and
  c) recovering the antibody from the cell or the cultivation medium and thereby producing the antibody.

V. Examples

The following are examples of methods and compositions of the invention. It is understood that various other embodiments may be practiced, given the general description provided above.

Example 1. Original Generation and Characterization of Murine Anti-IL1Beta Antibody 1134

Materials—BALB/c female mice were obtained from Banting and Kingman (Freemont, Calif.). Complete and Incomplete Freud's Adjuvant (CFA and IFA) were from Difco (Detroit, Mich.). HB101 was from Hana Biologics, Inc. (Berkeley, Calif.). Dulbecco's Phosphate-Buffered Saline (PBS) without calcium and magnesium, and glutamine were from GIBCO Labs (Grand Island, N.Y.). Fetal bovine serum was from Hyclone Labs (Logan, Utah) and Hypoxanthine-Aminopterin-Thymidine (HAT) and Hypoxanthine-Thymidine (HT) supplements, and 50% polyethylene glycol (PEG) 1450 was from Bethesda Research Labs (Gaithersburg, Md.). Rabbit anti-mouse IgG+A+M peroxidase conjugate, streptavidin peroxidase, mouse Ig isotype identification kit and orthophenylene diamine (OPD) were from Zymed Labs (South San Francisco, Calif.). Sepharose protein-A and Sephadex G-25 were from Pharmacia (Piscataway, N.J.). Pristane (2,6,10,14-tetramethyl pentadecane) was from Aldrich Chem. Co. (Milwaukee, Wis.). $^{125}$I Bolton-Hunter reagent was from New England Nuclear (Boston, Mass.). All other chemicals were analytical grade from Sigma.

Hybridoma Production—Hybridomas to IL-1beta were produced using the method of Kohler and Milstein, supra as described by Lerner (1981) Yale J. Biol. Med., 54: 347. Twelve week old female BALB/c mice were injected intraperitoneally and in the hind footpads with 5 µg of purified MW 17,500 form of IL-1beta in CFA. Five booster injections in Incomplete Freund's Adjuvant (IFA) were given at 3-4 week intervals. Serum antibody titers were determined periodically by ELISA and after 5 injections a titer was detectable. The animal chosen for fusion received an intravenous (IV) boost of 10 µg of IL-1beta in sterile PBS. The spleen was removed 4 days later and the splenocytes fused with P3X63-Ag8.653 Myeloma cells using 50% PEG 1450. Cells were cultured in 96-well plates ($1*10^6$ cells/well) in HAT medium. Hybridoma supernatants were assayed for anti-IL-1beta activity by solid-phase antigen ELISA, solid-phase antibody RIA with $^{125}$IIL-1beta and inhibition of IL-1beta-induced thymocyte proliferation (see below). Hybridomas were cloned by limiting dilution in HAT medium with thymocytes ($5*10^5$/well) at least 3 times.

Antibody production and purification—Monoclonal antibody was produced in ascites by injecting $2*10^6$ hybridoma cells intraperitoneally into Pristane-treated mice (Kohler et al., supra). Ascites fluid was collected and antibody purified by sepharose-protein A chromatography (Goding, J. Immunol. Methods 20 (1978) 241).

Monoclonal antibody ILB1-H34 was prepared from the corresponding cell lines as described above.

ELISA of IL-1beta antibody—Vinyl assay plates (Costar) were coated with 50 µL/well of a 5 µg/mL solution of antigen diluted in PBS and incubated overnight at 4 (degree) C. Wells were countercoated using 5% non-fat dry milk/ 0.05% Thimerosal/PBS one hour at room temperature. The wells were washed with 0.1% bovine serum albumin (BSA)/ 0.05% Thimerosal/PBS and 50 µL/well of anti-IL-1beta antibodies were incubated for 2 hours at room temperature. Antibody was detected by indirect ELISA using rabbit anti-mouse IgG+A+M peroxidase conjugate and OPD substrate solution. Alternatively, purified monoclonal antibody was biotinylated (Geusdon et al., J. Histochem. Cytochem. 27 (1979) 1131) and detected using streptavidin peroxidase and OPD substrate solution. Isotype of the monoclonal antibodies was identified by indirect ELISA using a mouse Ig isotype identification kit.

Thymocyte proliferation assay—IL-1beta and PHA (10 µg/ml) were added to cultures of C3H/HeJ mouse thymocytes ($1*10^6$/well) in MEM/5% fetal bovine serum (FBS)/ 100 µg/ml gentamicin, 2-mercaptoethanol ($2*10^{-5}$ M), 25 mM Hepes medium. After 48 hours at 37° C., 0.5 µCi/well of $^3$H thymidine was added and the cultures were incubated overnight. The cells were collected on glass fiber filters using a cell harvester and processed for scintillation counting.

Receptor binding assay—The 17,500 form of IL-1beta was labeled using diiodo $^{125}$I Bolton-Hunter reagent according to the manufacturer's instructions. One µg of IL-1beta in 10 µL of PBS was reacted with 1 mCi of reagent for 4 hours at 4° C.; 500 µL of PBS/0.2% gelatin was added and labeled IL-1beta was separated from free Bolton-Hunter reagent by chromatography on a $20*1$ cm column of Sephadex G-25 with PBS/0.2% gelatin. $^{125}$IIL-1beta was added to confluent monolayers of BALB/c 3T3 fibroblasts in DMEM/1% BSA/ 0.1% sodium azide/0.01% Triton X-100 in 24-well culture plates. After 1 hour at 37° C. the monolayers were washed extensively in media without labelled IL-1beta. The monolayers were removed using 0.1 N NaOH for gamma counting. Non-specific binding of $^{125}$IIL-1beta was measured by incubating in the presence of 200-fold molar excess of unlabeled IL-1beta.

Determination of antibody affinity—Monoclonal antibody affinity was determined from data obtained using an immunoprecipitation radioimmunoassay. Briefly, 5000 cpm/ tube of $^{125}$IIL-1beta was incubated with dilutions of purified monoclonal antibody in 0.3 ml of 1% non-fat dry milk/0.5% Thimerosal/PBS overnight at 4° C. Antigen-antibody complexes were precipitated by the addition of 100 µL/tube each of 10% normal mouse serum/PBS and 4 mg/ml goat anti mouse IgG sera in PBS. After 4 hours at 4° C., the 1/ml tube of ice-cold 2% polyethylene glycol-6000 was added and the tubes centrifuged at 3000*g for 20 min. at 4° C. The supernatants were aspirated and the pellets counted in a gamma counter. Affinity constants were calculated from bound/free ratios at different concentrations of antibody (Berson et al., Clin. Chim. Acta. 22 (1969) 51-69).

Affinity constants were calculated using data obtained from an immunoprecipitation radioimmunoassay (RIA) of $^{125}$IIL-1beta binding of different antibody concentrations as described above. The anti-IL-1beta antibody H34 has an affinity of $64*10^9$ L/mol for IL-1beta.

Example 2. Immunization of Mice

For immunization of NMRI mice, a RIMMS ("Rapid IMmunization, Multiple Sites") schedule was used.

Example 3. Determination of Anti-IL-1Beta Antibody Serum Titer

Human recombinant IL-1beta was immobilized on a 96-well NUNC Maxisorb plate at 2.5 µg/ml, 100 µl/well, in PBS, followed by: blocking of the plate with 2% CroteinC in PBS, 200 µl/well; application of serial dilutions of antisera, in duplicates, in 0.5% CroteinC in PBS, 100 µl/well; detection with HRP-conjugated goat anti-mouse IgG antibody (Jackson Immunoresearch) diluted 1:16,000 in 0.5% CroteinC in PBS, 100 µl/well. For all steps, plates were incubated for 1 hour at 37° C. Between all steps, plates were washed 3 times with 0.05 Tween 20 in PBS. Signal was developed by addition of BM Blue POD Substrate soluble (Roche Diagnostics GmbH, Mannheim, Germany), 100 µl/well; and stopped by addition of 1 M HCl, 100 µl/well. Absorbance was read out at 450 nm, against 690 nm as reference. Titer was defined as dilution of antisera resulting in half-maximal signal.

Example 4. Human IL-1Beta Binding ELISA

Variant 1

The binding analysis was carried out using an enzyme-linked immunosorbent assay (ELISA)-based technology. The antigen human IL-1beta (Peprotech Cat. No 200-01B) was immobilized at a concentration of 500 ng/mL in 25 µL in PBS on a 384 well microtiter plate (Thermo Scientific, Cat. No. 464718). Every of the following steps was followed by a washing routine of 3 times 90 µL PBS with dispense and aspiration: 1) blocking step: saturating unbound surface (1 hour, 2% BSA); 2) anti-IL-1beta antibody in increasing concentrations for 1 hour; 3) detection antibody, dilution=1: 2000 (Donkey F(ab)$_2$ anti-rabbit IgG POD, Amersham, NA9340V or sheep IgG anti-mouse IgG POD, Amersham RPN4201). 20-30 min. after adding the substrate 3,3',5,5'- tetramethylbenzidine (TMB, Roche Diagnostics GmbH, Mannheim, Germany, Cat. No 11835033001) the optical density was determined at 370 nm. The $EC_{50}$ was calculated with a four parameter logistic model using GraphPad Prism 6.0 software.

Variant 2

The binding analysis was carried out using an enzyme-linked immunosorbent assay (ELISA)-based technology. The antigen His-tagged human IL-1beta (Sino Biologics, Cat. No. 10139-H07E) was immobilized at a concentration of 0.25 µg/mL in 25 µL in PBS on a 384 well microtiter plate (Thermo Scientific, Cat. No. 464718). Every of the following steps was followed by a washing routine of 3 times 90 µL PBS, 0.5% BSA, 0.05 Tween with dispense and aspiration: 1) blocking step: saturating unbound surface (1 hour, 2% BSA); 2) anti-IL-1beta antibody in increasing concentrations for 1 hour; 3) detection antibody, dilution=1:2000 (Donkey F(ab)$_2$ anti-rabbit IgG POD, Amersham, NA9340V or sheep IgG anti-mouse IgG POD, Amersham RPN4201). 20-30 min. after adding the substrate 3,3',5,5'-tetramethylbenzidine (TMB, Roche Diagnostics GmbH, Mannheim, Germany, Cat. No 11835033001) the optical density was determined at 370 nm. The $EC_{50}$ was calculated with a four parameter logistic model using GraphPad Prism 6.0 software.

Example 5. Cynomolgus IL-1Beta Binding ELISA

The binding analysis was carried out using an enzyme-linked immunosorbent assay (ELISA)-based technology. The antigen human IL-1beta (Sino Biologics, Cat. No. 90010CNAE) was immobilized at a concentration of 0.5 µg/mL in 25 µL in PBS on a 384 well microtiter plate (Thermo Scientific, Cat. No. 464718). Every of the following steps was followed by a washing routine of 3 times 90 µL PBS, 0.5% BSA, 0.05% Tween with dispense and aspiration: 1) blocking step: saturating unbound surface (1 hour, 2% BSA); 2) anti-IL-1beta antibody in increasing concentrations for 1 hour; 3) detection antibody, dilution=1:2000 (Donkey F(ab)$_2$ anti-rabbit IgG POD, Amersham, NA9340V or sheep IgG anti-mouse IgG POD, Amersham RPN4201). 20-30 min. after adding the substrate 3,3',5,5'-tetramethylbenzidine (TMB, Roche Diagnostics GmbH, Mannheim, Germany, Cat. No 11835033001) the optical density was determined at 370 nm. The $EC_{50}$ was calculated with a four parameter logistic model using GraphPad Prism 6.0 software.

Example 6. Murine IL-1beta Binding ELISA

The binding analysis was carried out using an enzyme-linked immunosorbent assay (ELISA)-based technology. The antigen murine IL-1beta (Sino Biologics, Cat. No. 50101-MNAE) was immobilized at a concentration of 0.5 µg/mL in 25 µL in PBS on a 384 well microtiter plate (Thermo Scientific, Cat. No. 464718). Every of the following steps was followed by a washing routine of 3 times 90 µL PBS, 0.5% BSA, 0.05% Tween with dispense and aspiration: 1) blocking step: saturating unbound surface (1 hour, 2% BSA); 2) anti-IL-1beta antibody in increasing concentrations for 1 hour; 3) detection antibody, dilution=1:2000 (Donkey F(ab)$_2$ anti-rabbit IgG POD, Amersham, NA9340V or sheep IgG anti-mouse IgG POD, Amersham RPN4201). 20-30 min. after adding the substrate 3,3',5,5'-tetramethylbenzidine (TMB, Roche Diagnostics GmbH, Mannheim, Germany, Cat. No 11835033001) the optical density was determined at 370 nm. The $EC_{50}$ was calculated with a four parameter logistic model using GraphPad Prism 6.0 software.

Example 7. Protein-Protein Interaction Inhibition Assay: Human IL-1Beta:Human IL-1 Receptor Type 1

The protein-protein interaction inhibition analysis of human IL-1beta to the human IL-1 receptor type I was carried out using an enzyme-linked immunosorbent assay (ELISA)-based technology. The human His-tagged IL-1beta protein (Sino Biologics, Cat. No. 10139-H07E) was immobilized at a concentration of 1 µg/mL in 25 µL in PBS, 0.5% BSA and 0.05% Tween on a 384 well microtiter plate (Thermo Scientific Cat. No. 464718). Every of the following steps was followed by a washing routine of 3 times 90 µL PBS with dispense and aspiration: 1) blocking step saturating unbound surface (1 hour, 2% BSA); 2) 12.5 µL anti-IL-1beta antibody in increasing concentrations was incubated with 12.5 µL Fc-tagged human IL-1beta receptor (Sino Biologics, Ca. No 10126-H02H) at 300 ng/mL in a volume of 250 µL for 1 hour; 3) detection was achieved using peroxidase-labeled anti huFc antibody (Goat F(ab)$_2$) anti-human FC POD, Jackson, Cat. No 109-036-098). 10-30 min. after adding the substrate 3,3',5,5'-tetramethylbenzidine (TMB, Roche Diagnostics GmbH, Cat. No. 11835033001) the optical density was determined at 370 nm. The $IC_{50}$ was calculated with a four parameter logistic model using GraphPad Prism 6.0 software.

Example 8. Protein-Protein Interaction Inhibition Assay: Human IL-1Beta:Human IL-1 Receptor Type 2

The protein-protein interaction inhibition analysis of human IL-1beta to the human IL-1 receptor type II was carried out using an enzyme-linked immunosorbent assay (ELISA)-based technology. The human His-tagged IL-1beta protein (Sino Biologics, Cat. No. 10139-H07E) was immobilized at a concentration of 1 µg/mL in 25 µL in PBS, 0.5% BSA and 0.05% Tween on a 384 well microtiter plate (Thermo Scientific, Cat. No. 464718). Every of the following steps was followed by a washing routine of 3 times 90 µL PBS with dispense and aspiration: 1) blocking step: saturating unbound surface (1 hour, 2% BSA); 2) 12.5 µL anti-IL-1beta antibody in increasing concentrations was incubated with 12.5 µL Fc-tagged human IL-1beta receptor (RnD, Ca. No. 663-2R-50) at 30 ng/mL in a volume of 250 µL for 1 hour; 3) detection was achieved using peroxidase-labeled anti-huFc antibody (Goat F(ab)$_2$) anti-human FC POD, Jackson, Cat. No 109-036-098). 10-30 min. after adding the substrate 3,3',5,5'-tetramethylbenzidine (TMB, Roche Diagnostics GmbH, Mannheim, Germany, Cat. No. 11835033001) the optical density was determined at 370 nm. The $IC_{50}$ was calculated with a four parameter logistic model using GraphPad Prism 6.0 software.

Example 9. Expression of Mouse Hybridoma H34 Murine Anti-IL-1Beta Antibody Producing Hybridoma Medium contains following reagents: RPMI (PAN), 20% foetal calf serum, 2 mM Glutamine (PAN), 1× Sodium pyruvate (PAN), 1×NEAS (PAN)

Pre-thaw the frozen cell-containing-vial by placing the tube in a 37° C. water bath for 60 seconds. With 2 ml pre-warmed (37° C.) medium cells have been quickly resuspended and transferred from the vial into a 10 ml flask (CellStar); already containing 8 ml medium. Centrifuge flask for 5 minutes at 1000 rpm (25° C.). Then discard supernatant and resuspend gently cell-pellet by up-and-down-pipetting in 10 ml pre-warmed (37° C.) medium. Fill the whole solution in a T25-flask and place flask in an incubator (37° C., 7% $CO_2$, 85% humidity) for 2 days.

Split the cells the next 5 days each 2-3 days, by dilution in new medium, with a density of $1-2 \times 10^5$ cells/ml. Then start the following days to reduce part of foetal calf serum from 20% in a first step to 10%. After two splits in 10% foetal calf serum, mix medium (RPMI (PAN), 10% foetal calf serum, 2 mM Glutamine (PAN), 1× Sodium pyruvate (PAN), 1×NEAS (PAN)) 1:1 with Hyclone-ADCF-MAb-medium (Thermo-Scientific) and use this medium for another two splits. Then rise ratio of Hyclone: RPMI-with-10% foetal calf serum to 3:1 and seed cells with a higher density of $2-3 \times 10^5$ cells/ml. At least split cells in 100% Hyclone-medium added by Nutridoma CS (Roche Diagnostics GmbH, Mannheim, Germany).

Then expand volume of cells-solution to 20 ml (T75 flask) for 5 splits. For antibody-production fill 15 ml cells, with a density of $2.0 \times 10^6$ cell/ml in Celline CL1000 reactor and incubate for 8-9 days (37° C., 7% $CO_2$, 85% humidity). For harvesting, fill the supernatant in a 50 ml falcon and centrifuge with 4000 rpm 4 times (after each cycle the supernatant will be filled in a new 50 ml falcon). Finally freeze cell-free-supernatant at $-20°$ C.

Example 10. Antibody Purification from Murine Hybridoma

Antibody-containing H34 hybridoma supernatant was filtered and purified by two chromatographic steps. The antibodies were captured by affinity chromatography using HiTrap Protein G (GE Healthcare) equilibrated with PBS (1 mM $KH_2PO_4$, 10 mM $Na_2HPO_4$, 137 mM NaCl, 2.7 mM KCl), pH 7.4. Unbound proteins were removed by washing with equilibration buffer, and the antibody was recovered with 25 mM citrate buffer, pH 3.0, and immediately after elution neutralized to pH 6.0 with 1 M Tris-base, pH 9.0. Size exclusion chromatography on Superdex 200™ (GE Healthcare) was used as second purification step. The size exclusion chromatography was performed in 20 mM histidine buffer, 0.14 M NaCl, pH 6.0. The antibody containing solutions were concentrated with an Ultrafree-CL centrifugal filter unit equipped with a Biomax-SK membrane (Millipore, Billerica, Mass.) and stored at $-80°$ C.

Antibody-containing hybridoma supernatant was filtered and purified by two chromatographic steps. The supernatants were mixed with 50% v/v 2 M glycine, pH 8.6, 600 mM NaCl and were captured by affinity chromatography using HiTrap MabSelectSuRe (GE Healthcare) equilibrated with 1 M glycine, pH 8.6, 300 mM NaCl. Unbound proteins were removed by washing with equilibration buffer, and the antibody was recovered with 100 mM citrate buffer, pH 2.8 and immediately after elution neutralized to pH 6.0 with 1 M Tris-base, pH 8.5. Size exclusion chromatography on Superdex 200™ (GE Healthcare) was used as second purification step. The size exclusion chromatography was performed in 20 mM histidine buffer, 0.14 M NaCl, pH 6.0. The antibody containing solutions were concentrated with an Ultrafree-CL centrifugal filter unit equipped with a Biomax-SK membrane (Millipore, Billerica, Mass.) and stored at $-80°$ C.

Example 11. Transfection and Transient Expression of the Humanized Antibodies in HEK Cells Transient expression of antibodies in suspension-adapted HEK293F (FreeStyle 293-F cells; Invitrogen) cells with Transfection Reagent 293-free (Novagen).

Cells have been passaged, by dilution, at least four times (volume 30 ml) after thawing in a 125 ml shake flask (Incubate/Shake at 37° C., 7% $CO_2$, 85% humidity, 135 rpm).

The cells were expanded to $3 \times 10^5$ cells/ml in 250 ml volume. Three days later, cells have been split and new seeded with a density of $7*10^5$ cells/ml in a 250 ml volume in a 1 liter shake flask. Transfection will be 24 hours later at a cell density around $1.4-2.0 \times 10^6$ cells/ml.

Before transfection dilute 250 µg plasmid-DNA (122 µg light and 128 µg heavy chain) in a final volume of 10 ml with pre-heated (water bath; 37° C.) Opti-MEM (Gibco). Mix solution gentle and incubate at room temperature for not longer than 5 min. Then add 333.3 µl 293-free transfection reagent to DNA-OptiMEM-solution. Mix gently and incubate at room temperature for 15-20 minutes. Add whole volume of mixture to 1 L shake flask with 250 ml HEK-cell-culture-volume. Incubate/Shake at 37° C., 7% $CO_2$, 85% humidity, 135 rpm for 6 or 7 days.

Harvest supernatant by a first centrifugation-step at 2,000 rpm, 4° C., for 10 minutes. Then transfer the supernatant in a new centrifugation-flask for a second centrifuge at 4,000 rpm, 4° C., for 20 minutes. Thereafter the cell-free-supernatant is filtered through a 0.22 µm bottle-top-filter and stored in a freezer ($-20°$ C.).

Example 12. Antibody Purification from HEK Supernatant

The antibody-containing culture supernatants were filtered and purified by two chromatographic steps. The antibodies were captured by affinity chromatography using HiTrap MabSelectSuRe (GE Healthcare) equilibrated with PBS (1 mM $KH_2PO_4$, 10 mM $Na_2HPO_4$, 137 mM NaCl, 2.7 mM KCl), pH 7.4. Unbound proteins were removed by washing with equilibration buffer, and the antibody was recovered with 50 mM citrate buffer, pH 2.8, and immediately after elution neutralized to pH 6.0 with 1 M Tris-base, pH 9.0. Size exclusion chromatography on Superdex 200™ (GE Healthcare) was used as second purification step. The size exclusion chromatography was performed in 20 mM histidine buffer, 0.14 M NaCl, pH 6.0. The antibody containing solutions were concentrated with an Ultrafree-CL centrifugal filter unit equipped with a Biomax-SK membrane (Millipore, Billerica, Mass.) and stored at $-80°$ C.

Example 13. Analytics of Antibody Preparations

The protein concentration of antibody preparations was determined by measuring the optical density (OD) at 280 nm, using the molar extinction coefficient calculated on the basis of the amino acid sequence.

Purity and integrity of the antibodies were analyzed by CE-SDS using a LabChip GX II (PerkinElmer) with Protein Express Chip and HT Protein Express Reagents Kit.

Aggregate content of antibody preparations was determined by high-performance SEC using a TSK-GEL QC-PAK GFC 300 using 2×PBS, pH 7.4 as running buffer or by high-performance SEC using a BioSuite High Resolution SEC, 250 Å, 5 μm analytical size-exclusion column (Waters GmbH) using 200 mM $K_2HPO_4/KH_2PO_4$, 250 mM KCl, pH 7.0 as running buffer.

Example 14. Preparation of Fab Fragment from an Antibody and Analytics 12 mg antibody (1 mg/ml in 20 mM Histidine, 140 mM NaCl, pH 6.0) were incubated with 240 μl L-cysteine solution (Merck Millipore; 250 mM in 20 mM Histidine, 140 mM NaCl, pH 6.0) and 327 μl Papain (Roche Life Science; 0.001 U/mg antibody) for 120 min at 37° C. After cleavage, affinity chromatography using HiTrap MabSelect-SuRe (GE Healthcare) equilibrated with PBS (1 mM $KH_2PO_4$, 10 mM $Na_2HPO_4$, 137 mM NaCl, 2.7 mM KCl), pH 7.4 was used for removal of intact IgG and Fc fragment. Subsequently, flow-through of MabSelectSuRe chromatography was further purified using size exclusion chromatography on Superdex 200™ (GE Healthcare) as second purification step. The size exclusion chromatography was performed in 20 mM histidine buffer, 0.14 M NaCl, pH 6.0. The Fab fragment containing solutions were concentrated with an Ultrafree-CL centrifugal filter unit equipped with a Biomax-SK membrane (Millipore, Billerica, Mass.) and stored at −80° C.

The protein concentrations of the Fab-fragments were determined by measuring the optical density (OD) at 280 nm, using the molar extinction coefficient calculated on the basis of the amino acid sequence.

Purity and integrity of the Fab-fragments were analyzed by SDS-PAGE (NuPAGE 4-12% Bis-Tris Gel, Invitrogen) in the presence and absence of a reducing agent (5 mM 1.4-dithioreitol) and staining with Simply Blue Safe Stain (Invitrogen).

Aggregate content of Fab preparations was determined by high-performance SEC using a BioSuite High Resolution SEC, 250 Å, 5 μm analytical size-exclusion column (Waters GmbH) using 200 mM $K_2HPO_4/KH_2PO_4$, 250 mM KCl, pH 7.0 as running buffer.

Example 15. ICAM-1 Expression after IL-1Beta Stimulation of A549 Cells

A549 cells (10,000/well) were gown overnight in RPMI 1640 supplemented with 10% FCS. Thereafter the medium was replaced by Hunger medium supplemented with 0.5% serum.

The anti-IL-1beta antibody was incubated for 2 hours with IL-1beta at 250 pg/ml and different concentrations of the antibody (1000, 100, 10, 1, 0.1, 0 ng/ml). Thereafter A549 cells were incubated overnight with the IL-1beta/antibody mixture in quadruplicates.

The cells were washed four times with ice cold PBS and thereafter fixed with PFA for 20 minutes. Thereafter the cells were blocked with GSDB, non-permeabilizing. After incubation for 2 hours with anti-ICAM-1 antibody (R&D Systems, 5 μg/ml) the sample was washed four times with PBS. For staining the sample was incubated for 1 hour with anti-mouse antibody-HRP conjugate (Amersham) diluted 1:1000. Afterwards the sample was washed four times with PBS and incubated for 2 hours with ABTS. Absorption was measured at 405 nm with a reference at 495 nm.

Example 16. IL-6 Determination after IL-1Beta Stimulation of A549 Cells (Quantikine ELISA, R&D Systems)

A549 cells (10,000/well) were gown overnight in RPMI 1640 supplemented with 10% FCS. Thereafter the medium was replaced by Hunger medium supplemented with 0.5% serum and the cultivation continued for 96 hours.

The anti-IL-1beta antibody (1 μg/ml) was incubated for 2 hours with IL-1beta at 250 pg/ml. Thereafter A549 cells were incubated overnight with the IL-1beta/antibody mixture in duplicates.

A sample of 100 μl of the cultivation supernatant was taken for further analysis.

A 96 well plate coated with a monoclonal anti-human IL-6 antibody was blocked for 15 min. with assay diluent RD1W. Thereafter the supernatant sample was added and incubated for 2 hours at RT. The wells were washed four times with 200 μl wash buffer each. Thereafter the wells were incubated with polyclonal anti-human IL-6 antibody conjugated to HRP at RT for two hours. The wells were washed four times with 200 μl wash buffer each. Afterwards the wells were incubated for 20 min. with tetramethyl benzidine and H2O2. The reaction was stopped by the addition of 2 N sulfuric acid after 20 min. Absorption was determined at 450 nm with a reference wavelength of 570 nm.

Example 17. Bioactivity Assay

Murine helper T lymphocyte (Th-2) D10.G4.1 line has been used extensively as a reliable and sensitive assay for IL-1 (interleukin-1) bioactivity, since D10 cells will proliferate only minimally to con A in the absence of IL-1 or feeder cells (see Symons, J. A., et al. in Lymphokines and Interferons, a Practical Approach. Clemens, M. J. et al. (Eds): IRL Press. 272 (1987)). The $ED_{50}$ for this effect is typically <12 pg/mL.

35,000 D10.G4.1 T-Cells/well (freshly thawed) are stimulated for 72 hours in IL-1beta (1 ng/ml) containing media (RPMI/2.5 m/ml ConA/10% FCS).

Readout was determined by CellTiterGlo® Luminescent Cell Viability Assay according to the manufacturer's instructions.

Example 18. ICAM-1 Up-Regulation on HUVEC Cells Induced by IL-1Beta

HUVEC cells (Lonza, Cat #00191027) in corresponding media EBM/EGM (Cat #CC-4176) were seeded out in a 96 well culture plate (Costar, Cat #3596) at 40,000 cells/well in EBM+2% BSA 200 μl/well. Cells were incubated to recover in a 5%-$CO_2$ incubator at 37° C. for 24 h. Two dilution series 40 fold concentrated as finally requested were performed: one with the anti-IL-1b antibody huH34-2 and the other with recombinant human IL-1beta (R&D Systems, Cat #201-LB) in EBM+2% BSA. The two series were mixed against each other 1:1 and incubated for one hour at RT. 10 μl of this IL-1beta/anti-IL-1beta antibody mix was added to the cells and gently mixed. Incubation was performed in a 5%-$CO_2$ incubator at 37° C. for 20 hours. Thereafter all the media was removed from the cells and the cells were washed twice with PBS. After one wash with Cell Dissociation Solution Non-enzymatic 1× (Sigma, Cat #C5914) an incubation with 100 μl of the Cell Dissociation Solution at 37° C. was done. Detachment was checked by observing by microscope every 5 minutes. When 80% of the cells became globate, cells were transferred into a FACS-Plate (96 well, 340 μl Storage, PP, V-bottom Plate (Falcon Cat #353263)). The remaining cells were detached from the culture plate with 100 μl PBS+1% BSA by aspirating 4 times and also added to the FACS-plate. After 5 min. centrifugation by 300×g the supernatant was discarded. Pellets were resuspended in 100 μl PBS+1% BSA+10 µg/ml human IgG (Sigma; Cat #12511) AND Incubated for 15 min. at RT. 10 µl of anti-human ICAM-1 Fluorescein conjugate (CD54) (R&D Systems, Cat#BBA20) was added followed by an incubation at 4° C. for 30-45 min. After 5 min. centrifugation by 300×g the supernatant was discarded. The pellet was resuspended in 110 µl PBS+1% BSA and measured on LSRII.

Example 19. MSU Induced TNFalpha Production in THP1 Cells

THP1 cells (Invitrogen, Cat. No. thp-null) were grown until a density of $1\times10^6$ cells/ml in growth medium, RPMI 1640 (Gibco, Cat #A10491) supplemented with 10% FBS (heat inactivated) and transferred into a Falcon tube. PMA (phorbol myristate acetate, Invitrogen, Cat #tlrl-pma) was added with a final concentration of 300 ng/ml and incubated in the 5%-$CO_2$ incubator at 37° C. for 3 hours. Cells were washed once with PBS (5 min. centrifugation at 300×g, supernatant discarded) and resuspended with a density of $1.33\times10^6$ cells/ml in Hunger RPMI (Gibco, Cat #31870-025) supplemented with 2 mM L-Glutamine and 10% FBS (heat inactivated). 150 µl/well of the cell suspension was seeded out in a 96 well culture plate (Costar, Cat #3596) at $2\times10^5$ cells/well. Overnight incubation was performed in a 5%-$CO_2$ incubator at 37° C. 50 µl of a 4-fold concentrated MSU suspension, (monosodium urate crystals, Invitrogen, Cat #tlrl-msu) final concentration 250 µg/ml in Hunger medium, was added and incubated in the 5%-$CO_2$ incubator at 37° C. for 6 hours. Dilution series of the anti-IL-1beta antibodies were performed in growth medium. Supernatants from the THP1 cells were discarded and the wells were washed once with PBS. Then the prepared anti-IL-1b antibody dilution series were added to the wells. Overnight incubation was performed in a 5%-$CO_2$ incubator at 37° C. Supernatants were collected and analyzed by TNFalpha singleplex.

Example 20. Chemical Degradation Test

Samples were split into three aliquots and re-buffered into 20 mM His/His*HCl, 140 mM NaCl, pH 6.0 or into PBS, respectively, and stored at 40° C. (His/NaCl) or 37° C. (PBS). A control sample was stored at −80° C.

After incubation ended, samples were analyzed for relative active concentration (BIAcore), aggregation (SEC) and fragmentation (capillary electrophoresis or SDS-PAGE) and compared with the untreated control.

Example 21. Thermal Stability

Samples were prepared at a concentration of 1 mg/mL in 20 mM Histidine/Histidine chloride, 140 mM NaCl, pH 6.0, transferred into an optical 384-well plate by centrifugation through a 0.4 µm filter plate and covered with paraffin oil. The hydrodynamic radius was measured repeatedly by dynamic light scattering on a DynaPro Plate Reader (Wyatt) while the samples were heated with a rate of 0.05° C./min from 25° C. to 80° C.

Alternatively, samples were transferred into a 10 µL micro-cuvette array and static light scattering data as well as fluorescence data upon excitation with a 266 nm laser were recorded with an Optim1000 instrument (Avacta Inc.), while they were heated at a rate of 0.1° C./min from 25° C. to 90° C.

The aggregation onset temperature is defined as the temperature at which the hydrodynamic radius (DLS) or the scattered light intensity (Optim1000) starts to increase.

The melting temperature is defined as the inflection point in fluorescence intensity vs. wavelength graph.

Example 22. Immunization

For immunization of mice (NMRI mice) and rabbits (human Ig locus transgenic rabbits) a RIMMS ("Rapid IMmunization, Multiple Sites") based schedule was used. The antigen was human PDGF-BB (Cell Signaling Tech.).

Example 23. Determination of Anti-PDGF-B Antibody Serum Titer

Human recombinant PDGF-B was immobilized on a 96-well NUNC Maxisorb plate at 2.5 µg/ml (mouse) or 1.0 µg/ml (rabbit), 100 µl/well, in PBS, followed by: blocking of the plate with 2% CroteinC in PBS, 200 µl/well; application of serial dilutions of antisera, in duplicates, in 0.5% CroteinC in PBS, 100 µl/well; detection with HRP-conjugated goat anti-mouse IgG antibody (Jackson Immunoresearch) diluted 1:16,000 in 0.5% CroteinC in PBS for mouse sera or with biotinylated goat anti-human kappa antibody (Southern Biotech) diluted 1:5,000 and HRP-conjugated streptavidin diluted 1:8,000 in 0.5% CroteinC in PBS for rabbit sera, 100 µl/well. For all steps, plates were incubated for 1 hour at 37° C. Between all steps, plates were washed 3 times with 0.05% Tween 20 in PBS. Signal was developed by addition of BM Blue POD Substrate soluble (Roche Diagnostics GmbH, Mannheim, Germany), 100 µl/well; and stopped by addition of 1 M HCl, 100 µl/well. Absorbance was read out at 450 nm, against 690 nm as reference. Titer was defined as dilution of antisera resulting in half-maximal signal.

Example 24. B-Cell Cloning from Rabbits

Isolation of Rabbit Peripheral Blood Mononuclear Cells (PBMC)

Blood samples were taken of three immunized rabbits. EDTA containing whole blood was diluted twofold with 1×PBS (PAA, Pasching, Austria) before density centrifugation using lympholyte mammal (Cedarlane Laboratories, Burlington, Ontario, Canada) according to the specifications of the manufacturer. The PBMCs were washed twice with 1×PBS.

EL-4B5 Medium

RPMI 1640 (Pan Biotech, Aidenbach, Germany) supplemented with 10% FCS (Hyclone, Logan, Utah, USA), 2 mM Glutamine, 1% penicillin/streptomycin solution (PAA, Pasching, Austria), 2 mM sodium pyruvate, 10 mM HEPES (PAN Biotech, Aidenbach, Germany) and 0.05 mM β-mercaptoethanol (Gibco, Paisley, Scotland) was used.

Coating of Plates

Sterile cell culture 6-well plates were coated with either PBGF-BB (2 µg/ml) or a mixture of PDGF-AA and PDGF-CC proteins (1 µg/ml PDGF-AA and PDGF-CC) in carbonate buffer (0.1 M sodium bicarbonate, 34 mM disodium hydrogen carbonate, pH 9.55) overnight at 4° C. Plates were washed in sterile PBS three times before use.

Depletion of Macrophages/Monocytes

The PBMCs of half of the blood sample were seeded on sterile 6-well plates (cell culture grade) to deplete macrophages and monocytes through unspecific adhesion.

The remaining 50% of the PBMCs were seeded in plates that were pre-coated with a mixture of PDGF-AA and PDGF-CC proteins in order to remove B-cells binding to these proteins and to remove macrophages and monocytes in one step.

Each well was filled at maximum with 4 ml medium and up to $6\times10^6$ PBMCs from the immunized rabbit and were allowed to bind for 1 h at 37° C. in the incubator.

The cells in the supernatant (peripheral blood lymphocytes (PBLs)) were used for the antigen panning step.

Enrichment of B Cells on the PDGF BB Protein 6-well tissue culture plates coated with PDGF-BB protein were seeded with up to $6\times10^6$ PBLs per 4 ml medium and allowed to bind for 1 h at 37° C. in the incubator. Non-adherent cells were removed by carefully washing the wells 1-2 times with 1×PBS. The remaining sticky cells were detached by trypsin for 10 min at 37° C. in the incubator. Trypsination was stopped with EL-4B5 medium. The cells were kept on ice until the immune fluorescence staining.

Immune Fluorescence Staining and Flow Cytometry

The anti-IgG FITC (AbD Serotec, Dusseldorf, Germany) was used for single cell sorting. For surface staining, cells from the depletion and enrichment step were incubated with the anti-IgG antibody conjugated to FITC in PBS and incubated for 45 min in the dark at 4° C. After staining the PBMCs were washed two fold with ice cold PBS. Finally the PBMCs were resuspended in ice cold PBS and immediately subjected to the FACS analyses. Propidium iodide in a concentration of 5 µg/ml (BD Pharmingen, San Diego, Calif., USA) was added prior to the FACS analyses to discriminate between dead and live cells.

A Becton Dickinson FACSAria equipped with a computer and the FACSDiva software (BD Biosciences, USA) were used for single cell sort.

B-Cell Cultivation

Briefly, single sorted rabbit B-cells were incubated in 96-well plates with 200 µl/well EL-4B5 medium containing Pansorbin Cells (1:100,000) (Calbiochem (Merck), Darmstadt, Deutschland), 5% rabbit thymocyte supernatant (MicroCoat, Bernried, Germany) and gamma-irradiated murine EL-4B5 thymoma cells ($2.5\times10^4$ cells/well) for 7 days at 37° C. in the incubator. The supernatants of the B-cell cultivation were removed for screening and the remaining cells were harvested immediately and were frozen at −80° C. in 100 µl RLT buffer (Qiagen, Hilden, Germany).

Example 25. Hybridoma Generation

Cell Culture

The mouse myeloma cell line P3×63-Ag8.653 was used fusion partner for the generation of mouse-mouse hybridomas. The cells are thawed about 14 days prior to fusion and cultured in the presence of 8-azaguanine. Every 3 to 4 days the cells are split and adjusted to a concentration of $1-2\times10^5$ cells/m.

Cell Fusion

Material:

mouse hybridoma medium (RPMI 1640 (PAN), FBS ultra-low-IgG, 2 mM L-glutamine, 1 mM Na-pyruvate, NEAA, Nutridoma-CS with mulL-6, HAZ (SIGMA, #A9666), adjusted to RT RPMI 1640 medium (37° C.)

RPMI 1640 medium (4° C.)

PEG (37° C.)

Prior to fusion about the myeloma cells are centrifuged (250 rpm, 7 min.). The cell pellet is resuspended in culture medium. For one spleen about $1\text{-}5*10^7$ cells are required.

For cell fusion a ratio of lymphocytes to myeloma cells of about 5:1 should be used. P3×63-Ag8.653-cells are resuspended in 50 ml RPMI 1640 medium and centrifuged (250 rpm, 7 min.). The supernatant is removed. Thereafter the cells are added to the spleen cells.

During fusion the temperature is adjusted to 37° C. in a water bath.

The PEG solution (37° C.) is added drop wise to the cells.

The fusion mixture is incubated between 15 and 120 minutes at 37° C. in an incubator. Thereafter the fusion mixture is centrifuged (250 rpm, 7 min.) and resuspended in 1200 µl medium resuspended. 100 µl cell suspension was added to 50 ml semi-solid hybridoma-medium, homogenized and each 4 ml added per well of a 6-well plate. After 9-13 days of cultivation single clones are picked.

Example 26. Hybridoma Cultivation

About $5\times10^6$ cells are suspended in 50 ml Hyclone medium. The cultivation mixture is incubated for 96 hours. Thereafter 75 ml Hyclone medium was added. The cultivation was continued for 7 days. If the viability fell below 40% the cell suspension was filtered through a 0.22µ filter and the filtrate was used for purification.

Example 27. B-Cell Cloning

PCR Amplification of V-Domains

Total RNA was prepared from B-cell lysate (resuspended in RLT buffer—Qiagen—Cat. N° 79216) using the NucleoSpin 8/96 RNA kit (Macherey&Nagel; 740709.4, 740698) according to manufacturer's protocol. RNA was eluted with 60 µl RNAse free water. 6 µl of RNA was used to generate cDNA by reverse transcriptase reaction using the Superscript III First-Strand Synthesis SuperMix (Invitrogen 18080-400) and an oligo dT-primer according to the manufacturer's instructions. All steps were performed on a Hamilton ML Star System. 4 µl of cDNA were used to amplify the immunoglobulin heavy and light chain variable regions (VH and VL) with the AccuPrime SuperMix (Invitrogen 12344-040) in a final volume of 50 µl using the primers rbHC.up and rbHC.do for the heavy chain, rbLC.up and rbLC.do for the light chain of wild-type rabbit B-cells and BcPCR_FHLC_leader.fw and BcPCR_huCkappa.rev for the light chain of transgenic rabbit B-cells. All forward primers were specific for the signal peptide (of respectively VH and VL) whereas the reverse primers were specific for the constant regions (of respectively VH and VL). The PCR conditions for the RbVH+RbVL were as follows: Hot start at 94° C. for 5 min; 35 cycles of 20 s at 94° C., 20s at 70° C., 45 s at 68° C., and a final extension at 68° C. for 7 min. The PCR conditions for the HuVL were as follows: Hot start at 94° C. for 5 min; 40 cycles of 20 s at 94° C., 20 s at 52° C., 45s at 68° C., and a final extension at 68° C. for 7 min.

rbHC.up

SEQ ID NO: 111

AAGCTTGCCACCATGGAGACTGGGCTGCGC

TGGCTTC rbHCf.do

SEQ ID NO: 112

CCATTGGTGAGGGTGCCCGAG

-continued rbLC.up
SEQ ID NO: 113
AAGCTTGCCACCATGGACAYGAGGGCCCCC
ACTC rbLC.do
SEQ ID NO: 114
CAGAGTRCTGCTGAGGTTGTAGGTAC BcPCR_FHLC_leader.fw
SEQ ID NO: 115
ATGGACATGAGGGTCCCCGC BcPCR_huCkappa.rev
SEQ ID NO: 116
GATTTCAACTGCTCATCAGATGGC 8 µl of 50 µl PCR solution were loaded on a 48 E-Gel 2% (Invitrogen G8008-02). Positive PCR reactions were cleaned using the NucleoSpin Extract II kit (Macherey&Nagel; 740609250) according to manufacturer's protocol and eluted in 50 µl elution buffer. All cleaning steps were performed on a Hamilton ML Starlet System.

Example 28. Recombinant Expression of Rabbit Monoclonal Bivalent Antibodies

For recombinant expression of rabbit monoclonal bivalent antibodies, PCR-products coding for VH or VL were cloned as cDNA into expression vectors by the overhang cloning method (R S Haun et al., BioTechniques 13 (1992) 515-518; MZ Li et al., Nature Methods 4 (2007) 251-256). The expression vectors contained an expression cassette consisting of a 5' CMV promoter including intron A, and a 3' BGH poly adenylation sequence. In addition to the expression cassette, the plasmids contained a pUC-derived origin of replication and a beta-lactamase gene conferring ampicillin resistance for plasmid amplification in E. coli. Three variants of the basic plasmid were used: one plasmid containing the rabbit IgG constant region designed to accept the VH regions; two plasmids containing rabbit or human kappa LC constant region to accept the VL regions.

Linearized expression plasmids coding for the kappa or gamma constant region and VL/VH inserts were amplified by PCR using overlapping primers.

Purified PCR products were incubated with T4 DNA-polymerase, which generated single-strand overhangs. The reaction was stopped by dCTP addition.

In the next step, plasmid and insert were combined and incubated with recA which induced site specific recombination. The recombined plasmids were transformed into E. coli. The next day the grown colonies were picked and tested for correct recombined plasmid by plasmid preparation, restriction analysis and DNA-sequencing.

For antibody expression, the isolated HC and LC plasmids were transiently co-transfected into HEK293 cells and the supernatants were harvested after 1 week.

Example 29. Recombinant Expression of Rabbit Monoclonal Monovalent Antibodies

For recombinant expression of selected candidates as monoclonal monovalent antibodies rabbit constant regions of all VH chains were converted into human constant regions enclosing the Knob-mutation in the CH3 segment. For VL chains derived from rabbit wild type B-cells, rabbit C kappa constant regions were converted into human. 4 µl of cDNA of the selected candidates were used to amplify the immunoglobulin heavy and light chain variable regions with the AccuPrime SuperMix (Invitrogen 12344-040) in a final volume of 50 µl with forward primers specific for the signal peptide and reverse primers specific for the CDR3-J region with (at the 3' end) overlap sequence (20 bp) homologous to the human constant regions (respectively of VH and VL). The PCR conditions for the VH and VL chain amplification were as follows: Hot start at 94° C. for 5 min; 35 cycles of 20 s at 94° C., 20s at 68° C., 45 s at 68° C., and a final extension at 68° C. for 7 min.

PCR-products coding for VH or VL were cloned as cDNA into expression vectors by the overhang cloning method (R S Haun et al., BioTechniques 13 (1992) 515-518; M Z Li et al., Nature Methods 4 (2007) 251-256). The expression vectors contained an expression cassette consisting of a 5' CMV promoter including intron A, and a 3' BGH poly adenylation sequence. In addition to the expression cassette, the plasmids contained a pUC-derived origin of replication and a beta-lactamase gene conferring ampicillin resistance for plasmid amplification in E. coli. Two variants of the basic plasmid were used: one plasmid containing the human IgG constant region designed to accept the new amplified VH chain and a second plasmid containing the human kappa LC constant region to accept the VL chain.

Linearized expression plasmids coding for the kappa or gamma constant region and VL/VH inserts were amplified by PCR using overlapping primers.

Purified PCR products were incubated with T4 DNA-polymerase, which generated single-strand overhangs. The reaction was stopped by dCTP addition.

In the next step, plasmid and insert were combined and incubated with recA which induced site specific recombination. The recombined plasmids were transformed into E. coli. The next day the grown colonies were picked and tested for correct recombined plasmid by plasmid preparation, restriction analysis and DNA-sequencing.

Example 30. Human PDGF-BB Binding ELISA

The binding analysis was carried out using an enzyme-linked immunosorbent assay (ELISA)-based technology. The antigen human PDGF-BB (Cell Signaling, Cat. No. 8921BF) was immobilized at a concentration of 125 ng/mL in 25 µL in PBS, 0.5% BSA and 0.05% Tween on a 384 well microtiter plate (Thermo Scientific, Cat. No. 464718). Every of the following steps was followed by a washing routine of 3 times 90 µL PBS with dispense and aspiration: 1) blocking step: saturating unbound surface (1 hour, 2% BSA); 2) anti-PDGF-BB antibody in increasing concentrations for 1 hour; 3) detection antibody, dilution=1:3000 (ECL anti-rabbit IgG-POD, NA9340V+ECL anti-human IgG-POD, NA933V or alternatively for murine antibodies ECL anti-mouse IgG-POD; NA 9310V). 20-30 min. after adding the substrate 3,3',5,5'-tetramethylbenzidine (TMB, Piercenet, Cat. No. 34021) the optical density was determined at 370 nm. The $EC_{50}$ was calculated with a four parameter logistic model using GraphPad Prism 6.0 software.

Example 31. Cynomolgus PDGF-BB Binding ELISA

The binding analysis was carried out using an enzyme-linked immunosorbent assay (ELISA)-based technology. The antigen human PDGF-BB was immobilized at a concentration of 125 ng/mL in 25 µL in PBS, 0.5% BSA and 0.05% Tween on a 384 well microtiter plate (Thermo Scientific, Cat. No. 464718). Every of the following steps was followed by a washing routine of 3 times 90 μL PBS, 0.5% BSA, 0.05% Tween with dispense and aspiration: 1) blocking step: saturating unbound surface (1 hour, 2% BSA); 2) anti-PDGF-BB antibody in increasing concentrations for 1 hour; 3) detection antibody, dilution=1:3000 (ECL anti-rabbit IgG-POD, NA9340V+ECL anti-human IgG-POD, NA933V or alternatively for murine antibodies ECL anti-mouse IgG-POD; NA 9310V). 20-30 min. after adding the substrate 3,3',5,5'-tetramethylbenzidine (TMB, Piercenet, 34021) the optical density was determined at 370 nm. The $EC_{50}$ was calculated with a four parameter logistic model using GraphPad Prism 6.0 software.

Example 32. Murine PDGF-BB Binding ELISA

The binding analysis was carried out using an enzyme-linked immunosorbent assay (ELISA)-based technology. The antigen murine PDGF-BB (Peprotech 315-18) was immobilized at a concentration of 125 ng/mL in 25 μL in PBS, 0.5% BSA and 0.05% Tween on a 384 well microtiter plate (Thermo Scientific, Cat. No. 464718). Every of the following steps was followed by a washing routine of 3 times 90 μL PBS, 0.5% BSA, 0.05 Tween with dispense and aspiration: 1) blocking step: saturating unbound surface (1 hour, 2% BSA); 2) anti-PDGF-BB antibody in increasing concentrations for 1 hour; 3) detection antibody, dilution=1:3000 (ECL anti-rabbit IgG-POD, NA9340V+ECL anti-human IgG-POD, NA933V or alternatively for murine antibodies ECL anti-mouse IgG-POD; NA 9310V). 20-30 min. after adding the substrate 3,3',5,5'-tetramethylbenzidine (TMB, Piercenet, 34021) the optical density was determined at 370 nm. The $EC_{50}$ was calculated with a four parameter logistic model using GraphPad Prism 6.0 software.

Example 33. Rat PDGF-BB Binding ELISA

The binding analysis was carried out using an enzyme-linked immunosorbent assay (ELISA)-based technology. The antigen rat PDGF-BB (R&D, 520-BB) was immobilized at a concentration of 125 ng/mL in 25 μL in PBS, 0.5% BSA and 0.05% Tween on a 384 well microtiter plate (Thermo Scientific, Cat. No. 464718). Every of the following steps was followed by a washing routine of 3 times 90 μL PBS, 0.5% BSA, 0.05 Tween with dispense and aspiration: 1) blocking step: saturating unbound surface (1 hour, 2% BSA); 2) anti-PDGF-BB antibody in increasing concentrations for 1 hour; 3) detection antibody, dilution=1:3000 (ECL anti-rabbit IgG-POD, NA9340V+ECL anti-human IgG-POD, NA933V or alternatively for murine antibodies ECL anti-mouse IgG-POD; NA 9310V). 20-30 min. after adding the substrate 3,3',5,5'-tetramethylbenzidine (TMB, Piercenet, 34021) the optical density was determined at 370 nm. The $EC_{50}$ was calculated with a four parameter logistic model using GraphPad Prism 6.0 software.

Example 34. Human PDGF-AA Binding ELISA

The binding analysis was carried out using an enzyme-linked immunosorbent assay (ELISA)-based technology. The antigen human PDGF-AA (Peprotech, Cat. No. AF-100-13A) was immobilized at a concentration of 125 ng/mL in 25 μL in PBS, 0.5% BSA and 0.05% Tween on a 384 well microtiter plate (Thermo Scientific, Cat. No. 464718). Every of the following steps was followed by a washing routine of 3 times 90 μL PBS, 0.5% BSA, 0.05% Tween with dispense and aspiration: 1) blocking step: saturating unbound surface (1 hour, 2% BSA); 2) anti-PDGF-BB antibody in increasing concentrations for 1 hour; 3) detection antibody, dilution=1:3000 (ECL anti-rabbit IgG-POD, NA9340V+ECL anti-human IgG-POD, NA933V or alternatively for murine antibodies ECL anti-mouse IgG-POD; NA 9310V). 20-30 min. after adding the substrate 3,3',5,5'-tetramethylbenzidine (TMB, Piercenet, 34021) the optical density was determined at 370 nm. The $EC_{50}$ was calculated with a four parameter logistic model using GraphPad Prism 6.0 software.

Example 35. Human PDGF-CC Binding ELISA

The binding analysis was carried out using an enzyme-linked immunosorbent assay (ELISA)-based technology. The antigen human PDGF-CC (Peprotech AF-100-00C) was immobilized at a concentration of 125 ng/mL in 25 μL in PBS, 0.5% BSA and 0.05% Tween on a 384 well microtiter plate (Thermo Scientific, Cat. No. 464718). Every of the following steps was followed by a washing routine of 3 times 90 μL PBS, 0.5% BSA, 0.05 Tween with dispense and aspiration: 1) blocking step: saturating unbound surface (1 hour, 2% BSA); 2) anti-PDGF-BB antibody in increasing concentrations for 1 hour; 3) detection antibody, dilution=1:3000 (ECL anti-rabbit IgG-POD, NA9340V+ECL anti-human IgG-POD, NA933V or alternatively for murine antibodies ECL anti-mouse IgG-POD; NA 9310V). 20-30 min. after adding the substrate 3,3',5,5'-tetramethylbenzidine (TMB, Piercenet, 34021) the optical density was determined at 370 nm. The $EC_{50}$ was calculated with a four parameter logistic model using GraphPad Prism 6.0 software.

Example 36. Protein-Protein Interaction Inhibition Assay: Human PDGF-B:Human PDGF-BB Receptor The protein-protein interaction inhibition analysis of human PDGF-BB to the human PDGF-BB receptor was carried out using an enzyme-linked immunosorbent assay (ELISA)-based technology. The human Fc-tagged PDGF-BB receptor protein (RnD, Cat. No. 385-PR-100) was immobilized at a concentration of 750 μg/mL in 25 μL in PBS, 0.5% BSA and 0.05% Tween on a 384 well microtiter plate (Thermo Scientific Cat. No. 464718). Every of the following steps was followed by a washing routine of 3 times 90 μL PBS with dispense and aspiration: 1) blocking step saturating unbound surface (1 hour, 2% BSA); 2) 15 μL anti-PDGF-BB antibody in increasing concentrations was incubated with 15 μL biotinylated human PDGF-BB (Cell Signaling, 8921BF) at 75 nM in a volume of 30 μL for 1 hour; 3) detection was achieved using peroxidase-labeled streptavidin (Roche Diagnostics GmbH, Mannheim, Germany, 11089153001). 20-30 min. after adding the substrate 3,3',5,5'-tetramethylbenzidine (TMB, Piercenet, 34021) the optical density was determined at 370 nm. The $IC_{50}$ was calculated with a four parameter logistic model using Graph-Pad Prism 6.0 software.

Example 37. Antibody Purification from Murine Hybridoma

Antibody-containing hybridoma supernatant is filtered and purified by two chromatographic steps. The antibodies are captured by affinity chromatography using HiTrap Protein G (GE Healthcare) equilibrated with PBS (1 mM $KH_2PO_4$, 10 mM $Na_2HPO_4$, 137 mM NaCl, 2.7 mM KCl), pH 7.4. Unbound proteins are removed by washing with equilibration buffer, and the antibody is recovered with 25 mM citrate buffer, pH 3.0, and immediately after elution neutralized to pH 6.0 with 1 M Tris-base, pH 9.0. Size exclusion chromatography on Superdex 200™ (GE Healthcare) is used as second purification step. The size exclusion chromatography is performed in 20 mM histidine buffer, 0.14 M NaCl, pH 6.0. The antibody containing solutions are concentrated with an Ultrafree-CL centrifugal filter unit equipped with a Biomax-SK membrane (Millipore, Billerica, Mass.) and stored at −80° C.

Antibody-containing hybridoma supernatant is filtered and purified by two chromatographic steps. The supernatants are mixed with 50% v/v 2 M glycine, pH 8.6, 600 mM NaCl and are captured by affinity chromatography using HiTrap MabSelectSuRe (GE Healthcare) equilibrated with 1 M glycine, pH 8.6, 300 mM NaCl. Unbound proteins are removed by washing with equilibration buffer, and the antibody is recovered with 100 mM citrate buffer, pH 2.8 and immediately after elution neutralized to pH 6.0 with 1 M Tris-base, pH 8.5. Size exclusion chromatography on Superdex 200™ (GE Healthcare) is used as second purification step. The size exclusion chromatography is performed in 20 mM histidine buffer, 0.14 M NaCl, pH 6.0. The antibody containing solutions are concentrated with an Ultrafree-CL centrifugal filter unit equipped with a Biomax-SK membrane (Millipore, Billerica, Mass.) and stored at −80° C.

Example 38. Human PDGF-BB Binding Surface Plasmon Resonance Spectroscopy Assay The binding analysis was carried out using a surface plasmon resonance spectroscopy-based technology applying a BIAcore B4000 system (GE Healthcare). The antigen human PDGF-BB (Cell Signaling, 8921BF) was immobilized at a concentration of 1 µg/mL in PBS, 0.1% BSA, 0.05% Tween using amine coupling chemistry on a C1 sensor chip (GE Healthcare, BR-1005-35). Anti-PDGF-BB antibody in increasing concentrations was applied in 10 mM HEPES pH 7.2, 150 mM NaCl. Utilizing a read out time of 180 sec. association phase and 600 sec. dissociation phase the apparent $k_a$ and apparent $k_d$ were calculated. The apparent $K_D$ (avidity) was calculated using the BIAcore T200 v2.0 fitting software.

Example 39. Cynomolgus PDGF-BB Binding Surface Plasmon Resonance Spectroscopy Assay The binding analysis was carried out using a surface plasmon resonance spectroscopy-based technology applying a BIAcore B4000 system (GE Healthcare). The antigen cynomolgus PDGF-BB was immobilized at a concentration of 1 µg/mL in PBS, 0.1% BSA, 0.05% Tween using amine coupling chemistry on a C1 sensor chip (GE Healthcare, BR-1005-35). Anti-PDGF-BB antibody in increasing concentrations was applied in 10 mM HEPES pH 7.2, 150 mM NaCl. Utilizing a read out time of 180 sec. association phase and 600 sec. dissociation phase the apparent $k_a$ and apparent $k_d$ were calculated. The apparent $K_D$ (avidity) was calculated using the BIAcore T200 v2.0 fitting software.

Example 40. Transfection and Transient Expression of the Humanized Antibodies in HEK Cells Transient expression of antibodies in suspension-adapted HEK293F (FreeStyle 293-F cells; Invitrogen) cells with Transfection Reagent 293-free (Novagen).

Cells have been passaged, by dilution, at least four times (volume 30 ml) after thawing in a 125 ml shake flask (Incubate/Shake at 37° C., 7% $CO_2$, 85% humidity, 135 rpm).

The cells were expanded to $3 \times 10^5$ cells/ml in 250 ml volume. Three days later, cells have been split and new seeded with a density of $7 \times 10^5$ cells/ml in a 250 ml volume in a 1 liter shake flask. Transfection will be 24 hours later at a cell density around $1.4$-$2.0 \times 10^6$ cells/ml.

Before transfection dilute 250 µg plasmid-DNA (122 µg light and 128 µg heavy chain) in a final volume of 10 ml with pre-heated (water bath; 37° C.) Opti-MEM (Gibco). Mix solution gentle and incubate at room temperature for not longer than 5 min. Then add 333.3 µl 293-free transfection reagent to DNA-OptiMEM-solution. Mix gently and incubate at room temperature for 15-20 minutes. Add whole volume of mixture to 1 L shake flask with 250 ml HEK-cell-culture-volume.

Incubate/Shake at 37° C., 7% $CO_2$, 85% humidity, 135 rpm for 6 or 7 days.

Harvest supernatant by a first centrifugation-step at 2,000 rpm, 4° C., for 10 minutes. Then transfer the supernatant in a new centrifugation-flask for a second centrifuge at 4,000 rpm, 4° C., for 20 minutes. Thereafter the cell-free-supernatant is filtered through a 0.22 µm bottle-top-filter and stored in a freezer (−20° C.).

Example 41. Preparation of Fab Fragment from an Antibody and Analytics 5 mg antibody (about 1 mg/ml in 20 mM Histidine, 140 mM NaCl, pH 6.0) were incubated with 90 µl L-cysteine solution (Merck Millipore; 250 mM in 20 mM Histidine, 140 mM NaCl, pH 6.0) and 12 µl Papain (Roche Life Science; 3.2 U/mg antibody) for 120 min at 37° C. After cleavage, affinity chromatography using HiTrap MabSelectSuRe (GE Healthcare) equilibrated with PBS (1 mM $KH_2PO_4$, 10 mM $Na_2HPO_4$, 137 mM NaCl, 2.7 mM KCl), pH 7.4 was used for removal of intact IgG and Fc fragment. Subsequently, flow-through of MabSelectSuRe chromatography was further purified using size exclusion chromatography on Superdex 200™ (GE Healthcare) as second purification step. The size exclusion chromatography was performed in 20 mM histidine buffer, 0.14 M NaCl, pH 6.0. The Fab fragment containing solutions were concentrated with an Ultrafree-CL centrifugal filter unit equipped with a Biomax-SK membrane (Millipore, Billerica, Mass.) and stored at −80° C.

The protein concentrations of the Fab-fragments were determined by measuring the optical density (OD) at 280 nm, using the molar extinction coefficient calculated on the basis of the amino acid sequence.

Purity and integrity of the Fab-fragments were analyzed by SDS-PAGE (NuPAGE 4-12% Bis-Tris Gel, Invitrogen) in the presence and absence of a reducing agent (5 mM 1.4-dithiothreitol) and staining with Simply Blue Safe Stain (Invitrogen).

Aggregate content of Fab preparations was determined by high-performance SEC using a Superdex 200 10/300 GL analytical size-exclusion column (GE Healthcare) using 2×PBS, pH 7.4 as running buffer.

Example 42. 3T3 Cell Proliferation ELISA

For the determination of proliferation inhibition a BrdU colorimetric assay according to the manufacturer's manual was used (Roche Diagnostics GmbH, Mannheim, Germany, #11 647 229 001). In the assay 5 ng/ml human PDGF-BB and antibody was used.

Example 43. Phospho-PDGF-R Beta (Tyr751) Sandwich ELISA 10,000 3T3-cells/well were cultivated for 24 h in DMEM-medium supplemented with 10% Newborn Calf Serum. Thereafter the cells were incubated for 24 h in Hunger medium (DMEM-medium with 0.5% Newborn Calf Serum).

Prior to addition the antibody (1 µg/ml) was pre-incubated for 2 h in medium containing 5 ng/ml PDGF-BB. The 3T3 cells were incubated for 10 min. in Hunger medium with 5 ng/ml human PDGF-BB and antibody.

Prior to lysis the cells were washed 4 times with PBS. Lysis of the cells was performed in 100 µl lysis buffer.

The lysis solution was incubated overnight at 4° C. in the wells of a rabbit anti-PDGF-R beta antibody coated 96-well plate. Thereafter the wells were washed 4 times with PBS. After incubation for 1 hour with mouse anti-Phospho-PDGF receptor beta antibody the wells are washed 4 times with wash buffer. For detection the wells were incubated for 30 min. with 100 µl TMB substrate solution. The reaction was stopped by addition of 100 µl stop solution. The absorption was determined at 450 nm.

Example 44. Cell Migration Assay

Use of CIM-Plate 16 (ACEA Biosciences Inc., n° 05665817001, pore size membrane 8 µm).
Protocol
Starvation (in CellSystems CSC Serum-free Medium without Growth Factor (b° SF-4ZR-500-S) overnight of Primary Human Retinal Pericyte Cells ((ACBRI 183 Cell-Systems), immortalized with hTERT) before use (50-70% confluence)
Plate Preparation
Upper Chamber: (50 µl Medium+100 µl cells suspension)
Coating both sides with Fibronectin (Sigma n° F.0895-2 mg) 20 µg/ml in PBS:
Add 40 µl of fibronectin solution on the sensor side (bottom side) of each well, incubate the upper-chamber in the hood for 30 minutes. Carefully aspirate the fibronectin solution from the sensor side, avoid touching the electrodes. Turn the UC over such that the well side up and the sensor side is down. Add 50 µl of fibronectin solution in the well and incubate 30 minutes under the hood at RT. Carefully aspirate the solution from inside the well. Add 50 µl CSC Serum-free Medium without Growth Factor in the well.
Lower Chamber: 160 µl/well of your sample to test (1× concentrated)
All dilutions in CellSystems CSC Serum-free Medium without Growth Factor (n°SF-4ZR-500-S); incubate 2 h in the hood the mix of sample/antibody; add 160 µl/well of the sample; assemble the UC and LC using the CIM-Plate 16 Assembly Tool; place the CIM-Plate 16 in the incubator at 37° C. for 1 h to equilibrate; place the CIM-Plate 16 on the RTCA DP Analyser; start background measurement by initiating Step 1 in the RTCA software.
Cell Preparation
Detach the cells with cell dissociation buffer and resuspend the cells in CellSystems CSC Serum-free Medium without Growth Factor (n° SF-4ZR-500-S) at $1.5 \times 10^5$ cells/ml; remove the CIM-Plate 16 from the RTCA Analyser and add in the UC, 15,000 Primary Human Retinal Pericyte Cells ((ACBRI 183 CellSystems)), immortalized with hTERT)/100 µl in Basal Medium (Cell Systems CSC Serum-free Medium without Growth Factor n° SF-4ZR-500-S); place back the plate in the RTCA Analyser and start immediately the measurement during 10-20 hours.

Example 45. Cell Proliferation Assay

CellTiter 96 Aqueous One Solution Cell Proliferation Assay (Promega, G3580).
Primary Human Retinal Pericyte Cells ((ACBRI 183 CellSystems)), immortalized with hTERT), 2500 cells/well/ 100 µl
Media
Growth medium=CSC complete medium, culture boost (ACBRI n° 4Z=–500)
Assay medium=CSC Serum Free medium without growth factors (ACBRI n° SF-4ZR-500-S)
Balbc3T3, 5000 cells/well/100 µl
Media
Growth medium=DMEM (Gibco n° 41966), 10% NBCS
Assay medium=DMEM (Gibco n° 41966), 0.4% NBCS
Proliferation Assay
Seed cells in growth medium 24-48 hours before assay. When cells are 80-90% confluent, harvest the cells with Trypsin solution. Resuspend the cells in growth medium at $0.25 \times 10^5$ cells/ml (or $0.5 \times 10^5$ cells/ml). Add 100 µl cell suspension to each well of 96-well plate. Incubate for 24 hours at 37□. Remove growth medium, add 100 µl assay medium to each well. Incubate for 24 hours. Add 100 µl standards or samples to each well (2× concentrated, diluted in assay medium). Incubate for 72 hours at 37□ with 5% $CO_2$. Add 40 µl of dye solution on cells and incubate at 37° C. Read at 490 nm at different times (1 h to 8 h).

Example 46. Anti-PDGF-BB Antibodies Kinetic Screening

Binding of anti-PDGF-BB antibodies to human PDGF-BB was investigated by surface plasmon resonance using a BIACORE T200 instrument (GE Healthcare). Around 20 resonance units (RU) of recombinant human PDGF-BB (5 µg/ml; ordering code 220-BB; R&D Systems) were coupled on a Series S C1 chip (GE Healthcare BR-1005-35) at pH 4.0 by using an amine coupling kit supplied by GE Healthcare. Running buffer for immobilization was HBS-N pH 7.4 (10 mM HEPES, 150 mM NaCl, pH 7.4, GE Healthcare). For the following kinetic characterization, running and dilution buffer was HBS-P pH 7.4 (10 mM HEPES, 150 mM NaCl, 0.05% Surfactant P20, pH 7.4, GE Healthcare). The flow cell was set to 25° C.—and the sample block set to 12° C.—and primed with running buffer twice.

Association was measured by injection of the anti-PDGF-BB antibodies in concentrations of 30 nM and 3 nM in solution for 30 sec. at a flow rate of 100 µl/min. The dissociation phase was monitored for up to 600 sec. and triggered by switching from the sample solution to running buffer. The surface was regenerated by washing with two consecutive injections of 0.85% $H_3PO_4$ (phosphoric acid) solution for 60 sec. at a flow rate of 5 µl/min. Bulk refractive index differences were corrected by subtracting the response obtained from a blank surface. Blank injections were also subtracted (=double referencing). For calculation of $K_D$ and other kinetic parameters the Langmuir 1:1 model was used.

Example 47. Anti-PDGF-BB Fabs Kinetic Characterization

Binding of anti-PDGF-BB Fab samples to human PDGF-BB was investigated by surface plasmon resonance using a BIACORE T200 instrument (GE Healthcare). Around 50 resonance units (RU) of recombinant human PDGF-BB (0.5 µg/ml; ordering code 220-BB; R&D Systems) were coupled on a Series S CM3 chip (GE Healthcare BR-1005-36) at pH 4.0 by using an amine coupling kit supplied by GE Healthcare. Running buffer for Immobilization was HBS-N pH 7.4 (10 mM HEPES, 150 mM NaCl, pH 7.4, GE Healthcare). For the following kinetic characterization, running and dilution buffer was HBS-P pH 7.4 (10 mM HEPES, 150 mM NaCl, 0.05% Surfactant P20, pH 7.4, GE Healthcare). The flow cell was set to 25° C.—and the sample block set to 12° C.—and primed with running buffer twice.

Association was measured by injection of the anti-PDGF-BB Fabs in various concentrations in solution for 180 sec. at a flow rate of 30 µl/min starting with 300 nM in serial 1:3 dilutions. The dissociation phase was monitored for up to 900 sec. and triggered by switching from the sample solution to running buffer. The surface was regenerated by washing with a 0.85% $H_3PO_4$ (phosphoric acid) solution for 60 sec. at a flow rate of 5 µl/min. Bulk refractive index differences were corrected by subtracting the response obtained from a blank surface. Blank injections were also subtracted (=double referencing). For calculation of KD and other kinetic parameters the Langmuir 1:1 model was used.

Example 48. Preparation of Fab Fragment from an Antibody and Analytics 12 mg antibody (1 mg/ml in 20 mM Histidine, 140 mM NaCl, pH 6.0) were incubated with 240 µl L-cysteine solution (Merck Millipore; 250 mM in 20 mM Histidine, 140 mM NaCl, pH 6.0) and 327 µl Papain (Roche Life Science; 0.001 U/mg antibody) for 120 min at 37° C. After cleavage, affinity chromatography using HiTrap MabSelect-SuRe (GE Healthcare) equilibrated with PBS (1 mM $KH_2PO_4$, 10 mM $Na_2HPO_4$, 137 mM NaCl, 2.7 mM KCl), pH 7.4 was used for removal of intact IgG and Fc fragment. Subsequently, flow-through of MabSelectSuRe chromatography was further purified using size exclusion chromatography on Superdex 200™ (GE Healthcare) as second purification step. The size exclusion chromatography was performed in 20 mM histidine buffer, 0.14 M NaCl, pH 6.0. The Fab fragment containing solutions were concentrated with an Ultrafree-CL centrifugal filter unit equipped with a Biomax-SK membrane (Millipore, Billerica, Mass.) and stored at –80° C.

The protein concentrations of the Fab-fragments were determined by measuring the optical density (OD) at 280 nm, using the molar extinction coefficient calculated on the basis of the amino acid sequence.

Purity and integrity of the Fab-fragments were analyzed by SDS-PAGE (NuPAGE 4-12% Bis-Tris Gel, Invitrogen) in the presence and absence of a reducing agent (5 mM 1.4-dithiotreitol) and staining with Simply Blue Safe Stain (Invitrogen).

Aggregate content of Fab preparations was determined by high-performance SEC using a BioSuite High Resolution SEC, 250 Å, 5 µm analytical size-exclusion column (Waters GmbH) using 200 mM $K_2HPO_4$/$KH_2PO_4$, 250 mM KCl, pH 7.0 as running buffer.

Example 49. ANG2 Binding Kinetics and Cross-Reactivity of Maturated XFabs

Binding of the maturated XFabs to human ANG2-RBD-Fc-region fusion was investigated by surface plasmon resonance using a BIACORE T200 instrument (GE Healthcare). Around 4000 RU of anti-human antibody (10 µg/ml anti-human IgG (Fc) antibody; ordering code BR-1008-39; GE Healthcare) were coupled on a Series S CM5 chip (GE Healthcare BR-1005-30) at pH 5.0 by using an amine coupling kit supplied by the GE Healthcare. HBS-N (10 mM HEPES, 150 mM NaCl pH 7.4, GE Healthcare) was used as running buffer during the immobilization procedure. For the following kinetic characterization, sample and running buffer was FIBS-P (10 mM HEPES, 150 mM NaCl pH 7.4, 0.05% Surfactant P20; GE Healthcare). The flow cell was set to 25° C.—and the sample block set to 12° C.—and primed with running buffer twice prior to kinetic characterization.

Human or cynomolgus ANG2-RBD-Fc-region fusion was captured by injecting a 1 µg/ml solution for 30 sec. at a flow rate of 5 µl/min. Association was measured by injection of the XFabs in various concentrations in solution for 90 sec. at a flow rate of 90 µl/min starting with 300 nM in serial 1:3 dilutions. The dissociation phase was monitored for up to 600 sec. and triggered by switching from the sample solution to running buffer. All surfaces were regenerated by 60 sec. washing with a 3 M $MgCl_2$ solution at a flow rate of 5 µl/min. Bulk refractive index differences were corrected by subtracting the response obtained from an anti-human IgG antibody (Fc) surface. Blank injections were also subtracted (=double referencing). For calculation of KD and other kinetic parameters the Langmuir 1:1 model was Example 50. Biological Activity The method determines the capacity of an antibody to inhibit binding of ANG2 to its receptor Tie2. For expression of the Tie2 receptor tyrosine kinase on the cell surface the HEK293 cell line, a human embryonic kidney cell line, was stably transfected with the expression vector for human Tie2 resulting in the cell line HEK293 Tie2.

The cells are stimulated with ANG2 that binds to the Tie2 receptor and induces the autophosphorylation of the receptor. The binding to Tie2 can be inhibited by addition of an anti-ANG2 antibody as reported herein. The grade of phosphorylation is analyzed by an ELISA. The OD values correlate with the amount of phosphorylated Tie2 and are plotted against the antibody concentrations. The $EC_{50}$ value is determined and reported relative to the reference standard on the same plate as relative biological activity (RBA).

A multi-well plate was coated with antibody against the human Tie2 receptor (100 µl of 10 µg/ml; R&D Systems, Cat #MAB3132; 96 well Maxisorb immuno plate, incubated overnight at room temperature; coated plates were washed three times, volume 250 µl; thereafter incubated with 200 µl blocking 1-2 hours at room temperature).

Separately the HEK293_Tie2 cells (40 µl; $5 \times 10^6$ cells/ml; DMEM/F12) were added to a pre-incubated mixture (80 µl) of dilution series of the antibody in question and ANG2 (R&D Systems, Cat #623-CF). After 10 minutes the cells were lysed (60 µl lysis buffer added; incubated for 15 min.) and the cell lysate was transferred to the coated plate for the ELISA.

The Tie2 receptor of the lysate binds to the capture anti-Tie2 antibody (100 µl lysate; incubated for 90 min. at RT). The phosphorylated tyrosins on the Tie2 receptor were detected by anti-phosphotyrosine antibody conjugated to biotin (100 µl; 0.3 µg/ml anti-phosphotyrosine antibody, clone 4G10®, biotin conjugate, Upstate, Cat #16-103; incubated for 60 min. at RT). Biotin residues were bound by the streptavidin-horseradish peroxidase conjugate (100 µl; 100 mU/ml; Roche Diagnostics GmbH, Mannheim, Germany, Cat #11089153001; incubated for 30 min. at RT). The peroxidase substrate TMB (100 µl; Roche Diagnostics GmbH, Mannheim, Germany, Cat #11835033001) was added and the optical density was measured after 5-10 min at 450 nm.

Example 51. Production and Purification of Bispecific Antibodies

Transient expression of bispecific antibodies in suspension-adapted HEK293F (FreeStyle 293-F cells; Invitrogen) cells after transfection of DNA with Transfection Reagent 293-free (Novagen). Cells have been passaged every third or fourth day, by dilution, at least four times (volume 30 ml) after thawing in a 125 ml shake flask (incubate/Shake at 37° C., 7% CO2, 85% humidity, 135 rpm). The cells were expanded by seeding the cells with a cell density of $3\times10^5$ cells/ml in 250 ml medium. Three days later, cells have been split and newly seeded with a density of $2*10^5$ cells/ml in 500 ml medium. Four days later, cells have been split and newly seeded with a density of $7*10^5$ cells/ml in 1 liter medium (incubate/Shake at 37° C., 7% CO2, 85% humidity, 110 rpm). Transfection was done 24 hours later at a cell density around $1.4\text{-}2.0\times10^6$ cells/ml.

Before transfection 1000 µg plasmid-DNA (2×250 µg light encoding plasmid DNA and 2×250 µg heavy chain encoding plasmid DNA) were diluted in a final volume of 40 ml with pre-heated (water bath; 37° C.) Opti-MEM (Gibco). The solutions were gently mixed and incubated at room temperature for not longer than 5 min. Then 1333 µl 293-free transfection reagent were added to the DNA-Opti-MEM-solution. The mixture was gently mixed and incubated at room temperature for 15-20 minutes. The whole volume of mixture was carefully added to the 1 liter HEK-cell-culture. The cells were further incubated with shaking at 110 rpm at 37° C., 7% CO2, 85% humidity, for 7 days.

The supernatant was harvested after 7 days by a first centrifugation-step at 2000 rpm, 4° C., for 10 minutes. Then the supernatant was transferred into a new centrifugation-flask for a second centrifugation-step at 4000 rpm, 4° C., for 20 minutes. The cell-free-supernatant was filtered through a 0.22 µm filter (Millipore) and stored in a freezer (−20° C.) until purification-procedure was started.

The antibody-containing culture supernatants were filtered and purified by at least two chromatographic steps. The antibodies were captured by affinity chromatography using CaptureSelect Pre-packed Column IgG-CH1 (life technologies, #494320005) equilibrated with PBS (1 mM KH2PO4, 10 mM Na2HPO4, 137 mM NaCl, 2.7 mM KCl), pH 7.4. Unbound proteins were removed by washing with equilibration buffer, and antibodies were recovered with 25 mM citrate buffer, pH 3.0 and immediately after elution neutralized to pH 6.0 with 1 M Tris-base, pH 9.0.

Size exclusion chromatography on Superdex 200™ (GE Healthcare) was used as second purification step. The size exclusion chromatography was performed in 20 mM histidine buffer, 0.14 M NaCl, pH 6.0. The antibody containing solutions were concentrated with an Ultrafree-CL centrifugal filter unit equipped with a Biomax-SK membrane (Millipore, Billerica, Mass.) and stored at −80° C.

The anti-PDGF-B/ANG2 antibody (clone 0144-0004) was further purified using a hydrophobic interaction chromatography (HIC). Ammonium sulfate was added to final concentration of 1 M to the antibody containing solution. The solution was applied to a Butyl Sepharose 4 Fast Flow (GE Healthcare) column equilibrated in 1 M ammonium sulfate, 35 mM acetate, pH 5.6. The antibody was eluted in a linear gradient (0-100%) with 35 mM acetate, pH 5.6. Antibody containing fractions were pooled and applied to size exclusion chromatography.

The protein concentration of antibody preparations was determined by measuring the optical density (OD) at 280 nm, using the molar extinction coefficient calculated on the basis of the amino acid sequence.

Purity and integrity of the antibodies were analyzed by CE-SDS using a LabChip GX II (PerkinElmer) with Protein Express Chip and HT Protein Express Reagents Kit.

Aggregate content of antibody preparations was determined by high-performance SEC using a BioSuite High Resolution SEC, 250 Å, 5 µm analytical size-exclusion column (Waters GmbH) using 200 mM $K_2HPO_4/KH_2PO_4$, 250 mM KCl, pH 7.0 as running buffer.

TABLE 70

| antibody | scale [l] | yield [mg] | yield [mg/l supernatant] | Monomer (SE-HPLC) [%] | Monomer (CE-SDS) [%] | columns |
|---|---|---|---|---|---|---|
| anti-PDGF-B/ANG2 antibody | 0144 | 1.5 | 37.7 | 25.1 | >98 | >95 | CH1 select, HIC, SEC |
| anti-PDGF-B/VEGF antibody | 0117 | 1 | 46.3 | 46.3 | >98 | >95 | CH1 select, SEC |
| anti-PDGF-B/ANG2 antibody | 0145 | 1 | 21.5 | 21.5 | >98 | >95 | CH1 select/SEC |
| anti-PDGF-B/ANG2 antibody | 0146 | 0.5 | 14.6 | 29.2 | >98 | >95 | CH1 select/SEC |
| anti-IL-1beta/ANG2 antibody | 0031 | 1 | 29.2 | 29.2 | >98 | >95 | CH1 select, SEC |
| anti-IL-1beta/VEGF antibody | 0032 | 1.5 | 23.6 | 15.7 | >98 | >95 | CH1 select, IEX, SEC |

Antibody 0144 is a CrossMab antibody comprising an ANG2 binding site of SEQ ID NO: 117 (VH) and SEQ ID NO: 118 (VL) and a PDGF-B binding site of SEQ ID NO: 92 (VH) and SEQ ID NO: 97 (VL).

Antibody 0117 is a CrossMab antibody comprising a VEGF binding site of SEQ ID NO: 119 (VH) and SEQ ID NO: 120 (VL) and a PDGF-B binding site of SEQ ID NO: 92 (VH) and SEQ ID NO: 97 (VL).

Antibody 0145 is a CrossMab antibody comprising an ANG2 binding site of SEQ ID NO: 119 (VH) and SEQ ID NO: 120 (VL) and a PDGF-B binding site of SEQ ID NO: 101 (VH) and SEQ ID NO: 106 (VL).

Antibody 0146 is a CrossMab antibody comprising an ANG2 binding site of SEQ ID NO: 117 (VH) and SEQ ID NO: 118 (VL) and a PDGF-B binding site of SEQ ID NO: 121 (VH) and SEQ ID NO: 122 (VL).

Antibody 0031 is a CrossMab antibody comprising an IL-1beta binding site of SEQ ID NO: 06 (VH) and SEQ ID NO: 16 (VL) and an ANG2 binding site of SEQ ID NO: 140 (VH) and SEQ ID NO: 141 (VL).

Antibody 0032 is a CrossMab antibody comprising a VEGF binding site of SEQ ID NO: 142 (VH) and SEQ ID NO: 143 (VL) and an IL-1beta binding site of SEQ ID NO: 06 (VH) and SEQ ID NO: 16 (VL).

Example 52. Bispecific Antibody Kinetic Characterization

PDGF-BB

Binding of bispecific anti-PDGF-BB/ANG2 antibodies to human PDGF-BB was investigated by surface plasmon resonance using a BIACORE T200 instrument (GE Healthcare). Around 50 resonance units (RU) of recombinant human PDGF-BB (0.5 µg/ml; ordering code 220-BB; R&D Systems) were coupled on a Series S CM3 chip (GE Healthcare BR-1005-36) at pH 4.0 by using an amine coupling kit supplied by GE Healthcare. Running buffer for Immobilization was HBS-N pH 7.4 (10 mM HEPES, 150 mM NaCl, pH 7.4, GE Healthcare). For the following kinetic characterization, running and dilution buffer was HBS-P pH 7.4 (10 mM HEPES, 150 mM NaCl, 0.05% Surfactant P20, pH 7.4, GE Healthcare). The flow cell was set to 25° C.—and the sample block set to 12° C.—and primed with running buffer twice.

Association was measured by injection of the bispecific antibody in various concentrations in solution for 180 sec. at a flow rate of 30 µl/min starting with 300 nM in serial 1:3 dilutions. The dissociation phase was monitored for up to 900 sec. and triggered by switching from the sample solution to running buffer. The surface was regenerated by washing with a 0.85% $H_3PO_4$ (phosphoric acid) solution for 60 sec. at a flow rate of 5 µl/min. Bulk refractive index differences were corrected by subtracting the response obtained from a blank surface. Blank injections were also subtracted (=double referencing). For calculation of KD and other kinetic parameters the Langmuir 1:1 model was used.

ANG2:

Binding of the bispecific antibody to human ANG2-RBD-mouse Fc-region fusion was investigated by surface plasmon resonance using a BIACORE T200 instrument (GE Healthcare). Around 4000 RU of anti-mouse Fc-region antibody (10 µg/ml anti-mouse (Fc) antibody) were coupled on a Series S CM5 chip (GE Healthcare BR-1005-30) at pH 5.0 by using an amine coupling kit supplied by the GE Healthcare. HBS-N (10 mM HEPES, 150 mM NaCl pH 7.4, GE Healthcare) was used as running buffer during the immobilization procedure. For the following kinetic characterization, sample and running buffer was HBS-P (10 mM HEPES, 150 mM NaCl pH 7.4, 0.05% Surfactant P20; GE Healthcare). The flow cell was set to 25° C.—and the sample block set to 12° C.—and primed with running buffer twice prior to kinetic characterization.

Human ANG2-RBD-murine Fc-region fusion was captured by injecting a 1 µg/ml solution for 30 sec. at a flow rate of 5 µl/min. Association was measured by injection of the bispecific antibody in various concentrations in solution for 90 sec. at a flow rate of 90 µl/min starting with 300 nM in serial 1:3 dilutions. The dissociation phase was monitored for up to 600 sec. and triggered by switching from the sample solution to running buffer. All surfaces were regenerated by 60 sec. washing with a 3 M MgCl2 solution at a flow rate of 5 µl/min. Bulk refractive index differences were corrected by subtracting the response obtained from an anti-mouse IgG antibody (Fc) surface. Blank injections were also subtracted (=double referencing). For calculation of KD and other kinetic parameters the Langmuir 1:1 model was

VEGF:

Binding of the bispecific antibody to human VEGF isoform 121 was investigated by surface plasmon resonance using a BIACORE T200 instrument (GE Healthcare). An anti-hexa-histidine antibody was coupled on a CM5 chip (GE Healthcare BR-1005-30) according to the manufacturer's instructions by using an amine coupling kit supplied by the GE Healthcare. HBS-N (10 mM HEPES, 150 mM NaCl pH 7.4, GE Healthcare) was used as running buffer during the immobilization procedure. For the following kinetic characterization, sample and running buffer was HBS-P (10 mM HEPES, 150 mM NaCl pH 7.4, 0.05% Surfactant P20; GE Healthcare). The flow cell was set to 25° C.—and the sample block set to 12° C.—and primed with running buffer twice prior to kinetic characterization.

Histidine-tag comprising human VEGF isoform 121 was captured by injecting a solution for 30 sec. at a flow rate of 5 µl/min. Association was measured by injection of the bispecific antibody in various concentrations in solution for 90 sec. at a flow rate of 90 µl/min starting with 300 nM in serial 1:3 dilutions. The dissociation phase was monitored for up to 600 sec. and triggered by switching from the sample solution to running buffer. All surfaces were regenerated by 60 sec. washing with a 3 M $MgCl_2$ solution at a flow rate of 5 µl/min. Bulk refractive index differences were corrected by subtracting the response obtained from an anti-hexa-histidine antibody surface. Blank injections were also subtracted (=double referencing). For calculation of KD and other kinetic parameters the Langmuir 1:1 model was used.

IL-1beta:

Binding kinetics of anti-IL-1beta antibodies to human IL-1beta were investigated by surface plasmon resonance using a BIACORE T200 instrument (GE Healthcare). All experiments were performed at 25° C. using HBS-P (10 mM His, 140 mM NaCl, 0.05% Tween 20 pH 7.4) as running and dilution buffer. Anti-human Fc antibodies were immobilized on a Series S CM5 Sensor Chip (GE Healthcare) using standard amine coupling chemistry. Bispecific antibodies were captured on the surface leading to a capturing response of 100-200 RU. Human IL-1beta was injected for 90 s with concentrations from 0.74 up to 60 nM (1:3 dilution series) onto the surface (association phase). The dissociation phase was monitored for 600 sec by washing with running buffer. The surface was regenerated by injecting 3 M MgCl2 (for anti-human Fc antibody) or 10 mM Glycine pH 1.5 (for anti-mouse Fc antibody) for 60 sec at a flow rate of 5 µl/min. Bulk refractive index differences were corrected by subtracting the response obtained from a mock surface. Blank injections were subtracted (double referencing). The derived curves were fitted to a 1:1 Langmuir binding model using the BIAevaluation software.

Example 53. X-Ray Structure Determination

Apo Fab Fragment H34

Crystallization screening for Fab fragment H34 was performed at a concentration of 32 mg/ml. Crystallization droplets were set up at 21° C. by mixing 0.1 µl of protein solution with 0.1 µl reservoir solution in vapor diffusion sitting drop experiments. Crystals appeared out of various conditions containing PEG as precipitating agent. Crystals used to determine the structure of H34 appeared within 2 days out of 0.1 M HEPES pH 7.0, 20% PEG 4000 and out of 0.1M sodium cacodylate, 15% PEG4000.

Crystals were harvested with dried Paraffin oil as cryo-protectant and then flash-cooled in liquid $N_2$. Diffraction images were collected with a Pilatus 6M detector at a temperature of 100K at the beam line X10SA of the Swiss Light Source and processed with the XDS package (Kabsch, W. Automatic processing of rotation diffraction data from crystals of initially unknown symmetry and cell constants. J. Appl. Cryst. 26 (1993) 795-800). Data from two crystals were merged to yield a 1.64 Å resolution data set in space group P1 and two Fab per crystallographic asymmetric unit (see Table below).

The structure was determined by molecular replacement using the Fab 577 from Roche-internal PDB-ID 1htfr as search model. The Fab was split into constant and variable domains and both used for separate searches in the CCP4 program PHASER CCP4 (CCP4 (Collaborative Computational Project, N. The CCP4 suite: programs for protein crystallography. Acta Crystallogr. D, (1994) 760-763) to account for possible changes in the elbow angle. The model was rebuilt in COOT (Emsley, P., Lohkamp, B., Scott, W G. & Cowtan, K. Features and development of COOT. Acta Crystallogr. D Biol. Crystallogr. 60 (2010) 486-501) and refined with CCP4 program.

TABLE 71

Data collection and structure refinement statistics for H34 Fab apo-crystal

| Data Collection | |
| --- | --- |
| Wavelength (Å) | 1.0 |
| Resolution[1] (Å) | 48.27-1.64 (1.699-1.64) |
| Space group | P1 |
| Unit cell (Å, °) | 50.03 69.72 80.58 93.389 95.059 110.195 |
| Total reflections | 424699 (40316) |
| Unique reflections | 123149 (12254) |
| Multiplicity | 3.4 (3.3) |
| Completeness (%) | 0.99 (0.99) |
| Mean I/σ(I) | 5.95 (0.59) |
| Wilson B-factor | 28.27 |
| R-merge [2] | 0.1151 (1.612) |
| R-meas | 0.1352 (1.908) |
| CC1/2 | 0.991 (0.332) |
| CC* | 0.998 (0.706) |
| Refinement | |
| Reflections used in refinement | 123149 (12068) |
| Reflections used for R-free | 6101 (592) |
| R-work [3] | 0.2005 (0.3964) |
| R-free [4] | 0.2350 (0.4117) |
| CC(work) | 0.959 (0.593) |
| CC(free) | 0.943 (0.586) |
| Number of non-hydrogen atoms | 7574 |
| macromolecules | 6622 |
| Protein residues | 859 |
| RMS bonds (Å) | 0.007 |
| RMS angles (°) | 1.09 |
| Ramachandran favored (%) | 97 |
| Ramachandran allowed (%) | 2.7 |

TABLE 71-continued

Data collection and structure refinement statistics for H34 Fab apo-crystal

| | |
| --- | --- |
| Ramachandran outliers (%) | 0.23 |
| Rotamer outliers (%) | 1.1 |
| Clashscore | 1.30 |
| Average B-factor (Å$^2$) | 32.58 |
| macromolecules | 31.78 |
| solvent | 38.12 |

All data computed with Phenix.
[1]Values in parentheses refer to the highest resolution bins.
[2] $R_{merge} = \Sigma|I - <I>|/\Sigma I$ where I is intensity.
[3] $R_{work} = \Sigma|F_o - <F_c|/\Sigma F_o$ where $F_o$ is the observed and $F_c$ is the calculated structure factor amplitude.
[4] $R_{free}$ was calculated based on 5% of the total data omitted during refinement.

Complex Fab Fragment H34 with Human Il-1beta

Prior to crystallization screening Fab fragment H34 was mixed with IL-1beta (Peprotech) in a molar ratio of 1.2:1. The protein mixture was incubated at 21° C. for 2 h. Protein concentration used in crystallization experiments was 32 mg/ml. Crystallization droplets were set up at 21° C. by mixing 0.1 µl of protein with 0.1 µl reservoir solutions in vapor diffusion sitting drop experiments. Crystals appeared out of 0.1 M Tris pH 8.0, 20% PEG 4000 within 2 days and grew to a final size of 0.15 mm×0.06 mm×0.01 mm within 4 days.

Crystals were harvested without addition of cryo-protectant and then flash frozen in liquid N2. Diffraction images were collected with a Pilatus 6M detector at a temperature of 100K at the beam line X10SA of the Swiss Light Source and processed with the XDS package (Kabsch, W. Automatic processing of rotation diffraction data from crystals of initially unknown symmetry and cell constants. J. Appl. Cryst. 26 (1993) 795-800 (1993)). Data collection and processing followed the same route as for the H34 apo crystal (see above). Statistics are collected in the Table above. Data from two crystals were merged to obtain a more complete dataset. Molecular replacement was successful using the H34 Fab structure and interleukin-1beta (PDB-ID 1l2h) as search models. Model building and refinement was performed as described above.

TABLE 72

Data collection and structure refinement statistics for H34 Fab IL-1beta complex crystal

| Data Collection | |
| --- | --- |
| Wavelength | 1 |
| Resolution range [1] | 48.22-1.36 (1.409-1.36) |
| Space group | P 1 |
| Unit cell | 41.1 48.92 70.36 96.162 101.938 96.035 |
| Total reflections | 564817 (55575) |
| Unique reflections | 113220 (11310) |
| Multiplicity | 5.0 (4.9) |
| Completeness (%) | 0.99 (1.00) |
| Mean I/σ(I) | 9.82 (0.78) |
| Wilson B-factor | 17.64 |
| R-merge [2] | 0.09016 (2.448) |
| R-meas | 0.1007 (2.744) |
| CC1/2 | 0.999 (0.277) |
| CC* | 1 (0.659) |
| Refinement | |
| Reflections used in refinement | 113220 (10997) |
| Reflections used for R-free | 5663 (564) |
| R-work | 0.1559 (0.3786) |
| R-free | 0.2063 (0.4137) |
| CC(work) | 0.979 (0.659) |

TABLE 72-continued

Data collection and structure refinement statistics for H34 Fab IL-1beta complex crystal

| | |
|---|---|
| CC(free) | 0.971 (0.626) |
| Number of non-hydrogen atoms | 5318 |
| macromolecules | 4570 |
| Protein residues | 576 |
| RMS(bonds) | 0.005 |
| RMS(angles) | 1.09 |
| Ramachandran favored (%) | 98 |
| Ramachandran allowed (%) | 1.9 |
| Ramachandran outliers (%) | 0 |
| Rotamer outliers (%) | 1.3 |
| Clashscore | 1.86 |
| Average B-factor | 28.68 |
| macromolecules | 26.52 |
| solvent | 41.85 |

All data computed with Phenix.
[1] Values in parentheses refer to the highest resolution bins.
[2] $R_{merge} = \Sigma |I - <I>|/\Sigma I$ where I is intensity.
[3] $R_{work} = \Sigma |F_o - <F_c>|/\Sigma F_o$ where $F_o$ is the observed and $F_c$ is the calculated structure factor amplitude.
[4] $R_{free}$ was calculated based on 5% of the total data omitted during refinement.

Example 54. Binding Kinetics and Cross-Reactivity of Anti-IL-1Beta Antibodies Binding kinetics of anti-IL-1beta antibodies to human, cynomolgus, rat and murine IL-1beta as well as cross-reactivity to human IL-1beta and human IL-1alpha were investigated by surface plasmon resonance using a BIACORE T200 instrument (GE Healthcare). All experiments were performed at 25° C. using HBS-P (10 mM His, 140 mM NaCl, 0.05% Tween 20 pH 7.4) as running and dilution buffer. Anti-human or anti-mouse Fc antibodies were immobilized on a Series S CM5 Sensor Chip (GE Healthcare) using standard amine coupling chemistry. Anti-IL-1beta antibodies were captured on the surface leading to a capturing response of 100-200 RU. IL-1beta molecules were injected for 90 s with concentrations from 0.74 up to 60 nM (1:3 dilution series) onto the surface (association phase). The dissociation phase was monitored for 600 sec by washing with running buffer. Cross-reactivity to human IL-1beta and human IL-1α was determined by a single injection of 100 nM antigen according to the conditions described above. The surface was regenerated by injecting 3 M MgCl2 (for anti-human Fc antibody) or 10 mM Glycine pH 1.5 (for anti-mouse Fc antibody) for 60 sec at a flow rate of 5 µl/min. Bulk refractive index differences were corrected by subtracting the response obtained from a mock surface. Blank injections were subtracted (double referencing). The derived curves were fitted to a 1:1 Langmuir binding model using the BIAevaluation software.

Example 55. Binding Kinetics of Anti-IL-1Beta IgG Compared to Anti-IL-1Beta Fab Binding of anti-IL-1beta IgG and Fab to human IL-1beta was investigated by surface plasmon resonance using a BIACORE T200 instrument (GE Healthcare). All experiments were performed at 25° C. using HBS-P (10 mM His, 140 mM NaCl, 0.05% Tween 20 pH 7.4) as running and dilution buffer. Anti-human Fc or anti-human Fab antibodies were immobilized on a Series S CM5 Sensor Chip (GE Healthcare) using standard amine coupling chemistry. Anti-IL-1beta IgG and Fab was captured on the surface leading to a capturing response of approximately 100 and 50 RU, respectively. Human IL-1beta was injected for 90 s with concentrations from 0.74 up to 60 nM (1:3 dilution series) onto the surface (association phase) at a flow rate of 30 µl/min. The dissociation phase was monitored for 600 sec by washing with running buffer. The surface was regenerated by injecting 3 M MgCl2 (for anti-human Fc antibody) or 10 mM Glycine pH 1.5 (for anti-mouse Fc antibody) for 60 sec at a flow rate of 5 µl/min. Bulk refractive index differences were corrected by subtracting the response obtained from a mock surface. Blank injections were subtracted (double referencing). The derived curves were fitted to a 1:1 Langmuir binding model using the BIAevaluation software.

Example 56. Mode of Action Analysis of Anti-IL-1Beta Antibodies

Binding inhibition of anti-IL-1beta to human IL-1RI was investigated by surface plasmon resonance using a BIACORE T200 instrument (GE Healthcare). All experiments were performed at 25° C. using HBS-P (10 mM His, 140 mM NaCl, 0.05% Tween 20 pH 7.4) as running and dilution buffer. Human IL-1RI was immobilized on a Series S CM5 Sensor Chip (GE Healthcare) using standard amine coupling chemistry. 10 nM of human IL-1beta were pre-incubated with anti-IL-1beta antibodies concentrations from 100 nM down to 0.098 nM (1:2 dilution series). The IL-1beta/anti-IL-1beta antibody mixtures were injected onto the flow cell at 5 µl/min and the binding response (RU) after 60 s was used to monitor inhibition. The surface was regenerated by injecting 10 mM NaOH for 60 sec at a flow rate of 5 µl/min. Bulk refractive index differences were corrected by subtracting the response obtained from a mock surface.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A bispecific antibody that specifically binds to human IL-1beta and a second antigen selected from the group consisting of human ANG2, human VEGF, and human PDGF-B, comprising a human IL-1beta-specific heavy chain variable domain comprising a HVR-H1, a HVR-H2, and a HVR-H3 selected from the group consisting of:
   (a) a HVR-H1 comprising the amino acid sequence of SEQ ID NO: 02, a HVR-H2 comprising the amino acid sequence of SEQ ID NO: 03, and a HVR-H3 comprising the amino acid sequence of SEQ ID NO: 05,
   (b) a HVR-H1 comprising the amino acid sequence of SEQ ID NO: 07, a HVR-H2 comprising the amino acid sequence of SEQ ID NO: 08, and a HVR-H3 comprising the amino acid sequence of SEQ ID NO: 10, and
   (c) a HVR-H1 comprising the amino acid sequence of SEQ ID NO: 12, a HVR-H2 comprising the amino acid sequence of SEQ ID NO: 13, and a HVR-H3 comprising the amino acid sequence of SEQ ID NO: 15, and comprising a human IL-1beta-specific light chain variable domain comprising (a) a HVR-L1 comprising the amino acid sequence of SEQ ID NO: 17; (b) a HVR-L2 comprising the amino acid sequence of SEQ ID NO: 18; and (c) HVR-L3 comprising the amino acid sequence of SEQ ID NO: 19.

2. The bispecific antibody of claim 1, wherein the antibody further specifically binds to human ANG-2, further comprising:
   i) a human ANG-2-specific heavy chain variable domain comprising (a) a HVR-H1 comprising the amino acid sequence of SEQ ID NO: 57, (b) a HVR-H2 comprising the amino acid sequence of SEQ ID NO: 58, and (c) a HVR-H3 comprising the amino acid sequence of SEQ ID NO: 60, and a human ANG-2-specific light chain variable domain comprising (a) a HVR-L1 comprising the amino acid sequence of SEQ ID NO: 62; (b) a HVR-L2 comprising the amino acid sequence of SEQ ID NO: 63; and (c) HVR-L3 comprising the amino acid sequence of SEQ ID NO: 64, or ii) a human ANG-2-specific heavy chain variable domain comprising (a) a HVR-H1 comprising the amino acid sequence of SEQ ID NO: 66, (b) a HVR-H2 comprising the amino acid sequence of SEQ ID NO: 67, and (c) a HVR-H3 comprising the amino acid sequence of SEQ ID NO: 69, and a human ANG-2-specific light chain variable domain comprising (a) a HVR-L1 comprising the amino acid sequence of SEQ ID NO: 71; (b) a HVR-L2 comprising the amino acid sequence of SEQ ID NO: 72; and (c) HVR-L3 comprising the amino acid sequence of SEQ ID NO: 73, or iii) a human ANG-2-specific heavy chain variable domain comprising (a) a HVR-H1 comprising the amino acid sequence of SEQ ID NO: 75, (b) a HVR-H2 comprising the amino acid sequence of SEQ ID NO: 76, and (c) a HVR-H3 comprising the amino acid sequence of SEQ ID NO: 78, and a human ANG-2-specific light chain variable domain comprising (a) a HVR-L1 comprising the amino acid sequence of SEQ ID NO: 80; (b) a HVR-L2 comprising the amino acid sequence of SEQ ID NO: 81; and (c) HVR-L3 comprising the amino acid sequence of SEQ ID NO: 82, or iv) a human ANG-2-specific heavy chain variable domain comprising (a) a HVR-H1 comprising the amino acid sequence of SEQ ID NO: 84, (b) a HVR-H2 comprising the amino acid sequence of SEQ ID NO: 85, and (c) a HVR-H3 comprising the amino acid sequence of SEQ ID NO: 87, and a human ANG-2-specific light chain variable domain comprising (a) a HVR-L1 comprising the amino acid sequence of SEQ ID NO: 89; (b) a HVR-L2 comprising the amino acid sequence of SEQ ID NO: 90; and (c) HVR-L3 comprising the amino acid sequence of SEQ ID NO: 91.

3. The bispecific antibody of claim 1, wherein the antibody further specifically binds to human VEGF, further comprising:
   a) the HVR-H1, HVR-H2 and HVR-H3 as contained in the human VEGF-specific heavy chain variable domain of SEQ ID NO: 107 and the HVR-L1, HVR-L2 and HVR-L3 as contained in the human VEGF-specific light chain variable domain of SEQ ID NO: 108, or
   b) the HVR-H1, HVR-H2 and HVR-H3 as contained in the human VEGF-specific heavy chain variable domain of SEQ ID NO: 109 and the HVR-L1, HVR-L2 and HVR-L3 as contained in the human VEGF-specific light chain variable domain of SEQ ID NO: 110.

4. A bispecific antibody that specifically binds to human IL-1beta and a second antigen selected from the group consisting of human ANG2, human VEGF, and human PDGF-B, comprising:
   a) a human IL-1beta-specific heavy chain variable domain comprising a HVR-H1 comprising the amino acid sequence of SEQ ID NO: 21, (b) a HVR-H2 comprising the amino acid sequence of SEQ ID NO: 22, and (c) a HVR-H3 comprising the amino acid sequence of SEQ ID NO: 24, and a human IL-1beta-specific light chain variable domain comprising (a) a HVR-L1 comprising the amino acid sequence of SEQ ID NO: 26; (b) a HVR-L2 comprising the amino acid sequence of SEQ ID NO: 27; and (c) HVR-L3 comprising the amino acid sequence of SEQ ID NO: 28.

5. The bispecific antibody of claim 4, wherein the antibody further specifically binds to human ANG-2, further comprising:

i) a human ANG-2-specific heavy chain variable domain comprising (a) a HVR-H1 comprising the amino acid sequence of SEQ ID NO: 57, (b) a HVR-H2 comprising the amino acid sequence of SEQ ID NO: 58, and (c) a HVR-H3 comprising the amino acid sequence of SEQ ID NO: 60, and a human ANG-2-specific light chain variable domain comprising (a) a HVR-L1 comprising the amino acid sequence of SEQ ID NO: 62; (b) a HVR-L2 comprising the amino acid sequence of SEQ ID NO: 63; and (c) HVR-L3 comprising the amino acid sequence of SEQ ID NO: 64, or ii) a human ANG-2-specific heavy chain variable domain comprising (a) a HVR-H1 comprising the amino acid sequence of SEQ ID NO: 66, (b) a HVR-H2 comprising the amino acid sequence of SEQ ID NO: 67, and (c) a HVR-H3 comprising the amino acid sequence of SEQ ID NO: 69, and a human ANG-2-specific light chain variable domain comprising (a) a HVR-L1 comprising the amino acid sequence of SEQ ID NO: 71; (b) a HVR-L2 comprising the amino acid sequence of SEQ ID NO: 72; and (c) HVR-L3 comprising the amino acid sequence of SEQ ID NO: 73, or iii) a human ANG-2-specific heavy chain variable domain comprising (a) a HVR-H1 comprising the amino acid sequence of SEQ ID NO: 75, (b) a HVR-H2 comprising the amino acid sequence of SEQ ID NO: 76, and (c) a HVR-H3 comprising the amino acid sequence of SEQ ID NO: 78, and a human ANG-2-specific light chain variable domain comprising (a) a HVR-L1 comprising the amino acid sequence of SEQ ID NO: 80; (b) a HVR-L2 comprising the amino acid sequence of SEQ ID NO: 81; and (c) HVR-L3 comprising the amino acid sequence of SEQ ID NO: 82, or iv) a human ANG-2-specific heavy chain variable domain comprising (a) a HVR-H1 comprising the amino acid sequence of SEQ ID NO: 84, (b) a HVR-H2 comprising the amino acid sequence of SEQ ID NO: 85, and (c) a HVR-H3 comprising the amino acid sequence of SEQ ID NO: 87, and a human ANG-2-specific light chain variable domain comprising (a) a HVR-L1 comprising the amino acid sequence of SEQ ID NO: 89; (b) a HVR-L2 comprising the amino acid sequence of SEQ ID NO: 90; and (c) HVR-L3 comprising the amino acid sequence of SEQ ID NO: 91.

6. The bispecific antibody of claim 4, wherein the antibody further specifically binds to human VEGF, further comprising:
   a) the HVR-H1, HVR-H2 and HVR-H3 as contained in the human VEGF-specific heavy chain variable domain of SEQ ID NO: 107 and the HVR-L1, HVR-L2 and HVR-L3 as contained in the human VEGF-specific light chain variable domain of SEQ ID NO: 108, or
   b) the HVR-H1, HVR-H2 and HVR-H3 as contained in the human VEGF-specific heavy chain variable domain of SEQ ID NO: 109 and the HVR-L1, HVR-L2 and HVR-L3 as contained in the human VEGF-specific light chain variable domain of SEQ ID NO: 110.

7. A bispecific antibody that specifically binds to human IL-1beta and human PDGF-B, comprising:
   A) a first binding site specifically binding to human IL-1beta comprising:
      i) a heavy chain variable domain comprising a HVR-H1, a HVR-H2, and a HVR-H3 selected from the group consisting of:
         (a) a HVR-H1 comprising the amino acid sequence of SEQ ID NO: 02, a HVR-H2 comprising the amino acid sequence of SEQ ID NO: 03, and a HVR-H3 comprising the amino acid sequence of SEQ ID NO: 05,
(b) a HVR-H1 comprising the amino acid sequence of SEQ ID NO: 07, a HVR-H2 comprising the amino acid sequence of SEQ ID NO: 08, and a HVR-H3 comprising the amino acid sequence of SEQ ID NO: 10, and
(c) a HVR-H1 comprising the amino acid sequence of SEQ ID NO: 12, a HVR-H2 comprising the amino acid sequence of SEQ ID NO: 13, and a HVR-H3 comprising the amino acid sequence of SEQ ID NO: 15,
and comprising a light chain variable domain comprising (a) a HVR-L1 comprising the amino acid sequence of SEQ ID NO: 17; (b) a HVR-L2 comprising the amino acid sequence of SEQ ID NO: 18; and (c) HVR-L3 comprising the amino acid sequence of SEQ ID NO: 19, or
ii) a heavy chain variable domain comprising (a) a HVR-H1 comprising the amino acid sequence of SEQ ID NO: 21, (b) a HVR-H2 comprising the amino acid sequence of SEQ ID NO: 22, and (c) a HVR-H3 comprising the amino acid sequence of SEQ ID NO: 24, and a light chain variable domain comprising (a) a HVR-L1 comprising the amino acid sequence of SEQ ID NO: 26; (b) a HVR-L2 comprising the amino acid sequence of SEQ ID NO: 27; and (c) HVR-L3 comprising the amino acid sequence of SEQ ID NO: 28; and
B) a second binding site specifically binding to human PDGF-B comprising:
i) a heavy chain variable domain comprising (a) a HVR-H1 comprising the amino acid sequence of SEQ ID NO: 30, (b) a HVR-H2 comprising the amino acid sequence of SEQ ID NO: 31, and (c) a HVR-H3 comprising the amino acid sequence of SEQ ID NO: 33, and a light chain variable domain comprising (a) a HVR-L1 comprising the amino acid sequence of SEQ ID NO: 35; (b) a HVR-L2 comprising the amino acid sequence of SEQ ID NO: 36; and (c) HVR-L3 comprising the amino acid sequence of SEQ ID NO: 37, or
ii) a heavy chain variable domain comprising (a) a HVR-H1 comprising the amino acid sequence of SEQ ID NO: 39, (b) a HVR-H2 comprising the amino acid sequence of SEQ ID NO: 40, and (c) a HVR-H3 comprising the amino acid sequence of SEQ ID NO: 42, and a light chain variable domain comprising (a) a HVR-L1 comprising the amino acid sequence of SEQ ID NO: 44; (b) a HVR-L2 comprising the amino acid sequence of SEQ ID NO: 45; and (c) HVR-L3 comprising the amino acid sequence of SEQ ID NO: 46, or
iii) a heavy chain variable domain comprising (a) a HVR-H1 comprising the amino acid sequence of SEQ ID NO: 48, (b) a HVR-H2 comprising the amino acid sequence of SEQ ID NO: 49, and (c) a HVR-H3 comprising the amino acid sequence of SEQ ID NO: 51, and a light chain variable domain comprising (a) a HVR-L1 comprising the amino acid sequence of SEQ ID NO: 53; (b) a HVR-L2 comprising the amino acid sequence of SEQ ID NO: 54; and (c) HVR-L3 comprising the amino acid sequence of SEQ ID NO: 55.

8. The antibody of any one of claims 1, 4, 2, 5, 3, 6, and 7, wherein the antibody is a bivalent, bispecific antibody comprising:
a) a first light chain and a first heavy chain of an antibody specifically binding to a first antigen, and
b) a second light chain and a second heavy chain of an antibody specifically binding to a second antigen, wherein the variable domains VL and VH of the second light chain and the second heavy chain are replaced by each other.

9. The antibody of any one of claims 1, 4, 2, 5, 3, 6, and 7, wherein the antibody is a bivalent, bispecific antibody comprising:
a) a first light chain and a first heavy chain of an antibody specifically binding to a first antigen, and
b) a second light chain and a second heavy chain of an antibody specifically binding to a second antigen, wherein the variable domains VL and VH of the second light chain and the second heavy chain are replaced by each other,
wherein the antibody further comprises:
i) in the constant domain CL of the first light chain under a) the amino acid at position 124 is substituted independently by lysine (K), arginine (R) or histidine (H) (numbering according to Kabat), and wherein in the constant domain CH1 of the first heavy chain under a) the amino acid at position 147 or the amino acid at position 213 is substituted independently by glutamic acid (E) or aspartic acid (D) (numbering according to Kabat EU index), or
ii) in the constant domain CL of the second light chain under b) the amino acid at position 124 is substituted independently by lysine (K), arginine (R) or histidine (H) (numbering according to Kabat), and wherein in the constant domain CH1 of the second heavy chain under b) the amino acid at position 147 or the amino acid at position 213 is substituted independently by glutamic acid (E) or aspartic acid (D) (numbering according to Kabat EU index).

10. The antibody of any one of claims 1, 4, 2, 5, 3, 6, and 7, wherein the antibody is a bivalent, bispecific antibody, comprising:
a) a first light chain and a first heavy chain of an antibody specifically binding to a first antigen, and
b) a second light chain and a second heavy chain of an antibody specifically binding to a second antigen, wherein the constant domains CL and CH1 of the second light chain and the second heavy chain are replaced by each other.

11. The antibody according to any one of claims 1, 4, 2, 5, 3, 6, and 7, wherein the antibody comprises a first Fc-region polypeptide and a second Fc-region polypeptide, and wherein
i) the first Fc-region polypeptide is a human IgG1 Fc-region polypeptide and the second Fc-region polypeptide is a human IgG1 Fc-region polypeptide, or
ii) the first Fc-region polypeptide is a human IgG1 Fc-region polypeptide with the mutations L234A, L235A and the second Fc-region polypeptide is a human IgG1 Fc-region polypeptide with the mutations L234A, L235A, or
iii) the first Fc-region polypeptide is a human IgG1 Fc-region polypeptide with the mutations L234A, L235A, P329G and the second Fc-region polypeptide is a human IgG1 Fc-region polypeptide with the mutations L234A, L235A, P329G, or
iv) the first Fc-region polypeptide is a human IgG1 Fc-region polypeptide with the mutations L234A, L235A, S354C, T366W and the second Fc-region polypeptide is a human IgG1 Fc-region polypeptide with the mutations L234A, L235A, Y349C, T366S, L368A, Y407V, or v) the first Fc-region polypeptide is a human IgG1 Fc-region polypeptide with the mutations L234A, L235A, P329G, S354C, T366W and the second Fc-region polypeptide is a human IgG1 Fc-region polypeptide with the mutations L234A, L235A, P329G, Y349C, T366S, L368A, Y407V, or vi) the first Fc-region polypeptide is a human IgG4 Fc-region polypeptide and the second Fc-region polypeptide is a human IgG4 Fc-region polypeptide, or vii) the first Fc-region polypeptide is a human IgG4 Fc-region polypeptide with the mutations S228P, L235E and the second Fc-region polypeptide is a human IgG4 Fc-region polypeptide with the mutations S228P, L235E, or viii) the first Fc-region polypeptide is a human IgG4 Fc-region polypeptide with the mutations S228P, L235E, P329G and the second Fc-region polypeptide is a human IgG4 Fc-region polypeptide with the mutations S228P, L235E, P329G, or ix) the first Fc-region polypeptide is a human IgG4 Fc-region polypeptide with the mutations S228P, L235E, S354C, T366W and the second Fc-region polypeptide is a human IgG4 Fc-region polypeptide with the mutations S228P, L235E, Y349C, T366S, L368A, Y407V, or x) the first Fc-region polypeptide is a human IgG4 Fc-region polypeptide with the mutations S228P, L235E, P329G, S354C, T366W and the second Fc-region polypeptide is a human IgG4 Fc-region polypeptide with the mutations S228P, L235E, P329G, Y349C, T366S, L368A, Y407V.

12. The antibody of any one of claims 1, 4, 2, 5, 3, 6, and 7, wherein the antibody comprises a first Fc-region polypeptide and a second Fc-region polypeptide, and
   wherein the antibody comprises the combination of mutations
   i) I253A, H310A, and H435A, or
   ii) H310A, H433A, and Y436A, or
   iii) L251D, L314D, and L432D, or
   iv) combinations of i) to iii)
   in the first Fc-region polypeptide and in the second Fc-region polypeptide.

13. A pharmaceutical composition comprising the antibody according to any one of claims 1, 4, 2, 5, 3, 6, and 7 and a pharmaceutically acceptable carrier.

\* \* \* \* \*